US012590304B2

(12) United States Patent
Zhang et al.

(10) Patent No.: US 12,590,304 B2
(45) Date of Patent: *Mar. 31, 2026

(54) NUCLEIC ACID, PHARMACEUTICAL COMPOSITION, CONJUGATE, PREPARATION METHOD, AND USE

(71) Applicant: SUZHOU RIBO LIFE SCIENCE CO., LTD., Suzhou (CN)

(72) Inventors: Hongyan Zhang, Suzhou (CN); Shan Gao, Suzhou (CN); Daiwu Kang, Suzhou (CN)

(73) Assignee: SUZHOU RIBO LIFE SCIENCE CO., LTD., Suzhou (CN)

( * ) Notice: Subject to any disclaimer, the term of this patent is extended or adjusted under 35 U.S.C. 154(b) by 1062 days.

This patent is subject to a terminal disclaimer.

(21) Appl. No.: 17/595,621

(22) PCT Filed: May 21, 2020

(86) PCT No.: PCT/CN2020/091614
§ 371 (c)(1),
(2) Date: Nov. 19, 2021

(87) PCT Pub. No.: WO2020/233680
PCT Pub. Date: Nov. 26, 2020

(65) Prior Publication Data
US 2024/0200060 A1 Jun. 20, 2024

(30) Foreign Application Priority Data
May 22, 2019 (CN) ......................... 201910430606.1

(51) Int. Cl.
*C12N 15/113* (2010.01)
*A61K 47/54* (2017.01)
*A61P 31/04* (2006.01)

(52) U.S. Cl.
CPC .......... *C12N 15/113* (2013.01); *A61K 47/549* (2017.08); *A61P 31/04* (2018.01); *C12N 2310/14* (2013.01); *C12N 2310/315* (2013.01); *C12N 2310/322* (2013.01)

(58) Field of Classification Search
CPC .............. C12N 15/113; C12N 2310/14; C12N 2310/315; C12N 2310/322; C12N 2310/351; C12N 2320/11; C12N 2330/30; C12N 2310/343; C12N 2310/346; C12N 2310/3517; C12N 2320/32; A61K 47/549; A61K 31/713; A61K 47/54; A61P 31/04; A61P 21/00; A61P 21/04; A61P 37/00; C07H 21/02
See application file for complete search history.

(56) References Cited

U.S. PATENT DOCUMENTS

| | | | | |
|---|---|---|---|---|
| 8,030,474 | B2 | 10/2011 | Khvorova et al. | |
| 8,106,022 | B2 | 1/2012 | Manoharan et al. | |
| 8,334,372 | B2 | 12/2012 | Freier et al. | |
| 8,344,125 | B2 | 1/2013 | Manoharan et al. | |
| 9,428,751 | B2 | 8/2016 | Macdonald et al. | |
| 9,670,492 | B2 | 6/2017 | Freier et al. | |
| 10,130,651 | B2 | 11/2018 | Wooddell et al. | |
| 10,246,708 | B2 | 4/2019 | Kasperkovitz et al. | |
| 10,294,477 | B2 | 5/2019 | Swayze | |
| 10,370,453 | B2 | 8/2019 | Sexton et al. | |
| 10,934,544 | B2 | 3/2021 | Akinc et al. | |
| 11,084,884 | B2 | 8/2021 | Sexton et al. | |
| 11,414,661 | B2 | 8/2022 | Zhang et al. | |
| 11,414,665 | B2 | 8/2022 | Zhang et al. | |
| 11,492,620 | B2 | 11/2022 | Zhang et al. | |
| 11,633,482 | B2 * | 4/2023 | Zhang ................ | C12N 15/1131 514/25 |

(Continued)

FOREIGN PATENT DOCUMENTS

| | | | |
|---|---|---|---|
| AU | 2014208251 | A1 | 8/2014 |
| CA | 2930393 | A1 | 6/2009 |

(Continued)

OTHER PUBLICATIONS

Fakhr, E., Zare, F., & Teimoori-Toolabi, L. (2016). Precise and efficient siRNA design: a key point in competent gene silencing. Cancer Gene Therapy, 23(4), 73-82. https://doi.org/10.1038/cgt.2016.4 (Year: 2016).*

NCBI Gene ID: 3827, dating to GRCh37.p13 human genome assembly on Jun. 28, 2013 (Year: 2013).*

Fakhr, E., et al. "Precise and Efficient siRNA Design: A Key Point in Competent Gene Silencing." Cancer Gene Therapy, vol. 23, No. 4, Apr. 2016, pp. 73-82. DOI.org (Crossref), https://doi.org/10.1038/cgt.2016.4. (Year: 2016).*

Dana H, . . . Gharagouzlo E. Molecular Mechanisms and Biological Functions of siRNA. Int J Biomed Sci. Jun. 2017;13(2):48-57. PMID: 28824341; PMCID: PMC5542916. (Year: 2017).*

Willoughby, Jennifer L. S., et al. "Evaluation of GalNAc-siRNA Conjugate Activity in Pre-Clinical Animal Models with Reduced Asialoglycoprotein Receptor Expression." Molecular Therapy, vol. 26, No. 1, Jan. 2018, pp. 105-114. DOI.org (Crossref), https://doi.org/10.1016/j.ymthe.2017.08.019. (Year: 2018).*

(Continued)

*Primary Examiner* — J. E. Angell
*Assistant Examiner* — Sarah E Allen
(74) *Attorney, Agent, or Firm* — Panitch Schwarze Belisario & Nadel LLP

(57) ABSTRACT

An siRNA which inhibits kininogen (KNG) gene expression, a pharmaceutical composition containing the siRNA, and an siRNA conjugate. Each nucleotide in the siRNA is independently a modified or unmodified nucleotide. The siRNA contains a sense strand and an antisense strand. The sense strand contains nucleotide sequence I, nucleotide sequence I having the same length as the nucleotide sequence shown in SEQ ID NO: 1, with no more than three nucleotide differences. The antisense strand contains nucleotide sequence II, nucleotide sequence II having the same length as the nucleotide sequence shown in SEQ ID NO: 2, with no more than three nucleotide differences. The siRNA, the pharmaceutical composition thereof and the siRNA conjugate can effectively treat and/or prevent septicemia.

8 Claims, 4 Drawing Sheets

Specification includes a Sequence Listing.

(56) References Cited

U.S. PATENT DOCUMENTS

| | | | | |
|---|---|---|---|---|
| 11,660,347 | B2 * | 5/2023 | Zhang | A61P 3/06 536/1.11 |
| 11,896,674 | B2 * | 2/2024 | Zhang | A61K 47/555 |
| 11,918,600 | B2 | 3/2024 | Zhang et al. | |
| 12,084,661 | B2 * | 9/2024 | Zhang | C12N 15/1131 |
| 2003/0206887 | A1 | 11/2003 | Morrissey et al. | |
| 2004/0266707 | A1 | 12/2004 | Leake et al. | |
| 2005/0245475 | A1 | 11/2005 | Khvorova et al. | |
| 2005/0246794 | A1 | 11/2005 | Khvorova et al. | |
| 2005/0255487 | A1 | 11/2005 | Khvorova et al. | |
| 2008/0113351 | A1 | 5/2008 | Naito et al. | |
| 2008/0146788 | A1 | 6/2008 | Bhat et al. | |
| 2010/0063132 | A1 | 3/2010 | Kim et al. | |
| 2010/0137414 | A1 | 6/2010 | Freier et al. | |
| 2011/0015252 | A1 | 1/2011 | Fitzgerald et al. | |
| 2011/0039914 | A1 | 2/2011 | Pavco et al. | |
| 2011/0054005 | A1 | 3/2011 | Naito et al. | |
| 2012/0052487 | A9 | 3/2012 | Khvorova et al. | |
| 2012/0108803 | A1 | 5/2012 | Han et al. | |
| 2012/0172412 | A1 | 7/2012 | Rozema et al. | |
| 2012/0184595 | A1 | 7/2012 | Macdonald et al. | |
| 2012/0201756 | A1 | 8/2012 | Sexton | |
| 2012/0227119 | A1 | 9/2012 | Doran et al. | |
| 2013/0005793 | A1 | 1/2013 | Chin et al. | |
| 2013/0023579 | A1 | 1/2013 | Crooke et al. | |
| 2013/0041133 | A1 | 2/2013 | Aaronson et al. | |
| 2013/0096288 | A1 | 4/2013 | Han et al. | |
| 2013/0123482 | A1 | 5/2013 | Xi et al. | |
| 2013/0158021 | A1 | 6/2013 | Dong et al. | |
| 2013/0190484 | A1 | 7/2013 | Rozema et al. | |
| 2014/0099666 | A1 | 4/2014 | Rossomando et al. | |
| 2014/0128453 | A1 | 5/2014 | Mullick et al. | |
| 2014/0179768 | A1 | 6/2014 | Bettencourt et al. | |
| 2014/0194489 | A1 | 7/2014 | Bumcrot et al. | |
| 2014/0343123 | A1 | 11/2014 | Prakash et al. | |
| 2015/0093444 | A1 | 4/2015 | Zhang et al. | |
| 2015/0152436 | A1 | 6/2015 | Musunuru et al. | |
| 2015/0174260 | A1 | 6/2015 | Yang et al. | |
| 2015/0191726 | A1 | 7/2015 | Manoharan et al. | |
| 2015/0247143 | A1 | 9/2015 | Fitzgerald et al. | |
| 2015/0263948 | A1 | 9/2015 | Jan et al. | |
| 2015/0291958 | A1 | 10/2015 | Albaek et al. | |
| 2015/0315584 | A1 | 11/2015 | Macdonald et al. | |
| 2015/0315594 | A1 | 11/2015 | Prakash et al. | |
| 2016/0017335 | A1 | 1/2016 | Borodovsky et al. | |
| 2016/0186180 | A1 | 6/2016 | Bettencourt et al. | |
| 2016/0237438 | A1 | 8/2016 | Brown et al. | |
| 2016/0283653 | A1 | 9/2016 | Staudt et al. | |
| 2016/0354404 | A1 | 12/2016 | Hinkle et al. | |
| 2017/0000815 | A1 | 1/2017 | Fitzgerald et al. | |
| 2017/0002094 | A1 | 1/2017 | Sexton et al. | |
| 2017/0114341 | A1 | 4/2017 | Bradshaw et al. | |
| 2018/0087054 | A1 | 3/2018 | Querbes et al. | |
| 2018/0148722 | A1 | 5/2018 | Fitzgerald et al. | |
| 2018/0216114 | A1 | 8/2018 | Fitzgerald et al. | |
| 2018/0245077 | A1 | 8/2018 | Chiu et al. | |
| 2019/0062749 | A1 | 2/2019 | Zhang | |
| 2019/0078088 | A1 | 3/2019 | Li et al. | |
| 2019/0202855 | A1 | 7/2019 | Sakamuri et al. | |
| 2019/0255091 | A1 | 8/2019 | Li et al. | |
| 2019/0292547 | A1 | 9/2019 | Li et al. | |
| 2020/0199591 | A1 | 6/2020 | Fitzgerald et al. | |
| 2020/0338201 | A1 | 10/2020 | Zhang et al. | |
| 2020/0360522 | A1 | 11/2020 | Zhang et al. | |
| 2021/0032623 | A1 | 2/2021 | Zhang et al. | |
| 2021/0275564 | A1 | 9/2021 | Zhang et al. | |
| 2021/0277400 | A1 | 9/2021 | Zhang et al. | |
| 2021/0401994 | A1 | 12/2021 | Zhang et al. | |
| 2022/0049249 | A1 | 2/2022 | Zhang et al. | |
| 2022/0062427 | A1 | 3/2022 | Zhang et al. | |
| 2022/0186221 | A1 | 6/2022 | Zhang et al. | |
| 2022/0235359 | A1 | 7/2022 | Zhang et al. | |
| 2022/0315929 | A1 | 10/2022 | Zhang et al. | |
| 2022/0356474 | A1 | 11/2022 | Zhang et al. | |
| 2022/0389428 | A1 | 12/2022 | Zhang et al. | |
| 2022/0395526 | A1 | 12/2022 | Zhang et al. | |
| 2023/0076803 | A1 | 3/2023 | Zhang et al. | |
| 2023/0132756 | A1 | 5/2023 | Zhang et al. | |
| 2023/0193277 | A1 * | 6/2023 | Zhang | A61K 47/18 514/44 A |
| 2023/0257827 | A1 | 8/2023 | Zhang et al. | |
| 2023/0313195 | A1 | 10/2023 | Zhang et al. | |
| 2024/0200060 | A1 | 6/2024 | Zhang et al. | |
| 2024/0200076 | A1 | 6/2024 | Zhang et al. | |
| 2025/0057870 | A1 | 2/2025 | Liang et al. | |

FOREIGN PATENT DOCUMENTS

| | | | |
|---|---|---|---|
| CA | 2 677 068 | A1 | 3/2011 |
| CN | 101603042 | A | 12/2009 |
| CN | 102006890 | A | 4/2011 |
| CN | 102016036 | A | 4/2011 |
| CN | 102124107 | A | 7/2011 |
| CN | 102140458 | A | 8/2011 |
| CN | 102140459 | A | 8/2011 |
| CN | 102140460 | A | 8/2011 |
| CN | 102140461 | A | 8/2011 |
| CN | 102344477 | A | 2/2012 |
| CN | 102439148 | A | 5/2012 |
| CN | 102719434 | A | 10/2012 |
| CN | 102753186 | A | 10/2012 |
| CN | 102869774 | A | 1/2013 |
| CN | 103380113 | A | 10/2013 |
| CN | 102083983 | B | 4/2014 |
| CN | 103890000 | A | 6/2014 |
| CN | 104107437 | A | 10/2014 |
| CN | 104232644 | A | 12/2014 |
| CN | 104328121 | A | 2/2015 |
| CN | 104717982 | A | 6/2015 |
| CN | 104854242 | A | 8/2015 |
| CN | 104922141 | A | 9/2015 |
| CN | 105324485 | A | 2/2016 |
| CN | 105378082 | A | 3/2016 |
| CN | 105392488 | A | 3/2016 |
| CN | 105452465 | A | 3/2016 |
| CN | 105517556 | A | 4/2016 |
| CN | 105713092 | A | 6/2016 |
| CN | 105814204 | A | 7/2016 |
| CN | 106132442 | A | 11/2016 |
| CN | 106146591 | A | 11/2016 |
| CN | 106232831 | A | 12/2016 |
| CN | 106255755 | A | 12/2016 |
| CN | 106460025 | A | 2/2017 |
| CN | 107075516 | A | 8/2017 |
| CN | 107109405 | A | 8/2017 |
| CN | 107250362 | A | 10/2017 |
| CN | 107854478 | A | 3/2018 |
| CN | 108271386 | A | 3/2018 |
| CN | 108064294 | A | 5/2018 |
| CN | 108064313 | A | 5/2018 |
| CN | 108220293 | A | 6/2018 |
| CN | 108239644 | A | 7/2018 |
| CN | 108265052 | A | 7/2018 |
| CN | 108348541 | A | 7/2018 |
| CN | 110945131 | A | 3/2020 |
| CN | 110959011 | A | 4/2020 |
| CN | 111050807 | A | 4/2020 |
| CN | 111973617 | A | 11/2020 |
| CN | 111973618 | A | 11/2020 |
| CN | 111973619 | A | 11/2020 |
| CN | 111979237 | A | 11/2020 |
| CN | 112423795 | A | 2/2021 |
| CN | 113330117 | A | 8/2021 |
| EP | 1 752 536 | A1 | 2/2007 |
| EP | 2 194 128 | A1 | 6/2010 |
| EP | 2 213 738 | A2 | 8/2010 |
| EP | 2 376 641 | | 10/2011 |
| EP | 2 669 377 | A2 | 12/2013 |
| EP | 2 990 410 | A1 | 3/2016 |
| EP | 3 312 281 | A2 | 4/2018 |
| EP | 3 315 608 | A1 | 5/2018 |
| EP | 3 335 715 | A2 | 6/2018 |
| EP | 3409780 | A1 | 12/2018 |
| EP | 3 719 128 | A1 | 10/2020 |

(56) References Cited

FOREIGN PATENT DOCUMENTS

| | | | |
|---|---|---|---|
| EP | 3 862 024 | A1 | 8/2021 |
| JP | 2013523149 | A | 6/2013 |
| JP | 2013537423 | A | 10/2013 |
| JP | 2016501195 | A | 1/2016 |
| JP | 2016523087 | A | 8/2016 |
| JP | 2017521045 | A | 8/2017 |
| JP | 2017534290 | A | 11/2017 |
| RU | 2013 134 745 | A | 2/2015 |
| RU | 2 558 258 | C2 | 7/2015 |
| RU | 2015 133 167 | A | 3/2017 |
| TW | 201925471 | A | 7/2019 |
| TW | 201929905 | A | 8/2019 |
| WO | 00/27795 | A1 | 5/2000 |
| WO | 2004/045543 | A2 | 6/2004 |
| WO | 2004/078181 | A1 | 9/2004 |
| WO | 2005/116204 | A1 | 12/2005 |
| WO | 2006/006948 | A2 | 1/2006 |
| WO | 2006/096018 | A1 | 9/2006 |
| WO | 2007/134161 | A2 | 11/2007 |
| WO | 2008/011431 | A2 | 1/2008 |
| WO | 2008/109472 | A2 | 9/2008 |
| WO | 2009/073809 | A2 | 6/2009 |
| WO | 2009/082607 | A2 | 7/2009 |
| WO | 2009/134487 | A2 | 11/2009 |
| WO | 2010/012244 | A1 | 2/2010 |
| WO | 2010/045509 | A2 | 4/2010 |
| WO | 2010/068978 | A1 | 6/2010 |
| WO | 2010/083615 | A1 | 7/2010 |
| WO | 2010/101951 | A1 | 9/2010 |
| WO | 2010/121074 | A1 | 10/2010 |
| WO | 2010/131916 | A2 | 11/2010 |
| WO | 2010/147992 | A1 | 12/2010 |
| WO | 2011005793 | A1 | 1/2011 |
| WO | 2011/028938 | A1 | 3/2011 |
| WO | 2011/085271 | A2 | 7/2011 |
| WO | 2011/104169 | A1 | 9/2011 |
| WO | 2011126974 | A1 | 10/2011 |
| WO | 2011/139702 | A2 | 11/2011 |
| WO | 2011/154331 | A1 | 12/2011 |
| WO | 2012/013127 | A1 | 2/2012 |
| WO | 2012024170 | A2 | 2/2012 |
| WO | 2012/037254 | A1 | 3/2012 |
| WO | 2012/068176 | A1 | 5/2012 |
| WO | 2012/083185 | A2 | 6/2012 |
| WO | 2012/089352 | A1 | 7/2012 |
| WO | 2012/130086 | A1 | 10/2012 |
| WO | 2012/139081 | A2 | 10/2012 |
| WO | 2012/139469 | A1 | 10/2012 |
| WO | 2012/177784 | A2 | 12/2012 |
| WO | 2013/060261 | A1 | 5/2013 |
| WO | 2013/070771 | A1 | 5/2013 |
| WO | 2013061295 | A1 | 5/2013 |
| WO | 2013/166155 | A1 | 11/2013 |
| WO | 2014/025805 | A1 | 2/2014 |
| WO | 2014076195 | A1 | 5/2014 |
| WO | 2014/089313 | A1 | 6/2014 |
| WO | 2014/118267 | A2 | 11/2014 |
| WO | 2014/179626 | A2 | 11/2014 |
| WO | 2014/179627 | A2 | 11/2014 |
| WO | 2014/179629 | A2 | 11/2014 |
| WO | 2014205451 | A1 | 12/2014 |
| WO | 2015/006498 | A2 | 1/2015 |
| WO | 2015/006740 | A2 | 1/2015 |
| WO | 2015/015496 | A1 | 2/2015 |
| WO | 2015/031679 | A2 | 3/2015 |
| WO | 2015/051366 | A2 | 4/2015 |
| WO | 2015/100394 | A1 | 7/2015 |
| WO | 2015/113922 | A1 | 8/2015 |
| WO | 2015/148580 | A2 | 10/2015 |
| WO | 2015/168532 | A2 | 11/2015 |
| WO | 2015168589 | A1 | 11/2015 |
| WO | 2015/188197 | A2 | 12/2015 |
| WO | 2016/077321 | A2 | 12/2015 |
| WO | 2015188194 | A1 | 12/2015 |
| WO | 2015/011123 | A1 | 1/2016 |
| WO | 2016/028649 | A1 | 2/2016 |
| WO | 2016/040589 | A1 | 3/2016 |
| WO | 2016/081444 | A1 | 5/2016 |
| WO | 2016077349 | A1 | 5/2016 |
| WO | 2016/099982 | A2 | 6/2016 |
| WO | 2016/149331 | A2 | 9/2016 |
| WO | 2016/154127 | A2 | 9/2016 |
| WO | 2016/168286 | A1 | 10/2016 |
| WO | 2016/179342 | A2 | 11/2016 |
| WO | 2016/188473 | A1 | 12/2016 |
| WO | 2016/201301 | A1 | 12/2016 |
| WO | 2016/206626 | A1 | 12/2016 |
| WO | 2017/015175 | A1 | 1/2017 |
| WO | 2017/019660 | A1 | 2/2017 |
| WO | 2017/019891 | A2 | 2/2017 |
| WO | 2017/035340 | A1 | 3/2017 |
| WO | 2017/055627 | A1 | 4/2017 |
| WO | 2017/100542 | A1 | 6/2017 |
| WO | 2017/120397 | A1 | 7/2017 |
| WO | 2017131236 | A1 | 8/2017 |
| WO | 2017/184689 | A1 | 10/2017 |
| WO | 2017/189813 | A1 | 11/2017 |
| WO | 2018/027106 | A2 | 2/2018 |
| WO | 2018/035380 | A1 | 2/2018 |
| WO | 2018/044350 | A1 | 3/2018 |
| WO | 2018/075658 | A1 | 4/2018 |
| WO | 2018/140920 | A1 | 8/2018 |
| WO | 2018/191278 | A2 | 10/2018 |
| WO | 2018/209848 | A1 | 11/2018 |
| WO | 2018/223073 | A1 | 12/2018 |
| WO | 2019/105403 | A1 | 6/2019 |
| WO | 2019/105404 | A1 | 6/2019 |
| WO | 2019/105418 | A1 | 6/2019 |
| WO | 2019/105419 | A1 | 6/2019 |
| WO | 2019/105435 | A1 | 6/2019 |
| WO | 2019/105437 | A1 | 6/2019 |
| WO | 2019/128611 | A1 | 7/2019 |
| WO | 2020038377 | A1 | 2/2020 |
| WO | 2020/063198 | A1 | 4/2020 |
| WO | 2020/093053 | A1 | 5/2020 |
| WO | 2020/135581 | A1 | 7/2020 |
| WO | 2020/147847 | A1 | 7/2020 |
| WO | 2020233651 | A1 | 11/2020 |
| WO | 2020233655 | A1 | 11/2020 |
| WO | 2020233680 | A1 | 11/2020 |
| WO | 2020238763 | A1 | 12/2020 |
| WO | 2020238766 | A1 | 12/2020 |

OTHER PUBLICATIONS

*Homo sapiens* Kininogen 1 (KNG1), Transcript Variant 3, mRNA. 2, Mar. 27, 2025. NCBI Nucleotide Database, 1676317709, NCBI Nucleotide, http://www.ncbi.nlm.nih.gov/nuccore/NM_001166451.2. (Year: 2025).*

Chen et al., "Proof-of-concept Studies for siRNA-mediated Gene Silencing for Coagulation Factors in Rat and Rabbit", Molecular Therapy—Nucleic Acids, Jan. 27, 2015, vol. 4, No. 1, p. e224.

Ferrone et al., "IONIS-PKK Rx a Novel Antisense Inhibitor of Prekallikrein and Bradykinin Production", Nucleic Acid Therapeutics, Apr. 1, 2019, vol. 29, No. 2, pp. 82-91.

Ghosh et al., "Effectiveness and Safety of Inclisiran, A Novel Long-Acting RNA Therapeutic Inhibitor of Proprotein Convertase Subtilisin/Kexin 9", American Journal of Cardiology, Cahners Publishing Co., Newton, MA, US, Jul. 3, 2018, vol. 122, No. 7, pp. 1272-1277.

Joshi et al., "siRNA: novel therapeutics from functional genomics", Biotechnology and Genetic Engineering Reviews, Jan. 2, 2014, vol. 30, No. 1, pp. 1-30.

Pawluczyk et al., "Kallikrein gene 'knock-down' by small interfering RNA transfection induces a profibrotic phenotype in rat mesangial cells", Journal of Hypertension, Lippincott Williams & Wilkens, Ltd., Jan. 1, 2008, vol. 26, No. 1, pp. 93-101.

Revenko et al., "Selective depletion of plasma prekallikrein or coagulation factor XII inhibits thrombosis in mice without increased risk of bleeding", Blood, American Society of Hematology, Nov. 10, 2011, vol. 118, No. 19, pp. 5302-5311.

(56) References Cited

OTHER PUBLICATIONS

Yamasaki et al., "Novel molecular targets regulated by tumor suppressors microRNA-1 and microRNA-133a in bladder cancer", International Journal of Oncology, Feb. 29, 2012, vol. 40, pp. 1821-1830.
Supplementary European Search Report issued on Jun. 14, 2023, by the European Patent Office in European Patent Application No. 20809702.2 (12 pages).
Supplementary European Search Report issued on Jun. 16, 2023, by the European Patent Office in European Patent Application No. 20814338.8 (10 pages).
Partial Supplementary European Search Report issued on Jul. 5, 2023, by the European Patent Office in European Patent Application No. 20810635.1 (13 pages).
Partial Supplementary European Search Report issued on Jul. 10, 2023, by the European Patent Office in European Patent Application No. 20815633.1 (17 pages).
Bertrand, et al., "Comparison of antisense oligonucleotides and siRNAs in cell culture and in vivo," Biochemical and Biophysical Research Communications, 2002, vol. 296, Issue 4, pp. 1000-1004, ISSN 0006-291X.
Durnov, et al., "Children's Oncology", Paediatric Oncology, Second Edition, Moscow Publishing House Medicine, 2002, p. 139 and its English translation. Cited in Office Action issued on Oct. 10, 2022 in Russian Application No. 2020121741). (4 pages).
Dysop, "Chemistry of Synthetic Drugs", Publishing House MIR, 1964, pp. 12-19 and its English translation. Cited in Office Action issued on Oct. 10, 2022 in Russian Application No. 2020121741). (18 pages).
Belikov, V.G., "Pharmaceutical Chemistry", textbook, Moscow, 11th Edition, MEDpress-inform, 2007, pp. 27-29 and its English translation. (Cited in Office Action issued on Oct. 10, 2022 in Russian Application No. 2020121741). (8 pages).
The First Office Action issued on Jan. 30, 2022, by the State Intellectual Property Office of the People's Republic of China in Chinese Patent Application No. 201880049520.8 and an English translation of the Action. (11 pages).
Decision of Rejection issued on Mar. 3, 2022, by the State Intellectual Property Office of the People's Republic of China in Chinese Patent Application No. 202010426194.7 and an English translation of the Action. (20 pages).
The Second Office Action issued on Mar. 16, 2022, by the State Intellectual Property Office of the People's Republic of China in Chinese Patent Application No. 201980046892.X and an English translation of the Action. (24 pages).
The Second Office Action issued on Mar. 21, 2022, by the State Intellectual Property Office of the People's Republic of China in Chinese Patent Application No. 201980046893.4 and an English translation of the Action. (19 pages).
The First Office Action issued on May 7, 2022, by the State Intellectual Property Office of the People's Republic of China in Chinese Patent Application No. 201980010095.6 and an English translation of the Action. (27 pages).
The First Office Action issued on May 7, 2022, by the State Intellectual Property Office of the People's Republic of China in Chinese Patent Application No. 201980010175.1 and an English translation of the Action. (30 pages).
The First Office Action issued on May 7, 2022, by the State Intellectual Property Office of the People's Republic of China in Chinese Patent Application No. 201880049190.2 and an English translation of the Action. (31 pages).
The First Office Action issued on May 7, 2022, by the State Intellectual Property Office of the People's Republic of China in Chinese Patent Application No. 201880049191.7 and an English translation of the Action. (30 pages).
The First Office Action issued on May 7, 2022, by the State Intellectual Property Office of the People's Republic of China in Chinese Patent Application No. 202080007282.1 and an English translation of the Action. (33 pages).
The First Office Action issued on May 7, 2022, by the State Intellectual Property Office of the People's Republic of China in Chinese Patent Application No. 201880049564.0 and an English translation of the Action. (29 pages).
The First Office Action issued on May 7, 2022, by the State Intellectual Property Office of the People's Republic of China in Chinese Patent Application No. 201880049586.7 and an English translation of the Action. (33 pages).
The First Office Action issued on May 7, 2022, by the State Intellectual Property Office of the People's Republic of China in Chinese Patent Application No. 201880048597.3 and an English translation of the Action. (34 pages).
The First Office Action issued on May 7, 2022, by the State Intellectual Property Office of the People's Republic of China in Chinese Patent Application No. 201880048600.1 and an English translation of the Action. (34 pages).
The First Office Action issued on May 7, 2022, by the State Intellectual Property Office of the People's Republic of China in Chinese Patent Application No. 202080009787.1 and an English translation of the Action. (50 pages).
The First Office Action issued on May 7, 2022, by the State Intellectual Property Office of the People's Republic of China in Chinese Patent Application No. 201880048949.5 and an English translation of the Action. (33 pages).
The First Office Action issued on May 20, 2021, by the State Intellectual Property Office of the People's Republic of China in Chinese Patent Application No. 202010426194.7 and an English translation of the Action. (20 pages).
The First Office Action issued on Jun. 23, 2021, by the State Intellectual Property Office of the People's Republic of China in Chinese Patent Application No. 201980046892.X and an English translation of the Action. (13 pages).
The First Office Action issued on Jun. 23, 2021, by the State Intellectual Property Office of the People's Republic of China in Chinese Patent Application No. 201980046893.4 and an English translation of the Action. (12 pages).
The First Office Action issued on Jun. 29, 2022, by the State Intellectual Property Office of the People's Republic of China in Chinese Patent Application No. 201980046892.X and an English translation of the Action. (8 pages).
The First Office Action issued on Jun. 29, 2022, by the State Intellectual Property Office of the People's Republic of China in Chinese Patent Application No. 201980046893.4 and an English translation of the Action. (8 pages).
The First Office Action issued on Oct. 25, 2021, by the State Intellectual Property Office of the People's Republic of China in Chinese Patent Application No. 202010426196.6 and an English translation of the Action. (16 pages).
The Second Office Action issued on Nov. 12, 2021, by the State Intellectual Property Office of the People's Republic of China in Chinese Patent Application No. 202010426194.7 and an English translation of the Action. (16 pages).
The Extended European Search Report issued on Jun. 9, 2022, by the European Patent Office in European Patent Application Publication No. 19851738.5. (64 pages).
The Extended European Search Report issued on Jul. 19, 2022, by the European Patent Office in European Patent Application No. 19867686.8. (12 pages).
The Extended European Search Report and Supplementary European Search Report issued on Aug. 9, 2021, by the European Patent Office in European Patent Application Publication No. 18883362.8. (9 pages).
The Extended European Search Report issued on Sep. 16, 2021, by the European Patent Office in European Patent Application No. 18883803.1. (10 pages).
Extended European Search Report dated Sep. 17, 2021, issued by the European Patent Office in corresponding European Application No. 18883982.3. (9 pages).
Extended European Search Report dated Sep. 29, 2021, issued by the European Patent Office in corresponding European Application No. 18884492.2. (45 pages).

(56) References Cited

OTHER PUBLICATIONS

The Extended European Search Report issued on Oct. 7, 2021, by the European Patent Office in European Patent Application Publication No. 18896766.5. (19 pages).
Invitation to remedy deficiencies pursuant to Rule 30(3) EPC / Rule 163(3) EPC issued on Feb. 22, 2022, by the European Patent Office in European Patent Application No. 20809029.0. (2 pages).
Communication pursuant to Rule 159 and Rule 58 EPC Invitation to remedy deficiencies in the application documents issued on Jan. 24, 2022, by the European Patent Office in European Patent Application No. 20815633.1 (2 pages).
Supplementary European Search Report issued on Jul. 27, 2021, by the European Patent Office in European Patent Application No. 18883153. (7 pages).
Notification of Substantive Examination Result issued on Aug. 24, 2021, by the Intellectual Property Office of the Republic of Indonesia in Indonesian Patent Application No. P00202003131 and an English translation of the Notification. (6 pages).
Notification of Substantive Examination Result issued on Dec. 2, 2021, by the Intellectual Property Office of the Republic of Indonesia in Indonesian Patent Application No. P00202003125 and an English translation of the Notification. (6 pages).
Examination report under sections 12 & 13 of the Patents Act, 1970 and the Patents Rules, 2003 issued on Nov. 24, 2021, by the Intellectual Property Office of India in Indian Patent Application No. 202047017398 and English translation of the Report. (7 pages).
International Preliminary Report on Patentability issued on Jun. 11, 2020, by the International Bureau of WIPO in International Patent Application No. PCT/CN2018/118191. (7 pages).
International Preliminary Report on Patentability issued on Jul. 2, 2020, by the International Bureau of WIPO in International Patent Application No. PCT/CN2018/118232 and English translation of the Report. (14 pages).
International Preliminary Report on Patentability issued on Jul. 8, 2021, by the International Bureau of WIPO in International Patent Application No. PCT/CN2019/128686 and English translation of the Report. (17 pages).
International Preliminary Report on Patentability issued on Sep. 3, 2021, by the State Intellectual Property Office of the People's Republic of China in International Patent Application No. PCT/CN2020/091489 and English translation of the Report. (12 pages).
Written Opinion of the International Searching Authority and International Search Report issued on Feb. 20, 2019, by the State Intellectual Property Office of the People's Republic of China in International Patent Application No. PCT/CN2018/118107 and English translation. (22 pages).
Written Opinion of the International Searching Authority and International Search Report issued on Feb. 25, 2019, by the State Intellectual Property Office of the People's Republic of China in International Patent Application No. PCT/CN2018/118212 and English translation. (23 pages).
English translation of the Written Opinion of the International Searching Authority and International Search Report issued on Feb. 27, 2019, by the State Intellectual Property Office of the People's Republic of China in International Patent Application No. PCT/CN2018/118224. (13 pages).
Written Opinion of the International Searching Authority and International Search Report issued on Feb. 28, 2019, by the State Intellectual Property Office of the People's Republic of China in International Patent Application No. PCT/CN2018/118300 and English translation. (20 pages).
Written Opinion of the International Searching Authority and International Search Report issued on Mar. 6, 2019, by the State Intellectual Property Office of the People's Republic of China in International Patent Application No. PCT/CN2018/118106 and English translation. (20 pages).
Written Opinion of the International Searching Authority and International Search Report issued on Mar. 6, 2019, by the State Intellectual Property Office of the People's Republic of China in International Application No. PCT/CN2018/118191 and English translation. (17 pages).
Written Opinion of the International Searching Authority and International Search Report issued on Mar. 7, 2019, by the State Intellectual Property Office of the People's Republic of China in International Patent Application No. PCT/CN2018/118303 and English translation. (22 pages).
Written Opinion of the International Searching Authority and International Search Report issued on Mar. 7, 2019, by the State Intellectual Property Office of the People's Republic of China in International Patent Application No. PCT/CN2018/118232 and English translation. (24 pages).
Written Opinion of the International Searching Authority and International Search Report issued on Mar. 26, 2020, by the State Intellectual Property Office of the People's Republic of China in International Patent Application No. PCT/CN2019/129016 and English translation. (27 pages).
Written Opinion of the International Searching Authority and International Search Report issued on Mar. 26, 2020, by the State Intellectual Property Office of the People's Republic of China in International Patent Application No. PCT/CN2019/128686 and English translation. (27 pages).
Written Opinion of the International Searching Authority and International Search Report issued on Aug. 19, 2020, by the State Intellectual Property Office of the People's Republic of China in International Patent Application No. PCT/CN2020/091489 and English translation. (26 pages).
Written Opinion of the International Searching Authority and International Search Report issued on Aug. 21, 2020, by the State Intellectual Property Office of the People's Republic of China in International Patent Application No. PCT/CN2020/091484 and English translation. (29 pages).
Written Opinion of the International Searching Authority and International Search Report issued on Aug. 21, 2020, by the State Intellectual Property Office of the People's Republic of China in International Patent Application No. PCT/CN2020/091614 and English translation. (24 pages).
Written Opinion of the International Searching Authority and International Search Report issued on Aug. 24, 2020, by the State Intellectual Property Office of the People's Republic of China in International Patent Application No. PCT/CN2020/091624 and English translation. (26 pages).
Written Opinion of the International Searching Authority and International Search Report issued on Aug. 25, 2020, by the State Intellectual Property Office of the People's Republic of China in International Patent Application No. PCT/CN2020/091485 and English translation. (30 pages).
Written Opinion of the International Searching Authority and International Search Report issued on Aug. 28, 2020, by the State Intellectual Property Office of the People's Republic of China in International Patent Application No. PCT/CN2020/091649 and English translation. (25 pages).
Written Opinion of the International Searching Authority and International Search Report issued on Sep. 2, 2020, by the State Intellectual Property Office of the People's Republic of China in International Patent Application No. PCT/CN2020/091606 and English translation. (28 pages).
Written Opinion of the International Searching Authority and International Search Report issued on Nov. 21, 2019, by the State Intellectual Property Office of the People's Republic of China in International Patent Application No. PCT/CN2019/101653 and English translation. (23 pages).
Written Opinion of the International Searching Authority and International Search Report issued on Nov. 28, 2019, by the State Intellectual Property Office of the People's Republic of China in International Patent Application No. PCT/CN2019/101656 and English translation. (21 pages).
Written Opinion of the International Searching Authority and International Search Report issued on Apr. 17, 2020, by the State Intellectual Property Office of the People's Republic of China in International Patent Application No. PCT/CN2020/072813 and English translation. (32 pages).

(56) References Cited

OTHER PUBLICATIONS

Office Action issued on Mar. 9, 2022, by the Russian Agency for Patents and Trademarks in Russian Patent Application No. 2020118025/10(030488) and English translation of the Action. (14 pages).
Office Action issued on May 11, 2022, by the Russian Agency for Patents and Trademarks in Russian Patent Application No. 2020121741/04(037329) and English translation of the Action. (18 pages).
Office Action issued on Jan. 28, 2022, by the U.S. Patent and Trademark Office in U.S. Appl. No. 16/758,532. (28 pages).
Office Action issued on Mar. 11, 2022, by the U.S. Patent and Trademark Office in U.S. Appl. No. 16/758,720. (21 pages).
Notice of Allowance issued on Mar. 31, 2022, by the U.S. Patent and Trademark Office in U.S. Appl. No. 16/764,307. (7 pages).
Notice of Allowance issued on Apr. 5, 2022, by the U.S. Patent and Trademark Office in U.S. Appl. No. 16/763,058. (7 pages).
Office Action issued on May 27, 2022, by the U.S. Patent and Trademark Office in U.S. Appl. No. 16/758,532. (8 pages).
Notice of Allowance issued on Jul. 25, 2022, by the U.S. Patent and Trademark Office in U.S. Appl. No. 16/758,720. (5 pages).
Office Action issued on Aug. 24, 2022, by the U.S. Patent and Trademark Office in U.S. Appl. No. 16/758,532. (13 pages).
Office Action issued on Oct. 29, 2021, by the U.S. Patent and Trademark Office in U.S. Appl. No. 16/764,307. (17 pages).
Office Action issued on Nov. 16, 2021, by the U.S. Patent and Trademark Office in U.S. Appl. No. 16/763,058. (26 pages).
Office Action issued Aug. 14, 2020, by the Intellectual Property Office of Vietnam in Vietnamese Patent Application No. 1-2020-03065 and an English translation of the Action. (3 pages).
Office Action issued Aug. 28, 2020, by the Intellectual Property Office of Vietnam in Vietnamese Patent Application No. 1-2020-03777 and an English translation of the Action. (3 pages).
Payment and Certificate of Renewal issued on May 30, 2022 by the Patent Office of South Africa in South African Patent Application No. 2020/03833. (1 page).
Ahmad Dar et al., "siRNAmod: A database of experimentally validated chemically modified siRNAs," Scientific Reports, Jan. 28, 2016, vol. 6, No. 1. (8 pages).
Beaucage et al., "Advances in the Synthesis of Oligonucleotides by the Phosphoramidite Approach", Tetrahedron, 1992, vol. 48, No. 12, pp. 2223-2311.
Behlke, Mark A., "Chemical Modification of siRNAs for In Vivo Use," Oligonucleotides, 2008, vol. 18, pp. 305-320.
Berthold et al., "Cellular Delivery and Antisense Effects of Peptide Nucleic Acid Conjugated to Polyethyleneimine via Disulfide Linkers," Bioconjugate Chemistry, 2010, vol. 21, No. 10, pp. 1933-1938.
Chen et al., "Research progress on factor XI as a novel target for antithrombotic therapy," Chinese Pharmacological Bulletin, Apr. 15, 2015, vol. 31, No. 5, with English abstract, pp. 619-622.
Dai et al., "A vital role for Angpll3 in the PAN-induced podocyte loss by affecting detachment and apoptosis in vitro," BMC Nephrology, 2015, vol. 16, No. 1. (10 pages).
Ding et al., "Limited role of kininogen in the host response during gram-negative pneumonia derived sepsis," American Journal of Physiology Lung Cellular and Molecular Physiology, Nov. 9, 2017. (33 pages).
Dong et al., "Lipopeptide nanoparticles for potent and selective siRNA delivery in rodents and nonhuman primates", Proceedings of the National Academy of Sciences, Feb. 2014, www.pnas.org/cgi/doi/10.1073/pnas.1322937111 (6 pages).
Dong et al., "A novel packaging system of recombinant AAV5/5 vector," Chinese Journal of Biotechnology, May 25, 2010, vol. 26, No. 5, pp. 679-686.
Common knowledge "RNAi technology," 2005, with English translation. (5 pages).
Foster et al., "Advanced siRNA Designs Further Improve In Vivo Performance of GalNAc-siRNA Conjugates," Molecular Therapy, Mar. 2018, vol. 26, No. 3, pp. 708-717.
Greene et al., "Protection for the Hydroxyl Group, Including 1,2- and 1,3-DIOLS", Protective Groups in Organic Synthesis, Third Edition, 1999 John Wiley & Sons, Inc. pp. 17-245, (229 pages).
"*Homo sapiens* Kininogen 1 (KNG1), Transcript Variant 1, mRNA" GenBank, May 2, 2018, NM 00102416.2. (8 pages).
Khaitmetova et al., "Synthesis and Study of the Properties of Polymer Complexes of Ethacizin with Carboxymethylcellulose," Chemistry of Plant Raw Materials, 2017, No. 4, with English translation. (18 pages).
Khan et al., "High-Molecular-Weight Kininogen Fragments Stimulate the Secretion of Cytokines and Chemokines Through uPAR, Mac-1, and gC1qR in Monocytes," Arteriosclerosis, Thrombosis, and Vascular Biology, Oct. 2006, vol. 26, No. 10, pp. 2260-2266.
Khvorova et al., "The chemical evolution of oligonucleotide therapies of clinical utility", Nature Biotechnology Advance Online Publication, Feb. 27, 2017; doi:10.1038/nbt.3765, (11 pages).
Kim et al., "Bifunctional compounds for targeted hepatic gene delivery," Gene Therapy, 2007, vol. 14, pp. 704-708.
Liu et al., "Determination of Human Plasma Pre-Kallikrein," Journal of China Medical University, 1988, vol. 17, No. 6, with English abstract, pp. 432-436.
Liu et al., "Coagulation factor XI induces Ca2+ response and accelerates cell migration in vascular smooth muscle cells via proteinase-activated receptor 1," American Journal of Physiology, Cell Physiology, Mar. 1, 2019, vol. 316, No. 3, pp. C377-C392.
Love et al., "Lipid-like materials for low-dose, in vivo gene silencing", Proceedings of the National Academy of Sciences, Feb. 2, 2010, vol. 107, No. 5, pp. 1864-1869. (7 pages).
Matsuda et al., "siRNA Conjugates Carrying Sequentially Assembled Trivalent N-Acetylgalactosamine Linked Through Nucleosides Elicit Robust Gene Silencing In Vivo in Hepatocytes", ACS Chemical Biology, 2015, DOI: 10.1021/cb501028c. (7 pages).
Montagne et al., "Pericyte degeneration causes white matter dysfunction in the mouse CNS," Nature Medicine, 2018, vol. 24, vol. 3, pp. 326-337.
Nair et al., "Multivalent N-Acetylgalactosamine-Conjugated siRNA Localizes in Hepatocytes and Elicits Robust RNAi-Mediated Gene Silencing", Journal of the American Chemical Society, 2014, vol. 136, pp. 16958-16961.
Nakagawa et al., "The RNAi-Mediated Silencing of Xanthine Dehydrogenase Impairs Growth and Fertility and Accelerates Leaf Senescence in Transgenic *Arabidopsis* Plants," Plant & Cell Physiology, 2007, vol. 48, No. 10, pp. 1484-1495.
Nakamoto et al., "Enhanced Intercellular Delivery of cRGD-siRNA Conjugates by an Additional Oligospermine Modification," ACS Omega, 2018, vol. 3, pp. 8226-8232. (7 pages).
Norata et al., "Gene silencing approaches for the management of dyslipidaemia," Trends in Pharmacological Sciences, Apr. 13, 2013, vol. 34, No. 4, pp. 198-205.
Nordestgaard et al., "Advances in lipid-lowering therapy through gene-silencing technologies," Nature Reviews, Feb. 8, 2018, vol. 15. (12 pages).
Nothisen et al., "Cationic siRNAs Provide Carrier-Free Gene Silencing in Animal Cells," Journal of the American Chemical Society, 2009, vol. 131, No. 29, pp. 17730-17731. (2 pages).
Papulov, Yu. G., "Relationship between Properties of Compounds with Their Structures: Math Modeling," Advances in Modern Natural Sciences, 2006, with English translation, pp. 75-76.
Paris et al., "Conjugating Phosphospermines to siRNAs for Improved Stability in Serum, Intracellular Delivery and RNAi-Mediated Gene Silencing," Molecular Pharmaceutics, 2012, vol. 9, No. 12, pp. 3464-3475.
Peña-Altamira, et al., "Release of soluble and vesicular purine nucleoside phosphorylase from rat astrocytes and microglia induced by pro-inflammatory stimulation with extracellular ATP via P2X7 receptors," Neurochemistry International, May 31, 2018, vol. 115, pp. 37-49.
Pessentheiner et al., "ANGPTL3 targeting: The power of versatile lipid-lowering," Atherosclerosis, Jan. 2018, vol. 268, pp. 185-187.
Prakash et al., "Comprehensive Structure-Activity Relationship of Triantennary N-Acetylgalactosamine Conjugated Antisense Oligonucleotides for Targeted Delivery to Hepatocytes," Journal of Medicinal Chemistry, 2016, vol. 59, pp. 2718-2733.

(56) References Cited

OTHER PUBLICATIONS

Rajeev et al., "Hepatocyte-Specific Delivery of siRNAs Conjugated to Novel Non-nucleosidic Trivalent N-Acetylgalactosamine Elicits Robust Gene Silencing in Vivo" ChemBioChem, 2015, vol. 16, pp. 903-908.

Ren et al., "Synthesis of bifunctional cationic compound for gene delivery," Tetrahedron Letters, 2001, vol. 42, pp. 1007-1010.

Ren et al., "Gene Expression Profile of Transgenic Mouse Kidney Reveals Pathogenesis of Hepatitis B Virus Associated Nephropathy," Journal of Medical Virology, 2006, vol. 78, pp. 551-560.

Ren et al., "Stable Inhibition of Hepatitis B Virus Expression and Replication by Expressed SIRNA", Biochemical and Biophysical Research Communications, Oct. 7, 2005, vol. 335, No. 4, with English abstract, pp. 1051-1058.

Springer et al., "GalNAc-siRNA Conjugates: Leading the Way for Delivery of RNAi Therapeutics," Nucleic Acid Therapeutics, May 2018, vol. 28, No. 3, pp. 109-118.

Su et al., "Progress on the Inhibition of Hepatitis B virus by siRNA Strategy," China Biotechnology, 2014, vol. 34, No. 9, with English abstract, pp. 102-107.

Tangkijvanich et al., "Low pretreatment serum HBsAg level and viral mutations as predictors of response to PEG-interferon alpha-2b therapy in chronic hepatitis B," Journal of Clinical Virology, vol. 46, 2009, pp. 117-123.

Ui-Tei et al., "Functional dissection of siRNA sequence by systematic DNA substitution: modified siRNA with a DNA seed arm is a powerful tool for mammalian gene silencing with significantly reduced off-target effect", Nucleic Acids Research, 2008, vol. 36, No. 7, pp. 2136-2151.

Watts et al., "Chemically modified siRNA: tools and applications," Drug Discovery Today, Oct. 2008, vol. 13, Nos. 19/20, pp. 842-855.

Wooddell et al.,"Hepatocyte-targeted RNAi Therapeutics for the Treatment of Chronic Hepatitis B Virus Infection," The American Society of Gene & Cell Therapy, 2013, doi:10.1038/mt.2013.31. (13 pages).

Wu et al., "Cleaved high molecular weight kininogen inhibits tube formation of endothelial progenitor cells via suppression of matrix metalloproteinase 2," Journal of Thrombosis and Haemostasis, 2010, vol. 8, pp. 185-193.

Wu et al., "Contact pathway of coagulation and inflammation," Thrombosis Journal, 2015, pp. 13-17.

Xu et al., "Role of angiopoielin-like 3 (ANGPTL3) in regulating plasma level of low-density lipoprotein cholesterol," Atherosclerosis, 2018, vol. 268, pp. 196-206.

Yang et al., "A critical role for plasma kallikrein in the pathogenesis of autoantibody-induced arthritis, Federation of American Societies for Experimental Biology," Nov. 2017, vol. 31, No. 12, pp. 5419-5431.

Yang et al., "An essential role of high-molecular-weight kininogen in endotoxemia," Journal of Experimental Medicine, Sep. 4, 2017, vol. 214, No. 9, pp. 2649-2670.

Fedin A.I. et al., "Review of clinical recommendations for treatment and prevention of ischemic stroke", S. S. Korsakov Journal of Neurology and Psychiatry, 2019, vol. 119, No. 8, pp. 91-96, doi: 10.17116/jnevro201911908291, with English abstract. (Cited in Office Action issued on Mar. 6, 2024, in corresponding Russian Application No. 2021130601) (6 pages).

Meijers J.C. et al., "High levels of coagulation factor XI as a risk factor for venous thrombosis", N. Engl. J. Med., 2000, vol. 342, No. 10, pp. 696-701, doi: 10.1056/NEJM200003093421004. (Cited in Office Action issued on Mar. 6, 2024, in corresponding Russian Application No. 2021130601) (6 pages).

Soodabeh S. et al., "From in vitro Experiments to in vivo and Clinical Studies; Pros and Cons", Curr. Drug Discov. Technol., 2015, vol. 12, No. 4, pp. 218-224. (Cited in Office Action issued on Mar. 6, 2024, in corresponding Russian Application No. 2021130601) (7 pages).

Shafer A.I. et al., "Thrombotic Disorders Diagnosis and Treatment", Am. Soc. Hematol. Educ. Program, 2003, v. 1, pp. 520-539, doi 10.1182asheducation-2003.1.520. (Cited in Office Action issued on Mar. 6, 2024, in corresponding Russian Application No. 2021130601) (20 pages).

Sehgal, Alfica et al., "Liver as a target for oligonucleotide therapeutics", Journal of hepatology, 2013, vol. 59, pp. 1354-1359. (Cited in Office Action issued on Mar. 11, 2024, in corresponding Taiwanese Patent Application No. 109116935) (6 pages).

Diaz-Torné, Cesar et al., "New medications in development for the treatment of hyperuricemia of gout", Current opinion in rheumatology. 2015, vol. 27, No. 2, pp. 164-169. (Cited in Office Action issued on Mar. 11, 2024, in corresponding Taiwanese Patent Application No. 109116934) (6 pages).

Kojima, S. et al., "Tumour suppressors miR-1 and miR-133a target the oncogenic functionphosphorylase (PNP) in prostate cancer", Br. J. Cancer, 2012, vol. 106(2), pp. 405-413. (Citedon May 21, 2024, in corresponding Japanese Patent Application No. JP2021-569112) (9 pages).

Examination Report No. 2 issued on Feb. 3, 2023, by the Australian Government IP Australia in Australian Patent Application No. 2018394875 (4 pages).

Ren et al., "Synthesis of Galactosyl Compounds for Targeted Gene Delivery", Bioorganic & Medicinal Chemistry, 2001, 9(11), pp. 2969-2978.

Extended European Search Report issued on Mar. 27, 2023, by the European Patent Office in European Patent Application No. 19902173.4 (11 pages).

Li et al., "The silencing of ApoC3 suppresses oxidative stress and inflammatory responses in placenta cells from mice with preeclampsia via inhibition of the NF-B signaling pathway", Biomedicine & Pharmacotherapy, Aug. 31, 2018, vol. 107, pp. 1377-1384.

Notice of Reasons for Refusal issued on Jun. 1, 2023, by the Japanese Patent Office in Japanese Patent Application No. 2021-537877, with an English translation of the Notice (6 pages).

Kanasty et al., "Delivery materials for siRNA therapeutics", Nature Materials, Nov. 2023, vol. 12, pp. 967-977.

Notice of Reasons for Refusal issued on Jun. 6, 2023, by the Japanese Patent Office in Japanese Patent Application No. 2021-509880, with an English translation of the Notice (6 pages).

Qui, S. et al., "Dickkopf 3 attenuates xanthine dehydrogenase expression to prevent oxidative stress-induced apoptosis," Genes to Cells, 2017, vol. 22, pp. 406-417. (cited in Extended European Search Report issued on Jan. 30, 2024, in European Patent Application No. 20813863.6).

Yasuda, T. et al., "Anti-Gout Agent Allopurinol Exerts Cytotoxicity to Human Hormone-Refractory Prostate Cancer Cells in Combination with Tumor Necrosis Factor-Related Apoptosis-Inducing Ligand," Mol Cancer Res, Dec. 2008, vol. 6, No. 12, pp. 1852-1860. (cited in Extended European Search Report issued on Jan. 30, 2024, in European Patent Application No. 20813863.6).

Hashimoto, K. et al., "Sulfotransferase-1A1-dependent bioactivation of aristolochic acid I and N-hydroxyaristolactam I in human cells," Carcinogenesis, 2016, vol. 37, No. 7, pp. 647-655. (cited in Extended European Search Report issued on Jan. 30, 2024, in European Patent Application No. 20813863.6).

Elbashir et al., "Functional anatomy of siRNAs for mediating efficient RNAi in *Drosophila melanogaster* embryo lysate," The EMBO Journal, vol. 20, No. 23, pp. 6877-6888 (2001).

Girardet et al., "Urate Crystal Deposition Disease and Gout—New Therapies for an Old Problem," Annual Reports in Medicinal Chemistry, vol. 49, pp. 151-164 (2014).

Kliuchnikov et al., "Improving the potency prediction for chemically modified siRNAs through insights from molecular modeing of individual sequence positions," Molecular Therapy: Nucleic Acids, vol. 36, pp. 1-14 (2025).

Lorenzer et al., "Going beyond the liver: Progress and Challenges of Targeted Delivery of siRNA Therapeutics," Journal of Controlled Release, vol. 203, pp. 1-15 (2015).

* cited by examiner

SEQUENCE LISTING

<160> NUMBER OF SEQ ID NOS: 401

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
aaaguaacaa ccaguuugu 19

<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
acaaacuggu uguuacuuu 19

<210> SEQ ID NO 3
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 3
aaaguaacaa ccaguuugn 19

<210> SEQ ID NO 4
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 4
ncaaacuggu uguuacuuug g 21

<210> SEQ ID NO 5
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 5
aaaguaacaa ccaguuugn 19

<210> SEQ ID NO 6
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 6
ncaaacuggu uguuacuuug g 21

<210> SEQ ID NO 7
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n=a, or g, or c, or u

<400> SEQUENCE: 7
ccaaaguaac aaccaguuug n 21

<210> SEQ ID NO 8
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 8
ncaaacuggu uguuacuuug guu 23

<210> SEQ ID NO 9
<211> LENGTH: 19
<212> TYPE: RNA
<213> ORGANISM: Artificial Sequence
<220> FEATURE:
<223> OTHER INFORMATION: Sense strand for siKNa1

<400> SEQUENCE: 9
aaaguaacaa ccaguuugu 19

<210> SEQ ID NO 10
<211> LENGTH: 21
<212> TYPE: RNA
<213> ORGANISM: Artificial Sequence
<220> FEATURE:
<223> OTHER INFORMATION: Antisense strand for siKNa1

<400> SEQUENCE: 10
acaaacuggu uguuacuuug g 21

<210> SEQ ID NO 11
<211> LENGTH: 21
<212> TYPE: RNA
<213> ORGANISM: Artificial Sequence
<220> FEATURE:
<223> OTHER INFORMATION: Sense strand for siKNa2

<400> SEQUENCE: 11
ccaaaguaac aaccaguuug u 21

-continued

<210> SEQ ID NO 12
<211> LENGTH: 23
<212> TYPE: RNA
<213> ORGANISM: Artificial Sequence
<220> FEATURE:
<223> OTHER INFORMATION: Antisense strand for siKNa2

<400> SEQUENCE: 12
acaaacuggu uguuacuuug guu 23

<210> SEQ ID NO 13
<211> LENGTH: 19
<212> TYPE: RNA
<213> ORGANISM: Artificial Sequence
<220> FEATURE:
<223> OTHER INFORMATION: Sense strand for siKNa1-M1

<400> SEQUENCE: 13
aaaguaacaa ccaguuugu 19

<210> SEQ ID NO 14
<211> LENGTH: 21
<212> TYPE: RNA
<213> ORGANISM: Artificial Sequence
<220> FEATURE:
<223> OTHER INFORMATION: Antisense strand for siKNa1-M1

<400> SEQUENCE: 14
acaaacuggu uguuacuuug g 21

<210> SEQ ID NO 15
<211> LENGTH: 19
<212> TYPE: RNA
<213> ORGANISM: Artificial Sequence
<220> FEATURE:
<223> OTHER INFORMATION: Sense strand for siKNa1-M2

<400> SEQUENCE: 15
aaaguaacaa ccaguuugu 19

<210> SEQ ID NO 16
<211> LENGTH: 21
<212> TYPE: RNA
<213> ORGANISM: Artificial Sequence
<220> FEATURE:
<223> OTHER INFORMATION: Antisense strand for siKNa1-M2

<400> SEQUENCE: 16
acaaacuggu uguuacuuug g 21

<210> SEQ ID NO 17
<211> LENGTH: 19
<212> TYPE: RNA
<213> ORGANISM: Artificial Sequence
<220> FEATURE:
<223> OTHER INFORMATION: Sense strand for siKNa1-M3

<400> SEQUENCE: 17
aaaguaacaa ccaguuugu 19

<210> SEQ ID NO 18
<211> LENGTH: 21
<212> TYPE: RNA
<213> ORGANISM: Artificial Sequence
<220> FEATURE:
<223> OTHER INFORMATION: Antisense strand for siKNa1-M3

<400> SEQUENCE: 18
acaaacuggu uguuacuuug g 21

<210> SEQ ID NO 19
<211> LENGTH: 21
<212> TYPE: RNA
<213> ORGANISM: Artificial Sequence
<220> FEATURE:
<223> OTHER INFORMATION: Sense strand for siKNa2-M1

<400> SEQUENCE: 19
ccaaaguaac aaccaguuug u 21

<210> SEQ ID NO 20
<211> LENGTH: 23
<212> TYPE: RNA
<213> ORGANISM: Artificial Sequence
<220> FEATURE:
<223> OTHER INFORMATION: Antisense strand for siKNa2-M1

<400> SEQUENCE: 20
acaaacuggu uguuacuuug guu 23

<210> SEQ ID NO 21
<211> LENGTH: 21
<212> TYPE: RNA
<213> ORGANISM: Artificial Sequence
<220> FEATURE:
<223> OTHER INFORMATION: Sense strand for siKNa2-M2

<400> SEQUENCE: 21
ccaaaguaac aaccaguuug u 21

<210> SEQ ID NO 22
<211> LENGTH: 23
<212> TYPE: RNA
<213> ORGANISM: Artificial Sequence
<220> FEATURE:
<223> OTHER INFORMATION: Antisense strand for siKNa2-M2

<400> SEQUENCE: 22
acaaacuggu uguuacuuug guu 23

<210> SEQ ID NO 23
<211> LENGTH: 21
<212> TYPE: RNA
<213> ORGANISM: Artificial Sequence
<220> FEATURE:
<223> OTHER INFORMATION: Sense strand for siKNa2-M3

<400> SEQUENCE: 23
ccaaaguaac aaccaguuug u 21

<210> SEQ ID NO 24
<211> LENGTH: 23
<212> TYPE: RNA
<213> ORGANISM: Artificial Sequence
<220> FEATURE:
<223> OTHER INFORMATION: Antisense strand for siKNa2-M3

<400> SEQUENCE: 24
acaaacuggu uguuacuuug guu 23

<210> SEQ ID NO 25

<211> LENGTH: 19
<212> TYPE: RNA
<213> ORGANISM: Artificial Sequence
<220> FEATURE:
<223> OTHER INFORMATION: Sense strand for siKNa1-M1S

<400> SEQUENCE: 25
aaaguaacaa ccaguuugu 19

<210> SEQ ID NO 26
<211> LENGTH: 21
<212> TYPE: RNA
<213> ORGANISM: Artificial Sequence
<220> FEATURE:
<223> OTHER INFORMATION: Antisense strand for siKNa1-M1S

<400> SEQUENCE: 26
acaaacuggu uguuacuuug g 21

<210> SEQ ID NO 27
<211> LENGTH: 19
<212> TYPE: RNA
<213> ORGANISM: Artificial Sequence
<220> FEATURE:
<223> OTHER INFORMATION: Sense strand for siKNa1-M2S

<400> SEQUENCE: 27
aaaguaacaa ccaguuugu 19

<210> SEQ ID NO 28
<211> LENGTH: 21
<212> TYPE: RNA
<213> ORGANISM: Artificial Sequence
<220> FEATURE:
<223> OTHER INFORMATION: Antisense strand for siKNa1-M2S

<400> SEQUENCE: 28
acaaacuggu uguuacuuug g 21

<210> SEQ ID NO 29
<211> LENGTH: 19
<212> TYPE: RNA
<213> ORGANISM: Artificial Sequence
<220> FEATURE:
<223> OTHER INFORMATION: Sense strand for siKNa1-M3S

<400> SEQUENCE: 29
aaaguaacaa ccaguuugu 19

<210> SEQ ID NO 30
<211> LENGTH: 21
<212> TYPE: RNA
<213> ORGANISM: Artificial Sequence
<220> FEATURE:
<223> OTHER INFORMATION: Antisense strand for siKNa1-M3S

<400> SEQUENCE: 30
acaaacuggu uguuacuuug g 21

<210> SEQ ID NO 31
<211> LENGTH: 21
<212> TYPE: RNA
<213> ORGANISM: Artificial Sequence
<220> FEATURE:
<223> OTHER INFORMATION: Sense strand for siKNa2-M1S

<400> SEQUENCE: 31
ccaaaguaac aaccaguuug u 21

<210> SEQ ID NO 32
<211> LENGTH: 23
<212> TYPE: RNA
<213> ORGANISM: Artificial Sequence
<220> FEATURE:
<223> OTHER INFORMATION: Antisense strand for siKNa2-M1S

<400> SEQUENCE: 32
acaaacuggu uguuacuuug guu 23

<210> SEQ ID NO 33
<211> LENGTH: 21
<212> TYPE: RNA
<213> ORGANISM: Artificial Sequence
<220> FEATURE:
<223> OTHER INFORMATION: Sense strand for siKNa2-M2S

<400> SEQUENCE: 33
ccaaaguaac aaccaguuug u 21

<210> SEQ ID NO 34
<211> LENGTH: 23
<212> TYPE: RNA
<213> ORGANISM: Artificial Sequence
<220> FEATURE:
<223> OTHER INFORMATION: Antisense strand for siKNa2-M2S

<400> SEQUENCE: 34
acaaacuggu uguuacuuug guu 23

<210> SEQ ID NO 35
<211> LENGTH: 21
<212> TYPE: RNA
<213> ORGANISM: Artificial Sequence
<220> FEATURE:
<223> OTHER INFORMATION: Sense strand for siKNa2-M3S

<400> SEQUENCE: 35
ccaaaguaac aaccaguuug u 21

<210> SEQ ID NO 36
<211> LENGTH: 23
<212> TYPE: RNA
<213> ORGANISM: Artificial Sequence
<220> FEATURE:
<223> OTHER INFORMATION: Antisense strand for siKNa2-M3S

<400> SEQUENCE: 36
acaaacuggu uguuacuuug guu 23

<210> SEQ ID NO 37
<211> LENGTH: 19
<212> TYPE: RNA
<213> ORGANISM: Artificial Sequence
<220> FEATURE:
<223> OTHER INFORMATION: Sense strand for siKNa1-M1P1

<400> SEQUENCE: 37
aaaguaacaa ccaguuugu 19

<210> SEQ ID NO 38
<211> LENGTH: 21
<212> TYPE: RNA

<213> ORGANISM: Artificial Sequence
<220> FEATURE:
<223> OTHER INFORMATION: Antisense strand for siKNa1-M1P1

<400> SEQUENCE: 38
acaaacuggu uguuacuuug g 21

<210> SEQ ID NO 39
<211> LENGTH: 19
<212> TYPE: RNA
<213> ORGANISM: Artificial Sequence
<220> FEATURE:
<223> OTHER INFORMATION: Sense strand for siKNa1-M2P1

<400> SEQUENCE: 39
aaaguaacaa ccaguuugu 19

<210> SEQ ID NO 40
<211> LENGTH: 21
<212> TYPE: RNA
<213> ORGANISM: Artificial Sequence
<220> FEATURE:
<223> OTHER INFORMATION: Antisense strand for siKNa1-M2P1

<400> SEQUENCE: 40
acaaacuggu uguuacuuug g 21

<210> SEQ ID NO 41
<211> LENGTH: 19
<212> TYPE: RNA
<213> ORGANISM: Artificial Sequence
<220> FEATURE:
<223> OTHER INFORMATION: Sense strand for siKNa1-M3P1

<400> SEQUENCE: 41
aaaguaacaa ccaguuugu 19

<210> SEQ ID NO 42
<211> LENGTH: 21
<212> TYPE: RNA
<213> ORGANISM: Artificial Sequence
<220> FEATURE:
<223> OTHER INFORMATION: Antisense strand for siKNa1-M3P1

<400> SEQUENCE: 42
acaaacuggu uguuacuuug g 21

<210> SEQ ID NO 43
<211> LENGTH: 21
<212> TYPE: RNA
<213> ORGANISM: Artificial Sequence
<220> FEATURE:
<223> OTHER INFORMATION: Sense strand for siKNa2-M1P1

<400> SEQUENCE: 43
ccaaaguaac aaccaguuug u 21

<210> SEQ ID NO 44
<211> LENGTH: 23
<212> TYPE: RNA
<213> ORGANISM: Artificial Sequence
<220> FEATURE:
<223> OTHER INFORMATION: Antisense strand for siKNa2-M1P1

<400> SEQUENCE: 44
acaaacuggu uguuacuuug guu 23

<210> SEQ ID NO 45
<211> LENGTH: 21
<212> TYPE: RNA
<213> ORGANISM: Artificial Sequence
<220> FEATURE:
<223> OTHER INFORMATION: Sense strand for siKNa2-M2P1

<400> SEQUENCE: 45
ccaaaguaac aaccaguuug u 21

<210> SEQ ID NO 46
<211> LENGTH: 23
<212> TYPE: RNA
<213> ORGANISM: Artificial Sequence
<220> FEATURE:
<223> OTHER INFORMATION: Antisense strand for siKNa2-M2P1

<400> SEQUENCE: 46
acaaacuggu uguuacuuug guu 23

<210> SEQ ID NO 47
<211> LENGTH: 21
<212> TYPE: RNA
<213> ORGANISM: Artificial Sequence
<220> FEATURE:
<223> OTHER INFORMATION: Sense strand for siKNa2-M3P1

<400> SEQUENCE: 47
ccaaaguaac aaccaguuug u 21

<210> SEQ ID NO 48
<211> LENGTH: 23
<212> TYPE: RNA
<213> ORGANISM: Artificial Sequence
<220> FEATURE:
<223> OTHER INFORMATION: Antisense strand for siKNa2-M3P1

<400> SEQUENCE: 48
acaaacuggu uguuacuuug guu 23

<210> SEQ ID NO 49
<211> LENGTH: 19
<212> TYPE: RNA
<213> ORGANISM: Artificial Sequence
<220> FEATURE:
<223> OTHER INFORMATION: Sense strand for siKNa1-M1SP1

<400> SEQUENCE: 49
aaaguaacaa ccaguuugu 19

<210> SEQ ID NO 50
<211> LENGTH: 21
<212> TYPE: RNA
<213> ORGANISM: Artificial Sequence
<220> FEATURE:
<223> OTHER INFORMATION: Antisense strand for siKNa1-M1SP1

<400> SEQUENCE: 50
acaaacuggu uguuacuuug g 21

<210> SEQ ID NO 51
<211> LENGTH: 19
<212> TYPE: RNA
<213> ORGANISM: Artificial Sequence
<220> FEATURE:

<223> OTHER INFORMATION: Sense strand for siKNa1-M2SP1

<400> SEQUENCE: 51
aaaguaacaa ccaguuugu 19

<210> SEQ ID NO 52
<211> LENGTH: 21
<212> TYPE: RNA
<213> ORGANISM: Artificial Sequence
<220> FEATURE:
<223> OTHER INFORMATION: Antisense strand for siKNa1-M2SP1

<400> SEQUENCE: 52
acaaacuggu uguuacuuug g 21

<210> SEQ ID NO 53
<211> LENGTH: 19
<212> TYPE: RNA
<213> ORGANISM: Artificial Sequence
<220> FEATURE:
<223> OTHER INFORMATION: Sense strand for siKNa1-M3SP1

<400> SEQUENCE: 53
aaaguaacaa ccaguuugu 19

<210> SEQ ID NO 54
<211> LENGTH: 21
<212> TYPE: RNA
<213> ORGANISM: Artificial Sequence
<220> FEATURE:
<223> OTHER INFORMATION: Antisense strand for siKNa1-M3SP1

<400> SEQUENCE: 54
acaaacuggu uguuacuuug g 21

<210> SEQ ID NO 55
<211> LENGTH: 21
<212> TYPE: RNA
<213> ORGANISM: Artificial Sequence
<220> FEATURE:
<223> OTHER INFORMATION: Sense strand for siKNa2-M1SP1

<400> SEQUENCE: 55
ccaaaguaac aaccaguuug u 21

<210> SEQ ID NO 56
<211> LENGTH: 23
<212> TYPE: RNA
<213> ORGANISM: Artificial Sequence
<220> FEATURE:
<223> OTHER INFORMATION: Antisense strand for siKNa2-M1SP1

<400> SEQUENCE: 56
acaaacuggu uguuacuuug guu 23

<210> SEQ ID NO 57
<211> LENGTH: 21
<212> TYPE: RNA
<213> ORGANISM: Artificial Sequence
<220> FEATURE:
<223> OTHER INFORMATION: Sense strand for siKNa2-M2SP1

<400> SEQUENCE: 57
ccaaaguaac aaccaguuug u 21

<210> SEQ ID NO 58
<211> LENGTH: 23
<212> TYPE: RNA
<213> ORGANISM: Artificial Sequence
<220> FEATURE:
<223> OTHER INFORMATION: Antisense strand for siKNa2-M2SP1

<400> SEQUENCE: 58
acaaacuggu uguuacuuug guu 23

<210> SEQ ID NO 59
<211> LENGTH: 21
<212> TYPE: RNA
<213> ORGANISM: Artificial Sequence
<220> FEATURE:
<223> OTHER INFORMATION: Sense strand for siKNa2-M3SP1

<400> SEQUENCE: 59
ccaaaguaac aaccaguuug u 21

<210> SEQ ID NO 60
<211> LENGTH: 23
<212> TYPE: RNA
<213> ORGANISM: Artificial Sequence
<220> FEATURE:
<223> OTHER INFORMATION: Antisense strand for siKNa2-M3SP1

<400> SEQUENCE: 60
acaaacuggu uguuacuuug guu 23

<210> SEQ ID NO 61
<211> LENGTH: 19
<212> TYPE: RNA
<213> ORGANISM: Artificial Sequence
<220> FEATURE:
<223> OTHER INFORMATION: siRNA

<400> SEQUENCE: 61
auugaacuuu cgaauuacc 19

<210> SEQ ID NO 62
<211> LENGTH: 19
<212> TYPE: RNA
<213> ORGANISM: Artificial Sequence
<220> FEATURE:
<223> OTHER INFORMATION: siRNA

<400> SEQUENCE: 62
gguaauucga aaguucaau 19

<210> SEQ ID NO 63
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 63
auugaacuuu cgaauuacn 19

<210> SEQ ID NO 64
<211> LENGTH: 19
<212> TYPE: RNA

-continued

<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 64
nguaauucga aaguucaau 19

<210> SEQ ID NO 65
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 65
auugaacuuu cgaauuacn 19

<210> SEQ ID NO 66
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 66
nguaauucga aaguucaauc c 21

<210> SEQ ID NO 67
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n=a, or g, or c, or u

<400> SEQUENCE: 67
ggauugaacu uucgaauuac n 21

<210> SEQ ID NO 68
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 68
nguaauucga aaguucaauc cag 23

<210> SEQ ID NO 69
<211> LENGTH: 19

<212> TYPE: RNA
<213> ORGANISM: Artificial Sequence
<220> FEATURE:
<223> OTHER INFORMATION: Sense strand for siKNb1

<400> SEQUENCE: 69
auugaacuuu cgaauuacc 19

<210> SEQ ID NO 70
<211> LENGTH: 21
<212> TYPE: RNA
<213> ORGANISM: Artificial Sequence
<220> FEATURE:
<223> OTHER INFORMATION: Antisense strand for siKNb1

<400> SEQUENCE: 70
gguaauucga aaguucaauc c 21

<210> SEQ ID NO 71
<211> LENGTH: 21
<212> TYPE: RNA
<213> ORGANISM: Artificial Sequence
<220> FEATURE:
<223> OTHER INFORMATION: Sense strand for siKNb2

<400> SEQUENCE: 71
ggauugaacu uucgaauuac c 21

<210> SEQ ID NO 72
<211> LENGTH: 23
<212> TYPE: RNA
<213> ORGANISM: Artificial Sequence
<220> FEATURE:
<223> OTHER INFORMATION: Antisense strand for siKNb2

<400> SEQUENCE: 72
gguaauucga aaguucaauc cag 23

<210> SEQ ID NO 73
<211> LENGTH: 19
<212> TYPE: RNA
<213> ORGANISM: Artificial Sequence
<220> FEATURE:
<223> OTHER INFORMATION: Sense strand for siKNb1-M1

<400> SEQUENCE: 73
auugaacuuu cgaauuacc 19

<210> SEQ ID NO 74
<211> LENGTH: 21
<212> TYPE: RNA
<213> ORGANISM: Artificial Sequence
<220> FEATURE:
<223> OTHER INFORMATION: Antisense strand for siKNb1-M1

<400> SEQUENCE: 74
gguaauucga aaguucaauc c 21

<210> SEQ ID NO 75
<211> LENGTH: 19
<212> TYPE: RNA
<213> ORGANISM: Artificial Sequence
<220> FEATURE:
<223> OTHER INFORMATION: Sense strand for siKNb1-M2

<400> SEQUENCE: 75
auugaacuuu cgaauuacc 19

<210> SEQ ID NO 76
<211> LENGTH: 21
<212> TYPE: RNA
<213> ORGANISM: Artificial Sequence
<220> FEATURE:
<223> OTHER INFORMATION: Antisense strand for siKNb1-M2

<400> SEQUENCE: 76
gguaauucga aaguucaauc c 21

<210> SEQ ID NO 77
<211> LENGTH: 19
<212> TYPE: RNA
<213> ORGANISM: Artificial Sequence
<220> FEATURE:
<223> OTHER INFORMATION: Sense strand for siKNb1-M3

<400> SEQUENCE: 77
auugaacuuu cgaauuacc 19

<210> SEQ ID NO 78
<211> LENGTH: 21
<212> TYPE: RNA
<213> ORGANISM: Artificial Sequence
<220> FEATURE:
<223> OTHER INFORMATION: Antisense strand for siKNb1-M3

<400> SEQUENCE: 78
gguaauucga aaguucaauc c 21

<210> SEQ ID NO 79
<211> LENGTH: 21
<212> TYPE: RNA
<213> ORGANISM: Artificial Sequence
<220> FEATURE:
<223> OTHER INFORMATION: Sense strand for siKNb2-M1

<400> SEQUENCE: 79
ggauugaacu uucgaauuac c 21

<210> SEQ ID NO 80
<211> LENGTH: 23
<212> TYPE: RNA
<213> ORGANISM: Artificial Sequence
<220> FEATURE:
<223> OTHER INFORMATION: Antisense strand for siKNb2-M1

<400> SEQUENCE: 80
gguaauucga aaguucaauc cag 23

<210> SEQ ID NO 81
<211> LENGTH: 21
<212> TYPE: RNA
<213> ORGANISM: Artificial Sequence
<220> FEATURE:
<223> OTHER INFORMATION: Sense strand for siKNb2-M2

<400> SEQUENCE: 81
ggauugaacu uucgaauuac c 21

<210> SEQ ID NO 82
<211> LENGTH: 23
<212> TYPE: RNA
<213> ORGANISM: Artificial Sequence
<220> FEATURE:
<223> OTHER INFORMATION: Antisense strand for siKNb2-M2

<400> SEQUENCE: 82 ggua auucga aaguucaauc cag 23

<210> SEQ ID NO 83
<211> LENGTH: 21
<212> TYPE: RNA
<213> ORGANISM: Artificial Sequence
<220> FEATURE:
<223> OTHER INFORMATION: Sense strand for siKNb2-M3

<400> SEQUENCE: 83
ggauugaacu uucgaauuac c 21

<210> SEQ ID NO 84
<211> LENGTH: 23
<212> TYPE: RNA
<213> ORGANISM: Artificial Sequence
<220> FEATURE:
<223> OTHER INFORMATION: Antisense strand for siKNb2-M3

<400> SEQUENCE: 84
gguaauucga aaguucaauc cag 23

<210> SEQ ID NO 85
<211> LENGTH: 19
<212> TYPE: RNA
<213> ORGANISM: Artificial Sequence
<220> FEATURE:
<223> OTHER INFORMATION: Sense strand for siKNb1-M1S

<400> SEQUENCE: 85
auugaacuuu cgaauuacc 19

<210> SEQ ID NO 86
<211> LENGTH: 21
<212> TYPE: RNA
<213> ORGANISM: Artificial Sequence
<220> FEATURE:
<223> OTHER INFORMATION: Antisense strand for siKNb1-M1S

<400> SEQUENCE: 86
gguaauucga aaguucaauc c 21

<210> SEQ ID NO 87
<211> LENGTH: 19
<212> TYPE: RNA
<213> ORGANISM: Artificial Sequence
<220> FEATURE:
<223> OTHER INFORMATION: Sense strand for siKNb1-M2S

<400> SEQUENCE: 87
auugaacuuu cgaauuacc 19

<210> SEQ ID NO 88
<211> LENGTH: 21
<212> TYPE: RNA
<213> ORGANISM: Artificial Sequence
<220> FEATURE:
<223> OTHER INFORMATION: Antisense strand for siKNb1-M2S

<400> SEQUENCE: 88
gguaauucga aaguucaauc c 21

-continued

<210> SEQ ID NO 89
<211> LENGTH: 19
<212> TYPE: RNA
<213> ORGANISM: Artificial Sequence
<220> FEATURE:
<223> OTHER INFORMATION: Sense strand for siKNb1-M3S

<400> SEQUENCE: 89
auugaacuuu cgaauuacc 19

<210> SEQ ID NO 90
<211> LENGTH: 21
<212> TYPE: RNA
<213> ORGANISM: Artificial Sequence
<220> FEATURE:
<223> OTHER INFORMATION: Antisense strand for siKNb1-M3S

<400> SEQUENCE: 90
gguaauucga aaguucaauc c 21

<210> SEQ ID NO 91
<211> LENGTH: 21
<212> TYPE: RNA
<213> ORGANISM: Artificial Sequence
<220> FEATURE:
<223> OTHER INFORMATION: Sense strand for siKNb2-M1S

<400> SEQUENCE: 91
ggauugaacu uucgaauuac c 21

<210> SEQ ID NO 92
<211> LENGTH: 23
<212> TYPE: RNA
<213> ORGANISM: Artificial Sequence
<220> FEATURE:
<223> OTHER INFORMATION: Antisense strand for siKNb2-M1S

<400> SEQUENCE: 92
gguaauucga aaguucaauc cag 23

<210> SEQ ID NO 93
<211> LENGTH: 19
<212> TYPE: RNA
<213> ORGANISM: Artificial Sequence
<220> FEATURE:
<223> OTHER INFORMATION: Sense strand for siKNb2-M2S

<400> SEQUENCE: 93
auugaacuuu cgaauuacc 19

<210> SEQ ID NO 94
<211> LENGTH: 23
<212> TYPE: RNA
<213> ORGANISM: Artificial Sequence
<220> FEATURE:
<223> OTHER INFORMATION: Antisense strand for siKNb2-M2S

<400> SEQUENCE: 94
gguaauucga aaguucaauc cag 23

<210> SEQ ID NO 95
<211> LENGTH: 21
<212> TYPE: RNA
<213> ORGANISM: Artificial Sequence
<220> FEATURE:
<223> OTHER INFORMATION: Sense strand for siKNb2-M3S

<400> SEQUENCE: 95
ggauugaacu uucgaauuac c 21

<210> SEQ ID NO 96
<211> LENGTH: 23
<212> TYPE: RNA
<213> ORGANISM: Artificial Sequence
<220> FEATURE:
<223> OTHER INFORMATION: Antisense strand for siKNb2-M3S

<400> SEQUENCE: 96
gguaauucga aaguucaauc cag 23

<210> SEQ ID NO 97
<211> LENGTH: 19
<212> TYPE: RNA
<213> ORGANISM: Artificial Sequence
<220> FEATURE:
<223> OTHER INFORMATION: Sense strand for siKNb1-M1P1

<400> SEQUENCE: 97
auugaacuuu cgaauuacc 19

<210> SEQ ID NO 98
<211> LENGTH: 21
<212> TYPE: RNA
<213> ORGANISM: Artificial Sequence
<220> FEATURE:
<223> OTHER INFORMATION: Antisense strand for siKNb1-M1P1

<400> SEQUENCE: 98
gguaauucga aaguucaauc c 21

<210> SEQ ID NO 99
<211> LENGTH: 19
<212> TYPE: RNA
<213> ORGANISM: Artificial Sequence
<220> FEATURE:
<223> OTHER INFORMATION: Sense strand for siKNb1-M2P1

<400> SEQUENCE: 99
auugaacuuu cgaauuacc 19

<210> SEQ ID NO 100
<211> LENGTH: 21
<212> TYPE: RNA
<213> ORGANISM: Artificial Sequence
<220> FEATURE:
<223> OTHER INFORMATION: Antisense strand for siKNb1-M2P1

<400> SEQUENCE: 100
gguaauucga aaguucaauc c 21

<210> SEQ ID NO 101
<211> LENGTH: 19
<212> TYPE: RNA
<213> ORGANISM: Artificial Sequence
<220> FEATURE:
<223> OTHER INFORMATION: Sense strand for siKNb1-M3P1

<400> SEQUENCE: 101
auugaacuuu cgaauuacc 19

<210> SEQ ID NO 102

<211> LENGTH: 21
<212> TYPE: RNA
<213> ORGANISM: Artificial Sequence
<220> FEATURE:
<223> OTHER INFORMATION: Antisense strand for siKNb1-M3P1

<400> SEQUENCE: 102 ggudaauucga aaguucaauc c 21

<210> SEQ ID NO 103
<211> LENGTH: 21
<212> TYPE: RNA
<213> ORGANISM: Artificial Sequence
<220> FEATURE:
<223> OTHER INFORMATION: Sense strand for siKNb2-M1P1

<400> SEQUENCE: 103
ggauugaacu uucgaauuac c 21

<210> SEQ ID NO 104
<211> LENGTH: 23
<212> TYPE: RNA
<213> ORGANISM: Artificial Sequence
<220> FEATURE:
<223> OTHER INFORMATION: Antisense strand for siKNb2-M1P1

<400> SEQUENCE: 104
gguaauucga aaguucaauc cag 23

<210> SEQ ID NO 105
<211> LENGTH: 21
<212> TYPE: RNA
<213> ORGANISM: Artificial Sequence
<220> FEATURE:
<223> OTHER INFORMATION: Sense strand for siKNb2-M2P1

<400> SEQUENCE: 105
ggauugaacu uucgaauuac c 21

<210> SEQ ID NO 106
<211> LENGTH: 23
<212> TYPE: RNA
<213> ORGANISM: Artificial Sequence
<220> FEATURE:
<223> OTHER INFORMATION: Antisense strand for siKNb2-M2P1

<400> SEQUENCE: 106
gguaauucga aaguucaauc cag 23

<210> SEQ ID NO 107
<211> LENGTH: 21
<212> TYPE: RNA
<213> ORGANISM: Artificial Sequence
<220> FEATURE:
<223> OTHER INFORMATION: Sense strand for siKNb2-M3P1

<400> SEQUENCE: 107
ggauugaacu uucgaauuac c 21

<210> SEQ ID NO 108
<211> LENGTH: 23
<212> TYPE: RNA
<213> ORGANISM: Artificial Sequence
<220> FEATURE:
<223> OTHER INFORMATION: Antisense strand for siKNb2-M3P1

<400> SEQUENCE: 108

-continued gguaauucga aaguucaauc cag 23

<210> SEQ ID NO 109
<211> LENGTH: 19
<212> TYPE: RNA
<213> ORGANISM: Artificial Sequence
<220> FEATURE:
<223> OTHER INFORMATION: Sense strand for siKNb1-M1SP1

<400> SEQUENCE: 109
auugaacuuu cgaauuacc 19

<210> SEQ ID NO 110
<211> LENGTH: 21
<212> TYPE: RNA
<213> ORGANISM: Artificial Sequence
<220> FEATURE:
<223> OTHER INFORMATION: Antisense strand for siKNb1-M1SP1

<400> SEQUENCE: 110
gguaauucga aaguucaauc c 21

<210> SEQ ID NO 111
<211> LENGTH: 19
<212> TYPE: RNA
<213> ORGANISM: Artificial Sequence
<220> FEATURE:
<223> OTHER INFORMATION: Sense strand for siKNb1-M2SP1

<400> SEQUENCE: 111
auugaacuuu cgaauuacc 19

<210> SEQ ID NO 112
<211> LENGTH: 21
<212> TYPE: RNA
<213> ORGANISM: Artificial Sequence
<220> FEATURE:
<223> OTHER INFORMATION: Antisense strand for siKNb1-M2SP1

<400> SEQUENCE: 112
gguaauucga aaguucaauc c 21

<210> SEQ ID NO 113
<211> LENGTH: 19
<212> TYPE: RNA
<213> ORGANISM: Artificial Sequence
<220> FEATURE:
<223> OTHER INFORMATION: Sense strand for siKNb1-M3SP1

<400> SEQUENCE: 113
auugaacuuu cgaauuacc 19

<210> SEQ ID NO 114
<211> LENGTH: 21
<212> TYPE: RNA
<213> ORGANISM: Artificial Sequence
<220> FEATURE:
<223> OTHER INFORMATION: Antisense strand for siKNb1-M3SP1

<400> SEQUENCE: 114
gguaauucga aaguucaauc c 21

<210> SEQ ID NO 115
<211> LENGTH: 21
<212> TYPE: RNA

<213> ORGANISM: Artificial Sequence
<220> FEATURE:
<223> OTHER INFORMATION: Sense strand for siKNb2-M1SP1

<400> SEQUENCE: 115
ggauugaacu uucgaauuac c 21

<210> SEQ ID NO 116
<211> LENGTH: 23
<212> TYPE: RNA
<213> ORGANISM: Artificial Sequence
<220> FEATURE:
<223> OTHER INFORMATION: Antisense strand for siKNb2-M1SP1

<400> SEQUENCE: 116
gguaauucga aaguucaauc cag 23

<210> SEQ ID NO 117
<211> LENGTH: 21
<212> TYPE: RNA
<213> ORGANISM: Artificial Sequence
<220> FEATURE:
<223> OTHER INFORMATION: Sense strand for siKNb2-M2SP1

<400> SEQUENCE: 117
ggauugaacu uucgaauuac c 21

<210> SEQ ID NO 118
<211> LENGTH: 23
<212> TYPE: RNA
<213> ORGANISM: Artificial Sequence
<220> FEATURE:
<223> OTHER INFORMATION: Antisense strand for siKNb2-M2SP1

<400> SEQUENCE: 118
gguaauucga aaguucaauc cag 23

<210> SEQ ID NO 119
<211> LENGTH: 21
<212> TYPE: RNA
<213> ORGANISM: Artificial Sequence
<220> FEATURE:
<223> OTHER INFORMATION: Sense strand for siKNb2-M3SP1

<400> SEQUENCE: 119
ggauugaacu uucgaauuac c 21

<210> SEQ ID NO 120
<211> LENGTH: 23
<212> TYPE: RNA
<213> ORGANISM: Artificial Sequence
<220> FEATURE:
<223> OTHER INFORMATION: Antisense strand for siKNb2-M3SP1

<400> SEQUENCE: 120
gguaauucga aaguucaauc cag 23

<210> SEQ ID NO 121
<211> LENGTH: 19
<212> TYPE: RNA
<213> ORGANISM: Artificial Sequence
<220> FEATURE:
<223> OTHER INFORMATION: siRNA

<400> SEQUENCE: 121
ucgaauuacc uacucaauu 19

<210> SEQ ID NO 122
<211> LENGTH: 19
<212> TYPE: RNA
<213> ORGANISM: Artificial Sequence
<220> FEATURE:
<223> OTHER INFORMATION: siRNA

<400> SEQUENCE: 122
aauugaguag guaauucga 19

<210> SEQ ID NO 123
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 123
ucgaauuacc uacucaaun 19

<210> SEQ ID NO 124
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 124
nauugaguag guaauucga 19

<210> SEQ ID NO 125
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 125
ucgaauuacc uacucaaun 19

<210> SEQ ID NO 126
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 126
nauugaguag guaauucgaa a 21

<210> SEQ ID NO 127

```
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n=a, or g, or c, or u

<400> SEQUENCE: 127

uuucgaauua ccuacucaau n                                              21


<210> SEQ ID NO 128
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 128

nauugaguag guaauucgaa agu                                            23


<210> SEQ ID NO 129
<211> LENGTH: 19
<212> TYPE: RNA
<213> ORGANISM: Artificial Sequence
<220> FEATURE:
<223> OTHER INFORMATION: Sense strand for siKNc1

<400> SEQUENCE: 129

ucgaauuacc uacucaauu                                                 19


<210> SEQ ID NO 130
<211> LENGTH: 21
<212> TYPE: RNA
<213> ORGANISM: Artificial Sequence
<220> FEATURE:
<223> OTHER INFORMATION: Antisense strand for siKNc1

<400> SEQUENCE: 130

aauugaguag guaauucgaa a                                              21


<210> SEQ ID NO 131
<211> LENGTH: 21
<212> TYPE: RNA
<213> ORGANISM: Artificial Sequence
<220> FEATURE:
<223> OTHER INFORMATION: Sense strand for siKNc2

<400> SEQUENCE: 131

uuucgaauua ccuacucaau u                                              21


<210> SEQ ID NO 132
<211> LENGTH: 23
<212> TYPE: RNA
<213> ORGANISM: Artificial Sequence
<220> FEATURE:
<223> OTHER INFORMATION: Antisense strand for siKNc2

<400> SEQUENCE: 132

aauugaguag guaauucgaa agu                                            23
```

-continued

<210> SEQ ID NO 133
<211> LENGTH: 19
<212> TYPE: RNA
<213> ORGANISM: Artificial Sequence
<220> FEATURE:
<223> OTHER INFORMATION: Sense strand for siKNc1-M1

<400> SEQUENCE: 133
ucgaauuacc uacucaauu 19

<210> SEQ ID NO 134
<211> LENGTH: 21
<212> TYPE: RNA
<213> ORGANISM: Artificial Sequence
<220> FEATURE:
<223> OTHER INFORMATION: Antisense strand for siKNc1-M1

<400> SEQUENCE: 134
aauugaguag guaauucgaa a 21

<210> SEQ ID NO 135
<211> LENGTH: 19
<212> TYPE: RNA
<213> ORGANISM: Artificial Sequence
<220> FEATURE:
<223> OTHER INFORMATION: Sense strand for siKNc1-M2

<400> SEQUENCE: 135
ucgaauuacc uacucaauu 19

<210> SEQ ID NO 136
<211> LENGTH: 21
<212> TYPE: RNA
<213> ORGANISM: Artificial Sequence
<220> FEATURE:
<223> OTHER INFORMATION: Antisense strand for siKNc1-M2

<400> SEQUENCE: 136
aauugaguag guaauucgaa a 21

<210> SEQ ID NO 137
<211> LENGTH: 19
<212> TYPE: RNA
<213> ORGANISM: Artificial Sequence
<220> FEATURE:
<223> OTHER INFORMATION: Sense strand for siKNc1-M3

<400> SEQUENCE: 137
ucgaauuacc uacucaauu 19

<210> SEQ ID NO 138
<211> LENGTH: 21
<212> TYPE: RNA
<213> ORGANISM: Artificial Sequence
<220> FEATURE:
<223> OTHER INFORMATION: Antisense strand for siKNc1-M3

<400> SEQUENCE: 138
aauugaguag guaauucgaa a 21

<210> SEQ ID NO 139
<211> LENGTH: 21
<212> TYPE: RNA
<213> ORGANISM: Artificial Sequence
<220> FEATURE:
<223> OTHER INFORMATION: Sense strand for siKNc2-M1

<400> SEQUENCE: 139
uuucgaauua ccuacucaau u 21

<210> SEQ ID NO 140
<211> LENGTH: 23
<212> TYPE: RNA
<213> ORGANISM: Artificial Sequence
<220> FEATURE:
<223> OTHER INFORMATION: Antisense strand for siKNc2-M1

<400> SEQUENCE: 140
aauugaguag guaauucgaa agu 23

<210> SEQ ID NO 141
<211> LENGTH: 21
<212> TYPE: RNA
<213> ORGANISM: Artificial Sequence
<220> FEATURE:
<223> OTHER INFORMATION: Sense strand for siKNc2-M2

<400> SEQUENCE: 141
uuucgaauua ccuacucaau u 21

<210> SEQ ID NO 142
<211> LENGTH: 23
<212> TYPE: RNA
<213> ORGANISM: Artificial Sequence
<220> FEATURE:
<223> OTHER INFORMATION: Antisense strand for siKNc2-M2

<400> SEQUENCE: 142
aauugaguag guaauucgaa agu 23

<210> SEQ ID NO 143
<211> LENGTH: 21
<212> TYPE: RNA
<213> ORGANISM: Artificial Sequence
<220> FEATURE:
<223> OTHER INFORMATION: Sense strand for siKNc2-M3

<400> SEQUENCE: 143
uuucgaauua ccuacucaau u 21

<210> SEQ ID NO 144
<211> LENGTH: 23
<212> TYPE: RNA
<213> ORGANISM: Artificial Sequence
<220> FEATURE:
<223> OTHER INFORMATION: Antisense strand for siKNc2-M3

<400> SEQUENCE: 144
aauugaguag guaauucgaa agu 23

<210> SEQ ID NO 145
<211> LENGTH: 19
<212> TYPE: RNA
<213> ORGANISM: Artificial Sequence
<220> FEATURE:
<223> OTHER INFORMATION: Sense strand for siKNc1-M1S

<400> SEQUENCE: 145
ucgaauuacc uacucaauu 19

<210> SEQ ID NO 146
<211> LENGTH: 21

<212> TYPE: RNA
<213> ORGANISM: Artificial Sequence
<220> FEATURE:
<223> OTHER INFORMATION: Antisense strand for siKNc1-M1S

<400> SEQUENCE: 146
aauugaguag guaauucgaa a 21

<210> SEQ ID NO 147
<211> LENGTH: 19
<212> TYPE: RNA
<213> ORGANISM: Artificial Sequence
<220> FEATURE:
<223> OTHER INFORMATION: Sense strand for siKNc1-M2S

<400> SEQUENCE: 147
ucgaauuacc uacucaauu 19

<210> SEQ ID NO 148
<211> LENGTH: 21
<212> TYPE: RNA
<213> ORGANISM: Artificial Sequence
<220> FEATURE:
<223> OTHER INFORMATION: Antisense strand for siKNc1-M2S

<400> SEQUENCE: 148
aauugaguag guaauucgaa a 21

<210> SEQ ID NO 149
<211> LENGTH: 19
<212> TYPE: RNA
<213> ORGANISM: Artificial Sequence
<220> FEATURE:
<223> OTHER INFORMATION: Sense strand for siKNc1-M3S

<400> SEQUENCE: 149
ucgaauuacc uacucaauu 19

<210> SEQ ID NO 150
<211> LENGTH: 21
<212> TYPE: RNA
<213> ORGANISM: Artificial Sequence
<220> FEATURE:
<223> OTHER INFORMATION: Antisense strand for siKNc1-M3S

<400> SEQUENCE: 150
aauugaguag guaauucgaa a 21

<210> SEQ ID NO 151
<211> LENGTH: 21
<212> TYPE: RNA
<213> ORGANISM: Artificial Sequence
<220> FEATURE:
<223> OTHER INFORMATION: Sense strand for siKNc2-M1S

<400> SEQUENCE: 151
uuucgaauua ccuacucaau u 21

<210> SEQ ID NO 152
<211> LENGTH: 23
<212> TYPE: RNA
<213> ORGANISM: Artificial Sequence
<220> FEATURE:
<223> OTHER INFORMATION: Antisense strand for siKNc2-M1S

<400> SEQUENCE: 152
aauugaguag guaauucgaa agu 23

<210> SEQ ID NO 153
<211> LENGTH: 21
<212> TYPE: RNA
<213> ORGANISM: Artificial Sequence
<220> FEATURE:
<223> OTHER INFORMATION: Sense strand for siKNc2-M2S

<400> SEQUENCE: 153
uuucgaauua ccuacucaau u 21

<210> SEQ ID NO 154
<211> LENGTH: 23
<212> TYPE: RNA
<213> ORGANISM: Artificial Sequence
<220> FEATURE:
<223> OTHER INFORMATION: Antisense strand for siKNc2-M2S

<400> SEQUENCE: 154
aauugaguag guaauucgaa agu 23

<210> SEQ ID NO 155
<211> LENGTH: 21
<212> TYPE: RNA
<213> ORGANISM: Artificial Sequence
<220> FEATURE:
<223> OTHER INFORMATION: Sense strand for siKNc2-M3S

<400> SEQUENCE: 155
uuucgaauua ccuacucaau u 21

<210> SEQ ID NO 156
<211> LENGTH: 23
<212> TYPE: RNA
<213> ORGANISM: Artificial Sequence
<220> FEATURE:
<223> OTHER INFORMATION: Antisense strand for siKNc2-M3S

<400> SEQUENCE: 156
aauugaguag guaauucgaa agu 23

<210> SEQ ID NO 157
<211> LENGTH: 19
<212> TYPE: RNA
<213> ORGANISM: Artificial Sequence
<220> FEATURE:
<223> OTHER INFORMATION: Sense strand for siKNc1-M1P1

<400> SEQUENCE: 157
ucgaauuacc uacucaauu 19

<210> SEQ ID NO 158
<211> LENGTH: 21
<212> TYPE: RNA
<213> ORGANISM: Artificial Sequence
<220> FEATURE:
<223> OTHER INFORMATION: Antisense strand for siKNc1-M1P1

<400> SEQUENCE: 158
aauugaguag guaauucgaa a 21

<210> SEQ ID NO 159
<211> LENGTH: 19
<212> TYPE: RNA
<213> ORGANISM: Artificial Sequence
<220> FEATURE:
<223> OTHER INFORMATION: Sense strand for siKNc1-M2P1

<400> SEQUENCE: 159
ucgaauuacc uacucaauu 19

<210> SEQ ID NO 160
<211> LENGTH: 21
<212> TYPE: RNA
<213> ORGANISM: Artificial Sequence
<220> FEATURE:
<223> OTHER INFORMATION: Antisense strand for siKNc1-M2P1

<400> SEQUENCE: 160
aauugaguag guaauucgaa a 21

<210> SEQ ID NO 161
<211> LENGTH: 19
<212> TYPE: RNA
<213> ORGANISM: Artificial Sequence
<220> FEATURE:
<223> OTHER INFORMATION: Sense strand for siKNc1-M3P1

<400> SEQUENCE: 161
ucgaauuacc uacucaauu 19

<210> SEQ ID NO 162
<211> LENGTH: 21
<212> TYPE: RNA
<213> ORGANISM: Artificial Sequence
<220> FEATURE:
<223> OTHER INFORMATION: Antisense strand for siKNc1-M3P1

<400> SEQUENCE: 162
aauugaguag guaauucgaa a 21

<210> SEQ ID NO 163
<211> LENGTH: 21
<212> TYPE: RNA
<213> ORGANISM: Artificial Sequence
<220> FEATURE:
<223> OTHER INFORMATION: Sense strand for siKNc2-M1P1

<400> SEQUENCE: 163
uuucgaauua ccuacucaau u 21

<210> SEQ ID NO 164
<211> LENGTH: 23
<212> TYPE: RNA
<213> ORGANISM: Artificial Sequence
<220> FEATURE:
<223> OTHER INFORMATION: Antisense strand for siKNc2-M1P1

<400> SEQUENCE: 164
aauugaguag guaauucgaa agu 23

<210> SEQ ID NO 165
<211> LENGTH: 21
<212> TYPE: RNA
<213> ORGANISM: Artificial Sequence
<220> FEATURE:
<223> OTHER INFORMATION: Sense strand for siKNc2-M2P1

<400> SEQUENCE: 165
uuucgaauua ccuacucaau u 21

<210> SEQ ID NO 166
<211> LENGTH: 23
<212> TYPE: RNA
<213> ORGANISM: Artificial Sequence
<220> FEATURE:
<223> OTHER INFORMATION: Antisense strand for siKNc2-M2P1

<400> SEQUENCE: 166
aauugaguag guaauucgaa agu 23

<210> SEQ ID NO 167
<211> LENGTH: 21
<212> TYPE: RNA
<213> ORGANISM: Artificial Sequence
<220> FEATURE:
<223> OTHER INFORMATION: Sense strand for siKNc2-M3P1

<400> SEQUENCE: 167
uuucgaauua ccuacucaau u 21

<210> SEQ ID NO 168
<211> LENGTH: 23
<212> TYPE: RNA
<213> ORGANISM: Artificial Sequence
<220> FEATURE:
<223> OTHER INFORMATION: Antisense strand for siKNc2-M3P1

<400> SEQUENCE: 168
aauugaguag guaauucgaa agu 23

<210> SEQ ID NO 169
<211> LENGTH: 19
<212> TYPE: RNA
<213> ORGANISM: Artificial Sequence
<220> FEATURE:
<223> OTHER INFORMATION: Sense strand for siKNc1-M1SP1

<400> SEQUENCE: 169
ucgaauuacc uacucaauu 19

<210> SEQ ID NO 170
<211> LENGTH: 21
<212> TYPE: RNA
<213> ORGANISM: Artificial Sequence
<220> FEATURE:
<223> OTHER INFORMATION: Antisense strand for siKNc1-M1SP1

<400> SEQUENCE: 170
aauugaguag guaauucgaa a 21

<210> SEQ ID NO 171
<211> LENGTH: 19
<212> TYPE: RNA
<213> ORGANISM: Artificial Sequence
<220> FEATURE:
<223> OTHER INFORMATION: Sense strand for siKNc1-M2SP1

<400> SEQUENCE: 171
ucgaauuacc uacucaauu 19

<210> SEQ ID NO 172
<211> LENGTH: 21
<212> TYPE: RNA
<213> ORGANISM: Artificial Sequence
<220> FEATURE:
<223> OTHER INFORMATION: Antisense strand for siKNc1-M2SP1

<400> SEQUENCE: 172
aauugaguag guaauucgaa a 21

<210> SEQ ID NO 173
<211> LENGTH: 19
<212> TYPE: RNA
<213> ORGANISM: Artificial Sequence
<220> FEATURE:
<223> OTHER INFORMATION: Sense strand for siKNc1-M3SP1

<400> SEQUENCE: 173
ucgaauuacc uacucaauu 19

<210> SEQ ID NO 174
<211> LENGTH: 21
<212> TYPE: RNA
<213> ORGANISM: Artificial Sequence
<220> FEATURE:
<223> OTHER INFORMATION: Antisense strand for siKNc1-M3SP1

<400> SEQUENCE: 174
aauugaguag guaauucgaa a 21

<210> SEQ ID NO 175
<211> LENGTH: 21
<212> TYPE: RNA
<213> ORGANISM: Artificial Sequence
<220> FEATURE:
<223> OTHER INFORMATION: Sense strand for siKNc2-M1SP1

<400> SEQUENCE: 175
uuucgaauua ccuacucaau u 21

<210> SEQ ID NO 176
<211> LENGTH: 23
<212> TYPE: RNA
<213> ORGANISM: Artificial Sequence
<220> FEATURE:
<223> OTHER INFORMATION: Antisense strand for siKNc2-M1SP1

<400> SEQUENCE: 176
aauugaguag guaauucgaa agu 23

<210> SEQ ID NO 177
<211> LENGTH: 21
<212> TYPE: RNA
<213> ORGANISM: Artificial Sequence
<220> FEATURE:
<223> OTHER INFORMATION: Sense strand for siKNc2-M2SP1

<400> SEQUENCE: 177
uuucgaauua ccuacucaau u 21

<210> SEQ ID NO 178
<211> LENGTH: 23
<212> TYPE: RNA
<213> ORGANISM: Artificial Sequence
<220> FEATURE:
<223> OTHER INFORMATION: Antisense strand for siKNc2-M2SP1

<400> SEQUENCE: 178
aauugaguag guaauucgaa agu 23

<210> SEQ ID NO 179

<211> LENGTH: 21
<212> TYPE: RNA
<213> ORGANISM: Artificial Sequence
<220> FEATURE:
<223> OTHER INFORMATION: Sense strand for siKNc2-M3SP1

<400> SEQUENCE: 179
uuucgaauua ccuacucaau u 21

<210> SEQ ID NO 180
<211> LENGTH: 23
<212> TYPE: RNA
<213> ORGANISM: Artificial Sequence
<220> FEATURE:
<223> OTHER INFORMATION: Antisense strand for siKNc2-M3SP1

<400> SEQUENCE: 180
aauugaguag guaauucgaa agu 23

<210> SEQ ID NO 181
<211> LENGTH: 19
<212> TYPE: RNA
<213> ORGANISM: Artificial Sequence
<220> FEATURE:
<223> OTHER INFORMATION: siRNA

<400> SEQUENCE: 181
gauaaugcau acaucgaua 19

<210> SEQ ID NO 182
<211> LENGTH: 19
<212> TYPE: RNA
<213> ORGANISM: Artificial Sequence
<220> FEATURE:
<223> OTHER INFORMATION: siRNA

<400> SEQUENCE: 182
uaucgaugua ugcauuauc 19

<210> SEQ ID NO 183
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 183
gauaaugcau acaucgaun 19

<210> SEQ ID NO 184
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 184
naucgaugua ugcauuauc 19

-continued

<210> SEQ ID NO 185
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 185
gauaaugcau acaucgaun 19

<210> SEQ ID NO 186
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 186
naucgaugua ugcauuaucu g 21

<210> SEQ ID NO 187
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n=a, or g, or c, or u

<400> SEQUENCE: 187
cagauaaugc auacaucgau n 21

<210> SEQ ID NO 188
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 188
naucgaugua ugcauuaucu gua 23

<210> SEQ ID NO 189
<211> LENGTH: 19
<212> TYPE: RNA
<213> ORGANISM: Artificial Sequence
<220> FEATURE:
<223> OTHER INFORMATION: Sense strand for siKNd1

<400> SEQUENCE: 189
gauaaugcau acaucgaua 19

<210> SEQ ID NO 190
<211> LENGTH: 21
<212> TYPE: RNA

-continued

<213> ORGANISM: Artificial Sequence
<220> FEATURE:
<223> OTHER INFORMATION: Antisense strand for siKNd1

<400> SEQUENCE: 190
uaucgaugua ugcauuaucu g 21

<210> SEQ ID NO 191
<211> LENGTH: 21
<212> TYPE: RNA
<213> ORGANISM: Artificial Sequence
<220> FEATURE:
<223> OTHER INFORMATION: Sense strand for siKNd2

<400> SEQUENCE: 191
cagauaaugc auacaucgau a 21

<210> SEQ ID NO 192
<211> LENGTH: 23
<212> TYPE: RNA
<213> ORGANISM: Artificial Sequence
<220> FEATURE:
<223> OTHER INFORMATION: Antisense strand for siKNd2

<400> SEQUENCE: 192
uaucgaugua ugcauuaucu gua 23

<210> SEQ ID NO 193
<211> LENGTH: 19
<212> TYPE: RNA
<213> ORGANISM: Artificial Sequence
<220> FEATURE:
<223> OTHER INFORMATION: Sense strand for siKNd1-M1

<400> SEQUENCE: 193
gauaaugcau acaucgaua 19

<210> SEQ ID NO 194
<211> LENGTH: 21
<212> TYPE: RNA
<213> ORGANISM: Artificial Sequence
<220> FEATURE:
<223> OTHER INFORMATION: Antisense strand for siKNd1-M1

<400> SEQUENCE: 194
uaucgaugua ugcauuaucu g 21

<210> SEQ ID NO 195
<211> LENGTH: 19
<212> TYPE: RNA
<213> ORGANISM: Artificial Sequence
<220> FEATURE:
<223> OTHER INFORMATION: Sense strand for siKNd1-M2

<400> SEQUENCE: 195
gauaaugcau acaucgaua 19

<210> SEQ ID NO 196
<211> LENGTH: 21
<212> TYPE: RNA
<213> ORGANISM: Artificial Sequence
<220> FEATURE:
<223> OTHER INFORMATION: Antisense strand for siKNd1-M2

<400> SEQUENCE: 196
uaucgaugua ugcauuaucu g 21

<210> SEQ ID NO 197
<211> LENGTH: 19
<212> TYPE: RNA
<213> ORGANISM: Artificial Sequence
<220> FEATURE:
<223> OTHER INFORMATION: Sense strand for siKNd1-M3

<400> SEQUENCE: 197
gauaaugcau acaucgaua 19

<210> SEQ ID NO 198
<211> LENGTH: 21
<212> TYPE: RNA
<213> ORGANISM: Artificial Sequence
<220> FEATURE:
<223> OTHER INFORMATION: Antisense strand for siKNd1-M3

<400> SEQUENCE: 198
uaucgaugua ugcauuaucu g 21

<210> SEQ ID NO 199
<211> LENGTH: 21
<212> TYPE: RNA
<213> ORGANISM: Artificial Sequence
<220> FEATURE:
<223> OTHER INFORMATION: Sense strand for siKNd2-M1

<400> SEQUENCE: 199
cagauaaugc auacaucgau a 21

<210> SEQ ID NO 200
<211> LENGTH: 23
<212> TYPE: RNA
<213> ORGANISM: Artificial Sequence
<220> FEATURE:
<223> OTHER INFORMATION: Antisense strand for siKNd2-M1

<400> SEQUENCE: 200
uaucgaugua ugcauuaucu gua 23

<210> SEQ ID NO 201
<211> LENGTH: 21
<212> TYPE: RNA
<213> ORGANISM: Artificial Sequence
<220> FEATURE:
<223> OTHER INFORMATION: Sense strand for siKNd2-M2

<400> SEQUENCE: 201
cagauaaugc auacaucgau a 21

<210> SEQ ID NO 202
<211> LENGTH: 23
<212> TYPE: RNA
<213> ORGANISM: Artificial Sequence
<220> FEATURE:
<223> OTHER INFORMATION: Antisense strand for siKNd2-M2

<400> SEQUENCE: 202
uaucgaugua ugcauuaucu gua 23

<210> SEQ ID NO 203
<211> LENGTH: 21
<212> TYPE: RNA
<213> ORGANISM: Artificial Sequence
<220> FEATURE:

<223> OTHER INFORMATION: Sense strand for siKNd2-M3

<400> SEQUENCE: 203
cagauaaugc auacaucgau a 21

<210> SEQ ID NO 204
<211> LENGTH: 23
<212> TYPE: RNA
<213> ORGANISM: Artificial Sequence
<220> FEATURE:
<223> OTHER INFORMATION: Antisense strand for siKNd2-M3

<400> SEQUENCE: 204
uaucgaugua ugcauuaucu gua 23

<210> SEQ ID NO 205
<211> LENGTH: 19
<212> TYPE: RNA
<213> ORGANISM: Artificial Sequence
<220> FEATURE:
<223> OTHER INFORMATION: Sense strand for siKNd1-M1S

<400> SEQUENCE: 205
gauaaugcau acaucgaua 19

<210> SEQ ID NO 206
<211> LENGTH: 21
<212> TYPE: RNA
<213> ORGANISM: Artificial Sequence
<220> FEATURE:
<223> OTHER INFORMATION: Antisense strand for siKNd1-M1S

<400> SEQUENCE: 206
uaucgaugua ugcauuaucu g 21

<210> SEQ ID NO 207
<211> LENGTH: 19
<212> TYPE: RNA
<213> ORGANISM: Artificial Sequence
<220> FEATURE:
<223> OTHER INFORMATION: Sense strand for siKNd1-M2S

<400> SEQUENCE: 207
gauaaugcau acaucgaua 19

<210> SEQ ID NO 208
<211> LENGTH: 21
<212> TYPE: RNA
<213> ORGANISM: Artificial Sequence
<220> FEATURE:
<223> OTHER INFORMATION: Antisense strand for siKNd1-M2S

<400> SEQUENCE: 208
uaucgaugua ugcauuaucu g 21

<210> SEQ ID NO 209
<211> LENGTH: 19
<212> TYPE: RNA
<213> ORGANISM: Artificial Sequence
<220> FEATURE:
<223> OTHER INFORMATION: Sense strand for siKNd1-M3S

<400> SEQUENCE: 209
gauaaugcau acaucgaua 19

<210> SEQ ID NO 210
<211> LENGTH: 21
<212> TYPE: RNA
<213> ORGANISM: Artificial Sequence
<220> FEATURE:
<223> OTHER INFORMATION: Antisense strand for siKNd1-M3S

<400> SEQUENCE: 210
uaucgaugua ugcauuaucu g 21

<210> SEQ ID NO 211
<211> LENGTH: 21
<212> TYPE: RNA
<213> ORGANISM: Artificial Sequence
<220> FEATURE:
<223> OTHER INFORMATION: Sense strand for siKNd2-M1S

<400> SEQUENCE: 211
cagauaaugc auacaucgau a 21

<210> SEQ ID NO 212
<211> LENGTH: 23
<212> TYPE: RNA
<213> ORGANISM: Artificial Sequence
<220> FEATURE:
<223> OTHER INFORMATION: Antisense strand for siKNd2-M1S

<400> SEQUENCE: 212
uaucgaugua ugcauuaucu gua 23

<210> SEQ ID NO 213
<211> LENGTH: 21
<212> TYPE: RNA
<213> ORGANISM: Artificial Sequence
<220> FEATURE:
<223> OTHER INFORMATION: Sense strand for siKNd2-M2S

<400> SEQUENCE: 213
cagauaaugc auacaucgau a 21

<210> SEQ ID NO 214
<211> LENGTH: 23
<212> TYPE: RNA
<213> ORGANISM: Artificial Sequence
<220> FEATURE:
<223> OTHER INFORMATION: Antisense strand for siKNd2-M2S

<400> SEQUENCE: 214
uaucgaugua ugcauuaucu gua 23

<210> SEQ ID NO 215
<211> LENGTH: 21
<212> TYPE: RNA
<213> ORGANISM: Artificial Sequence
<220> FEATURE:
<223> OTHER INFORMATION: Sense strand for siKNd2-M3S

<400> SEQUENCE: 215
cagauaaugc auacaucgau a 21

<210> SEQ ID NO 216
<211> LENGTH: 23
<212> TYPE: RNA
<213> ORGANISM: Artificial Sequence
<220> FEATURE:
<223> OTHER INFORMATION: Antisense strand for siKNd2-M3S

<400> SEQUENCE: 216
uaucgaugua ugcauuaucu gua 23

<210> SEQ ID NO 217
<211> LENGTH: 19
<212> TYPE: RNA
<213> ORGANISM: Artificial Sequence
<220> FEATURE:
<223> OTHER INFORMATION: Sense strand for siKNd1-M1P1

<400> SEQUENCE: 217
gauaaugcau acaucgaua 19

<210> SEQ ID NO 218
<211> LENGTH: 21
<212> TYPE: RNA
<213> ORGANISM: Artificial Sequence
<220> FEATURE:
<223> OTHER INFORMATION: Antisense strand for siKNd1-M1P1

<400> SEQUENCE: 218
uaucgaugua ugcauuaucu g 21

<210> SEQ ID NO 219
<211> LENGTH: 19
<212> TYPE: RNA
<213> ORGANISM: Artificial Sequence
<220> FEATURE:
<223> OTHER INFORMATION: Sense strand for siKNd1-M2P1

<400> SEQUENCE: 219
gauaaugcau acaucgaua 19

<210> SEQ ID NO 220
<211> LENGTH: 21
<212> TYPE: RNA
<213> ORGANISM: Artificial Sequence
<220> FEATURE:
<223> OTHER INFORMATION: Antisense strand for siKNd1-M2P1

<400> SEQUENCE: 220
uaucgaugua ugcauuaucu g 21

<210> SEQ ID NO 221
<211> LENGTH: 19
<212> TYPE: RNA
<213> ORGANISM: Artificial Sequence
<220> FEATURE:
<223> OTHER INFORMATION: Sense strand for siKNd1-M3P1

<400> SEQUENCE: 221
gauaaugcau acaucgaua 19

<210> SEQ ID NO 222
<211> LENGTH: 21
<212> TYPE: RNA
<213> ORGANISM: Artificial Sequence
<220> FEATURE:
<223> OTHER INFORMATION: Antisense strand for siKNd1-M3P1

<400> SEQUENCE: 222
uaucgaugua ugcauuaucu g 21

<210> SEQ ID NO 223
<211> LENGTH: 21

<212> TYPE: RNA
<213> ORGANISM: Artificial Sequence
<220> FEATURE:
<223> OTHER INFORMATION: Sense strand for siKNd2-M1P1

<400> SEQUENCE: 223
cagauaaugc auacaucgau a 21

<210> SEQ ID NO 224
<211> LENGTH: 23
<212> TYPE: RNA
<213> ORGANISM: Artificial Sequence
<220> FEATURE:
<223> OTHER INFORMATION: Antisense strand for siKNd2-M1P1

<400> SEQUENCE: 224
uaucgaugua ugcauuaucu gua 23

<210> SEQ ID NO 225
<211> LENGTH: 21
<212> TYPE: RNA
<213> ORGANISM: Artificial Sequence
<220> FEATURE:
<223> OTHER INFORMATION: Sense strand for siKNd2-M2P1

<400> SEQUENCE: 225
cagauaaugc auacaucgau a 21

<210> SEQ ID NO 226
<211> LENGTH: 23
<212> TYPE: RNA
<213> ORGANISM: Artificial Sequence
<220> FEATURE:
<223> OTHER INFORMATION: Antisense strand for siKNd2-M2P1

<400> SEQUENCE: 226
uaucgaugua ugcauuaucu gua 23

<210> SEQ ID NO 227
<211> LENGTH: 21
<212> TYPE: RNA
<213> ORGANISM: Artificial Sequence
<220> FEATURE:
<223> OTHER INFORMATION: Sense strand for siKNd2-M3P1

<400> SEQUENCE: 227
cagauaaugc auacaucgau a 21

<210> SEQ ID NO 228
<211> LENGTH: 23
<212> TYPE: RNA
<213> ORGANISM: Artificial Sequence
<220> FEATURE:
<223> OTHER INFORMATION: Antisense strand for siKNd2-M3P1

<400> SEQUENCE: 228
uaucgaugua ugcauuaucu gua 23

<210> SEQ ID NO 229
<211> LENGTH: 19
<212> TYPE: RNA
<213> ORGANISM: Artificial Sequence
<220> FEATURE:
<223> OTHER INFORMATION: Sense strand for siKNd1-M1SP1

<400> SEQUENCE: 229
gauaaugcau acaucgaua 19

<210> SEQ ID NO 230
<211> LENGTH: 21
<212> TYPE: RNA
<213> ORGANISM: Artificial Sequence
<220> FEATURE:
<223> OTHER INFORMATION: Antisense strand for siKNd1-M1SP1

<400> SEQUENCE: 230
uaucgaugua ugcauuaucu g 21

<210> SEQ ID NO 231
<211> LENGTH: 19
<212> TYPE: RNA
<213> ORGANISM: Artificial Sequence
<220> FEATURE:
<223> OTHER INFORMATION: Sense strand for siKNd1-M2SP1

<400> SEQUENCE: 231
gauaaugcau acaucgaua 19

<210> SEQ ID NO 232
<211> LENGTH: 21
<212> TYPE: RNA
<213> ORGANISM: Artificial Sequence
<220> FEATURE:
<223> OTHER INFORMATION: Antisense strand for siKNd1-M2SP1

<400> SEQUENCE: 232
uaucgaugua ugcauuaucu g 21

<210> SEQ ID NO 233
<211> LENGTH: 19
<212> TYPE: RNA
<213> ORGANISM: Artificial Sequence
<220> FEATURE:
<223> OTHER INFORMATION: Sense strand for siKNd1-M3SP1

<400> SEQUENCE: 233
gauaaugcau acaucgaua 19

<210> SEQ ID NO 234
<211> LENGTH: 21
<212> TYPE: RNA
<213> ORGANISM: Artificial Sequence
<220> FEATURE:
<223> OTHER INFORMATION: Antisense strand for siKNd1-M3SP1

<400> SEQUENCE: 234
uaucgaugua ugcauuaucu g 21

<210> SEQ ID NO 235
<211> LENGTH: 21
<212> TYPE: RNA
<213> ORGANISM: Artificial Sequence
<220> FEATURE:
<223> OTHER INFORMATION: Sense strand for siKNd2-M1SP1

<400> SEQUENCE: 235
cagauaaugc auacaucgau a 21

<210> SEQ ID NO 236
<211> LENGTH: 23
<212> TYPE: RNA
<213> ORGANISM: Artificial Sequence

```
<220> FEATURE:
<223> OTHER INFORMATION: Antisense strand for siKNd2-M1SP1

<400> SEQUENCE: 236

uaucgaugua ugcauuaucu gua                                         23


<210> SEQ ID NO 237
<211> LENGTH: 21
<212> TYPE: RNA
<213> ORGANISM: Artificial Sequence
<220> FEATURE:
<223> OTHER INFORMATION: Sense strand for siKNd2-M2SP1

<400> SEQUENCE: 237

cagauaaugc auacaucgau a                                           21


<210> SEQ ID NO 238
<211> LENGTH: 23
<212> TYPE: RNA
<213> ORGANISM: Artificial Sequence
<220> FEATURE:
<223> OTHER INFORMATION: Antisense strand for siKNd2-M2SP1

<400> SEQUENCE: 238

uaucgaugua ugcauuaucu gua                                         23


<210> SEQ ID NO 239
<211> LENGTH: 21
<212> TYPE: RNA
<213> ORGANISM: Artificial Sequence
<220> FEATURE:
<223> OTHER INFORMATION: Sense strand for siKNd2-M3SP1

<400> SEQUENCE: 239

cagauaaugc auacaucgau a                                           21


<210> SEQ ID NO 240
<211> LENGTH: 23
<212> TYPE: RNA
<213> ORGANISM: Artificial Sequence
<220> FEATURE:
<223> OTHER INFORMATION: Antisense strand for siKNd2-M3SP1

<400> SEQUENCE: 240

uaucgaugua ugcauuaucu gua                                         23


<210> SEQ ID NO 241
<211> LENGTH: 19
<212> TYPE: RNA
<213> ORGANISM: Artificial Sequence
<220> FEATURE:
<223> OTHER INFORMATION: siRNA

<400> SEQUENCE: 241

gaauaacgca acuuucuau                                              19


<210> SEQ ID NO 242
<211> LENGTH: 19
<212> TYPE: RNA
<213> ORGANISM: Artificial Sequence
<220> FEATURE:
<223> OTHER INFORMATION: siRNA

<400> SEQUENCE: 242

auagaaaguu gcguuauuc                                              19
```

<210> SEQ ID NO 243
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 243
gaauaacgca acuuucuan 19

<210> SEQ ID NO 244
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 244
nuagaaaguu gcguuauuc 19

<210> SEQ ID NO 245
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 245
gaauaacgca acuuucuan 19

<210> SEQ ID NO 246
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 246
nuagaaaguu gcguuauucu c 21

<210> SEQ ID NO 247
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n=a, or g, or c, or u

<400> SEQUENCE: 247
gagaauaacg caacuuucua n 21

<210> SEQ ID NO 248
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 248
nuagaaaguu gcguuauucu cug 23

<210> SEQ ID NO 249
<211> LENGTH: 19
<212> TYPE: RNA
<213> ORGANISM: Artificial Sequence
<220> FEATURE:
<223> OTHER INFORMATION: Sense strand for siKNe1

<400> SEQUENCE: 249
gaauaacgca acuuucuau 19

<210> SEQ ID NO 250
<211> LENGTH: 21
<212> TYPE: RNA
<213> ORGANISM: Artificial Sequence
<220> FEATURE:
<223> OTHER INFORMATION: Antisense strand for siKNe1

<400> SEQUENCE: 250
auagaaaguu gcguuauucu c 21

<210> SEQ ID NO 251
<211> LENGTH: 21
<212> TYPE: RNA
<213> ORGANISM: Artificial Sequence
<220> FEATURE:
<223> OTHER INFORMATION: Sense strand for siKNe2

<400> SEQUENCE: 251
gagaauaacg caacuuucua u 21

<210> SEQ ID NO 252
<211> LENGTH: 23
<212> TYPE: RNA
<213> ORGANISM: Artificial Sequence
<220> FEATURE:
<223> OTHER INFORMATION: Antisense strand for siKNe2

<400> SEQUENCE: 252
auagaaaguu gcguuauucu cug 23

<210> SEQ ID NO 253
<211> LENGTH: 19
<212> TYPE: RNA
<213> ORGANISM: Artificial Sequence
<220> FEATURE:
<223> OTHER INFORMATION: Sense strand for siKNe1-M1

<400> SEQUENCE: 253
gaauaacgca acuuucuau 19

<210> SEQ ID NO 254

<211> LENGTH: 21
<212> TYPE: RNA
<213> ORGANISM: Artificial Sequence
<220> FEATURE:
<223> OTHER INFORMATION: Antisense strand for siKNe1-M1

<400> SEQUENCE: 254
auagaaaguu gcguuauucu c 21

<210> SEQ ID NO 255
<211> LENGTH: 19
<212> TYPE: RNA
<213> ORGANISM: Artificial Sequence
<220> FEATURE:
<223> OTHER INFORMATION: Sense strand for siKNe1-M2

<400> SEQUENCE: 255
gaauaacgca acuuucuau 19

<210> SEQ ID NO 256
<211> LENGTH: 21
<212> TYPE: RNA
<213> ORGANISM: Artificial Sequence
<220> FEATURE:
<223> OTHER INFORMATION: Antisense strand for siKNe1-M2

<400> SEQUENCE: 256
auagaaaguu gcguuauucu c 21

<210> SEQ ID NO 257
<211> LENGTH: 19
<212> TYPE: RNA
<213> ORGANISM: Artificial Sequence
<220> FEATURE:
<223> OTHER INFORMATION: Sense strand for siKNe1-M3

<400> SEQUENCE: 257
gaauaacgca acuuucuau 19

<210> SEQ ID NO 258
<211> LENGTH: 21
<212> TYPE: RNA
<213> ORGANISM: Artificial Sequence
<220> FEATURE:
<223> OTHER INFORMATION: Sense strand for siKNe1-M3

<400> SEQUENCE: 258
auagaaaguu gcguuauucu c 21

<210> SEQ ID NO 259
<211> LENGTH: 21
<212> TYPE: RNA
<213> ORGANISM: Artificial Sequence
<220> FEATURE:
<223> OTHER INFORMATION: Sense strand for siKNe2-M1

<400> SEQUENCE: 259
gagaauaacg caacuuucua u 21

<210> SEQ ID NO 260
<211> LENGTH: 23
<212> TYPE: RNA
<213> ORGANISM: Artificial Sequence
<220> FEATURE:
<223> OTHER INFORMATION: Antisense strand for siKNe2-M1

<400> SEQUENCE: 260
auagaaaguu gcguuauucu cug 23

<210> SEQ ID NO 261
<211> LENGTH: 21
<212> TYPE: RNA
<213> ORGANISM: Artificial Sequence
<220> FEATURE:
<223> OTHER INFORMATION: Sense strand for siKNe2-M2

<400> SEQUENCE: 261
gagaauaacg caacuuucua u 21

<210> SEQ ID NO 262
<211> LENGTH: 23
<212> TYPE: RNA
<213> ORGANISM: Artificial Sequence
<220> FEATURE:
<223> OTHER INFORMATION: Antisense strand for siKNe2-M2

<400> SEQUENCE: 262
auagaaaguu gcguuauucu cug 23

<210> SEQ ID NO 263
<211> LENGTH: 21
<212> TYPE: RNA
<213> ORGANISM: Artificial Sequence
<220> FEATURE:
<223> OTHER INFORMATION: Sense strand for siKNe2-M3

<400> SEQUENCE: 263
gagaauaacg caacuuucua u 21

<210> SEQ ID NO 264
<211> LENGTH: 23
<212> TYPE: RNA
<213> ORGANISM: Artificial Sequence
<220> FEATURE:
<223> OTHER INFORMATION: Antisense strand for siKNe2-M3

<400> SEQUENCE: 264
auagaaaguu gcguuauucu cug 23

<210> SEQ ID NO 265
<211> LENGTH: 19
<212> TYPE: RNA
<213> ORGANISM: Artificial Sequence
<220> FEATURE:
<223> OTHER INFORMATION: Sense strand for siKNe1-M1S

<400> SEQUENCE: 265
gaauaacgca acuuucuau 19

<210> SEQ ID NO 266
<211> LENGTH: 21
<212> TYPE: RNA
<213> ORGANISM: Artificial Sequence
<220> FEATURE:
<223> OTHER INFORMATION: Antisense strand for siKNe1-M1S

<400> SEQUENCE: 266
auagaaaguu gcguuauucu c 21

<210> SEQ ID NO 267
<211> LENGTH: 19
<212> TYPE: RNA

<213> ORGANISM: Artificial Sequence
<220> FEATURE:
<223> OTHER INFORMATION: Sense strand for siKNe1-M2S

<400> SEQUENCE: 267
gaauaacgca acuuucuau 19

<210> SEQ ID NO 268
<211> LENGTH: 21
<212> TYPE: RNA
<213> ORGANISM: Artificial Sequence
<220> FEATURE:
<223> OTHER INFORMATION: Antisense strand for siKNe1-M2S

<400> SEQUENCE: 268
auagaaaguu gcguuauucu c 21

<210> SEQ ID NO 269
<211> LENGTH: 19
<212> TYPE: RNA
<213> ORGANISM: Artificial Sequence
<220> FEATURE:
<223> OTHER INFORMATION: Sense strand for siKNe1-M3S

<400> SEQUENCE: 269
gaauaacgca acuuucuau 19

<210> SEQ ID NO 270
<211> LENGTH: 21
<212> TYPE: RNA
<213> ORGANISM: Artificial Sequence
<220> FEATURE:
<223> OTHER INFORMATION: Antisense strand for siKNe1-M3S

<400> SEQUENCE: 270
auagaaaguu gcguuauucu c 21

<210> SEQ ID NO 271
<211> LENGTH: 21
<212> TYPE: RNA
<213> ORGANISM: Artificial Sequence
<220> FEATURE:
<223> OTHER INFORMATION: Sense strand for siKNe2-M1S

<400> SEQUENCE: 271
gagaauaacg caacuuucua u 21

<210> SEQ ID NO 272
<211> LENGTH: 23
<212> TYPE: RNA
<213> ORGANISM: Artificial Sequence
<220> FEATURE:
<223> OTHER INFORMATION: Antisense strand for siKNe2-M1S

<400> SEQUENCE: 272
auagaaaguu gcguuauucu cug 23

<210> SEQ ID NO 273
<211> LENGTH: 21
<212> TYPE: RNA
<213> ORGANISM: Artificial Sequence
<220> FEATURE:
<223> OTHER INFORMATION: Sense strand for siKNe2-M2S

<400> SEQUENCE: 273
gagaauaacg caacuuucua u 21

<210> SEQ ID NO 274
<211> LENGTH: 23
<212> TYPE: RNA
<213> ORGANISM: Artificial Sequence
<220> FEATURE:
<223> OTHER INFORMATION: Antisense strand for siKNe2-M2S

<400> SEQUENCE: 274
auagaaaguu gcguuauucu cug 23

<210> SEQ ID NO 275
<211> LENGTH: 21
<212> TYPE: RNA
<213> ORGANISM: Artificial Sequence
<220> FEATURE:
<223> OTHER INFORMATION: Sense strand for siKNe2-M3S

<400> SEQUENCE: 275
gagaauaacg caacuuucua u 21

<210> SEQ ID NO 276
<211> LENGTH: 23
<212> TYPE: RNA
<213> ORGANISM: Artificial Sequence
<220> FEATURE:
<223> OTHER INFORMATION: Antisense strand for siKNe2-M3S

<400> SEQUENCE: 276
auagaaaguu gcguuauucu cug 23

<210> SEQ ID NO 277
<211> LENGTH: 19
<212> TYPE: RNA
<213> ORGANISM: Artificial Sequence
<220> FEATURE:
<223> OTHER INFORMATION: Sense strand for siKNe1-M1P1

<400> SEQUENCE: 277
gaauaacgca acuuucuau 19

<210> SEQ ID NO 278
<211> LENGTH: 21
<212> TYPE: RNA
<213> ORGANISM: Artificial Sequence
<220> FEATURE:
<223> OTHER INFORMATION: Antisense strand for siKNe1-M1P1

<400> SEQUENCE: 278
auagaaaguu gcguuauucu c 21

<210> SEQ ID NO 279
<211> LENGTH: 19
<212> TYPE: RNA
<213> ORGANISM: Artificial Sequence
<220> FEATURE:
<223> OTHER INFORMATION: Sense strand for siKNe1-M2P1

<400> SEQUENCE: 279
gaauaacgca acuuucuau 19

<210> SEQ ID NO 280
<211> LENGTH: 21
<212> TYPE: RNA
<213> ORGANISM: Artificial Sequence
<220> FEATURE:

<223> OTHER INFORMATION: Antisense strand for siKNe1-M2P1

<400> SEQUENCE: 280
auagaaaguu gcguuauucu c 21

<210> SEQ ID NO 281
<211> LENGTH: 19
<212> TYPE: RNA
<213> ORGANISM: Artificial Sequence
<220> FEATURE:
<223> OTHER INFORMATION: Sense strand for siKNe1-M3P1

<400> SEQUENCE: 281
gaauaacgca acuuucuau 19

<210> SEQ ID NO 282
<211> LENGTH: 21
<212> TYPE: RNA
<213> ORGANISM: Artificial Sequence
<220> FEATURE:
<223> OTHER INFORMATION: Antisense strand for siKNe1-M3P1

<400> SEQUENCE: 282
auagaaaguu gcguuauucu c 21

<210> SEQ ID NO 283
<211> LENGTH: 21
<212> TYPE: RNA
<213> ORGANISM: Artificial Sequence
<220> FEATURE:
<223> OTHER INFORMATION: Sense strand for siKNe2-M1P1

<400> SEQUENCE: 283
gagaauaacg caacuuucua u 21

<210> SEQ ID NO 284
<211> LENGTH: 23
<212> TYPE: RNA
<213> ORGANISM: Artificial Sequence
<220> FEATURE:
<223> OTHER INFORMATION: Antisense strand for siKNe2-M1P1

<400> SEQUENCE: 284
auagaaaguu gcguuauucu cug 23

<210> SEQ ID NO 285
<211> LENGTH: 21
<212> TYPE: RNA
<213> ORGANISM: Artificial Sequence
<220> FEATURE:
<223> OTHER INFORMATION: Sense strand for siKNe2-M2P1

<400> SEQUENCE: 285
gagaauaacg caacuuucua u 21

<210> SEQ ID NO 286
<211> LENGTH: 23
<212> TYPE: RNA
<213> ORGANISM: Artificial Sequence
<220> FEATURE:
<223> OTHER INFORMATION: Antisense strand for siKNe2-M2P1

<400> SEQUENCE: 286
auagaaaguu gcguuauucu cug 23

-continued

<210> SEQ ID NO 287
<211> LENGTH: 21
<212> TYPE: RNA
<213> ORGANISM: Artificial Sequence
<220> FEATURE:
<223> OTHER INFORMATION: Sense strand for siKNe2-M3P1

<400> SEQUENCE: 287
gagaauaacg caacuuucua u 21

<210> SEQ ID NO 288
<211> LENGTH: 23
<212> TYPE: RNA
<213> ORGANISM: Artificial Sequence
<220> FEATURE:
<223> OTHER INFORMATION: Antisense strand for siKNe2-M3P1

<400> SEQUENCE: 288
auagaaaguu gcguuauucu cug 23

<210> SEQ ID NO 289
<211> LENGTH: 19
<212> TYPE: RNA
<213> ORGANISM: Artificial Sequence
<220> FEATURE:
<223> OTHER INFORMATION: Sense strand for siKNe1-M1SP1

<400> SEQUENCE: 289
gaauaacgca acuuucuau 19

<210> SEQ ID NO 290
<211> LENGTH: 21
<212> TYPE: RNA
<213> ORGANISM: Artificial Sequence
<220> FEATURE:
<223> OTHER INFORMATION: Antisense strand for siKNe1-M1SP1

<400> SEQUENCE: 290
auagaaaguu gcguuauucu c 21

<210> SEQ ID NO 291
<211> LENGTH: 19
<212> TYPE: RNA
<213> ORGANISM: Artificial Sequence
<220> FEATURE:
<223> OTHER INFORMATION: Sense strand for siKNe1-M2SP1

<400> SEQUENCE: 291
gaauaacgca acuuucuau 19

<210> SEQ ID NO 292
<211> LENGTH: 21
<212> TYPE: RNA
<213> ORGANISM: Artificial Sequence
<220> FEATURE:
<223> OTHER INFORMATION: Antisense strand for siKNe1-M2SP1

<400> SEQUENCE: 292
auagaaaguu gcguuauucu c 21

<210> SEQ ID NO 293
<211> LENGTH: 19
<212> TYPE: RNA
<213> ORGANISM: Artificial Sequence
<220> FEATURE:
<223> OTHER INFORMATION: Sense strand for siKNe1-M3SP1

<400> SEQUENCE: 293
gaauaacgca acuuucuau 19

<210> SEQ ID NO 294
<211> LENGTH: 21
<212> TYPE: RNA
<213> ORGANISM: Artificial Sequence
<220> FEATURE:
<223> OTHER INFORMATION: Antisense strand for siKNe1-M3SP1

<400> SEQUENCE: 294
auagaaaguu gcguuauucu c 21

<210> SEQ ID NO 295
<211> LENGTH: 21
<212> TYPE: RNA
<213> ORGANISM: Artificial Sequence
<220> FEATURE:
<223> OTHER INFORMATION: Sense strand for siKNe2-M1SP1

<400> SEQUENCE: 295
gagaauaacg caacuuucua u 21

<210> SEQ ID NO 296
<211> LENGTH: 23
<212> TYPE: RNA
<213> ORGANISM: Artificial Sequence
<220> FEATURE:
<223> OTHER INFORMATION: Antisense strand for siKNe2-M1SP1

<400> SEQUENCE: 296
auagaaaguu gcguuauucu cug 23

<210> SEQ ID NO 297
<211> LENGTH: 21
<212> TYPE: RNA
<213> ORGANISM: Artificial Sequence
<220> FEATURE:
<223> OTHER INFORMATION: Sense strand for siKNe2-M2SP1

<400> SEQUENCE: 297
gagaauaacg caacuuucua u 21

<210> SEQ ID NO 298
<211> LENGTH: 23
<212> TYPE: RNA
<213> ORGANISM: Artificial Sequence
<220> FEATURE:
<223> OTHER INFORMATION: Antisense strand for siKNe2-M2SP1

<400> SEQUENCE: 298
auagaaaguu gcguuauucu cug 23

<210> SEQ ID NO 299
<211> LENGTH: 21
<212> TYPE: RNA
<213> ORGANISM: Artificial Sequence
<220> FEATURE:
<223> OTHER INFORMATION: Sense strand for siKNe2-M3SP1

<400> SEQUENCE: 299
gagaauaacg caacuuucua u 21

<210> SEQ ID NO 300
<211> LENGTH: 23

-continued

<212> TYPE: RNA
<213> ORGANISM: Artificial Sequence
<220> FEATURE:
<223> OTHER INFORMATION: Antisense strand for siKNe2-M3SP1

<400> SEQUENCE: 300
auagaaaguu gcguuauucu cug 23

<210> SEQ ID NO 301
<211> LENGTH: 19
<212> TYPE: RNA
<213> ORGANISM: Artificial Sequence
<220> FEATURE:
<223> OTHER INFORMATION: siRNA

<400> SEQUENCE: 301
aacuuucuau uucaagauu 19

<210> SEQ ID NO 302
<211> LENGTH: 19
<212> TYPE: RNA
<213> ORGANISM: Artificial Sequence
<220> FEATURE:
<223> OTHER INFORMATION: siRNA

<400> SEQUENCE: 302
aaucuugaaa uagaaaguu 19

<210> SEQ ID NO 303
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 303
aacuuucuau uucaagaun 19

<210> SEQ ID NO 304
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 304
naucuugaaa uagaaaguu 19

<210> SEQ ID NO 305
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n=a, or g, or c, or u

<400> SEQUENCE: 305
aacuuucuau uucaagaun 19

<210> SEQ ID NO 306
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 306
naucuugaaa uagaaaguug c 21

<210> SEQ ID NO 307
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n=a, or g, or c, or u

<400> SEQUENCE: 307
gcaacuuucu auuucaagau n 21

<210> SEQ ID NO 308
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n=a, or g, or c, or u

<400> SEQUENCE: 308
naucuugaaa uagaaaguug cgu 23

<210> SEQ ID NO 309
<211> LENGTH: 19
<212> TYPE: RNA
<213> ORGANISM: Artificial Sequence
<220> FEATURE:
<223> OTHER INFORMATION: Sense strand for siKNf1

<400> SEQUENCE: 309
aacuuucuau uucaagauu 19

<210> SEQ ID NO 310
<211> LENGTH: 21
<212> TYPE: RNA
<213> ORGANISM: Artificial Sequence
<220> FEATURE:
<223> OTHER INFORMATION: Antisense strand for siKNf1

<400> SEQUENCE: 310
aaucuugaaa uagaaaguug c 21

<210> SEQ ID NO 311
<211> LENGTH: 21
<212> TYPE: RNA
<213> ORGANISM: Artificial Sequence
<220> FEATURE:
<223> OTHER INFORMATION: Sense strand for siKNf2

<400> SEQUENCE: 311
gcaacuuucu auuucaagau u 21

<210> SEQ ID NO 312
<211> LENGTH: 23
<212> TYPE: RNA
<213> ORGANISM: Artificial Sequence
<220> FEATURE:
<223> OTHER INFORMATION: Antisense strand for siKNf2

<400> SEQUENCE: 312
aaucuugaaa uagaaaguug cgu 23

<210> SEQ ID NO 313
<211> LENGTH: 19
<212> TYPE: RNA
<213> ORGANISM: Artificial Sequence
<220> FEATURE:
<223> OTHER INFORMATION: Sense strand for siKNf1-M1

<400> SEQUENCE: 313
aacuuucuau uucaagauu 19

<210> SEQ ID NO 314
<211> LENGTH: 21
<212> TYPE: RNA
<213> ORGANISM: Artificial Sequence
<220> FEATURE:
<223> OTHER INFORMATION: Antisense strand for siKNf1-M1

<400> SEQUENCE: 314
aaucuugaaa uagaaaguug c 21

<210> SEQ ID NO 315
<211> LENGTH: 19
<212> TYPE: RNA
<213> ORGANISM: Artificial Sequence
<220> FEATURE:
<223> OTHER INFORMATION: Sense strand for siKNf1-M2

<400> SEQUENCE: 315
aacuuucuau uucaagauu 19

<210> SEQ ID NO 316
<211> LENGTH: 21
<212> TYPE: RNA
<213> ORGANISM: Artificial Sequence
<220> FEATURE:
<223> OTHER INFORMATION: Antisense strand for siKNf1-M2

<400> SEQUENCE: 316
aaucuugaaa uagaaaguug c 21

<210> SEQ ID NO 317
<211> LENGTH: 19
<212> TYPE: RNA
<213> ORGANISM: Artificial Sequence
<220> FEATURE:
<223> OTHER INFORMATION: Sense strand for siKNf1-M3

<400> SEQUENCE: 317
aacuuucuau uucaagauu 19

<210> SEQ ID NO 318
<211> LENGTH: 21
<212> TYPE: RNA
<213> ORGANISM: Artificial Sequence
<220> FEATURE:
<223> OTHER INFORMATION: Antisense strand for siKNf1-M3

<400> SEQUENCE: 318
aaucuugaaa uagaaaguug c 21

<210> SEQ ID NO 319
<211> LENGTH: 21
<212> TYPE: RNA
<213> ORGANISM: Artificial Sequence
<220> FEATURE:
<223> OTHER INFORMATION: Sense strand for siKNf2-M1

<400> SEQUENCE: 319
gcaacuuucu auuucaagau u 21

<210> SEQ ID NO 320
<211> LENGTH: 23
<212> TYPE: RNA
<213> ORGANISM: Artificial Sequence
<220> FEATURE:
<223> OTHER INFORMATION: Antisense strand for siKNf2-M1

<400> SEQUENCE: 320
aaucuugaaa uagaaaguug cgu 23

<210> SEQ ID NO 321
<211> LENGTH: 21
<212> TYPE: RNA
<213> ORGANISM: Artificial Sequence
<220> FEATURE:
<223> OTHER INFORMATION: Sense strand for siKNf2-M2

<400> SEQUENCE: 321
gcaacuuucu auuucaagau u 21

<210> SEQ ID NO 322
<211> LENGTH: 23
<212> TYPE: RNA
<213> ORGANISM: Artificial Sequence
<220> FEATURE:
<223> OTHER INFORMATION: Antisense strand for siKNf2-M2

<400> SEQUENCE: 322
aaucuugaaa uagaaaguug cgu 23

<210> SEQ ID NO 323
<211> LENGTH: 21
<212> TYPE: RNA
<213> ORGANISM: Artificial Sequence
<220> FEATURE:
<223> OTHER INFORMATION: Sense strand for siKNf2-M3

<400> SEQUENCE: 323
gcaacuuucu auuucaagau u 21

<210> SEQ ID NO 324
<211> LENGTH: 23
<212> TYPE: RNA
<213> ORGANISM: Artificial Sequence
<220> FEATURE:
<223> OTHER INFORMATION: Antisense strand for siKNf2-M3

<400> SEQUENCE: 324
aaucuugaaa uagaaaguug cgu 23

<210> SEQ ID NO 325
<211> LENGTH: 19
<212> TYPE: RNA
<213> ORGANISM: Artificial Sequence
<220> FEATURE:
<223> OTHER INFORMATION: Sense strand for siKNf1-M1S

<400> SEQUENCE: 325
aacuuucuau uucaagauu 19

<210> SEQ ID NO 326
<211> LENGTH: 21
<212> TYPE: RNA
<213> ORGANISM: Artificial Sequence
<220> FEATURE:
<223> OTHER INFORMATION: Antisense strand for siKNf1-M1S

<400> SEQUENCE: 326
aaucuugaaa uagaaaguug c 21

<210> SEQ ID NO 327
<211> LENGTH: 19
<212> TYPE: RNA
<213> ORGANISM: Artificial Sequence
<220> FEATURE:
<223> OTHER INFORMATION: Sense strand for siKNf1-M2S

<400> SEQUENCE: 327
aacuuucuau uucaagauu 19

<210> SEQ ID NO 328
<211> LENGTH: 21
<212> TYPE: RNA
<213> ORGANISM: Artificial Sequence
<220> FEATURE:
<223> OTHER INFORMATION: Antisense strand for siKNf1-M2S

<400> SEQUENCE: 328
aaucuugaaa uagaaaguug c 21

<210> SEQ ID NO 329
<211> LENGTH: 19
<212> TYPE: RNA
<213> ORGANISM: Artificial Sequence
<220> FEATURE:
<223> OTHER INFORMATION: Sense strand for siKNf1-M3S

<400> SEQUENCE: 329
aacuuucuau uucaagauu 19

<210> SEQ ID NO 330
<211> LENGTH: 21
<212> TYPE: RNA
<213> ORGANISM: Artificial Sequence
<220> FEATURE:
<223> OTHER INFORMATION: Antisense strand for siKNf1-M3S

<400> SEQUENCE: 330
aaucuugaaa uagaaaguug c 21

<210> SEQ ID NO 331

<211> LENGTH: 21
<212> TYPE: RNA
<213> ORGANISM: Artificial Sequence
<220> FEATURE:
<223> OTHER INFORMATION: Sense strand for siKNf2-M1S

<400> SEQUENCE: 331
gcaacuuucu auuucaagau u 21

<210> SEQ ID NO 332
<211> LENGTH: 23
<212> TYPE: RNA
<213> ORGANISM: Artificial Sequence
<220> FEATURE:
<223> OTHER INFORMATION: Antisense strand for siKNf2-M1S

<400> SEQUENCE: 332
aaucuugaaa uagaaaguug cgu 23

<210> SEQ ID NO 333
<211> LENGTH: 21
<212> TYPE: RNA
<213> ORGANISM: Artificial Sequence
<220> FEATURE:
<223> OTHER INFORMATION: Sense strand for siKNf2-M2S

<400> SEQUENCE: 333
gcaacuuucu auuucaagau u 21

<210> SEQ ID NO 334
<211> LENGTH: 23
<212> TYPE: RNA
<213> ORGANISM: Artificial Sequence
<220> FEATURE:
<223> OTHER INFORMATION: Antisense strand for siKNf2-M2S

<400> SEQUENCE: 334
aaucuugaaa uagaaaguug cgu 23

<210> SEQ ID NO 335
<211> LENGTH: 21
<212> TYPE: RNA
<213> ORGANISM: Artificial Sequence
<220> FEATURE:
<223> OTHER INFORMATION: Sense strand for siKNf2-M3S

<400> SEQUENCE: 335
gcaacuuucu auuucaagau u 21

<210> SEQ ID NO 336
<211> LENGTH: 23
<212> TYPE: RNA
<213> ORGANISM: Artificial Sequence
<220> FEATURE:
<223> OTHER INFORMATION: Antisense strand for siKNf2-M3S

<400> SEQUENCE: 336
aaucuugaaa uagaaaguug cgu 23

<210> SEQ ID NO 337
<211> LENGTH: 19
<212> TYPE: RNA
<213> ORGANISM: Artificial Sequence
<220> FEATURE:
<223> OTHER INFORMATION: Sense strand for siKNf1-M1P1

<400> SEQUENCE: 337

```
aacuuucuau uucaagauu                                             19


<210> SEQ ID NO 338
<211> LENGTH: 21
<212> TYPE: RNA
<213> ORGANISM: Artificial Sequence
<220> FEATURE:
<223> OTHER INFORMATION: Antisense strand for siKNf1-M1P1

<400> SEQUENCE: 338

aaucuugaaa uagaaaguug c                                          21


<210> SEQ ID NO 339
<211> LENGTH: 19
<212> TYPE: RNA
<213> ORGANISM: Artificial Sequence
<220> FEATURE:
<223> OTHER INFORMATION: Sense strand for siKNf1-M2P1

<400> SEQUENCE: 339

aacuuucuau uucaagauu                                             19


<210> SEQ ID NO 340
<211> LENGTH: 21
<212> TYPE: RNA
<213> ORGANISM: Artificial Sequence
<220> FEATURE:
<223> OTHER INFORMATION: Antisense strand for siKNf1-M2P1

<400> SEQUENCE: 340

aaucuugaaa uagaaaguug c                                          21


<210> SEQ ID NO 341
<211> LENGTH: 19
<212> TYPE: RNA
<213> ORGANISM: Artificial Sequence
<220> FEATURE:
<223> OTHER INFORMATION: Sense strand for siKNf1-M3P1

<400> SEQUENCE: 341

aacuuucuau uucaagauu                                             19


<210> SEQ ID NO 342
<211> LENGTH: 21
<212> TYPE: RNA
<213> ORGANISM: Artificial Sequence
<220> FEATURE:
<223> OTHER INFORMATION: Antisense strand for siKNf1-M3P1

<400> SEQUENCE: 342

aaucuugaaa uagaaaguug c                                          21


<210> SEQ ID NO 343
<211> LENGTH: 21
<212> TYPE: RNA
<213> ORGANISM: Artificial Sequence
<220> FEATURE:
<223> OTHER INFORMATION: Sense strand for siKNf2-M1P1

<400> SEQUENCE: 343

gcaacuuucu auuucaagau u                                          21


<210> SEQ ID NO 344
<211> LENGTH: 23
<212> TYPE: RNA
```

```
<213> ORGANISM: Artificial Sequence
<220> FEATURE:
<223> OTHER INFORMATION: Antisense strand for siKNf2-M1P1

<400> SEQUENCE: 344

aaucuugaaa uagaaaguug cgu                                             23


<210> SEQ ID NO 345
<211> LENGTH: 21
<212> TYPE: RNA
<213> ORGANISM: Artificial Sequence
<220> FEATURE:
<223> OTHER INFORMATION: Sense strand for siKNf2-M2P1

<400> SEQUENCE: 345

gcaacuuucu auuucaagau u                                               21


<210> SEQ ID NO 346
<211> LENGTH: 23
<212> TYPE: RNA
<213> ORGANISM: Artificial Sequence
<220> FEATURE:
<223> OTHER INFORMATION: Antisense strand for siKNf2-M2P1

<400> SEQUENCE: 346

aaucuugaaa uagaaaguug cgu                                             23


<210> SEQ ID NO 347
<211> LENGTH: 21
<212> TYPE: RNA
<213> ORGANISM: Artificial Sequence
<220> FEATURE:
<223> OTHER INFORMATION: Sense strand for siKNf2-M3P1

<400> SEQUENCE: 347

gcaacuuucu auuucaagau u                                               21


<210> SEQ ID NO 348
<211> LENGTH: 23
<212> TYPE: RNA
<213> ORGANISM: Artificial Sequence
<220> FEATURE:
<223> OTHER INFORMATION: Antisense strand for siKNf2-M3P1

<400> SEQUENCE: 348

aaucuugaaa uagaaaguug cgu                                             23


<210> SEQ ID NO 349
<211> LENGTH: 19
<212> TYPE: RNA
<213> ORGANISM: Artificial Sequence
<220> FEATURE:
<223> OTHER INFORMATION: Sense strand for siKNf1-M1SP1

<400> SEQUENCE: 349

aacuuucuau uucaagauu                                                  19


<210> SEQ ID NO 350
<211> LENGTH: 21
<212> TYPE: RNA
<213> ORGANISM: Artificial Sequence
<220> FEATURE:
<223> OTHER INFORMATION: Antisense strand for siKNf1-M1SP1

<400> SEQUENCE: 350

aaucuugaaa uagaaaguug c                                               21
```

<210> SEQ ID NO 351
<211> LENGTH: 19
<212> TYPE: RNA
<213> ORGANISM: Artificial Sequence
<220> FEATURE:
<223> OTHER INFORMATION: Sense strand for siKNf1-M2SP1

<400> SEQUENCE: 351
aacuuucuau uucaagauu 19

<210> SEQ ID NO 352
<211> LENGTH: 21
<212> TYPE: RNA
<213> ORGANISM: Artificial Sequence
<220> FEATURE:
<223> OTHER INFORMATION: Antisense strand for siKNf1-M2SP1

<400> SEQUENCE: 352
aaucuugaaa uagaaaguug c 21

<210> SEQ ID NO 353
<211> LENGTH: 19
<212> TYPE: RNA
<213> ORGANISM: Artificial Sequence
<220> FEATURE:
<223> OTHER INFORMATION: Sense strand for siKNf1-M3SP1

<400> SEQUENCE: 353
aacuuucuau uucaagauu 19

<210> SEQ ID NO 354
<211> LENGTH: 21
<212> TYPE: RNA
<213> ORGANISM: Artificial Sequence
<220> FEATURE:
<223> OTHER INFORMATION: Antisense strand for siKNf1-M3SP1

<400> SEQUENCE: 354
aaucuugaaa uagaaaguug c 21

<210> SEQ ID NO 355
<211> LENGTH: 21
<212> TYPE: RNA
<213> ORGANISM: Artificial Sequence
<220> FEATURE:
<223> OTHER INFORMATION: Sense strand for siKNf2-M1SP1

<400> SEQUENCE: 355
gcaacuuucu auuucaagau u 21

<210> SEQ ID NO 356
<211> LENGTH: 23
<212> TYPE: RNA
<213> ORGANISM: Artificial Sequence
<220> FEATURE:
<223> OTHER INFORMATION: Antisense strand for siKNf2-M1SP1

<400> SEQUENCE: 356
aaucuugaaa uagaaaguug cgu 23

<210> SEQ ID NO 357
<211> LENGTH: 21
<212> TYPE: RNA
<213> ORGANISM: Artificial Sequence
<220> FEATURE:

<223> OTHER INFORMATION: Sense strand for siKNf2-M2SP1

<400> SEQUENCE: 357
gcaacuuucu auuucaagau u 21

<210> SEQ ID NO 358
<211> LENGTH: 23
<212> TYPE: RNA
<213> ORGANISM: Artificial Sequence
<220> FEATURE:
<223> OTHER INFORMATION: Antisense strand for siKNf2-M2SP1

<400> SEQUENCE: 358
aaucuugaaa uagaaaguug cgu 23

<210> SEQ ID NO 359
<211> LENGTH: 21
<212> TYPE: RNA
<213> ORGANISM: Artificial Sequence
<220> FEATURE:
<223> OTHER INFORMATION: Sense strand for siKNf2-M3SP1

<400> SEQUENCE: 359
gcaacuuucu auuucaagau u 21

<210> SEQ ID NO 360
<211> LENGTH: 23
<212> TYPE: RNA
<213> ORGANISM: Artificial Sequence
<220> FEATURE:
<223> OTHER INFORMATION: Antisense strand for siKNf2-M3SP1

<400> SEQUENCE: 360
aaucuugaaa uagaaaguug cgu 23

<210> SEQ ID NO 361
<211> LENGTH: 19
<212> TYPE: RNA
<213> ORGANISM: Artificial Sequence
<220> FEATURE:
<223> OTHER INFORMATION: Sense strand for L10-siKNa1M1SP

<400> SEQUENCE: 361
aaaguaacaa ccaguuugu 19

<210> SEQ ID NO 362
<211> LENGTH: 21
<212> TYPE: RNA
<213> ORGANISM: Artificial Sequence
<220> FEATURE:
<223> OTHER INFORMATION: Antisense strand for L10-siKNa1M1SP

<400> SEQUENCE: 362
acaaacuggu uguuacuuug g 21

<210> SEQ ID NO 363
<211> LENGTH: 19
<212> TYPE: RNA
<213> ORGANISM: Artificial Sequence
<220> FEATURE:
<223> OTHER INFORMATION: Sense strand for L10-siKNb1M1SP

<400> SEQUENCE: 363
auugaacuuu cgaauuacc 19

<210> SEQ ID NO 364
<211> LENGTH: 21
<212> TYPE: RNA
<213> ORGANISM: Artificial Sequence
<220> FEATURE:
<223> OTHER INFORMATION: Antisense strand for L10-siKNb1M1SP

<400> SEQUENCE: 364
gguaauucga aaguucaauc c 21

<210> SEQ ID NO 365
<211> LENGTH: 19
<212> TYPE: RNA
<213> ORGANISM: Artificial Sequence
<220> FEATURE:
<223> OTHER INFORMATION: Sense strand for L10-siKNc1M1SP

<400> SEQUENCE: 365
ucgaauuacc uacucaauu 19

<210> SEQ ID NO 366
<211> LENGTH: 21
<212> TYPE: RNA
<213> ORGANISM: Artificial Sequence
<220> FEATURE:
<223> OTHER INFORMATION: Antisense strand for L10-siKNc1M1SP

<400> SEQUENCE: 366
aauugaguag guaauucgaa a 21

<210> SEQ ID NO 367
<211> LENGTH: 19
<212> TYPE: RNA
<213> ORGANISM: Artificial Sequence
<220> FEATURE:
<223> OTHER INFORMATION: Sense strand for L10-siKNd1M1SP

<400> SEQUENCE: 367
gauaaugcau acaucgaua 19

<210> SEQ ID NO 368
<211> LENGTH: 21
<212> TYPE: RNA
<213> ORGANISM: Artificial Sequence
<220> FEATURE:
<223> OTHER INFORMATION: Antisense strand for L10-siKNd1M1SP

<400> SEQUENCE: 368
uaucgaugua ugcauuaucu g 21

<210> SEQ ID NO 369
<211> LENGTH: 19
<212> TYPE: RNA
<213> ORGANISM: Artificial Sequence
<220> FEATURE:
<223> OTHER INFORMATION: Sense strand for L10-siKNe1M1SP

<400> SEQUENCE: 369
gaauaacgca acuuucuau 19

<210> SEQ ID NO 370
<211> LENGTH: 21
<212> TYPE: RNA
<213> ORGANISM: Artificial Sequence
<220> FEATURE:
<223> OTHER INFORMATION: Antisense strand for L10-siKNe1M1SP

<400> SEQUENCE: 370
auagaaaguu gcguuauucu c 21

<210> SEQ ID NO 371
<211> LENGTH: 19
<212> TYPE: RNA
<213> ORGANISM: Artificial Sequence
<220> FEATURE:
<223> OTHER INFORMATION: Sense strand for L10-siKNf1M1SP

<400> SEQUENCE: 371
aacuuucuau uucaagauu 19

<210> SEQ ID NO 372
<211> LENGTH: 21
<212> TYPE: RNA
<213> ORGANISM: Artificial Sequence
<220> FEATURE:
<223> OTHER INFORMATION: Antisense strand for L10-siKNf1M1SP

<400> SEQUENCE: 372
aaucuugaaa uagaaaguug c 21

<210> SEQ ID NO 373
<211> LENGTH: 19
<212> TYPE: RNA
<213> ORGANISM: Artificial Sequence
<220> FEATURE:
<223> OTHER INFORMATION: Sense strand for siKNa1M1S

<400> SEQUENCE: 373
aaaguaacaa ccaguuugu 19

<210> SEQ ID NO 374
<211> LENGTH: 21
<212> TYPE: RNA
<213> ORGANISM: Artificial Sequence
<220> FEATURE:
<223> OTHER INFORMATION: Antisense strand for siKNa1M1S

<400> SEQUENCE: 374
acaaacuggu uguuacuuug g 21

<210> SEQ ID NO 375
<211> LENGTH: 19
<212> TYPE: RNA
<213> ORGANISM: Artificial Sequence
<220> FEATURE:
<223> OTHER INFORMATION: Sense strand for siKNb1M1S

<400> SEQUENCE: 375
auugaacuuu cgaauuacc 19

<210> SEQ ID NO 376
<211> LENGTH: 21
<212> TYPE: RNA
<213> ORGANISM: Artificial Sequence
<220> FEATURE:
<223> OTHER INFORMATION: Antisense strand for siKNb1M1S

<400> SEQUENCE: 376
gguaauucga aaguucaauc c 21

<210> SEQ ID NO 377
<211> LENGTH: 19

<212> TYPE: RNA
<213> ORGANISM: Artificial Sequence
<220> FEATURE:
<223> OTHER INFORMATION: Sense strand for siKNc1M1S

<400> SEQUENCE: 377
ucgaauuacc uacucaauu 19

<210> SEQ ID NO 378
<211> LENGTH: 21
<212> TYPE: RNA
<213> ORGANISM: Artificial Sequence
<220> FEATURE:
<223> OTHER INFORMATION: Antisense strand for siKNc1M1S

<400> SEQUENCE: 378
aauugaguag guaauucgaa a 21

<210> SEQ ID NO 379
<211> LENGTH: 19
<212> TYPE: RNA
<213> ORGANISM: Artificial Sequence
<220> FEATURE:
<223> OTHER INFORMATION: Sense strand for siKNd1M1S

<400> SEQUENCE: 379
gauaaugcau acaucgaua 19

<210> SEQ ID NO 380
<211> LENGTH: 21
<212> TYPE: RNA
<213> ORGANISM: Artificial Sequence
<220> FEATURE:
<223> OTHER INFORMATION: Antisense strand for siKNd1M1S

<400> SEQUENCE: 380
uaucgaugua ugcauuaucu g 21

<210> SEQ ID NO 381
<211> LENGTH: 19
<212> TYPE: RNA
<213> ORGANISM: Artificial Sequence
<220> FEATURE:
<223> OTHER INFORMATION: Sense strand for siKNe1M1S

<400> SEQUENCE: 381
gaauaacgca acuuucuau 19

<210> SEQ ID NO 382
<211> LENGTH: 21
<212> TYPE: RNA
<213> ORGANISM: Artificial Sequence
<220> FEATURE:
<223> OTHER INFORMATION: Antisense strand for siKNe1M1S

<400> SEQUENCE: 382
auagaaaguu gcguuauucu c 21

<210> SEQ ID NO 383
<211> LENGTH: 19
<212> TYPE: RNA
<213> ORGANISM: Artificial Sequence
<220> FEATURE:
<223> OTHER INFORMATION: Sense strand for siKNf1M1S

<400> SEQUENCE: 383
aacuuucuau uucaagauu 19

<210> SEQ ID NO 384
<211> LENGTH: 21
<212> TYPE: RNA
<213> ORGANISM: Artificial Sequence
<220> FEATURE:
<223> OTHER INFORMATION: Antisense strand for siKNf1M1S

<400> SEQUENCE: 384
aaucuugaaa uagaaaguug c 21

<210> SEQ ID NO 385
<211> LENGTH: 19
<212> TYPE: RNA
<213> ORGANISM: Artificial Sequence
<220> FEATURE:
<223> OTHER INFORMATION: Sense strand for siKNa0

<400> SEQUENCE: 385
aaaguaacaa ccaguuugu 19

<210> SEQ ID NO 386
<211> LENGTH: 19
<212> TYPE: RNA
<213> ORGANISM: Artificial Sequence
<220> FEATURE:
<223> OTHER INFORMATION: Antisense strand for siKNa0

<400> SEQUENCE: 386
acaaacuggu uguuacuuu 19

<210> SEQ ID NO 387
<211> LENGTH: 19
<212> TYPE: RNA
<213> ORGANISM: Artificial Sequence
<220> FEATURE:
<223> OTHER INFORMATION: Sense strand for siKNc0

<400> SEQUENCE: 387
ucgaauuacc uacucaauu 19

<210> SEQ ID NO 388
<211> LENGTH: 19
<212> TYPE: RNA
<213> ORGANISM: Artificial Sequence
<220> FEATURE:
<223> OTHER INFORMATION: Antisense strand for siKNc0

<400> SEQUENCE: 388
aauugaguag guaauucga 19

<210> SEQ ID NO 389
<211> LENGTH: 19
<212> TYPE: RNA
<213> ORGANISM: Artificial Sequence
<220> FEATURE:
<223> OTHER INFORMATION: Sense strand for siKNa0-com

<400> SEQUENCE: 389
ccaaaguaac aaccaguuu 19

<210> SEQ ID NO 390
<211> LENGTH: 19
<212> TYPE: RNA
<213> ORGANISM: Artificial Sequence
<220> FEATURE:
<223> OTHER INFORMATION: Antisense strand for siKNa0-com

<400> SEQUENCE: 390
aaacugguug uuacuuugg 19

<210> SEQ ID NO 391
<211> LENGTH: 19
<212> TYPE: RNA
<213> ORGANISM: Artificial Sequence
<220> FEATURE:
<223> OTHER INFORMATION: Sense strand for NC

<400> SEQUENCE: 391
uucuccgaac gugucacgu 19

<210> SEQ ID NO 392
<211> LENGTH: 19
<212> TYPE: RNA
<213> ORGANISM: Artificial Sequence
<220> FEATURE:
<223> OTHER INFORMATION: Antisense strand for NC

<400> SEQUENCE: 392
acgugacacg uucggagaa 19

<210> SEQ ID NO 393
<211> LENGTH: 19
<212> TYPE: DNA
<213> ORGANISM: Artificial Sequence
<220> FEATURE:
<223> OTHER INFORMATION: Target sequence of the siKNa0

<400> SEQUENCE: 393
aaagtaacaa ccagtttgt 19

<210> SEQ ID NO 394
<211> LENGTH: 19
<212> TYPE: DNA
<213> ORGANISM: Artificial Sequence
<220> FEATURE:
<223> OTHER INFORMATION: Target sequence of the siKNc0

<400> SEQUENCE: 394
tcgaattacc tactcaatt 19

<210> SEQ ID NO 395
<211> LENGTH: 19
<212> TYPE: DNA
<213> ORGANISM: Artificial Sequence
<220> FEATURE:
<223> OTHER INFORMATION: Target sequence of the siKNa0-com

<400> SEQUENCE: 395
ccaaagtaac aaccagttt 19

<210> SEQ ID NO 396
<211> LENGTH: 590
<212> TYPE: DNA
<213> ORGANISM: Artificial Sequence
<220> FEATURE:
<223> OTHER INFORMATION: Target sequence of the siKNa1M1S

<400> SEQUENCE: 396
catggccacg gaaaacataa aaataaaggc aaaaagaatg gaaagcacaa tggttggaaa 60

-continued

```
acagagcatt tggcaagctc ttctgaagac agtactacac cttctgcaca gacacaagag    120

aagacagaag ggccaacacc catcccttcc ctagccaagc caggtgtaac agttaccttt    180

tctgactttc aggactctga tctcattgca actatgatgc ctcctatatc accagctccc    240

atacagagtg atgacgattg gatccctgat atccagatag acccaaatgg cctttcattt    300

aacccaatat cagattttcc agacacgacc tccccaaaat gtcctggacg cccctggaag    360

tcagttagtg aaattaatcc aaccacacaa atgaaagaat cttattattt cgatctcact    420

gatggccttt cttaatttaa gtggctatgg gtatttcttt catactttat taaagtatca    480

atatccctct ctccattgtc cagatgaaaa tatcctgata taatgcacca aaaaccatgc    540

agcttcggaa cagtctaaag agaagtggtg agactcccag tggagacacc              590
```

```
<210> SEQ ID NO 397
<211> LENGTH: 590
<212> TYPE: DNA
<213> ORGANISM: Artificial Sequence
<220> FEATURE:
<223> OTHER INFORMATION: Target sequence of siKNb1M1S, siKNb1M1S,
      siKNc1M1S, siKNd1M1S, siKNe1M1S, and siKNf1M1S

<400> SEQUENCE: 397

catggccacg gaaaacataa aaataaaggc aaaaagaatg gaaagcacaa tggttggaaa     60

acagagcatt tggcaagctc ttctgaagac agtactacac cttctgcaca gacacaagag    120

aagacagaag ggccaacacc catcccttcc ctagccaagc caggtgtaac agttaccttt    180

tctgactttc aggactctga tctcattgca actatgatgc ctcctatatc accagctccc    240

atacagagtg atgacgattg gatccctgat atccagatag acccaaatgg cctttcattt    300

aacccaatat cagattttcc agacacgacc tccccaaaat gtcctggacg cccctggaag    360

tcagttagtg aaattaatcc aaccacacaa atgaaagaat cttattattt cgatctcact    420

gatggccttt cttaatttaa gtggctatgg gtatttcttt catactttat taaagtatca    480

atatccctct ctccattgtc cagatgaaaa tatcctgata taatgcacca aaaaccatgc    540

agcttcggaa cagtctaaag agaagtggtg agactcccag tggagacacc              590


<210> SEQ ID NO 398
<211> LENGTH: 24
<212> TYPE: DNA
<213> ORGANISM: Artificial Sequence
<220> FEATURE:
<223> OTHER INFORMATION: Upstream primer for human KNG

<400> SEQUENCE: 398

ctacccagac ctgccagatt actc                                            24


<210> SEQ ID NO 399
<211> LENGTH: 23
<212> TYPE: DNA
<213> ORGANISM: Artificial Sequence
<220> FEATURE:
<223> OTHER INFORMATION: Downstream primer for human KNG

<400> SEQUENCE: 399

gatataggat gcacacagcc gag                                             23


<210> SEQ ID NO 400
<211> LENGTH: 23
<212> TYPE: DNA
<213> ORGANISM: Artificial Sequence
<220> FEATURE:
```

-continued

<223> OTHER INFORMATION: Upstream primer for β-actin

<400> SEQUENCE: 400
gtgctatgtt gctctagact tcg 23

<210> SEQ ID NO 401
<211> LENGTH: 20
<212> TYPE: DNA
<213> ORGANISM: Artificial Sequence
<220> FEATURE:
<223> OTHER INFORMATION: Downstream primer for β-actin

<400> SEQUENCE: 401
atgccacagg attccatacc 20

NUCLEIC ACID, PHARMACEUTICAL COMPOSITION, CONJUGATE, PREPARATION METHOD, AND USE

SEQUENCE LISTING

Incorporated by reference herein in its entirety is a computer-readable sequence listing submitted via EF S-Web and identified as follows: One (85,186 byte ASCII (Text)) file named "Amended Sequence Listing-20220913.txt" created on Sep. 13, 2022.

TECHNICAL FIELD

The present disclosure relates to a nucleic acid capable of inhibiting expression of a kininogen gene, and a pharmaceutical composition and an siRNA conjugate containing the nucleic acid. The present disclosure also relates to a preparation method and use of the nucleic acid, the pharmaceutical composition and the siRNA conjugate.

BACKGROUND

Septicemia (or Sepsis) refers to a systemic inflammatory response syndrome caused by infection, which is clinically confirmed to have bacteria or highly suspicious focus of infection. Although septicemia is caused by infection, once it happens, the occurrence and development of the septicemia follow pathological process and law thereof, so the septicemia is essentially a body's response to infectious factors.

A kininogen (KNG) gene may be expressed to produce activated high molecular weight kininogen (HMWKa), which may be combined with lipopolysaccharide (LPS) on surfaces of Gram-negative bacteria cells to prolong a half life thereof. By inhibiting the KNG expression, a life span of a pathogen can be effectively inhibited, so as to alleviate the progress of the septicemia and reverse the septicemia. Therefore, the KNG is closely related to the septicemia and other inflammations caused by pathogens, so the KNG is one of the key targets for treating the septicemia. Based on the mechanism of RNA interference (RNAi), small interfering RNA (siRNA) can inhibit or block the expression of interested target genes in a sequence-specific way, thus achieving the purpose of treating diseases.

One of the keys to developing siRNA drugs for inhibiting the expression of the KNG gene and treating the septicemia lies in finding a suitable siRNA and its modification and an effective delivery system.

SUMMARY

The inventors of the present disclosure have surprisingly found that the following siRNA and modification sequence thereof provided by the present disclosure, and the pharmaceutical composition or the siRNA conjugate containing the siRNA can specifically inhibit the expression of the KNG gene, and the siRNA conjugate can specifically target the liver, thereby inhibiting the expression of the KNG gene in the liver and realizing the treatment or prevention of the septicemia.

In some embodiments, the present disclosure provides a first siRNA capable of inhibiting expression of a KNG gene. The siRNA comprises a sense strand and an antisense strand, each nucleotide in the siRNA is independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; and the nucleotide sequence I and the nucleotide sequence II are selected from a group of sequences shown in the following i)-vi):

i) the nucleotide sequence I has the same length as and no more than three nucleotide differences from the nucleotide sequence shown in SEQ ID NO:1; and the nucleotide sequence II has the same length as and no more than three nucleotide differences from the nucleotide sequence shown in SEQ ID NO:2:

(SEQ ID NO: 1)
5'-AAAGUAACAACCAGUUUG$Z_1$-3';

(SEQ ID NO: 2)
5'-$Z_2$CAAACUGGUUGUUACUUU-3', wherein, $Z_1$ is U, $Z_2$ is A, the nucleotide sequence I comprises a nucleotide $Z_3$ at a corresponding site to $Z_1$, the nucleotide sequence II comprises a nucleotide $Z_4$ at a corresponding site to $Z_2$, and $Z_4$ is the first nucleotide from the 5' terminal of the antisense strand;

ii) the nucleotide sequence I has the same length as and no more than three nucleotide differences from the nucleotide sequence shown in SEQ ID NO: 61; and the nucleotide sequence II has the same length as and no more than three nucleotide differences from the nucleotide sequence shown in SEQ ID NO: 62:

(SEQ ID NO: 61)
5'-AUUGAACUUUCGAAUUAC$Z_5$-3';

(SEQ ID NO: 62)
5'-$Z_6$GUAAUUCGAAAGUUCAAU-3', wherein, $Z_5$ is C, $Z_6$ is G, the nucleotide sequence I comprises a nucleotide $Z_7$ at a corresponding site to $Z_5$, the nucleotide sequence II comprises a nucleotide $Z_5$ at a corresponding site to $Z_6$, and $Z_8$ is the first nucleotide from the 5' terminal of the antisense strand;

iii) the nucleotide sequence I has the same length as and no more than three nucleotide differences from the nucleotide sequence shown in SEQ ID NO: 121; and the nucleotide sequence II has the same length as and no more than three nucleotide differences from the nucleotide sequence shown in SEQ ID NO: 122:

(SEQ ID NO: 121)
5'-UCGAAUUACCUACUCAAU$Z_9$-3';

(SEQ ID NO: 122)
5'-$Z_{10}$AUUGAGUAGGUAAUUCGA-3', wherein, $Z_9$ is U, $Z_{10}$ is A, the nucleotide sequence I comprises a nucleotide Zn at a corresponding site to $Z_9$, the nucleotide sequence II comprises a nucleotide $Z_{12}$ at a corresponding site to $Z_{10}$, and $Z_{12}$ is the first nucleotide from the 5' terminal of the antisense strand;

iv) the nucleotide sequence I has the same length as and no more than three nucleotide differences from the nucleotide sequence shown in SEQ ID NO: 181; and the nucleotide sequence II has the same length as and no more than three nucleotide differences from the nucleotide sequence shown in SEQ ID NO: 182:

(SEQ ID NO: 181)
5'-GAUAAUGCAUACAUCGAU$Z_{13}$-3';

(SEQ ID NO: 182)
5'-$Z_{14}$AUCGAUGUAUGCAUUAUC-3', wherein, $Z_{13}$ is A, $Z_{14}$ is U, the nucleotide sequence I comprises a nucleotide $Z_{15}$ at a corresponding site to $Z_{13}$, the nucleotide sequence II comprises a nucleotide $Z_{16}$ at a corresponding site to $Z_{14}$, and $Z_{16}$ is the first nucleotide from the 5' terminal of the antisense strand;

v) the nucleotide sequence I has the same length as and no more than three nucleotide differences from the nucleotide sequence shown in SEQ ID NO: 241; and the nucleotide sequence II has the same length as and no more than three nucleotide differences from the nucleotide sequence shown in SEQ ID NO: 242:

(SEQ ID NO: 241)
5'-GAAUAACGCAACUUUCUA$Z_{17}$-3';

(SEQ ID NO: 242)
5'-$Z_{18}$UAGAAAGUUGCGUUAUUC-3', wherein, $Z_{17}$ is U, $Z_{18}$ is A, the nucleotide sequence I comprises a nucleotide $Z_{19}$ at a corresponding site to $Z_{17}$, the nucleotide sequence II comprises a nucleotide $Z_{20}$ at a corresponding site to $Z_{18}$, and $Z_{20}$ is the first nucleotide from the 5' terminal of the antisense strand; and vi) the nucleotide sequence I has the same length as and no more than three nucleotide differences from the nucleotide sequence shown in SEQ ID NO: 301; and the nucleotide sequence II has the same length as and no more than three nucleotide differences from the nucleotide sequence shown in SEQ ID NO: 302:

(SEQ ID NO: 301)
5'-AACUUUCUAUUUCAAGAU$Z_{21}$-3';

(SEQ ID NO: 302)
5'-$Z_{22}$AUCUUGAAAUAGAAAGUU-3', wherein, $Z_{21}$ is U, $Z_{22}$ is A, the nucleotide sequence I comprises a nucleotide $Z_{23}$ at a corresponding site to $Z_{21}$, the nucleotide sequence II comprises a nucleotide $Z_{24}$ at a corresponding site to $Z_{22}$, and $Z_{24}$ is the first nucleotide from the 5' terminal of the antisense strand.

In some embodiments, the present disclosure provides a pharmaceutical composition, wherein the pharmaceutical composition comprises the siRNA of the present disclosure and a pharmaceutically acceptable carrier.

In some embodiments, the present disclosure provides an siRNA conjugate, wherein the siRNA conjugate comprises the siRNA provided by the present disclosure and a conjugating group conjugated to the siRNA.

In some embodiments, the present disclosure provides use of the siRNA and/or the pharmaceutical composition and/or the siRNA conjugate according to the present disclosure in the manufacture of a medicament for treating and/or preventing septicemia caused by abnormal expression of the KNG gene.

In some embodiments, the present disclosure provides a method for treating and/or preventing septicemia, wherein the method comprises administering an effective amount of the siRNA and/or the pharmaceutical composition and/or the siRNA conjugate according to the present disclosure to a subject suffering from septicemia.

In some embodiments, the present disclosure provides a method for inhibiting expression of a KNG gene in a cell, wherein the method comprises contacting an effective amount of the siRNA and/or the pharmaceutical composition and/or the siRNA conjugate according to the present disclosure to the cell.

In some embodiments, the present disclosure provides a kit, wherein the kit comprises the siRNA and/or the pharmaceutical composition and/or the siRNA conjugate of the present disclosure.

INCORPORATED BY REFERENCE

All publications, patents and patent applications mentioned in this specification are incorporated herein by reference to the same extent as each individual publication, patent or patent application is specifically and individually incorporated herein by reference.

Advantageous Effects

The siRNA, the pharmaceutical composition and the siRNA conjugate provided by the present disclosure have better stability, higher KNG mRNA inhibitory activity and lower off-target effect, and/or can significantly treat or alleviate a septicemia symptom.

In some embodiments, the siRNA, the pharmaceutical composition or the siRNA conjugate provided by the present disclosure exhibits excellent target mRNA inhibitory activity in cell experiments in vitro. In some embodiments, the siRNA, the pharmaceutical composition or the siRNA conjugate provided by the present disclosure exhibits an inhibition percentage to target mRNA expression in hepatocytes of at least 20%, 30%, 40%, 50%, 60%, 70%, 80%, 90%, or 95%. In some embodiments, the siRNA conjugate provided by the present disclosure exhibits higher inhibitory activity in a psiCHECK system, and the $IC_{50}$ is between 0.0048 nM and 0.2328 nM.

The siRNA provided by the present disclosure has very high inhibitory activity to PKK mRNA in a psiCHECK system, and exhibits inhibition effects to KNG target sequences at different siRNA concentrations, and in particular, the inhibition percentage of the siRNA provided by the present disclosure to the expression of the KNG mRNA at the concentration of 0.1 nM can reach above 75%.

In some embodiments, the siRNA, the pharmaceutical composition or the siRNA conjugate provided by the present disclosure may exhibit higher stability and/or higher activity in vivo. In some embodiments, the siRNA, the pharmaceutical composition or the siRNA conjugate provided by the present disclosure exhibits an inhibition percentage to target gene expression of at least 20%, 30%, 40%, 50%, 60%, 70%, 80%, 90%, or 95% in vivo. In some embodiments, the siRNA, the pharmaceutical composition or the siRNA conjugate provided by the present disclosure exhibits an inhibition percentage to KNG gene expression of at least 20%, 30%, 40%, 50%, 60%, 70%, 80%, 90%, or 95% in vivo. In some embodiments, the siRNA, the pharmaceutical composition or the siRNA conjugate provided by the present disclosure exhibits an inhibition percentage to KNG gene expression in liver of at least 20%, 30%, 40%, 50%, 60%, 70%, 80%, 90%, or 95% in vivo. In some embodiments, the siRNA, the pharmaceutical composition or the siRNA conjugate provided by the present disclosure exhibits an inhibition percentage to KNG gene expression in liver in animal models of at least 20%, 30%, 40%, 50%, 60%, 70%, 80%, 90%, or 95% in vivo. In some embodiments, the siRNA, the pharmaceutical composition or the siRNA conjugate provided by the present disclosure exhibits an inhibition percentage to KNG gene expression in liver in human subjects of at least 20%, 30%, 40%, 50%, 60%, 70%, 80%, 90%, or 95% in vivo. In some embodiments, the siRNA conjugate provided by the present disclosure shows apparent inhibitory activity to KNG mRNA in humanized mice, and the inhibition percentage of the siRNA conjugate to the expression level of the KNG mRNA can reach 56%. In some embodiments, the siRNA conjugate provided by the present disclosure shows very high inhibitory activity in humanized mice, and the inhibition percentage to the expression level of the KNG mRNA can reach above 97%.

In some embodiments, the siRNA, the pharmaceutical composition or the siRNA conjugate provided by the present disclosure exhibits no significant off-target effect. An off-target effect may be, for example, inhibition on normal expression of a gene which is not the target gene. It is considered insignificant if the binding/inhibition of off-target gene expression is at a level of lower than 50%, 40%, 30%, 20%, or 10% of the on-target effect.

In this way, it is indicated that the siRNA, the pharmaceutical composition and the siRNA conjugate provided by the present disclosure can inhibit the expression of KNG mRNA, effectively treat and/or prevent the septicemia symptom, and have good application prospects.

Other features and advantages of the present disclosure will be described in detail in the detailed description section that follows.

DETAILED DESCRIPTION

Figure 1:
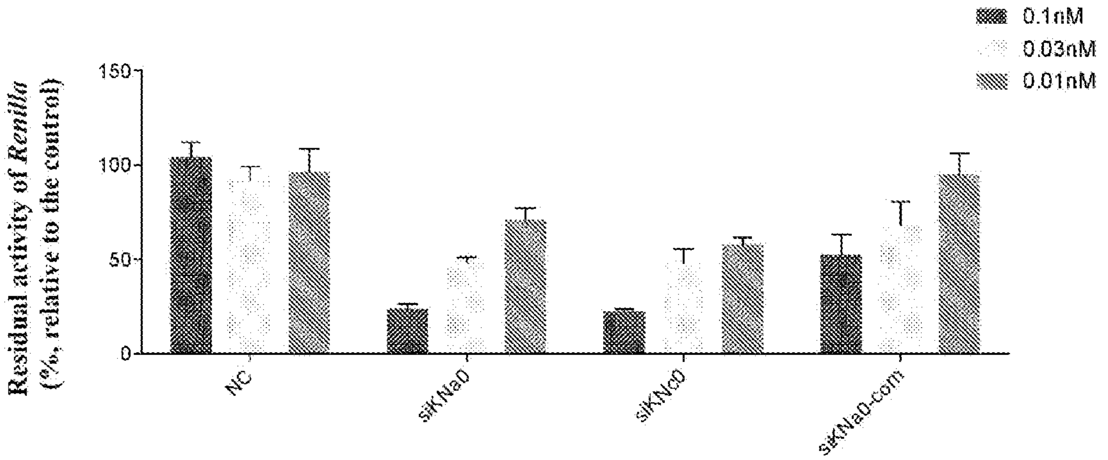
FIG. 1 is a histogram showing relative residual activity of *Renilla* in HEK293A cells in vitro after transfection of a plurality of siRNAs with different concentrations.
Figure 2A:
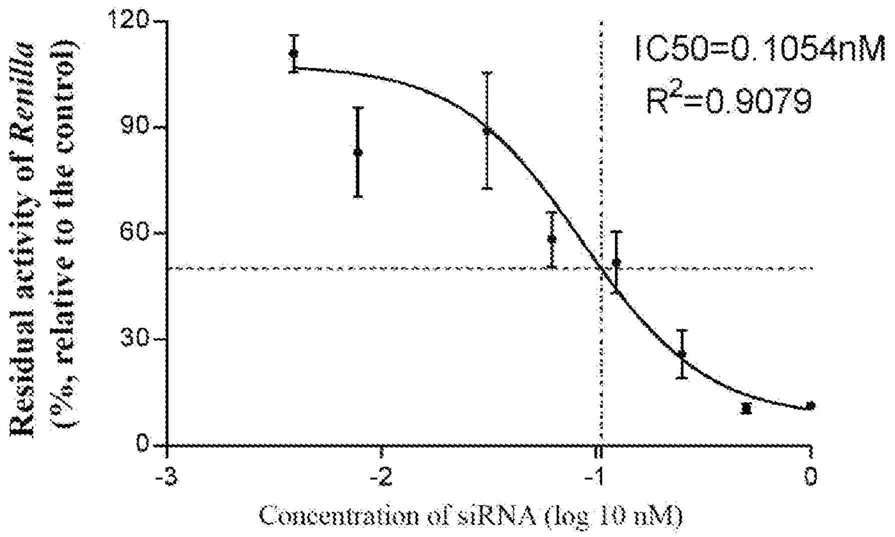
FIGS. 2A-2F show dose-response curves fitted according to the relative residual activity of *Renilla* in HEK293A cells after transfection of a plurality of siRNAs with different concentrations.
Figure 2B:
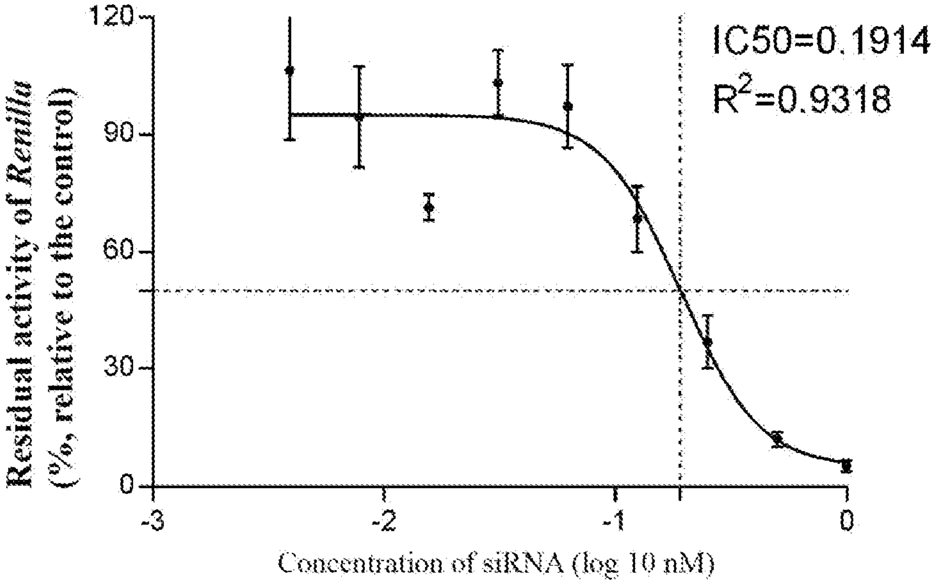
Figure 2C:
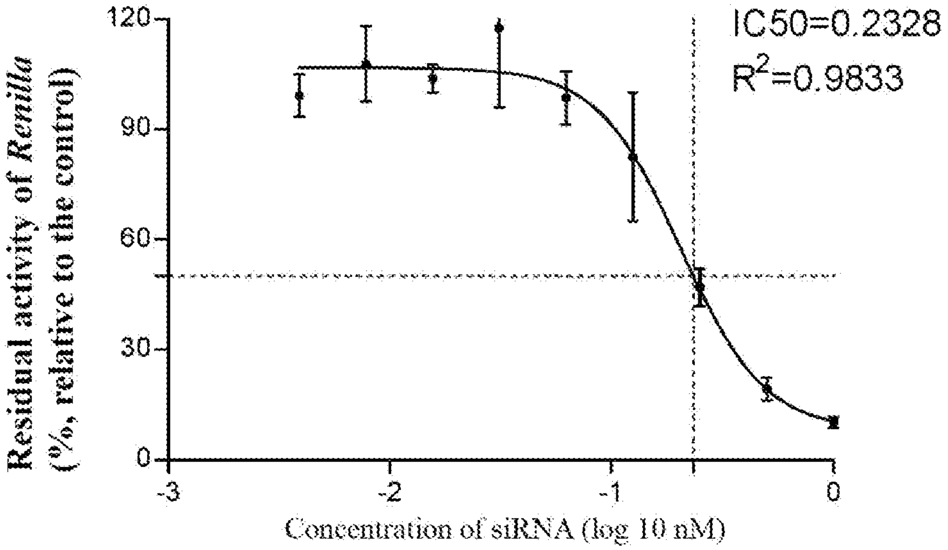
Figure 2D:
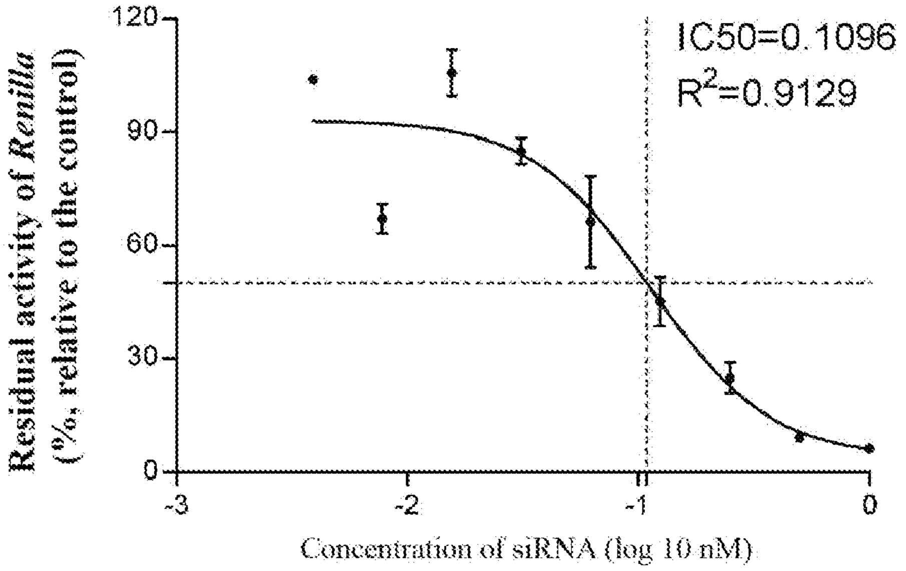
Figure 2E:
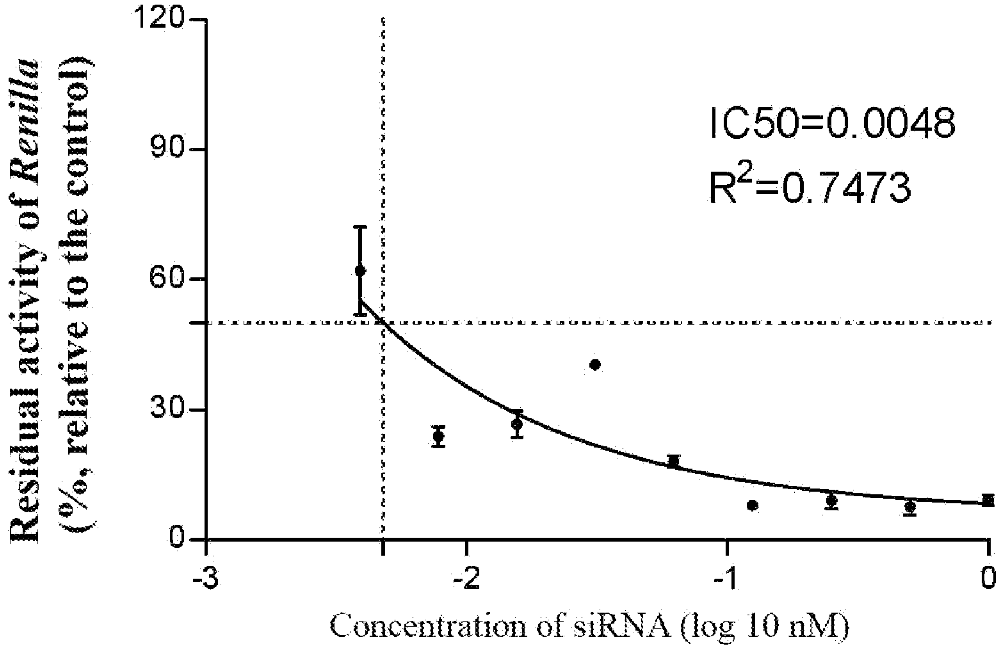
Figure 2F:
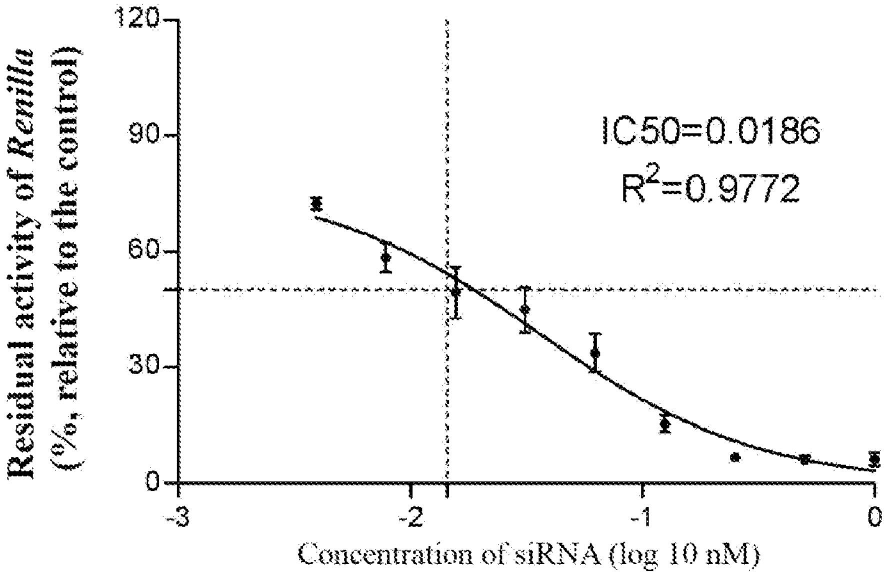

The specific embodiments of the present disclosure are described in detail as below. It should be understood that the specific embodiments described herein are only for the purpose of illustration and explanation of the present disclosure and are not intended to limit the present disclosure.

In the present disclosure, KNG mRNA refers to the mRNA with the sequence shown in Genbank registration number NM_001102416.2. Furthermore, unless otherwise stated, the term "target gene" used in the present disclosure refers to a gene capable of transcribing the above KNG mRNA, and the term "target mRNA" refers to the above KNG mRNA.

Definitions

In the context of the present disclosure, unless otherwise specified, capital letters C, G, U, and A indicate the base composition of the nucleotides; the lowercase m indicates that the nucleotide adjacent to the left side of the letter m is a methoxy modified nucleotide; the lowercase f indicates that the nucleotide adjacent to the left side of the letter f is a fluoro modified nucleotide; the lowercase letter s indicates that the two nucleotides adjacent to the left and right of the letter s are linked by phosphorothioate; P1 represents that the nucleotide adjacent to the right side of P1 is a 5'-phosphate nucleotide or a 5'-phosphate analogue modified nucleotide, the letter combination VP represents that the nucleotide adjacent to the right side of the letter combination VP is a vinyl phosphate modified nucleotide, the letter combination Ps represents that the nucleotide adjacent to the right side of the letter combination Ps is a phosphorothioate modified nucleotide, and the capital letter P represents that the nucleotide adjacent to the right side of the letter P is a 5'-phosphate nucleotide.

In the context of the present disclosure, the "fluoro modified nucleotide" refers to a nucleotide formed by substituting the 2'-hydroxy of the ribose group of the nucleotide with a fluoro, and the "non-fluoro modified nucleotide" refers to a nucleotide formed by substituting the 2'-hydroxy of the ribose group of the nucleotide with a non-fluoro group, or a nucleotide analogue. The "nucleotide analogue" refers to a group that can replace a nucleotide in a nucleic acid, while structurally differs from an adenine ribonucleotide, a guanine ribonucleotide, a cytosine ribonucleotide, a uracil ribonucleotide or a thymidine deoxyribonucleotide, such as an isonucleotide, a bridged nucleic acid (BNA) nucleotide or an acyclic nucleotide. The "methoxy modified nucleotide" refers to a nucleotide formed by substituting the 2'-hydroxy of the ribose group with a methoxy group.

In the context of the present disclosure, expressions "complementary" and "reverse complementary" can be interchangeably used, and have a well-known meaning in the art, namely, the bases in one strand are complementarily paired with those in the other strand of a double-stranded nucleic acid molecule. In DNA, a purine base adenine (A) is always paired with a pyrimidine base thymine (T) (or uracil (U) in RNAs); and a purine base guanine (G) is always paired with a pyrimidine base cytosine (C). Each base pair comprises a purine and a pyrimidine. While adenines in one strand are always paired with thymines (or uracils) in another strand, and guanines are always paired with cytosines, these two strands are considered as being complementary to each other; and the sequence of a strand may be deduced from the sequence of its complementary strand. Correspondingly, a "mispairing" means that in a double-stranded nucleic acid, the bases at corresponding sites are not presented in a manner of being complementarily paired.

In the context of the present disclosure, unless otherwise specified, "basically reverse complementary" means that there are no more than 3 base mispairings between two nucleotide sequences involved. "Substantially reverse complementary" means that there is no more than 1 base mispairing between two nucleotide sequences. "Completely complementary" means that there is no base mispairing between two nucleotide sequences.

In the context of the present disclosure, when a nucleotide sequence has "nucleotide difference" from another nucleotide sequence, the bases of the nucleotides at the same position therebetween are changed. For example, if a nucleotide base in the second sequence is A and the nucleotide base at the same position in the first sequence is U, C, G or T, these two nucleotide sequences are considered as having a nucleotide difference at this position. In some embodiments, if a nucleotide at a position is replaced with an abasic nucleotide or a nucleotide analogue, it is also considered that there is a nucleotide difference at the position.

In the context of the present disclosure, particularly in the description of the method for preparing the siRNA, the pharmaceutical composition or the siRNA conjugate of the present disclosure, unless otherwise specified, the nucleoside monomer refers to, according to the kind and sequence of the nucleotides in the siRNA or siRNA conjugate to be prepared, unmodified or modified RNA phosphoramidites used in a solid phase phosphoramidite synthesis (the RNA phosphoramidites are also called as Nucleoside phosphoramidites elsewhere). Solid phase phosphoramidite synthesis is a well-known method used in RNA synthesis to those skilled in the art. Nucleoside monomers used in the present disclosure can all be commercially available.

In the context of the present disclosure, unless otherwise stated, "conjugating" refers to two or more chemical moieties each with specific function being linked to each other via a covalent linkage. Correspondingly, a "conjugate" refers to a compound formed by covalent linkage of individual chemical moieties. Further, a "siRNA conjugate" represents a compound formed by covalently linking one or more chemical moieties with specific functions to siRNA. Hereinafter, the siRNA conjugate of the present disclosure is sometimes abbreviated as "conjugate". The siRNA conjugate should be understood according to the context as the generic term of a plurality of siRNA conjugates or siRNA conjugates shown in certain chemical formulae. In the context of the present disclosure, a "conjugating molecule" should be understood as a specific compound capable of being conjugated to an siRNA via reactions, thus finally forming the siRNA conjugate of the present disclosure.

As used herein, "optional" or "optionally" means that the subsequently described event or condition may or may not occur, and that the description includes instances wherein the event or condition may or may not occur. For example, "optionally substituted" "alkyl" encompasses both "alkyl" and "substituted alkyl" as defined below. Those skilled in the art would understand, with respect to any group containing one or more substituents, that such groups are not intended to introduce any substitution or substitution patterns that are sterically impractical, synthetically infeasible and/or inherently unstable.

As used herein, "alkyl" refers to straight chain and branched chain having the specified number of carbon atoms, usually 1 to 20 carbon atoms, for example 1 to 10 carbon atoms, such as 1 to 8 or 1 to 6 carbon atoms. For example, $C_1$-$C_6$ alkyl encompasses both straight and branched chain alkyl of 1 to 6 carbon atoms. When naming an alkyl residue having a specific number of carbon atoms, all branched and straight chain forms having that number of carbon atoms are intended to be encompassed; thus, for example, "butyl" is meant to include n-butyl, sec-butyl, isobutyl and t-butyl; and "propyl" includes n-propyl and isopropyl. Alkylene is a subset of alkyl, referring to the same residues as alkyl, but having two attachment points.

As used herein, "alkenyl" refers to an unsaturated branched or linear alkyl having at least one carbon-carbon double bond which is obtained by respectively removing one hydrogen molecule from two adjacent carbon atoms of the parent alkyl. The group may be in either cis or trans configuration of the double bond. Typical alkenyl groups include, but not limited to, ethenyl; propenyls such as prop-1-en-1-yl, prop-1-en-2-yl, prop-2-en-1-yl (allyl), and prop-2-en-2-yl; and butenyls such as but-1-en-1-yl, but-1-en-2-yl, 2-methyl-prop-1-en-1-yl, but-2-en-1-yl, but-2-en-2-yl, but-1,3-dien-1-yl, but-1,3-dien-2-yl, and the like. In certain embodiments, an alkenyl group has 2 to 20 carbon atoms, and in other embodiments, 2 to 10, 2 to 8, or 2 to 6 carbon atoms. Alkenylene is a subset of alkenyl, referring to the same residues as alkenyl, but having two attachment points.

As used herein, "alkynyl" refers to an unsaturated branched or linear alkyl having at least one carbon-carbon triple bond which is obtained by respectively removing two hydrogen molecules from two adjacent carbon atoms of the parent alkyl. Typical alkynyl groups include, but not limited to, ethynyl; propynyls such as prop-1-yn-1-yl, and prop-2-yn-1-yl; and butynyls such as but-1-yn-1-yl, but-1-yn-3-yl, but-3-yn-1-yl, and the like. In certain embodiments, an alkynyl group has 2 to 20 carbon atoms, and in other embodiments, 2 to 10, 2 to 8, or 2 to 6 carbon atoms. Alkynylene is a subset of alkynyl, referring to the same residues as alkynyl, but having two attachment points.

As used herein, "alkoxy" refers to an alkyl group of the specified number of carbon atoms attached through an oxygen bridge, such as, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. An alkoxy usually has 1 to 10, 1 to 8, 1 to 6, or 1 to 4 carbon atoms attached through oxygen bridge.

As used herein, "aryl" refers to a group derived from an aromatic monocyclic or multicyclic hydrocarbon ring system by removing a hydrogen atom from a ring carbon atom. The aromatic monocyclic or multicyclic hydrocarbon ring system contains only hydrogen and 6 to 18 carbon atoms, wherein at least one ring in the ring system is fully unsaturated, i.e., containing a cyclic, delocalized $(4n+2)\pi$-electron system in accordance with the Hückel theory. Aryl groups include, but not limited to, phenyl, fluorenyl, naphthyl and the like. Arylene is a subset of aryl, referring to the same residues as aryl, but having two attachment points.

As used herein, "halo substituent" or "halogen" refers to fluoro, chloro, bromo, and iodo, and the term "halogen" includes fluorine, chlorine, bromine, or iodine.

As used herein, "haloalkyl" refers to the alkyl as defined above with the specified number of carbon atoms being substituted with one or more halogen atoms, up to the maximum allowable number of halogen atoms. Examples of haloalkyl include, but not limited to, trifluoromethyl, difluoromethyl, 2-fluoroethyl, and pentafluoroethyl.

"Heterocyclyl" refers to a stable 3- to 18-membered non-aromatic ring radical that comprises 2-12 carbon atoms and 1-6 heteroatoms selected from nitrogen, oxygen or sulfur. Unless stated otherwise in the description, heterocyclyl is a monocyclic, bicyclic, tricyclic, or tetracyclic ring system, which may include fused or bridged ring systems. The heteroatoms in the heterocyclyl may be optionally oxidized. One or more nitrogen atoms, if present, are optionally quaternized. The heterocyclyl is partially or fully saturated. The heterocyclyl may be linked to the rest of the molecule through any atom of the ring. Examples of such heterocyclyl include, but not limited to, dioxanyl, thienyl[1,3]disulfonyl, decahydroisoquinolyl, imidazolinyl, imidazolidinyl, isothiazolidinyl, isoxazolidinyl, morpholinyl, octahydroindolyl, octahydroisoindolyl, 2-oxapiperazinyl, 2-oxapiperidinyl, 2-oxapyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

"Heteroaryl" refers to a group derived from a 3- to 18-membered aromatic ring radical that comprises 2 to 17 carbon atoms and 1 to 6 heteroatoms selected from nitrogen, oxygen and sulfur. As used herein, the heteroaryl may be a monocyclic, bicyclic, tricyclic or tetracyclic ring system, wherein at least one ring in the ring system is fully unsaturated, i.e., containing a cyclic, delocalized (4n+2)π-electron system in accordance with the Hückel theory. The heteroaryl includes fused or bridged ring systems. The heteroatoms in the heteroaryl are optionally oxidized. One or more nitrogen atoms, if present, are optionally quaternized. The heteroaryl may be linked to the rest of the molecule through any atom of the ring. Examples of such heteroaryl include, but not limited to, azepinyl, acridinyl, benzimidazolyl, benzindolyl, 1,3-benzodioxazolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothienyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[H]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, quinazolinyl, quinoxalinyl, quinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl/thienyl.

Various hydroxy protecting groups may be used in the present disclosure. In general, protecting groups render chemical functional groups insensitive to specific reaction conditions, and may be attached to and removed from such functional groups in a molecule without substantially damaging the remainder of the molecule. Representative hydroxy protecting groups are disclosed in Beaucage, et al., Tetrahedron 1992, 48, 2223-2311, and also in Greene and Wuts, Protective Groups in Organic Synthesis, Chapter 2, 2d ed, John Wiley & Sons, New York, 1991, each of which is hereby incorporated by reference in their entirety. In some embodiments, the protecting group is stable under basic conditions but can be removed under acidic conditions. In some embodiments, non-exclusive examples of the hydroxy protecting groups used herein include dimethoxytrityl (DMT), monomethoxytrityl, 9-phenylxanthen-9-yl (Pixyl), or 9-(p-methoxyphenyl)xanthen-9-yl (Mox). In some embodiments, non-exclusive examples of the hydroxy protecting groups used herein include Tr(trityl), MMTr(4-methoxytrityl), DMTr(4,4'-dimethoxytrityl), or TMTr(4,4',4"-trimethoxytrityl).

The term "subject", as used herein, refers to any animal, e.g., mammal or marsupial. The subject of the present disclosure includes, but not limited to, human, non-human primate (e.g., rhesus or other kinds of macaque), mouse, pig, horse, donkey, cow, sheep, rat or any kind of poultry.

As used herein, "treatment" refers to a method for obtaining advantageous or desired result, including but not limited to, therapeutic benefit. "Therapeutic benefit" means eradication or improvement of potential disorder to be treated. Moreover, the therapeutic benefit is achieved by eradicating or ameliorating one or more of physiological symptoms associated with the potential disorder such that an improvement is observed in the subject, notwithstanding that the subject may still be afflicted with the potential disorder.

As used herein, "prevention" refers to a method for obtaining advantageous or desired result, including but not limited to, prophylactic benefit. For obtaining the "prophylactic benefit", the siRNA, the siRNA conjugate or the pharmaceutical composition may be administered to the subject at risk of developing a particular disease, or to the subject reporting one or more physiological symptoms of a disease, even though the diagnosis of this disease may not have been made.

In one aspect, the present disclosure provides first to sixth siRNAs capable of inhibiting expression of a KNG gene. The siRNAs will be described in detail hereinafter.

The siRNA of the present disclosure comprises nucleotides as basic structural units. It is well-known to those skilled in the art that the nucleotide comprises a phosphate group, a ribose group and a base. Detailed illustrations relating to such groups are omitted herein.

The siRNA of the present disclosure comprises a sense strand and an antisense strand, wherein lengths of the sense strand and the antisense strand are the same or different, the length of the sense strand is 19-23 nucleotides, and the length of the antisense strand is 19-26 nucleotides. In this way, a length ratio of the sense strand to the antisense strand of the siRNA provided by the present disclosure may be 19/19, 19/20, 19/21, 19/22, 19/23, 19/24, 19/25, 19/26, 20/20, 20/21, 20/22, 20/23, 20/24, 20/25, 20/26, 21/20, 21/21, 21/22, 21/23, 21/24, 21/25, 21/26, 22/20, 22/21, 22/22, 22/23, 22/24, 22/25, 22/26, 23/20, 23/21, 23/22, 23/23, 23/24, 23/25 or 23/26. In some embodiments, the length ratio of the sense strand to the antisense strand of the siRNA is 19/21, 21/23 or 23/25.

First siRNA

According to the present disclosure, the siRNA may be the first siRNA.

The first siRNA comprises a sense strand and an antisense strand. Each nucleotide in the first siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length as and no more than three nucleotide differences from the nucleotide sequence shown in SEQ ID NO: 1; and the nucleotide sequence II has the same length as and no more than three nucleotide differences from the nucleotide sequence shown in SEQ ID NO: 2:

(SEQ ID NO: 1)
5'-AAAGUAACAACCAGUUUGZ$_1$-3';

(SEQ ID NO: 2)
5'-Z$_2$CAAACUGGUUGUUACUUU-3', wherein, $Z_1$ is U, $Z_2$ is A, the nucleotide sequence I comprises a nucleotide $Z_3$ at a corresponding site to $Z_1$, the nucleotide sequence II comprises a nucleotide $Z_4$ at a corresponding site to $Z_2$, and $Z_4$ is the first nucleotide from the 5' terminal of the antisense strand.

In this context, the term "corresponding site" means being at the same site in the nucleotide sequence by counting from the same terminal of the nucleotide sequence. For example, the first nucleotide at the 3' terminal of the nucleotide sequence I is a nucleotide at the corresponding site to the first nucleotide at the 3' terminal of SEQ ID NO: 1.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 1, and/or the nucleotide sequence II has no more than one nucleotide difference from the nucleotide sequence shown in SEQ ID NO: 2.

In some embodiments, the nucleotide difference between the nucleotide sequence II and the nucleotide sequence shown in SEQ ID NO: 2 comprises a difference at the site of $Z_4$, and $Z_4$ is selected from U, C or G. In some embodiments, the nucleotide difference is a difference at the site of $Z_4$, and $Z_4$ is selected from U, C or G. In some embodiments, $Z_3$ is a nucleotide complementary to $Z_4$. The siRNAs having the above nucleotide differences have higher ability to inhibit the target mRNA, and these siRNAs are also within the protection scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 3, and the nucleotide sequence II is the nucleotide sequence shown in SEQ ID NO: 4:

(SEQ ID NO: 3)
5'-AAAGUAACAACCAGUUUGZ$_3$-3';

(SEQ ID NO: 4)
5'-Z$_4$CAAACUGGUUGUUACUUUGG-3', wherein, $Z_4$ is the first nucleotide from 5' terminal of the antisense strand; $Z_4$ is selected from A, U, G or C; and $Z_3$ is a nucleotide complementary to $Z_4$; and in some embodiments, $Z_3$ is U, and $Z_4$ is A.

In some embodiments, the sense strand further comprises a nucleotide sequence III, the antisense strand further comprises a nucleotide sequence IV, and the nucleotide sequence III and the nucleotide sequence IV each has a length of 1-4 nucleotides; the nucleotide sequence III is equal in length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. In some embodiments, the nucleotide sequence IV is substantially reverse complementary or completely reverse complementary to the second nucleotide sequence, and the second nucleotide sequence refers to the nucleotide sequence adjacent to the 5' terminal of the nucleotide sequence represented by SEQ ID NO: 1 in the target mRNA and having the same length as the nucleotide sequence IV.

In some embodiments, the nucleotide sequence III and the nucleotide sequence IV both have a length of one nucleotide, and the base of the nucleotide sequence III is C, and the base of the nucleotide sequence IV is G; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is CC, and the base composition of the nucleotide sequence IV is GG; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is ACC, and the base composition of the nucleotide sequence IV is GGU; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is AACC, and the base composition of the nucleotide sequence IV is GGUU; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is CC, and the base composition of the nucleotide sequence IV is GG; in this case, the length ratio of the sense strand to the antisense strand is 21/21.

In some embodiments, the nucleotide sequence III is completely reverse complementary to the nucleotide sequence IV Thus, if the base(s) of the nucleotide sequence III is provided, the base(s) of the nucleotide sequence IV is also determined.

Second siRNA

According to the present disclosure, the siRNA may be the second siRNA. The second siRNA comprises a sense strand and an antisense strand. Each nucleotide in the siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length as and no more than three nucleotide differences from the nucleotide sequence shown in SEQ ID NO: 61; and the nucleotide sequence II has the same length as and no more than three nucleotide differences from the nucleotide sequence shown in SEQ ID NO: 62:

(SEQ ID NO: 61)
5'-AUUGAACUUUCGAAUUACZ$_5$-3';

(SEQ ID NO: 62)
5'-Z$_6$GUAAUUCGAAAGUUCAAU-3', wherein, $Z_5$ is C, $Z_6$ is G, the nucleotide sequence I comprises a nucleotide $Z_7$ at a corresponding site to $Z_5$, the nucleotide sequence II comprises a nucleotide $Z_5$ at a corresponding site to $Z_6$, and $Z_8$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 61, and/or the nucleotide sequence II has no more than one nucleotide difference from the nucleotide sequence shown in SEQ ID NO: 62.

In some embodiments, the nucleotide difference between the nucleotide sequence II and the nucleotide sequence shown in SEQ ID NO: 62 comprises a difference at the site of $Z_8$, and $Z_8$ is selected from A, U or C. In some embodiments, the nucleotide difference is a difference at the site of $Z_8$, and $Z_8$ is selected from A, U or C. In some embodiments, $Z_7$ is a nucleotide complementary to $Z_8$. The siRNAs having the above nucleotide differences have higher ability to inhibit the target mRNA, and these siRNAs comprising the nucleotide differences are also within the protection scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 63, and the nucleotide sequence II is the nucleotide sequence shown in SEQ ID NO: 64:

(SEQ ID NO: 63)
5'-AUUGAACUUUCGAAUUACZ$_7$-3';

(SEQ ID NO: 64)
5'-Z$_8$GUAAUUCGAAAGUUCAAU-3', wherein, $Z_8$ is the first nucleotide from 5' terminal of the antisense strand; $Z_8$ is selected from A, U, G or C; and $Z_7$ is a nucleotide complementary to $Z_8$; and in some embodiments, $Z_7$ is C, and $Z_8$ is G.

In some embodiments, the sense strand further comprises a nucleotide sequence III, the antisense strand further comprises a nucleotide sequence IV, and the nucleotide sequence III and the nucleotide sequence IV each has a length of 1-4 nucleotides; the nucleotide sequence III is equal in length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the second nucleotide sequence, and the second nucleotide sequence refers to the nucleotide sequence adjacent to the 5' terminal of the nucleotide sequence represented by SEQ ID NO: 61 in the target mRNA and having the same length as the nucleotide sequence IV.

In some embodiments, the nucleotide sequence III and the nucleotide sequence IV both have a length of one nucleotide, and the base of the nucleotide sequence III is G, and the base of the nucleotide sequence IV is C; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is GG, and the base composition of the nucleotide sequence IV is CC; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is UGG, and the base composition of the nucleotide sequence IV is CCA; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is CUGG, and the base composition of the nucleotide sequence IV is CCAG; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is GG, and the base composition of the nucleotide sequence IV is CC; in this case, the length ratio of the sense strand to the antisense strand is 21/21.

In some embodiments, the nucleotide sequence III is completely reverse complementary to the nucleotide sequence IV Thus, if the base(s) of the nucleotide sequence III is provided, the base(s) of the nucleotide sequence IV is also determined.

Third siRNA

According to the present disclosure, the siRNA may be the third siRNA.

The third siRNA comprises a sense strand and an antisense strand. Each nucleotide in the siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length as and no more than three nucleotide differences from the nucleotide sequence shown in SEQ ID NO: 121; and the nucleotide sequence II has the same length as and no more than three nucleotide differences from the nucleotide sequence shown in SEQ ID NO: 122:

(SEQ ID NO: 121)
5'-UCGAAUUACCUACUCAAUZ$_9$-3';

(SEQ ID NO: 122)
5'-Z$_{10}$AUUGAGUAGGUAAUUCGA-3', wherein, $Z_9$ is U, $Z_{10}$ is A, the nucleotide sequence I comprises a nucleotide $Z_{11}$ at a corresponding site to $Z_9$, the nucleotide sequence II comprises a nucleotide $Z_{12}$ at a corresponding site to $Z_{10}$, and $Z_{12}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 121, and/or the nucleotide sequence II has no more than one nucleotide difference from the nucleotide sequence shown in SEQ ID NO: 122.

In some embodiments, the nucleotide difference between the nucleotide sequence II and the nucleotide sequence shown in SEQ ID NO: 122 comprises a difference at the site of $Z_{12}$, and $Z_{12}$ is selected from U, C or G. In some embodiments, the nucleotide difference is a difference at the site of $Z_{12}$, and $Z_{12}$ is selected from U, C or G. In some embodiments, Zu is a nucleotide complementary to $Z_{12}$. The siRNAs having the above nucleotide differences have higher ability to inhibit the target mRNA, and these siRNAs comprising the nucleotide differences are also within the protection scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 123, and the nucleotide sequence II is the nucleotide sequence shown in SEQ ID NO: 124:

```
                         (SEQ ID NO: 123)
5'-UCGAAUUACCUACUCAAUZ11-3';

                         (SEQ ID NO: 124)
5'-Z12AUUGAGUAGGUAAUUCGA-3',
```

wherein, $Z_{12}$ is the first nucleotide from 5' terminal of the antisense strand; $Z_{12}$ is selected from A, U, G or C; and Zu is a nucleotide complementary to $Z_{12}$; and in some embodiments, $Z_{11}$ is U, and $Z_{12}$ is A.

In some embodiments, the sense strand further comprises a nucleotide sequence III, the antisense strand further comprises a nucleotide sequence IV, and the nucleotide sequence III and the nucleotide sequence IV each has a length of 1-4 nucleotides; the nucleotide sequence III is equal in length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the second nucleotide sequence, and the second nucleotide sequence refers to the nucleotide sequence adjacent to the 5' terminal of the nucleotide sequence represented by SEQ ID NO: 121 in the target mRNA and having the same length as the nucleotide sequence IV.

In some embodiments, the nucleotide sequence III and the nucleotide sequence IV both have a length of one nucleotide, the base of the nucleotide sequence III is U, and the base of the nucleotide sequence IV is A; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is UU, and the base composition of the nucleotide sequence IV is AA; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is CUU, and the base composition of the nucleotide sequence IV is AAG; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is ACUU, and the base composition of the nucleotide sequence IV is AAGU; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is UU, and the base composition of the nucleotide sequence IV is AA; in this case, the length ratio of the sense strand to the antisense strand is 21/21.

In some embodiments, the nucleotide sequence III is completely reverse complementary to the nucleotide sequence IV Thus, if the base(s) of the nucleotide sequence III is provided, the base(s) of the nucleotide sequence IV is also determined.

Fourth siRNA

According to the present disclosure, the siRNA may be the fourth siRNA.

The fourth siRNA comprises a sense strand and an antisense strand. Each nucleotide in the siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length as and no more than three nucleotide differences from the nucleotide sequence shown in SEQ ID NO: 181; and the nucleotide sequence II has the same length as and no more than three nucleotide differences from the nucleotide sequence shown in SEQ ID NO: 182:

```
                         (SEQ ID NO: 181)
5'-GAUAAUGCAUACAUCGAUZ13-3';

                         (SEQ ID NO: 182)
5'-Z14AUCGAUGUAUGCAUUAUC-3',
```

wherein, $Z_{13}$ is A, $Z_{14}$ is U, the nucleotide sequence I comprises a nucleotide $Z_{15}$ at a corresponding site to $Z_{13}$, the nucleotide sequence II comprises a nucleotide $Z_{16}$ at a corresponding site to $Z_{14}$, and $Z_{16}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 181, and/or the nucleotide sequence II has no more than one nucleotide difference from the nucleotide sequence shown in SEQ ID NO: 182.

In some embodiments, the nucleotide difference between the nucleotide sequence II and the nucleotide sequence shown in SEQ ID NO: 182 comprises a difference at the site of $Z_{16}$, and $Z_{16}$ is selected from A, C or G. In some embodiments, the nucleotide difference is a difference at the site of $Z_{16}$, and $Z_{16}$ is selected from A, C or G. In some embodiments, $Z_{15}$ is a nucleotide complementary to $Z_{16}$. The siRNAs having the above nucleotide differences have higher ability to inhibit the target mRNA, and these siRNAs comprising the nucleotide differences are also within the protection scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 183, and the nucleotide sequence II is the nucleotide sequence shown in SEQ ID NO: 184:

```
                         (SEQ ID NO: 183)
5'-GAUAAUGCAUACAUCGAUZ15-3';

                         (SEQ ID NO: 184)
5'-Z16AUCGAUGUAUGCAUUAUC-3',
```

wherein, $Z_{16}$ is the first nucleotide from 5' terminal of the antisense strand; $Z_{16}$ is selected from A, U, G or C; and $Z_{15}$ is a nucleotide complementary to $Z_{16}$; and in some embodiments, $Z_{15}$ is A, and $Z_{16}$ is U.

In some embodiments, the sense strand further comprises a nucleotide sequence III, the antisense strand further comprises a nucleotide sequence IV, and the nucleotide sequence III and the nucleotide sequence IV each has a length of 1-4 nucleotides; the nucleotide sequence III is equal in length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the second nucleotide sequence, and the second nucleotide sequence refers to the nucleotide sequence adjacent to the 5' terminal of the nucleotide sequence represented by SEQ ID NO: 181 in the target mRNA and having the same length as the nucleotide sequence IV.

In some embodiments, the nucleotide sequence III and the nucleotide sequence IV both have a length of one nucleotide, the base of the nucleotide sequence III is A, and the base of the nucleotide sequence IV is U; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is CA, and the base composition of the nucleotide sequence IV is UG; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is ACA, and the base composition of the nucleotide sequence IV is UGU; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is UACA, and the base composition of the nucleotide sequence IV is UGUA; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is CA, and the base composition of the nucleotide sequence IV is UG; in this case, the length ratio of the sense strand to the antisense strand is 21/21.

In some embodiments, the nucleotide sequence III is completely reverse complementary to the nucleotide sequence IV Thus, if the base(s) of the nucleotide sequence III is provided, the base(s) of the nucleotide sequence IV is also determined.

Fifth siRNA

According to the present disclosure, the siRNA may be the fifth siRNA. The fifth siRNA comprises a sense strand and an antisense strand. Each nucleotide in the siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length as and no more than three nucleotide differences from the nucleotide sequence shown in SEQ ID NO: 241; and the nucleotide sequence II has the same length as and no more than three nucleotide differences from the nucleotide sequence shown in SEQ ID NO: 242:

(SEQ ID NO: 241)
5'-GAAUAACGCAACUUUCUA$Z_{17}$-3';

(SEQ ID NO: 242)
5'-$Z_{18}$UAGAAAGUUGCGUUAUUC-3', wherein, $Z_{17}$ is U, $Z_{18}$ is A, the nucleotide sequence I comprises a nucleotide $Z_{19}$ at a corresponding site to $Z_{17}$, the nucleotide sequence II comprises a nucleotide $Z_{20}$ at a corresponding site to $Z_{18}$, and $Z_{20}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 241, and/or the nucleotide sequence II has no more than one nucleotide difference from the nucleotide sequence shown in SEQ ID NO: 242.

In some embodiments, the nucleotide difference between the nucleotide sequence II and the nucleotide sequence shown in SEQ ID NO: 242 comprises a difference at the site of $Z_{20}$, and $Z_{20}$ is selected from U, C or G. In some embodiments, the nucleotide difference is a difference at the site of $Z_{20}$, and $Z_{20}$ is selected from U, C or G. In some embodiments, $Z_{19}$ is a nucleotide complementary to $Z_{20}$. The siRNAs having the above nucleotide differences have higher ability to inhibit the target mRNA, and these siRNAs comprising the nucleotide differences are also within the protection scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 243, and the nucleotide sequence II is the nucleotide sequence shown in SEQ ID NO: 244:

(SEQ ID NO: 243)
5'-GAAUAACGCAACUUUCUA$Z_{19}$-3';

(SEQ ID NO: 244)
5'-$Z_{20}$UAGAAAGUUGCGUUAUUC-3', wherein, $Z_{20}$ is the first nucleotide from 5' terminal of the antisense strand; $Z_{20}$ is selected from A, U, G or C; and $Z_{19}$ is a nucleotide complementary to $Z_{20}$; and in some embodiments, $Z_{19}$ is U, and $Z_{20}$ is A.

In some embodiments, the sense strand further comprises a nucleotide sequence III, the antisense strand further comprises a nucleotide sequence IV, and the nucleotide sequence III and the nucleotide sequence IV each has a length of 1-4 nucleotides; the nucleotide sequence III is equal in length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the second nucleotide sequence, and the second nucleotide sequence refers to the nucleotide sequence adjacent to the 5' terminal of the nucleotide sequence represented by SEQ ID NO: 241 in the target mRNA and having the same length as the nucleotide sequence IV.

In some embodiments, the nucleotide sequence III and the nucleotide sequence IV both have a length of one nucleotide, the base of the nucleotide sequence III is A, and the base of the nucleotide sequence IV is U; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is GA, and the base composition of the nucleotide sequence IV is UC; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is AGA, and the base composition of the nucleotide sequence IV is UCU; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is CAGA, and the base composition of the nucleotide sequence IV is UCUG; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is CA, and the base composition of the nucleotide sequence IV is UG; in this case, the length ratio of the sense strand to the antisense strand is 21/21.

In some embodiments, the nucleotide sequence III is completely reverse complementary to the nucleotide sequence IV Thus, if the base(s) of the nucleotide sequence III is provided, the base(s) of the nucleotide sequence IV is also determined.

Sixth siRNA

According to the present disclosure, the siRNA may be the sixth siRNA.

The sixth siRNA comprises a sense strand and an antisense strand. Each nucleotide in the siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length as and no more than three nucleotide differences from the nucleotide sequence shown in SEQ ID NO: 301; and the nucleotide sequence II has the same length as and no more than three nucleotide differences from the nucleotide sequence shown in SEQ ID NO: 302:

(SEQ ID NO: 301)
5'-AACUUUCUAUUUCAAGAU$Z_{21}$-3';

(SEQ ID NO: 302)
5'-$Z_{22}$AUCUUGAAAUAGAAAGUU-3', wherein, $Z_{21}$ is U, $Z_{22}$ is A, the nucleotide sequence I comprises a nucleotide $Z_{23}$ at a corresponding site to $Z_{21}$, the nucleotide sequence II comprises a nucleotide $Z_{24}$ at a corresponding site to $Z_{22}$, and $Z_{24}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 301, and/or the nucleotide sequence II has no more than one nucleotide difference from the nucleotide sequence shown in SEQ ID NO: 302.

In some embodiments, the nucleotide difference between the nucleotide sequence II and the nucleotide sequence shown in SEQ ID NO: 302 comprises a difference at the site of $Z_{24}$, and $Z_{24}$ is selected from U, C or G. In some embodiments, the nucleotide difference is a difference at the site of $Z_{24}$, and $Z_{24}$ is selected from U, C or G. In some embodiments, $Z_{23}$ is a nucleotide complementary to $Z_{24}$. The siRNAs having the above nucleotide differences have higher ability to inhibit the target mRNA, and these siRNAs comprising the nucleotide differences are also within the protection scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 303, and the nucleotide sequence II is the nucleotide sequence shown in SEQ ID NO: 304:

(SEQ ID NO: 303)
5'-AACUUUCUAUUUCAAGAU$Z_{23}$-3';

(SEQ ID NO: 304)
5'-$Z_{24}$AUCUUGAAAUAGAAAGUU-3', wherein, $Z_{24}$ is the first nucleotide from 5' terminal of the antisense strand; $Z_{24}$ is selected from A, U, G or C; and $Z_{23}$ is a nucleotide complementary to $Z_{24}$; and in some embodiments, $Z_{23}$ is U, and $Z_{24}$ is A.

In some embodiments, the sense strand further comprises a nucleotide sequence III, the antisense strand further comprises a nucleotide sequence IV, and the nucleotide sequence III and the nucleotide sequence IV each has a length of 1-4 nucleotides; the nucleotide sequence III is equal in length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the second nucleotide sequence, and the second nucleotide sequence refers to the nucleotide sequence adjacent to the 5' terminal of the nucleotide sequence represented by SEQ ID NO: 301 in the target mRNA and having the same length as the nucleotide sequence IV.

In some embodiments, the nucleotide sequence III and the nucleotide sequence IV both have a length of one nucleotide, the base of the nucleotide sequence III is C, and the base of the nucleotide sequence IV is G; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is GC, and the base composition of the nucleotide sequence IV is GC; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is CGC, and the base composition of the nucleotide sequence IV is GCG; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is ACGC, and the base composition of the nucleotide sequence IV is GCGU; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is GC, and the base composition of the nucleotide sequence IV is GC; in this case, the length ratio of the sense strand to the antisense strand is 21/21.

In some embodiments, the nucleotide sequence III is completely reverse complementary to the nucleotide sequence IV Thus, if the base(s) of the nucleotide sequence III is provided, the base(s) of the nucleotide sequence IV is also determined.

The following description of the nucleotide sequence V, the nucleic acid sequence, the nucleotide modification and the modified sequence in the siRNA is applicable to any one of the first siRNA to the sixth siRNA. That is, unless otherwise specified, the following description of the siRNA should be regarded as describing the first siRNA, the second siRNA, the third siRNA, the fourth siRNA, the fifth siRNA, or the sixth siRNA one by one. For example, if no specific siRNA is specified, "the siRNA further comprises a nucleotide sequence V" means "the first siRNA, the second siRNA, the third siRNA, the fourth siRNA, the fifth siRNA, or the sixth siRNA further comprises a nucleotide sequence V".

In some embodiments, the antisense strand further comprises a nucleotide sequence V, which has a length of 1-3 nucleotides and is linked to the 3' terminal of the antisense strand, thereby constituting a 3' overhang of the antisense strand. As such, the length ratio of the sense strand to the antisense strand in the siRNA of the present disclosure may be 19/20, 19/21, 19/22, 20/21, 20/22, 20/23, 21/22, 21/23, 21/24, 22/23, 22/24, 22/25, 23/24, 23/25, or 23/26. In some embodiments, the nucleotide sequence V has a length of 2 nucleotides. As such, the length ratio of the sense strand to the antisense strand in the siRNA of the present disclosure may be 19/21, 21/23 or 23/25.

Each nucleotide in the nucleotide sequence V may be any nucleotide. In order to facilitate synthesis and save synthesis cost, the nucleotide sequence V is 2 continuous thymidine deoxyribonucleotides (dTdT) or 2 continuous uracil ribonucleotides (UU); or, in order to improve the affinity of the antisense strand of the siRNA to the target mRNA, the nucleotide sequence V is complementary to the nucleotides at the corresponding site of the target mRNA. Therefore, in some embodiments, the length ratio of the sense strand to the antisense strand of the siRNA of the present disclosure is 19/21 or 21/23. In this case, the siRNA of the present disclosure has better silencing activity against target mRNA.

The nucleotide at the corresponding site of the target mRNA refers to the nucleotide or nucleotide sequence adjacent to the third nucleotide sequence of the target mRNA at the 5' terminal. The third nucleotide sequence of the target mRNA is a segment of nucleotide sequence which is substantially reverse complementary or completely reverse complementary to the nucleotide sequence II, or substantially reverse complementary or completely reverse complementary to the nucleotide sequence formed by the nucleotide sequence II and the nucleotide sequence IV.

In some embodiments, for the first siRNA, the sense strand of the siRNA comprises the nucleotide sequence shown in SEQ ID NO: 5, and the antisense strand of the siRNA comprises the nucleotide sequence shown in SEQ ID NO: 6:

(SEQ ID NO: 5)
5'-AAAGUAACAACCAGUUUG$Z_3$-3';

(SEQ ID NO: 6)
5'-$Z_4$CAAACUGGUUGUUACUUUGG-3';

or, the sense strand of the siRNA comprises the nucleotide sequence shown in SEQ ID NO: 7, and the antisense strand of the siRNA comprises the nucleotide sequence shown in SEQ ID NO: 8;

(SEQ ID NO: 7)
5'-CCAAAGUAACAACCAGUUUG$Z_3$-3';

(SEQ ID NO: 8)
5'-$Z_4$CAAACUGGUUGUUACUUUGGUU-3';

wherein, $Z_4$ is the first nucleotide from 5' terminal of the antisense strand; $Z_4$ is selected from A, U, G or C; and $Z_3$ is a nucleotide complementary to $Z_4$.

In some embodiments, for the second siRNA, the sense strand of the siRNA comprises the nucleotide sequence shown in SEQ ID NO: 65, and the antisense strand of the siRNA comprises the nucleotide sequence shown in SEQ ID NO: 66:

(SEQ ID NO: 65)
5'-AUUGAACUUUCGAAUUAC$Z_7$-3';

(SEQ ID NO: 66)
5'-$Z_8$GUAAUUCGAAAGUUCAAUCC-3', or, the sense strand of the siRNA comprises the nucleotide sequence shown in SEQ ID NO: 67, and the antisense strand of the siRNA comprises the nucleotide sequence shown in SEQ ID NO: 68:

(SEQ ID NO: 67)
5'-GGAUUGAACUUUCGAAUUAC$Z_7$-3';

(SEQ ID NO: 68)
5'-$Z_8$GUAAUUCGAAAGUUCAAUCCAG-3', wherein, $Z_8$ is the first nucleotide from 5' terminal of the antisense strand; $Z_8$ is selected from A, U, G or C; and $Z_7$ is a nucleotide complementary to $Z_8$.

In some embodiments, for the third siRNA, the sense strand of the siRNA comprises the nucleotide sequence shown in SEQ ID NO: 125, and the antisense strand of the siRNA comprises the nucleotide sequence shown in SEQ ID NO: 126:

(SEQ ID NO: 125)
5'-UCGAAUUACCUACUCAAU$Z_{11}$-3';

(SEQ ID NO: 126)
5'-$Z_{12}$AUUGAGUAGGUAAUUCGAAA-3', or, the sense strand of the siRNA comprises the nucleotide sequence shown in SEQ ID NO: 127, and the antisense strand of the siRNA comprises the nucleotide sequence shown in SEQ ID NO: 128:

(SEQ ID NO: 127)
5'-UUUCGAAUUACCUACUCAAU$Z_{11}$-3';

(SEQ ID NO: 128)
5'-$Z_{12}$AUUGAGUAGGUAAUUCGAAAGU-3', wherein, $Z_{12}$ is the first nucleotide from 5' terminal of the antisense strand; $Z_{12}$ is selected from A, U, G or C; and Zu is a nucleotide complementary to $Z_{12}$.

In some embodiments, for the fourth siRNA, the sense strand of the siRNA comprises the nucleotide sequence shown in SEQ ID NO: 185, and the antisense strand of the siRNA comprises the nucleotide sequence shown in SEQ ID NO: 186:

(SEQ ID NO: 185)
5'-GAUAAUGCAUACAUCGAU$Z_{15}$-3';

(SEQ ID NO: 186)
5'-$Z_{16}$AUCGAUGUAUGCAUUAUCUG-3', or, the sense strand of the siRNA comprises the nucleotide sequence shown in SEQ ID NO: 187, and the antisense strand of the siRNA comprises the nucleotide sequence shown in SEQ ID NO: 188:

(SEQ ID NO: 187)
5'-CAGAUAAUGCAUACAUCGAU$Z_{15}$-3';

(SEQ ID NO: 188)
5'-$Z_{16}$AUCGAUGUAUGCAUUAUCUGUA-3', wherein, $Z_{16}$ is the first nucleotide from 5' terminal of the antisense strand; $Z_{16}$ is selected from A, U, G or C; and $Z_{15}$ is a nucleotide complementary to $Z_{16}$.

In some embodiments, for the fifth siRNA, the sense strand of the siRNA comprises the nucleotide sequence shown in SEQ ID NO: 245, and the antisense strand of the siRNA comprises the nucleotide sequence shown in SEQ ID NO: 246:

(SEQ ID NO: 245)
5'-GAAUAACGCAACUUUCUA$Z_{19}$-3';

(SEQ ID NO: 246)
5'-$Z_{20}$UAGAAAGUUGCGUUAUUCUC-3', or, the sense strand of the siRNA comprises the nucleotide sequence shown in SEQ ID NO: 247, and the antisense strand of the siRNA comprises the nucleotide sequence shown in SEQ ID NO: 248:

(SEQ ID NO: 247)
5'-GAGAAUAACGCAACUUUCUA$Z_{19}$-3';

(SEQ ID NO: 248)
5'-$Z_{20}$UAGAAAGUUGCGUUAUUCUCUG-3', wherein, $Z_{20}$ is the first nucleotide from 5' terminal of the antisense strand; $Z_{20}$ is selected from A, U, G or C; and $Z_{19}$ is a nucleotide complementary to $Z_{20}$.

In some embodiments, for the sixth siRNA, the sense strand of the siRNA comprises the nucleotide sequence shown in SEQ ID NO: 305, and the antisense strand of the siRNA comprises the nucleotide sequence shown in SEQ ID NO: 306:

(SEQ ID NO: 305)
5'-AACUUUCUAUUUCAAGAU$Z_{23}$-3';

(SEQ ID NO: 306)
5'-$Z_{24}$AUCUUGAAAUAGAAAGUUGC-3', or, the sense strand of the siRNA comprises the nucleotide sequence shown in SEQ ID NO: 307, and the antisense strand of the siRNA comprises the nucleotide sequence shown in SEQ ID NO: 308:

(SEQ ID NO: 307)
5'-GCAACUUUCUAUUUCAAGAU$Z_{23}$-3';

(SEQ ID NO: 308)
5'-$Z_{24}$AUCUUGAAAUAGAAAGUUGCGU-3', wherein, $Z_{24}$ is the first nucleotide from 5' terminal of the antisense strand; $Z_{24}$ is selected from A, U, G or C; and $Z_{23}$ is a nucleotide complementary to $Z_{24}$.

In some embodiments, the siRNA of the present disclosure is siKNa1, siKNa2, siKNb1, siKNb2, siKNc1, siKNc2, siKNd1, siKNd2, siKNe1, siKNe2, siKNf1 and siKNf2 listed in Tables 1a-1f.

As described above, the nucleotides in the siRNA of the present disclosure are each independently modified or unmodified nucleotides. In some embodiments, each nucleotide in the siRNA of the present disclosure is an unmodified nucleotide. In some embodiments, some or all nucleotides in the siRNA of the present disclosure are modified nucleotides. Such modifications on the nucleotides would not cause significant decrease or loss of the function of the siRNA of the present disclosure to inhibit the expression of KNG genes.

In some embodiments, the siRNA of the present disclosure comprises at least one modified nucleotide. In the context of the present disclosure, the term "modified nucleotide" employed herein refers to a nucleotide formed by substituting the 2'-hydroxy of the ribose group of a nucleotide with other groups, a nucleotide analogue, or a nucleotide with modified base. Such modified nucleotides would not cause significant decrease or loss of the function of the siRNA to inhibit the expression of genes. For example, the modified nucleotides disclosed in J. K. Watts, G. F. Deleavey and M. J. Damha, Chemically Modified siRNA: tools and applications. Drug Discov Today, 2008.13(19-20): p. 842-55 may be selected.

In some embodiments, at least one nucleotide in the sense strand or the antisense strand of the siRNA provided by the present disclosure is a modified nucleotide, and/or at least one phosphate group is a phosphate group with modified group. In other words, at least a portion of the phosphate groups and/or ribose groups in phosphate-sugar backbone of at least one single strand in the sense strand and the antisense strand are phosphate groups with modified groups and/or ribose groups with modified groups.

In some embodiments, all nucleotides in the sense strand and/or the antisense strand are modified nucleotides. In some embodiments, each nucleotide in the sense strand and the antisense strand of the siRNA provided by the present disclosure is independently a fluoro modified nucleotide or a non-fluoro modified nucleotide.

The inventors of the present disclosure have surprisingly found that the siRNA of the present disclosure has achieved a high degree of balance between the stability in serum and the gene silencing efficiency in animal experiments.

In some embodiments, the fluoro modified nucleotides are located in the nucleotide sequence I and the nucleotide sequence II; and in the direction from 5' terminal to 3' terminal, at least the nucleotides at positions 7, 8 and 9 of the nucleotide sequence I are fluoro modified nucleotides; and in the direction from 5' terminal to 3' terminal, at least the nucleotides at positions 2, 6, 14 and 16 of the nucleotide sequence II are fluoro modified nucleotides.

In some embodiments, the fluoro modified nucleotides are located in the nucleotide sequence I and the nucleotide sequence II; no more than 5 fluoro modified nucleotides are present in the nucleotide sequence I, and in the direction from 5' terminal to 3' terminal, at least the nucleotides at positions 7, 8 and 9 in the nucleotide sequence I are fluoro modified nucleotides; no more than 7 fluoro modified nucleotides are present in the nucleotide sequence II, and at least the nucleotides at positions 2, 6, 14 and 16 in the nucleotide sequence II are fluoro modified nucleotides.

In some embodiments, in the direction from 5' terminal to 3' terminal, the nucleotides at positions 7, 8 and 9 or at positions 5, 7, 8 and 9 of the nucleotide sequence I in the sense strand are fluoro modified nucleotides, and the nucleotides at the rest of positions in the sense strand are non-fluoro modified nucleotides; and in the direction from 5' terminal to 3' terminal, the nucleotides at positions 2, 6, 14 and 16 or at positions 2, 6, 8, 9, 14 and 16 of the nucleotide sequence II in the antisense strand are fluoro modified nucleotides, and the nucleotides at the rest of positions in the antisense strand are non-fluoro modified nucleotides.

In the context of the present disclosure, a "fluoro modified nucleotide" refers to a nucleotide which is formed by substituting the 2'-hydroxy of the ribose group of a nucleotide with fluoro, which has a structure as shown by Formula (7). A "non-fluoro modified nucleotide", refers to a nucleotide which is formed by substituting the 2'-hydroxy of the ribose group of a nucleotide with a non-fluoro group, or a nucleotide analogue. In some embodiments, each non-fluoro modified nucleotide is independently selected from a nucleotide formed by substituting the 2'-hydroxy of the ribose group of the nucleotide with the non-fluoro group, or the nucleotide analogue.

These nucleotides formed by substituting the 2'-hydroxy of the ribose group with the non fluoro group are well-known to those skilled in the art, and these nucleotides may be selected from one of a 2' alkoxy modified nucleotide, a 2'-substituted alkoxy modified nucleotide, a 2'-alkyl modified nucleotide, a 2'-substituted alkyl modified nucleotide, a 2'-amino modified nucleotide, a 2' substituted amino modified nucleotide and a 2'-deoxy nucleotide.

In some embodiments, the 2'-alkoxy modified nucleotide is a methoxy modified nucleotide (2'-OMe), as shown by Formula (8). In some embodiments, the 2'-substituted alkoxy modified nucleotide is, for example, a 2'-O-methoxyethoxy modified nucleotide (2'-MOE) as shown by Formula (9). In some embodiments, the 2'-amino modified nucleotide ($2'-NH_2$) is as shown by Formula (10). In some embodiments, the 2'-deoxy nucleotide (DNA) is as shown by Formula (11):

Formula (7)

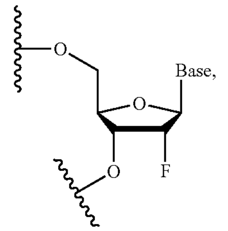

Formula (8)

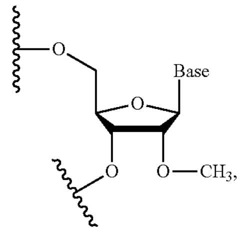

Formula (9)

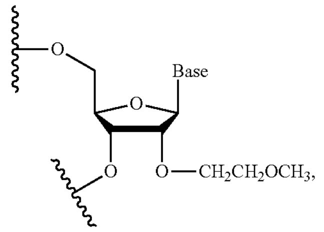

Formula (10)

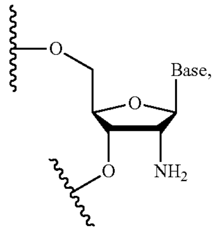

Formula (11)

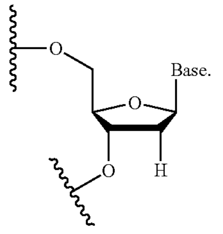

The nucleotide analogue refers to a group that can replace a nucleotide in a nucleic acid, while structurally differs from an adenine ribonucleotide, a guanine ribonucleotide, a cytosine ribonucleotide, a uracil ribonucleotide or a thymidine deoxyribonucleotide. In some embodiments, the nucleotide analogue may be an isonucleotide, a bridged nucleic acid (referred to as BNA) or an acyclic nucleotide.

The BNA is a nucleotide that is constrained or is not accessible. The BNA may contain a 5-membered ring, 6-membered ring or 7-membered ring bridged structure with "fixed" C3'-endo sugar puckering. The bridge is typically incorporated at the 2'- and 4'-position of the ribose to afford a 2',4'-BNA nucleotide. In some embodiments, the BNA may be LNA, ENA, cET BNA, etc., wherein the LNA is as shown by Formula (12), the ENA is as shown by Formula (13) and the cET BNA is as shown by Formula (14):

Formula (12)

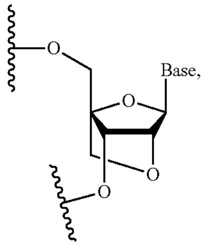

Formula (13)

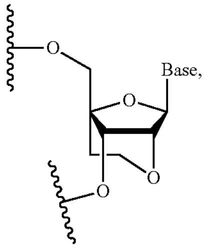

Formula (14)

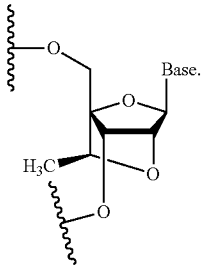

Acyclic nucleotides are a class of nucleotides formed by opening the sugar ring of nucleotides. In some embodiments, the acyclic nucleotide may be an unlocked nucleic acid (UNA) or a glycerol nucleic acid (GNA), wherein the UNA is as shown by Formula (15), and the GNA is as shown by Formula (16):

Formula (15)

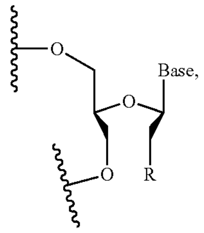

Formula (16)

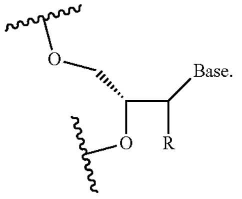

In the Formula (15) and the Formula (16), R is selected from H, OH or alkoxy (O-alkyl).

An isonucleotide is a compound which is formed by that in a nucleotide the position of a base on a ribose ring alters. In some embodiments, the isonucleotide may be a compound in which the base is transposed from position-1' to position-2' or position-3' on the ribose ring, as shown by Formula (17) or (18).

Formula (17)

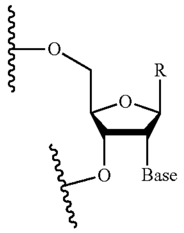

Formula (18)

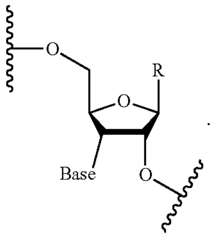

In the compounds as shown by the Formula (17) and Formula (18) above, Base represents a base, such as A, U, G, C or T; and R is selected from H, OH, F or a non-fluoro group described above.

In some embodiments, the nucleotide analogue is selected from one of an isonucleotide, an LNA, an ENA, a cET, a UNA and a GNA. In some embodiments, each non-fluoro modified nucleotide is a methoxy modified nucleotide. In the context of the present disclosure, the methoxy modified nucleotide refers to a nucleotide formed by substituting the 2'-hydroxy of the ribose group with a methoxy group.

In the context of the present disclosure, a “fluoro modified nucleotide”, a “2'-fluoro modified nucleotide”, a “nucleotide in which the 2'-hydroxy of the ribose group is substituted with fluoro” and a “nucleotide with 2'-fluororibosyl” have the same meaning, referring to a compound formed by substituting the 2'-hydroxy of the nucleotide with fluoro, having a structure as shown by Formula (7). A “methoxy modified nucleotide”, a “2'-methoxy modified nucleotide”, a “nucleotide in which the 2'-hydroxy of the ribose group is substituted with methoxy” and a “nucleotide with 2'-methoxyribosyl” have the same meaning, referring to a compound formed by substituting the 2'-hydroxy of the ribose group of the nucleotide with methoxy, having a structure as shown by Formula (8).

In some embodiments, the siRNA of the present disclosure is an siRNA with the following modifications: in the direction from 5' terminal to 3' terminal, the nucleotides at positions 7, 8 and 9 or at positions 5, 7, 8 and 9 of the nucleotide sequence I in the sense strand are fluoro modified nucleotides, and the nucleotides at the rest of positions in the sense strand are methoxy modified nucleotides; and the nucleotides at positions 2, 6, 14 and 16 or at positions 2, 6, 8, 9, 14 and 16 of the nucleotide sequence II in the antisense strand are fluoro modified nucleotides, and the nucleotides at the rest of positions in the antisense strand are methoxy modified nucleotides.

In some embodiments, the siRNA of the present disclosure is an siRNA with the following modifications: in the direction from 5' terminal to 3' terminal, the nucleotides at positions 5, 7, 8 and 9 of the nucleotide sequence I in the sense strand of the siRNA are fluoro modified nucleotides, and the nucleotides at the rest of positions in the sense strand of the siRNA are methoxy modified nucleotides; and, in the direction from 5' terminal to 3' terminal, the nucleotides at positions 2, 6, 8, 9, 14 and 16 of the nucleotide sequence II in the antisense strand of the siRNA are fluoro modified nucleotides, and the nucleotides at the rest of positions in the antisense strand of the siRNA are methoxy modified nucleotides;

or, in the direction from 5' terminal to 3' terminal, the nucleotides at positions 5, 7, 8 and 9 of the nucleotide sequence I in the sense strand of the siRNA are fluoro modified nucleotides, and the nucleotides at the rest of positions in the sense strand of the siRNA are methoxy modified nucleotides; and, in the direction from 5' terminal to 3' terminal, the nucleotides at positions 2, 6, 14 and 16 of the nucleotide sequence II in the antisense strand of the siRNA are fluoro modified nucleotides, and the nucleotides at the rest of positions in the antisense strand of the siRNA are methoxy modified nucleotides;

or, in the direction from 5' terminal to 3' terminal, the nucleotides at positions 7, 8 and 9 of the nucleotide sequence I in the sense strand of the siRNA are fluoro modified nucleotides, and the nucleotides at the rest of positions in the sense strand of the siRNA are methoxy modified nucleotides; and, in the direction from 5' terminal to 3' terminal, the nucleotides at positions 2, 6, 14 and 16 of the nucleotide sequence II in the antisense strand of the siRNA are fluoro modified nucleotides, and the nucleotides at the rest of positions in the antisense strand of the siRNA are methoxy modified nucleotides.

In some embodiments, the siRNA provided by the present disclosure is any one of siKNa1-M1, siKNa1-M2, siKNa1-M3, siKNa2-M1, siKNa2-M2, siKNa2-M3, siKNb1-M1, siKNb1-M2, siKNb1-M3, siKNb2-M1, siKNb2-M2, siKNb2-M3, siKNc1-M1, siKNc1-M2, siKNc1-M3, siKNc2-M1, siKNc2-M2, siKNc2-M3, siKNd1-M1, siKNd1-M2, siKNd1-M3, siKNd2-M1, siKNd2-M2, siKNd2-M3, siKNe1-M1, siKNe1-M2, siKNe1-M3, siKNe2-M1, siKNe2-M2, siKNe2-M3, siKNf1-M1, siKNf1-M2, siKNf1-M3, siKNf2-M1, siKNf2-M2 and siKNf2-M3 listed in Tables 1a-1f.

The siRNAs with the above modifications not only have low cost, but also allow the ribonucleases in the blood to be less liable to cleaving the nucleic acid so as to increase the stability of the nucleic acid and enable the nucleic acid to have stronger resistance against nuclease hydrolysis. Meanwhile, the modified siRNA above has higher activity of inhibiting the target mRNA.

In some embodiments, at least a portion of the phosphate groups in phosphate-sugar backbone of at least one single strand in the sense strand and the antisense strand of the siRNA provided by the present disclosure are phosphate groups with modified groups. In some embodiments, the phosphate group with modified group is a phosphorothioate group formed by substituting at least one oxygen atom in a phosphodiester bond in the phosphate group with a sulfur atom; and in some embodiments, the phosphate group with modified group is a phosphorothioate group having a structure as shown by Formula (1):

Formula (1)

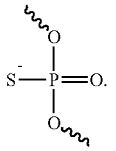

This modification can stabilize the double-stranded structure of the siRNA, thereby maintaining high specificity and high affinity for base pairing.

In some embodiments, in the siRNA provided by the present disclosure, phosphorothioate linkages exist in at least one of the groups consisting of the following positions: the position between the first nucleotide and second nucleotides at either terminal of the sense strand or antisense strand; the position between the second and third nucleotides at either terminal of the sense strand or antisense strand; or any combination thereof. In some embodiments, the phosphorothioate linkages exist at all the above positions except for 5' terminal of the sense strand. In some embodiments, the phosphorothioate linkages exist at all the above positions except for 3' terminal of the sense strand. In some embodiments, the phosphorothioate linkages exist in at least one of the following positions:

the position between the first nucleotide and the second nucleotide at 5' terminal of the sense strand;

the position between the second nucleotide and the third nucleotide at 5' terminal of the sense strand;

the position between the first nucleotide and the second nucleotide at 3' terminal of the sense strand;

the position between the second nucleotide and the third nucleotide at 3' terminal of the sense strand;

the position between the first nucleotide and the second nucleotide at 5' terminal of the antisense strand;

the position between the second nucleotide and the third nucleotide at 5' terminal of the antisense strand;

the position between the first nucleotide and the second nucleotide at 3' terminal of the antisense strand; and the position between the second nucleotide and the third nucleotide at 3' terminal of the antisense strand.

In some embodiments, the siRNA provided by the present disclosure is any one of siKNa1-M1S, siKNa1-M2S, siKNa1-M3S, siKNa2-M1S, siKNa2-M2S, siKNa2-M3S, siKNb1-M1S, siKNb1-M2S, siKNb1-M3S, siKNb2-M1S, siKNb2-M2S, siKNb2-M3S, siKNc1-M1S, siKNc1-M2S, siKNc1-M3S, siKNc2-M1S, siKNc2-M2S, siKNc2-M3S, siKNd1-M1S, siKNd1-M2S, siKNd1-M3S, siKNd2-M1S, siKNd2-M2S, siKNd2-M3S, siKNe1-M1S, siKNe1-M2S, siKNe1-M3S, siKNe2-M1S, siKNe2-M2S, siKNe2-M3S, siKNf1-M1S, siKNf1-M2S, siKNf1-M3S, siKNf2-M1S, siKNf2-M2S and siKNf2-M3S listed in Tables 1a-1f.

In some embodiments, the 5'-terminal nucleotide in the antisense strand of the siRNA is a 5'-phosphate nucleotide or a 5'-phosphate analogue modified nucleotide.

Common types of the 5'-phosphate nucleotides or 5'-phosphate analogue modified nucleotides are well known to those skilled in the art; for example, the 5'-phosphate nucleotides may have the following structure:

Formula (2)

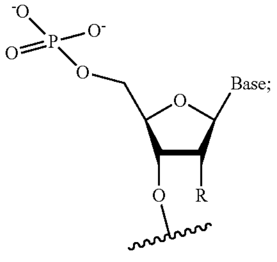

For another example, Anastasia Khvorova and Jonathan K. Watts, The chemical evolution of oligonucleotide therapies of clinical utility. Nature Biotechnology, 2017, 35(3): 238-48 disclose the following four 5'-phosphate analogue modified nucleotides:

Formula (3)

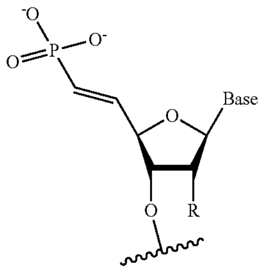

Formula (4)

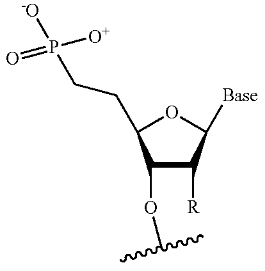

Formula (5)

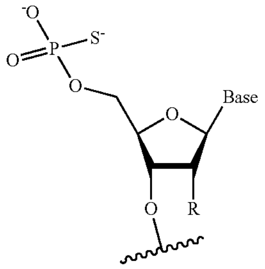

Formula (6)

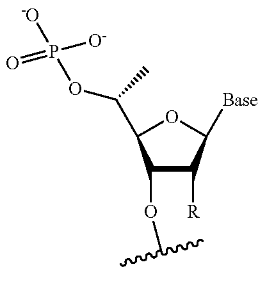

wherein, R is selected from H, OH, methoxy or F; and Base represents a base selected from A, U, C, G, or T.

In some embodiments, the 5'-phosphate nucleotide is a nucleotide with 5'-phosphate modification as shown by Formula (2); the 5'-phosphate analogue modified nucleotide is a nucleotide with 5'-(E)-vinylphosphonate (E-VP) modification as shown by Formula (3) or a phosphorothioate modified nucleotide as shown by Formula (5).

In some embodiments, the siRNA provided by the present disclosure is any one of siKNa1-M1P1, siKNa1-M2P1, siKNa1-M3P1, siKNa2-M1P1, siKNa2-M2P1, siKNa2-M3P1, siKNa1-M1SP1, siKNa1-M2SP1, siKNa1-M3SP1, siKNa2-M1SP1, siKNa2-M2SP1, siKNa2-M3SP1, siKNb1-M1P1, siKNb1-M2P1, siKNb1-M3P1, siKNb2-M1P1, siKNb2-M2P1, siKNb2-M3P1, siKNb1-M1SP1, siKNb1-M2SP1, siKNb1-M3SP1, siKNb2-M1SP1, siKNb2-M2SP1, siKNb2-M3SP1, siKNc1-M1P1, siKNc1-M2P1, siKNc1-M3P1, siKNc2-M1P1, siKNc2-M2P1, siKNc2-M3P1, siKNc1-M1SP1, siKNc1-M2SP1, siKNc1-M3SP1, siKNc2-M1SP1, siKNc2-M2SP1, siKNc2-M3SP1, siKNd1-M1P1, siKNd1-M2P1, siKNd1-M3P1, siKNd2-M1P1, siKNd2-M2P1, siKNd2-M3P1, siKNd1-M1SP1, siKNd1-M2SP1, siKNd1-M3SP1, siKNd2-M1SP1, siKNd2-M2SP1, siKNd2-M3SP1, siKNe1-M1P1, siKNe1-M2P1, siKNe1-M3P1, siKNe2-M1P1, siKNe2-M2P1, siKNe2-M3P1, siKNe1-M1SP1, siKNe1-M2SP1, siKNe1-M3SP1, siKNe2-M1SP1, siKNe2-M2SP1, siKNe2-M3SP1, siKNf1-M1P1, siKNf1-M2P1, siKNf1-M3P1, siKNf2-M1P1, siKNf2-M2P1, siKNf2-M3P1, siKNf1-M1SP1, siKNf1-M2SP1, siKNf1-M3SP1, siKNf2-M1SP1, siKNf2-M2SP1 and siKNf2-M3SP1 listed in Tables 1a-1f.

The inventors of the present disclosure have surprisingly found that the siRNA provided by the present disclosure not only has significantly enhanced plasma and lysosomal stability, but also has higher inhibitory activity of target mRNA.

The siRNA provided by the present disclosure can be obtained by conventional methods for preparing siRNAs in the art (e.g., solid phase synthesis and liquid phase synthesis methods). Commercial customization services have already been available for solid phase synthesis. Modified nucleotide groups can be introduced into the siRNAs of the present disclosure by using a nucleotide monomer having a corresponding modification, wherein the methods for preparing a nucleotide monomer having a corresponding modification and the methods for introducing a modified nucleotide group into an siRNA are also well-known to those skilled in the art.

Pharmaceutical Composition

The present disclosure provides a pharmaceutical composition, wherein the pharmaceutical composition comprises the siRNA described above as an active ingredient, and a pharmaceutically acceptable carrier.

The pharmaceutically acceptable carrier may be a carrier conventionally used in the field of siRNA administration, for example, but not limited to, one or more of magnetic nanoparticles (such as $Fe_3O_4$ or $Fe_2O_3$-based nanoparticle), carbon nanotubes, mesoporous silicon, calcium phosphate nanoparticles, polyethylenimine (PEI), polyamidoamine (PAMAM) dendrimer, poly(L-lysine) (PLL), chitosan, 1,2-dioleoyl-3-trimethylammonium-propane (DOTAP), poly (D&L-lactic/glycolic acid) copolymer (PLGA), poly(2-aminoethyl ethylene phosphate) (PPEEA), poly(2-dimethylaminoethyl methacrylate) (PDMAEMA), and derivatives thereof.

In the pharmaceutical composition, there are no special requirements for the contents of the siRNA and the pharmaceutically acceptable carrier, which may be the conventional content of each component. In some embodiments, the weight ratio of the siRNA to the pharmaceutically acceptable carrier is 1:(1-500), and in some embodiments, the weight ratio above is 1:(1-50).

In some embodiments, the pharmaceutical composition may also comprise other pharmaceutically acceptable excipients, which may be one or more of various conventional formulations or compounds in the art. For example, the other pharmaceutically acceptable excipients may comprise at least one of a pH buffer solution, a protective agent and an osmotic pressure regulator.

The pH buffer solution may be a tris(hydroxymethyl) aminomethane hydrochloride buffer solution with a pH of 7.5-8.5, and/or a phosphate buffer solution with a pH of 5.5-8.5, for example, it may be a phosphate buffer solution with a pH of 5.5-8.5.

The protective agent may be at least one of inositol, sorbitol, sucrose, trehalose, mannose, maltose, lactose, and glucose. The content of the protective agent may be from 0.01 wt % to 30 wt % on the basis of the total weight of the pharmaceutical composition.

The osmotic pressure regulator may be sodium chloride and/or potassium chloride. The content of the osmotic pressure regulator allows an osmotic pressure of the pharmaceutical composition to be 200-700 milliosmol/kg (mOsm/kg). Depending on the desired osmotic pressure, those skilled in the art can readily determine the content of the osmotic pressure regulator.

In some embodiments, the pharmaceutical composition may be a liquid formulation, for example, an injection solution; or a lyophilized powder for injection, which is mixed with a liquid excipient to form a liquid formulation during administration. The liquid formulation may be administered by, but not limited to, subcutaneous, intramuscular or intravenous injection routes, and also may be administered to, but not limited to, lung by spray, or other organs (such as liver) via lung by spray. In some embodiments, the pharmaceutical composition is administered by intravenous injection.

In some embodiments, the pharmaceutical composition may be in the form of a liposome formulation. In some embodiments, the pharmaceutically acceptable carrier used in the liposome formulation comprises an amine-containing transfection compound (hereinafter also referred to as an organic amine), a helper lipid and/or a pegylated lipid. The organic amine, the helper lipid and the pegylated lipid may be respectively selected from one or more of the amine-containing transfection compounds or the pharmaceutically acceptable salts or derivatives thereof, the helper lipids and the pegylated lipids as described in CN103380113A (which is incorporated herein by reference in its entirety).

In some embodiments, the organic amine may be a compound as shown by Formula (201) as described in CN103380113A or a pharmaceutically acceptable salt thereof:

Formula (201)

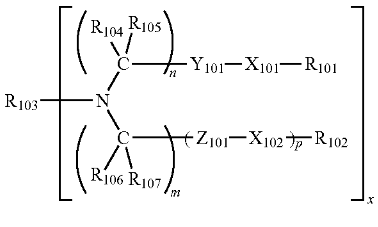

wherein:

each of $X_{101}$ or $X_{102}$ is independently O, S, N-A or C-A, wherein A is hydrogen or a C1-C20 hydrocarbon chain;

each of $Y_{101}$ or $Z_{101}$ is independently C═O, C═S, S═O, CH—OH or $SO_2$;

each of $R_{101}$, $R_{102}$, $R_{103}$, $R_{104}$, $R_{105}$, $R_{106}$ or $R_{107}$ is independently hydrogen; a cyclic or acyclic, substituted or unsubstituted, branched or linear aliphatic group; a cyclic or acyclic, substituted or unsubstituted, branched or linear heteroaliphatic group; a substituted or unsubstituted, branched or linear acyl group; a substituted or unsubstituted, branched or linear aryl; or a substituted or unsubstituted, branched or linear heteroaryl;

x is an integer of 1-10;

n is an integer of 1-3, m is an integer of 0-20, and p is 0 or 1, wherein if m=p=0, then $R_{102}$ is hydrogen, and if at least one of n or m is 2, then $R_{103}$ and the nitrogen in Formula (201) form a structure as shown by Formula (202) or (203):

Formula (202)

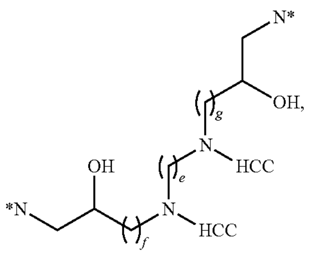

Formula (203)

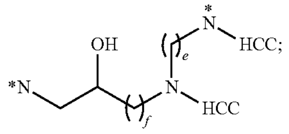

wherein g, e or f is each independently an integer of 1-6, "HCC" represents a hydrocarbon chain, and each *N represents a nitrogen atom shown in Formula (201).

In some embodiments, $R_{103}$ is a polyamine. In other embodiments, $R_{103}$ is a ketal. In some embodiments, each of $R_{101}$ and $R_{102}$ in the Formula (201) is independently any substituted or unsubstituted, branched or linear alkyl or alkenyl, wherein the alkyl or alkenyl has 3 to about 20 carbon atoms (such as 8 to about 18 carbon atoms) and 0 to 4 double bonds (such as 0 to 2 double bonds).

In some embodiments, if each of n and m is independently 1 or 3, $R_{103}$ may be any in the following Formulae (204)-(213):

Formula (204)

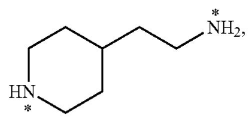

Formula (205)

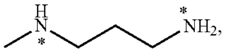

-continued

Formula (206)

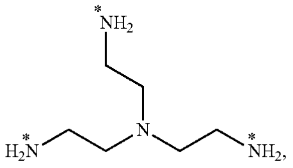

Formula (207)

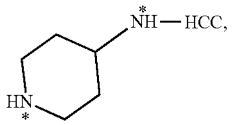

Formula (208)

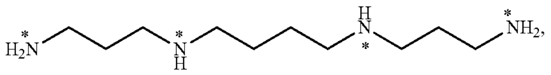

Formula (209)

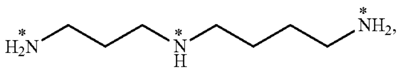

Formula (210)

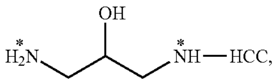

Formula (211)

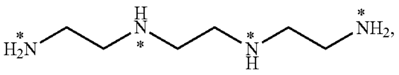

-continued

Formula (212)

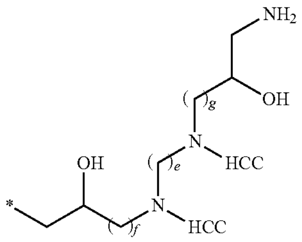

and

Formula (213)

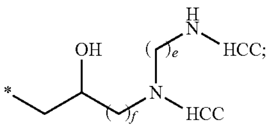

wherein, in Formula (204) to Formula (213), each of g, e and f is independently an integer of 1-6; each "HCC" represents a hydrocarbon chain, and each * represents a potential attachment point of $R_{103}$ to the nitrogen atom in Formula (201), wherein each H at any * position may be replaced to realize the attachment to the nitrogen atom in Formula (201).

Wherein, the compound as shown by (201) may be prepared as described in CN103380113A.

In some embodiments, the organic amine may be an organic amine as shown by Formula (214) and/or an organic amine as shown by Formula (215):

Formula (214)

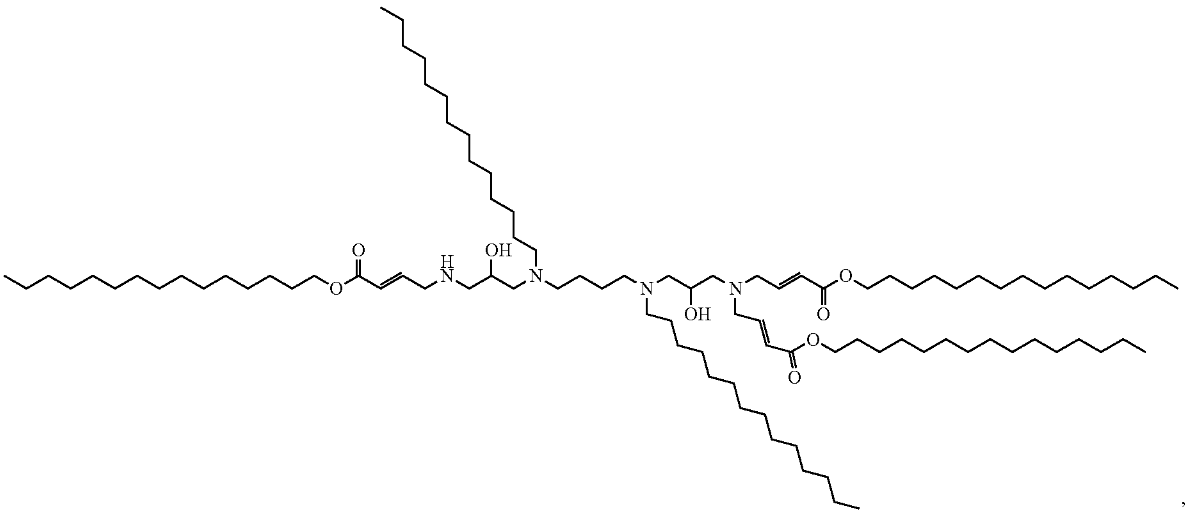

,

-continued

Formula (215)

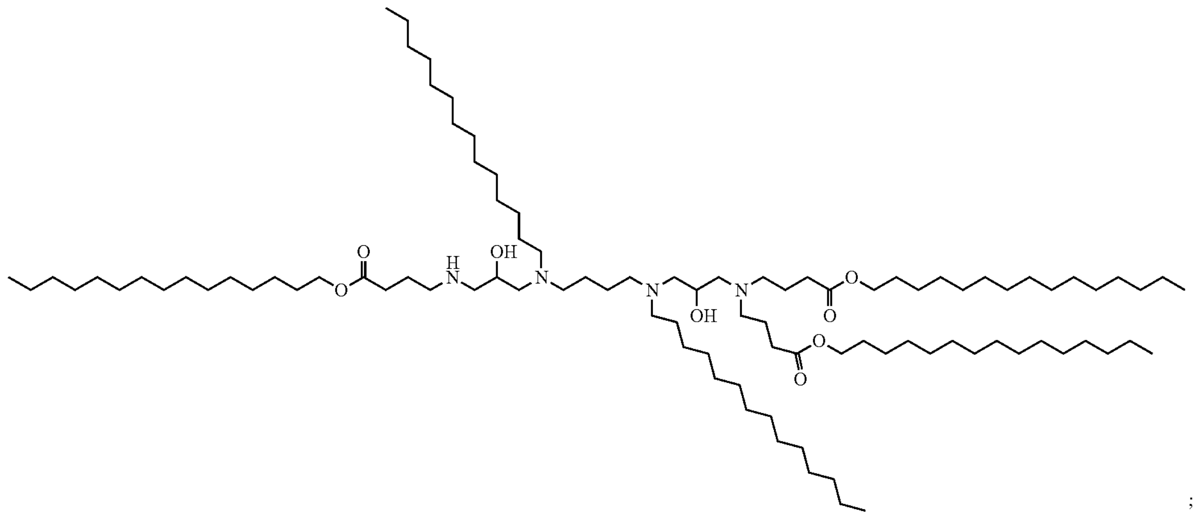

;

The helper lipid is a cholesterol, a cholesterol analogue and/or a cholesterol derivative.

The pegylated lipid is 1,2-dipalmitamide-sn-glycero-3-phosphatidylethanolamin e-N-[methoxy(polyethylene glycol)]-2000.

In some embodiments, the molar ratio among the organic amine, the helper lipid, and the pegylated lipid in the pharmaceutical composition is (19.7-80):(19.7-80):(0.3-50); for example, the molar ratio may be (50-70):(20-40):(3-20).

In some embodiments, the pharmaceutical compositions particles formed by the siRNA of the present disclosure and the above amine-containing transfection agent have an average diameter from about 30 nm to about 200 nm, typically from about 40 nm to about 135 nm, and more typically, the average diameter of the liposome particles is from about 50 nm to about 120 nm, from about 50 nm to about 100 nm, from about 60 nm to about 90 nm, or from about 70 nm to about 90 nm, for example, the average diameter of the liposome particles is about 30, 40, 50, 60, 70, 75, 80, 85, 90, 100, 110, 120, 130, 140, 150 or 160 nm.

In some embodiments, in the pharmaceutical composition formed by the siRNA of the present disclosure and the above amine-containing transfection agent, the weight ratio (weight/weight ratio) of the siRNA to total lipids (e.g., the organic amine, the helper lipid and/or the pegylated lipid), ranges from about 1:1 to about 1:50, from about 1:1 to about 1:30, from about 1:3 to about 1:20, from about 1:4 to about 1:18, from about 1:5 to about 1:17, from about 1:5 to about 1:15, from about 1:5 to about 1:12, from about 1:6 to about 1:12, or from about 1:6 to about 1:10. For example, the ratio of the siRNA of the present disclosure to the total lipids is about 1:5, 1:6, 1:7, 1:8, 1:9, 1:10, 1:11, 1:12, 1:13, 1:14, 1:15, 1:16, 1:17 or 1:18 by weight.

In some embodiments, the pharmaceutical composition may be marketed with each component being separate, and used in the form of a liquid formulation. In some embodiments, the pharmaceutical composition formed by the siRNA of the present disclosure and the above pharmaceutically acceptable carrier may be prepared by various known processes, except replacing the existing siRNA with the siRNA of the present disclosure. In some embodiments, the pharmaceutical composition may be prepared according to the following process.

The organic amines, helper lipids and pegylated lipids are suspended in alcohol at a molar ratio as described above and mixed homogeneously to yield a lipid solution; and the alcohol is used in an amount such that the resultant lipid solution is present at a total mass concentration of 2 to 25 mg/mL, e.g., the total mass concentration may be 8 to 18 mg/mL. The alcohol is selected from pharmaceutically acceptable alcohols, such as an alcohol that is in liquid form at about room temperature, for example, one or more of ethanol, propylene glycol, benzyl alcohol, glycerol, PEG 200, PEG 300, PEG 400, and for example, the alcohol may be ethanol.

The siRNA provided by the present disclosure is dissolved in a buffer salt solution to obtain an aqueous solution of the siRNA. The buffer salt solution has a concentration of 0.05-0.5 M, e.g., the concentration may be 0.1-0.2 M. The pH of the buffer salt solution is adjusted to 4.0-5.5, e.g., the pH may be 5.0-5.2. The buffer salt solution is used in an amount such that the siRNA is present at a concentration of no more than 0.6 mg/ml, e.g., the siRNA may present at a concentration of 0.2-0.4 mg/mL. The buffer salt may be one or more selected from the group consisting of soluble acetate and soluble citrate, such as sodium acetate and/or potassium acetate.

The lipid solution and the aqueous solution of the siRNA are mixed. The product obtained after mixing is incubated at a temperature of 40-60° C. for at least 2 minutes (e.g., 5-30 minutes) to produce an incubated lipid formulation. The volume ratio of the lipid solution to the aqueous solution of the siRNA is 1:(2-5).

The incubated liposome formulation is concentrated or diluted, purified to remove impurities, and then sterilized to obtain the pharmaceutical composition provided by the present disclosure, which has physicochemical parameters as follows: a pH of 6.5-8, an encapsulation percentage of no less than 80%, a particle size of 40-200 nm, a polydispersity index of no more than 0.30, and an osmotic pressure of 250-400 mOsm/kg; for example, the physicochemical parameters may be as follows: a pH of 7.2-7.6, an encapsulation percentage of no less than 90%, a particle size of 60-100 nm, a polydispersity index of no more than 0.20, and an osmotic pressure of 300-400 mOsm/kg.

Wherein, the concentration or dilution step may be performed before, after or simultaneously with the step of impurity removal. The method for removing impurities may be any of various existing methods, for example, ultrafiltration using tangential flow system with hollow fiber column under 100 KDa and using a phosphate buffer solution (PBS) at pH 7.4 as an ultrafiltration exchange solution. The method for sterilization may be any of various existing methods, such as filtration sterilization on a 0.22 μm filter.

siRNA Conjugate

The present disclosure provides an siRNA conjugate, wherein the siRNA conjugate comprises the siRNA described above and a conjugating group conjugated to the siRNA.

Generally, the conjugating group comprises at least one pharmaceutically acceptable targeting group and an optional linker. Moreover, the siRNA, the linker and the targeting group are linked in succession. In some embodiments, there are 1-6 targeting groups. In some embodiments, there are 2-4 targeting groups. The siRNA molecule may be non-covalently or covalently conjugated to the conjugating group, for example, the siRNA molecule may be covalently conjugated to the conjugating group. The conjugating site between the siRNA and the conjugating group may be at 3-terminal or 5'-terminal of the sense strand of the siRNA, or at 5'-terminal of the antisense strand, or within the internal sequence of the siRNA. In some embodiments, the conjugating site between the siRNA and the conjugating group is at 3' terminal of the sense strand of the siRNA.

In some embodiments, the conjugating group is linked to a phosphate group, the 2'-hydroxy or the base of a nucleotide. In some embodiments, the conjugating group may be linked to a 3'-hydroxy in which case the nucleotides are linked via a 2'-5'-phosphodiester bond. When the conjugating group is linked to a terminal of the siRNA, the conjugating group is typically linked to a phosphate group of a nucleotide; when the conjugating group is linked to an internal sequence of the siRNA, the conjugating group is typically linked to a ribose ring or a base. For various linking methods, reference may be made to: Muthiah Manoharan et. al., siRNA conjugates carrying sequentially assembled trivalent N-acetylgalactosamine linked through nucleosides elicit robust gene silencing in vivo in hepatocytes. ACS Chemical biology, 2015, 10(5):1181-7.

In some embodiments, the siRNA and the conjugating group may be linked by an acid labile or reducible chemical bond, and these chemical bonds may be degraded under the acidic environment of cell endosomes, thereby rendering the siRNA to be in a free state. For non-degradable conjugating methods, the conjugating group may be linked to the sense strand of the siRNA, thereby minimizing the effect of conjugating on the activity of the siRNA.

In some embodiments, the pharmaceutically acceptable targeting group may be a conventionally used ligand in the field of siRNA administration, for example, the various ligands as described in WO2009082607A2, which is incorporated herein by reference in its entirety.

In some embodiments, the pharmaceutically acceptable targeting group may be selected from one or more of the ligands formed by the following targeting molecules or derivatives thereof: lipophilic molecules, such as cholesterol, bile acids, vitamins (such as vitamin E), lipid molecules of different chain lengths; polymers, such as polyethylene glycol; polypeptides, such as cell-penetrating peptide; aptamers; antibodies; quantum dots; saccharides, such as lactose, polylactose, mannose, galactose, and N-acetylgalactosamine (GalNAc); folate; and receptor ligands expressed in hepatic parenchymal cells, such as asialoglycoprotein, asialo-sugar residue, lipoproteins (such as high density lipoprotein, low density lipoprotein), glucagon, neurotransmitters (such as adrenaline), growth factors, transferrin and the like.

In some embodiments, each ligand is independently selected from a ligand capable of binding to a cell surface receptor. In some embodiments, at least one ligand is a ligand capable of binding to a hepatocyte surface receptor. In some embodiments, at least one ligand is a ligand capable of binding to a mammalian cell surface receptor. In some embodiments, at least one ligand is a ligand capable of binding to a human hepatocyte surface receptor. In some embodiments, at least one ligand is a ligand capable of binding to a hepatic surface asialoglycoprotein receptor (ASGP-R). The types of these ligands are well-known to those skilled in the art and they typically serve the function of binding to specific receptors on the surface of the target cell, thereby mediating delivery of the siRNA linked to the ligand into the target cell.

In some embodiments, the pharmaceutically acceptable targeting group may be any ligand that binds to asialoglycoprotein receptors (ASGP-R) on the surface of mammalian hepatocytes. In one embodiment, each ligand is independently an asialoglycoprotein, such as asialoorosomucoid (ASOR) or asialofetuin (ASF). In some embodiments, the ligand is a saccharide or a saccharide derivative.

In some embodiments, at least one ligand is a saccharide. In some embodiments, each ligand is a saccharide. In some embodiments, at least one ligand is a monosaccharide, polysaccharide, modified monosaccharide, modified polysaccharide, or saccharide derivative. In some embodiments, at least one ligand may be a monosaccharide, disaccharide or trisaccharide. In some embodiments, at least one ligand is a modified saccharide. In some embodiments, each ligand is a modified saccharide. In some embodiments, each ligand is independently selected from the group consisting of polysaccharides, modified polysaccharides, monosaccharides, modified monosaccharides, polysaccharide derivatives or monosaccharide derivatives. In some embodiments, each ligand or at least one ligand is selected from the group consisting of the following saccharides: glucose and derivative thereof, mannose and derivative thereof, galactose and derivative thereof, xylose and derivative thereof, ribose and derivative thereof, fucose and derivative thereof, lactose and derivative thereof, maltose and derivative thereof, arabinose and derivative thereof, fructose and derivative thereof, and sialic acid.

In some embodiments, each ligand may be independently selected from following: D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, 3-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O-[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2- deoxy-1,5-dithio-α-D-glucoheptopyranoside, 2,5-anhydro-D-allononitrile, ribose, D-ribose, D-4-thioribose, L-ribose, or L-4-thioribose. Other ligand selections may be found, for example, in the description of CN105378082A, which is incorporated herein by reference in its entirety.

In some embodiments, the pharmaceutically acceptable targeting group in the siRNA conjugate may be galactose or N-acetylgalactosamine, wherein the galactose or N-acetylgalactosamine molecules may be monovalent, bivalent, trivalent and tetravalent. It should be understood that the terms monovalent, bivalent, trivalent and tetravalent described herein respectively mean that the molar ratio of the siRNA molecule to the galactose or N-acetylgalactosamine molecule in the siRNA conjugate is 1:1, 1:2, 1:3 or 1:4, wherein the siRNA conjugate is formed from the siRNA molecule and the conjugating group containing galactose or N-acetylgalactosamine as the targeting group. In some embodiments, the pharmaceutically acceptable targeting group is N-acetylgalactosamine. In some embodiments, when the siRNA of the present disclosure is conjugated to a conjugating group containing N-acetylgalactosamine, the N-acetylgalactosamine molecule is trivalent or tetravalent. In some embodiments, when the siRNA of the present disclosure is conjugated to a conjugating group containing N-acetylgalactosamine, the N-acetylgalactosamine molecule is trivalent.

The targeting group may be linked to the siRNA molecule via an appropriate linker, and the appropriate linker may be selected by those skilled in the art according to the specific type of the targeting group. The types of these linkers and targeting groups and the linking methods with the siRNA may be found in the disclosure of W2015006740A2, which is incorporated herein by reference in its entirety.

In some embodiments, when the targeting group is N-acetylgalactosamine, an appropriate linker may be a structure as shown by Formula (301):

Formula (301)

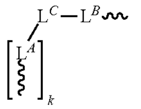

wherein, k is an integer of 1-3; and $L^A$ is an amide bond-containing chain moiety with a structure as shown by Formula (302), each the $L^A$ being respectively linked to the targeting group and the $L^C$ moiety through ether bonds at two terminals thereof:

Formula (302)

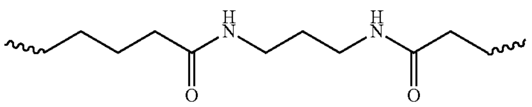

$L^B$ is an N-acylpyrrolidine-containing chain moiety with a structure as shown by Formula (303), the chain moiety having a carbonyl at one terminal thereof and being linked to the $L^C$ moiety through an amide bond, and having an oxy-group at the other terminal thereof and being linked to the siRNA via a phosphoester bond:

Formula (303)

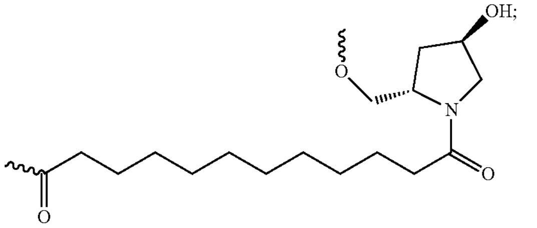

$L^C$ is a bivalent to tetravalent linking group based on hydroxymethyl aminomethane, dihydroxymethyl aminomethane or trihydroxymethyl aminomethane, the $L^C$ being linked to each of the $L^A$ moieties through an ether bond via an oxygen atom, and being linked to the $L^B$ moiety through an amide bond via a nitrogen atom.

In some embodiments, when n=3 and $L^C$ is a tetravalent linking group based on trihydroxymethyl aminomethane, the siRNA conjugate formed by linking an N-acetylgalactosamine molecule with an siRNA molecule via $-(L^A)_3$-trihydroxymethyl aminomethane-$L^B$- as a linker has a structure as shown by Formula (304):

Formula (304)

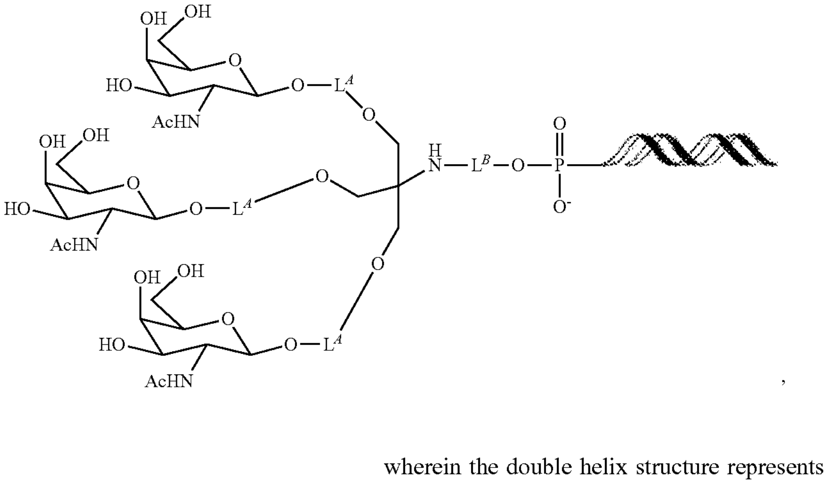

, wherein the double helix structure represents an siRNA.

Likewise, the conjugating site between the siRNA and the conjugating group nay be at the 3'-terminal or 5'-terminal of the sense strand of the siRNA, or at the 5'-terminal of the antisense strand, or within the internal sequence of the siRNA.

In some embodiments, the 3'-terminal of the sense strand of the siRNA of the present disclosure is covalently conjugated to three N-acetylgalactosamine (GalNAc) molecules via a linker $-(L^A)_3$-trihydroxymethyl aminomethane-$L^B$- to obtain an siRNA conjugate in which the molar ratio of the siRNA molecule to the GalNAc molecule is 1:3, which may also be hereinafter referred to as $(GalNAc)_3$-siRNA, and the siRNA conjugate has a structure as shown by Formula (305):

Formula (305)

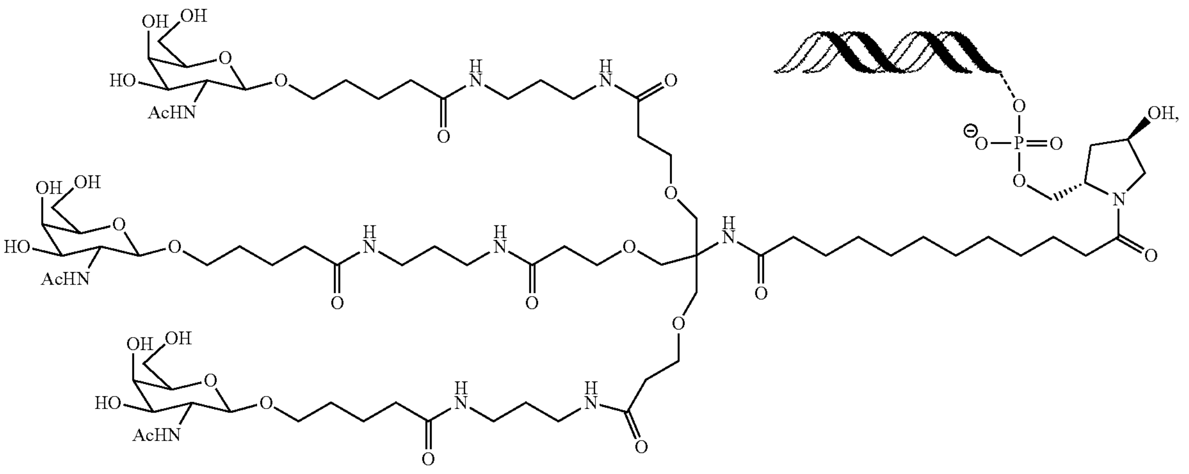

wherein the double helix structure represents an siRNA; and the linker is linked to the 3' terminal of the sense strand of the siRNA.

In some embodiments, when the targeting group is N-acetylgalactosamine, an appropriate linker may be a structure as shown by Formula (306):

Formula (306)

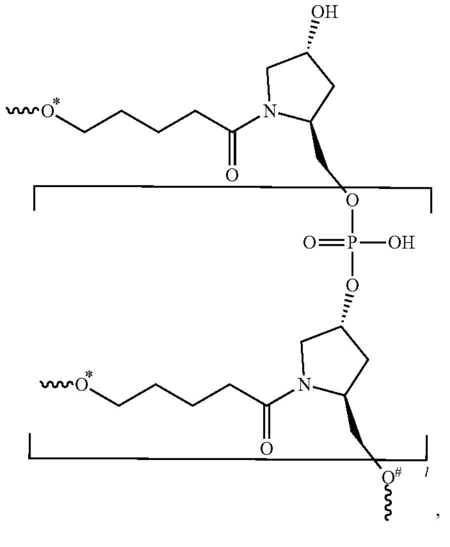

, wherein, 1 is an integer of 0-3;

* represents a site linked to the targeting group via an ether bond on the linker; and # represents a site linked to the siRNA via a phosphoester bond on the linker.

In some embodiments, when 1=2, the siRNA conjugate has a structure as shown by Formula (307):

Formula (307)

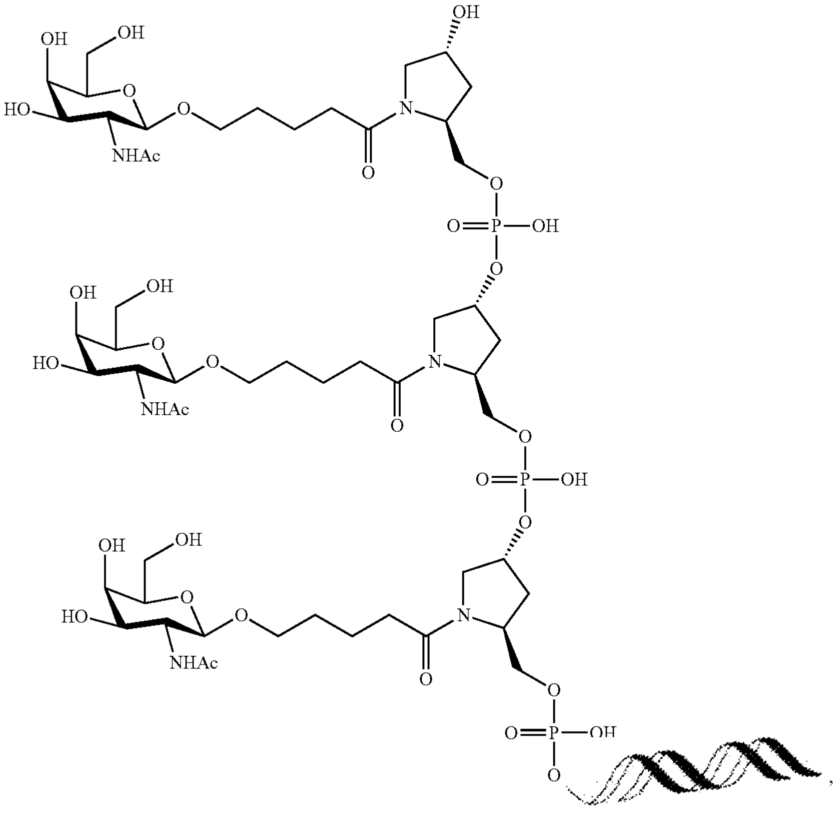

wherein the double helix structure represents an siRNA; and the linker is linked to the 3' terminal of the sense strand of the siRNA.

The above conjugates may be synthesized according to the methods described in detail in the prior art. For example, WO2015006740A2 describes the method of preparing various conjugates in detail. The siRNA conjugate of the present disclosure may be obtained by methods well known to those skilled in the art. For example, WO2014025805A1 describes the preparation method of the conjugate having a structure as shown by Formula (305). Rajeev et al., describes the preparation method of the conjugate having a structure as shown by Formula (307) in ChemBioChem 2015, 16, 903-908.

In some embodiments, the siRNA conjugate has a structure as shown by Formula (308):

Formula (308)

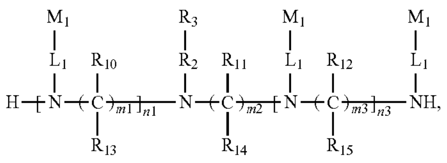

wherein:

n1 is an integer selected from 1-3, and n3 is an integer selected from 0-4;

m1, m2, or m3 is independently an integer selected from 2-10;

$R_{10}$, $R_{11}$, $R_{12}$, $R_{13}$, $R_{14}$ or $R_{15}$ is independently H or selected from the group consisting of $C_1$-$C_{10}$ alkyl, $C_1$-$C_{10}$ haloalkyl and $C_1$-$C_{10}$ alkoxy; and $R_3$ is a group having a structure as shown by Formula A59:

(A59)

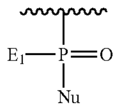

wherein, $E_1$ is OH, SH or $BH_2$, and Nu is the siRNA of the present disclosure;

$R_2$ is a linear alkylene of 1-20 carbon atoms in length, wherein one or more carbon atoms are optionally replaced with any one or more of the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene; and wherein $R_2$ may optionally have any one or more substituents in the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo substituent, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —$CO_2H$, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH$($C_1$-$C_{10}$ alkyl), —$SO_2NH$(phenyl), —$NHSO_2$($C_1$-$C_{10}$ alkyl), —$NHSO_2$(phenyl), and —$NHSO_2$($C_1$-$C_{10}$ haloalkyl); and each $L_1$ is independently a linear alkylene of 1-70 carbon atoms in length, wherein one or more carbon atoms are optionally replaced with any one or more of the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene; and wherein $L_1$ may optionally have any one or more substituents in the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo substituent, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —$CO_2H$, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH$($C_1$-$C_{10}$ alkyl), —$SO_2NH$(phenyl), —$NHSO_2$($C_1$-$C_{10}$ alkyl), —$NHSO_2$(phenyl), and —$NHSO_2$($C_1$-$C_{10}$ haloalkyl).

In some embodiments, $L_1$ may be selected from the group consisting of groups A1-A26 and any combination thereof, wherein the structures and definitions of A1-A26 are as follows:

(A1)

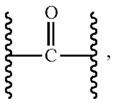

(A2)

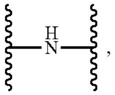

(A3)

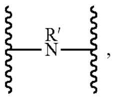

-continued (A4)

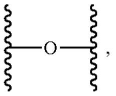

(A5)

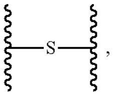

(A6)

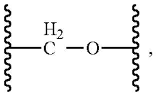

(A7)

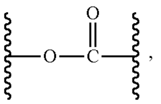

(A8)

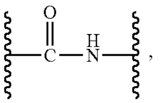

(A9)

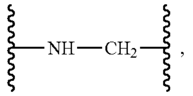

(A10)

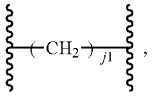

(A11)

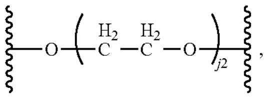

(A12)

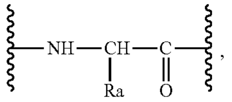

(A13)

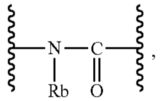

(A14)

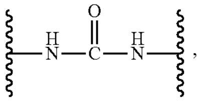

(A15)

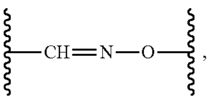

(A16)

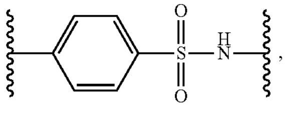

(A17)

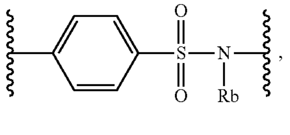

-continued
(A18)
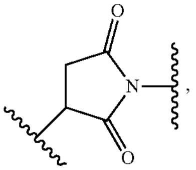
(A19)
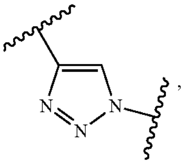
(A20)
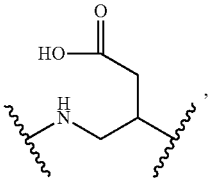
(A21)
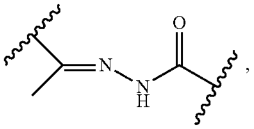
(A22)
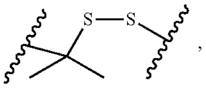
(A23)
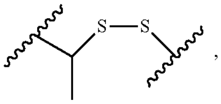
(A24)
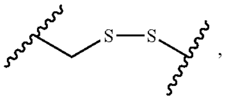
(A25)
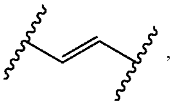
(A26)
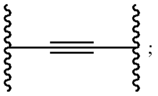
wherein, each j1 is independently an integer of 1-20; and each j2 is independently an integer of 1-20;
each R' is independently a $C_1$-$C_{10}$ alkyl; and
each Ra is independently selected from the group consisting of groups A27-A45 and any combinations thereof:
(A27)
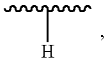
-continued
(A28)
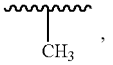
(A29)
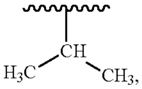
(A30)
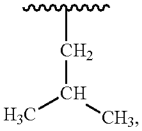
(A31)
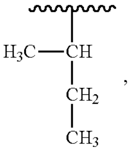
(A32)
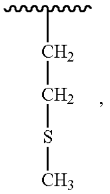
(A33)
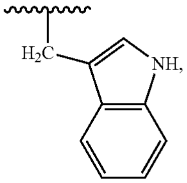
(A34)
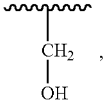
(A35)
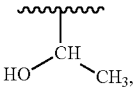
(A36)
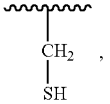
(A37)
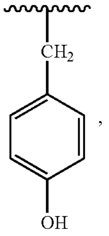
(A38)
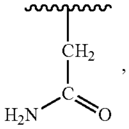

-continued (A39)

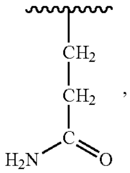

, (A40)

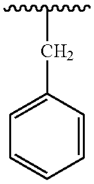

, (A41)

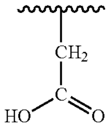

, (A42)

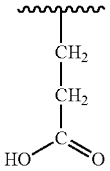

, (A43)

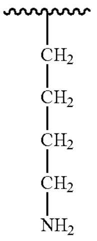

, (A44)

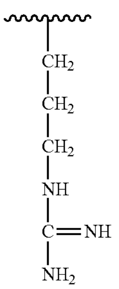

or (A45)

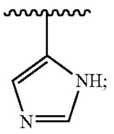

each Rb is independently a $C_1$-$C_{10}$ alkyl; and ∿∿∿ represents a site where the group is covalently linked.

Those skilled in the art would understand that, though $L_1$ is defined as a linear alkylene for convenience, but it may not be a linear group or be named differently, such as an amine or alkenyl produced by the above replacement and/or substitution. For the purpose of the present disclosure, the length of $L_1$ is the number of the atoms in the chain connecting the two attaching points. For this purpose, a ring obtained by replacement of a carbon atom of the linear alkylene, such as a heterocyclylene or heteroarylene, is counted as one atom.

$M_1$ represents a targeting group, of which the definitions and options are the same as those described above. In some embodiments, each $M_1$ is independently selected from one of the ligands that have affinity to the asialoglycoprotein receptor on the surface of mammalian hepatocytes.

When $M_1$ is a ligand that has affinity to the asialoglycoprotein receptor on the surface of mammalian hepatocytes, in some embodiments, n1 may be an integer of 1-3, and n3 may be an integer of 0-4 to ensure that the number of the $M_1$ targeting group in the siRNA conjugate may be at least 2. In some embodiments, n1+n3>2, such that the number of the $M_1$ targeting group may be at least 3, thereby allowing the $M_1$ targeting group to more conveniently bind to the asialoglycoprotein receptor on the surface of hepatocytes, which may facilitate the endocytosis of the siRNA conjugate into cells. Experiments have shown that when the number of the $M_1$ targeting group is greater than 3, the ease of binding the $M_1$ targeting group to the asialoglycoprotein receptor on the surface of hepatocytes is not significantly increased. Therefore, in view of various aspects such as synthesis convenience, structure/process costs and delivery efficiency, in some embodiments, n1 is an integer of 1-2, n3 is an integer of 0-1, and n+n3=2-3.

In some embodiments, when m1, m2, or m3 is independently selected from an integer of 2-10, the steric mutual positions among a plurality of $M_1$ targeting groups may be fit for binding the $M_1$ targeting groups to the asialoglycoprotein receptor on the surface of hepatocytes. In order to make the siRNA conjugate provided by the present disclosure simpler, easier to synthesis and/or have reduced cost, in some embodiments, m1, m2 or m3 is each independently an integer of 2-5, and in some embodiments, m1=m2=m3.

Those skilled in the art would understand that when $R_{10}$, $R_{11}$, $R_{12}$, $R_{13}$, $R_{14}$, or $R_{15}$ is each independently selected from one of H, $C_1$-$C_{10}$ alkyl, $C_1$-$C_{10}$ haloalkyl, and $C_1$-$C_{10}$ alkoxy, they would not change the properties of the siRNA conjugate of the present disclosure and could all achieve the purpose of the present disclosure. In some embodiments, $R_{10}$, $R_{11}$, $R_{12}$, $R_{13}$, $R_{14}$, or $R_{15}$ is each independently selected from selected from H, methyl or ethyl. In some embodiments, $R_{10}$, $R_{11}$, $R_{12}$, $R_{13}$, $R_{14}$, or $R_{15}$ is H.

$R_3$ is a group having the structure as shown by Formula A59, wherein $E_1$ is OH, SH or $BH_2$, and considering the availability of starting materials, in some embodiments, $E_1$ is OH or SH.

$R_2$ is selected to achieve the linkage between the A59 and the N atom on a nitrogenous backbone. In the context of the present disclosure, the "nitrogenous backbone" refers to a chain structure in which the carbon atoms attached to $R_{10}$, $R_{11}$, $R_{12}$, $R_{13}$, $R_{14}$, and $R_{15}$ and the N atoms are linked to each other. Therefore, $R_2$ may be any linking group capable of attaching the group as shown by Formula A59 to the N atom on a nitrogenous backbone by suitable means. In some embodiments, in the case where the siRNA conjugate as shown by Formula (308) is prepared by a solid phase synthesis process, $R_2$ group needs to have both a site linking to the N atom on the nitrogenous backbone and a site linking to the P atom in $R_3$. In some embodiments, in $R_2$, the site linking to the N atom on the nitrogenous backbone forms an amide bond with the N atom, and the site linking to the P atom in $R_3$ forms a phosphoester bond with the P atom. In some embodiments, $R_2$ may be B5, B6, B5' or B6':

(B5)

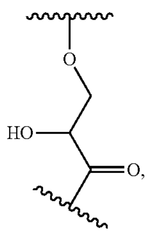

(B6)

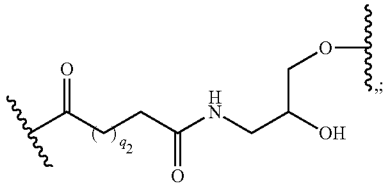

(B5′)

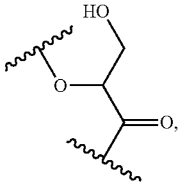

(B6′)

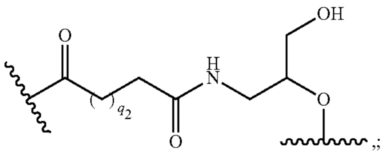

wherein, ∿∿∿ represents a site where the group is covalently linked.

A value range of q2 may be an integer of 1-10; and in some embodiments, q2 is an integer of 1-5.

$L_1$ is used to link the $M_1$ targeting group to the N on the nitrogenous backbone, thereby providing liver targeting function for the siRNA conjugate as shown by Formula (308). In some embodiments, $L_1$ is selected from the connection combinations of one or more of groups as shown by Formulae A1-A26. In some embodiments, $L_1$ is selected from the connection combinations of one or more of A1, A4, A5, A6, A8, A10, A11, and A13. In some embodiments, $L_1$ is selected from the connection combinations of at least two of A1, A4, A8, A10, and A11. In some embodiments, $L_1$ is selected from the connection combinations of at least two of A1, A8, and A10.

In some embodiments, the length of $L_1$ may be 3-25 atoms, 3-20 atoms, 4-15 atoms or 5-12 atoms. In some embodiments, the length of $L_1$ is 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 atoms.

In some embodiments, j1 is an integer of 2-10, and in some embodiments, j1 is an integer of 3-5. In some embodiments, j2 is an integer of 2-10, and in some embodiments, j2 is an integer of 3-5. R' is a $C_1$-$C_4$ alkyl, and in some embodiments, R' is one of methyl, ethyl, and isopropyl. Ra is one of A27, A28, A29, A30, and A31, and in some embodiments, Ra is A27 or A28. Rb is a $C_1$-$C_5$ alkyl, and in some embodiments, Rb is one of methyl, ethyl, isopropyl, and butyl. In some embodiments, j1, j2, R', Ra, and Rb of Formulae A1-A26 are respectively selected to achieve the linkage between the $M_1$ targeting group and the N atom on the nitrogenous backbone, and to make the steric mutual position among the $M_1$ targeting group more suitable for binding the $M_1$ targeting group to the asialoglycoprotein receptor on the surface of hepatocytes.

In some embodiments, the siRNA conjugate has a structure as shown by Formula (403), (404), (405), (406), (407), (408), (409), (410), (411), (412), (413), (414), (415), (416), (417), (418), (419), (420), (421) or (422):

Formula (403)

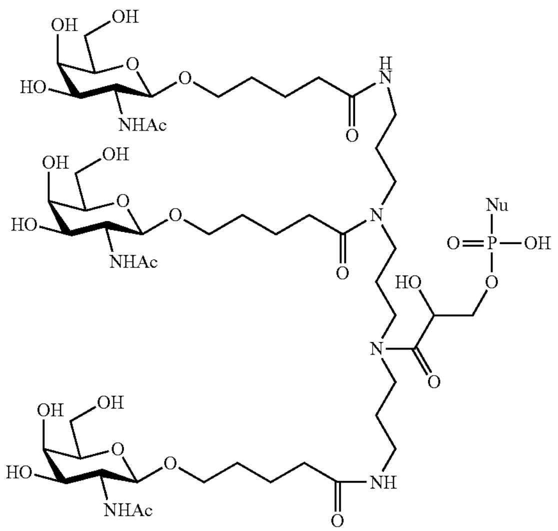

-continued
Formula (404)
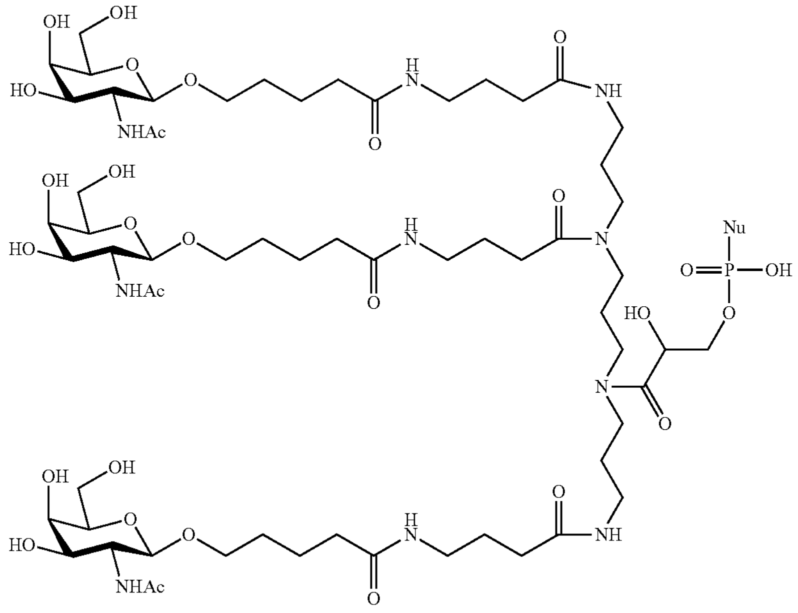
Formula (405)
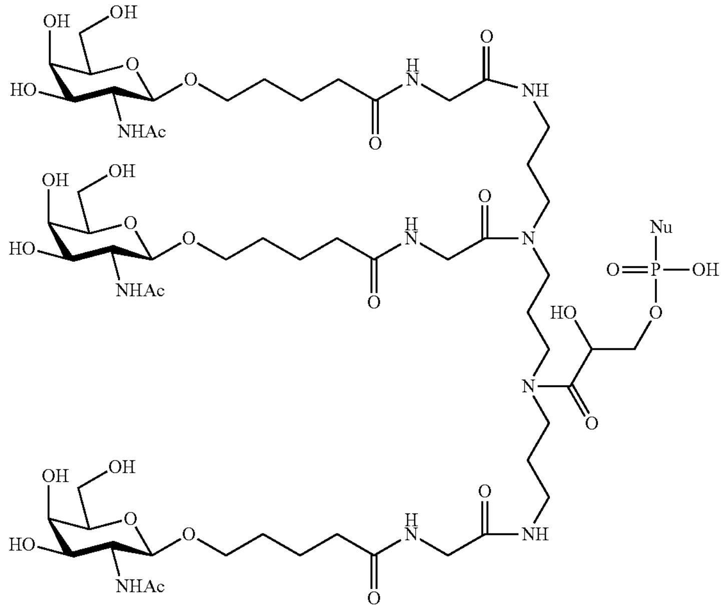

-continued
Formula (406)
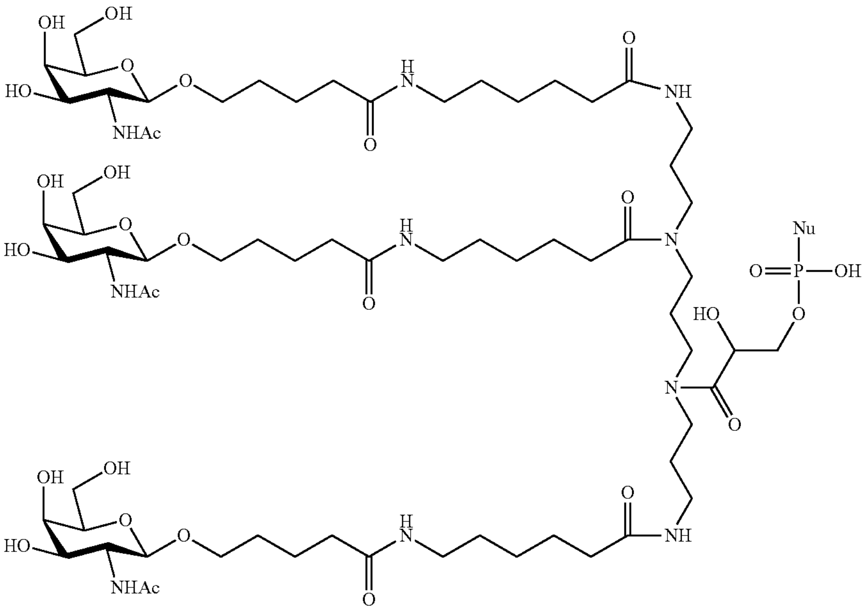
Formula (407)
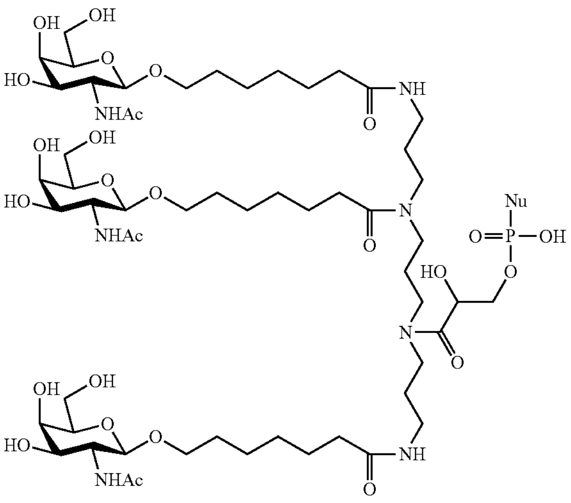
Formula (408)
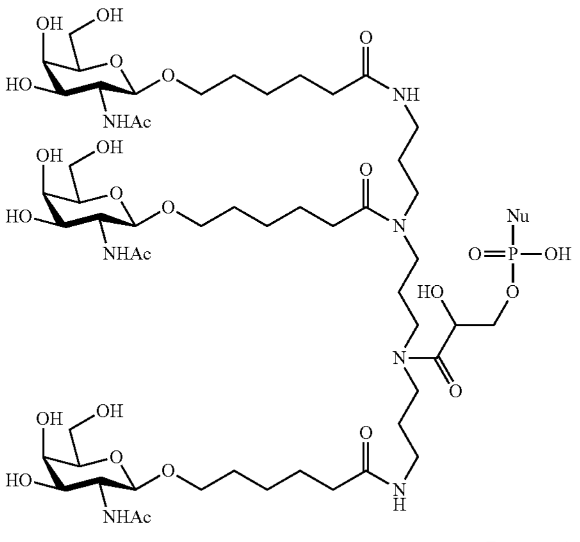
Formula (409)
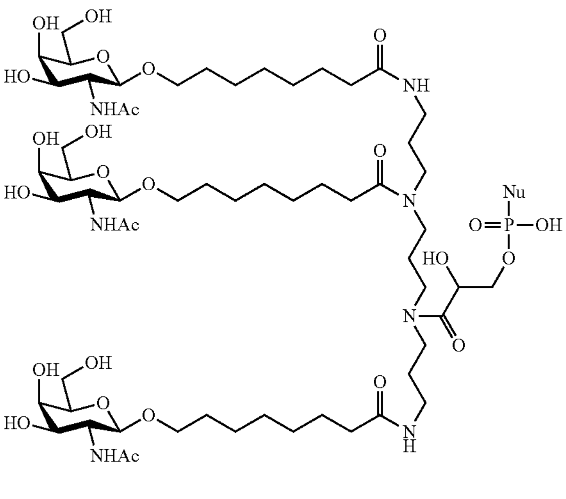
Formula (410)
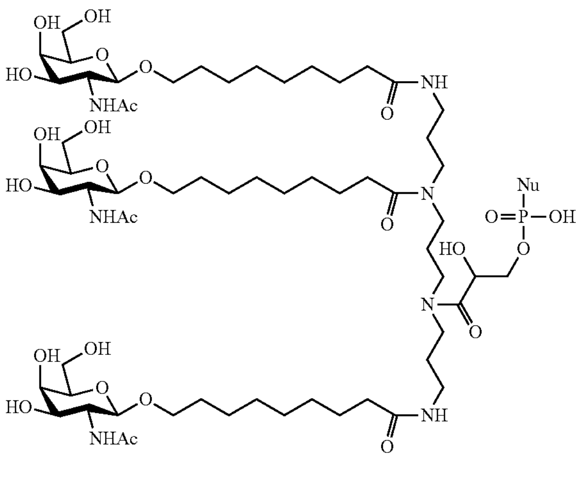

-continued
Formula (411)
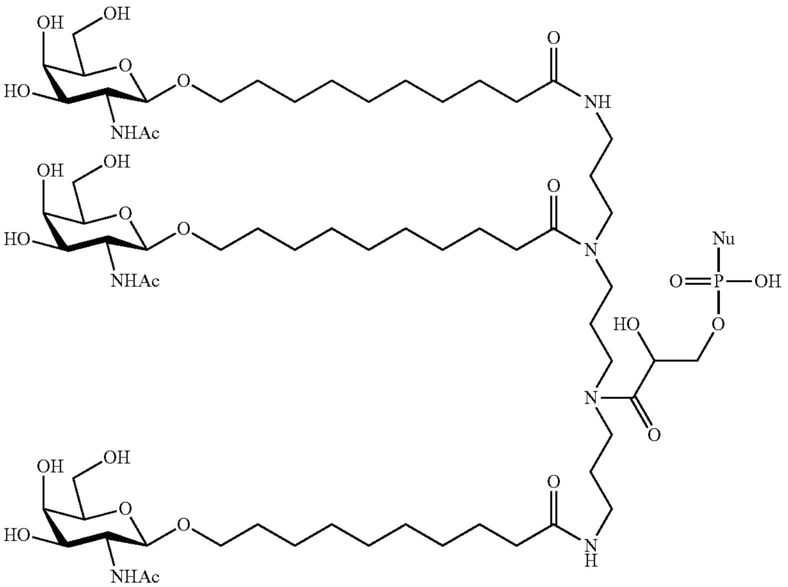
Formula (412)
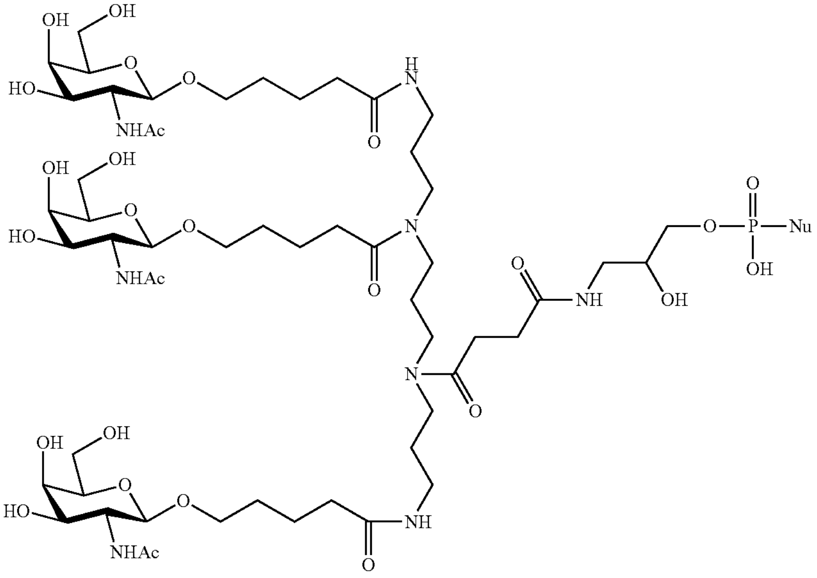

-continued
Formula (413)
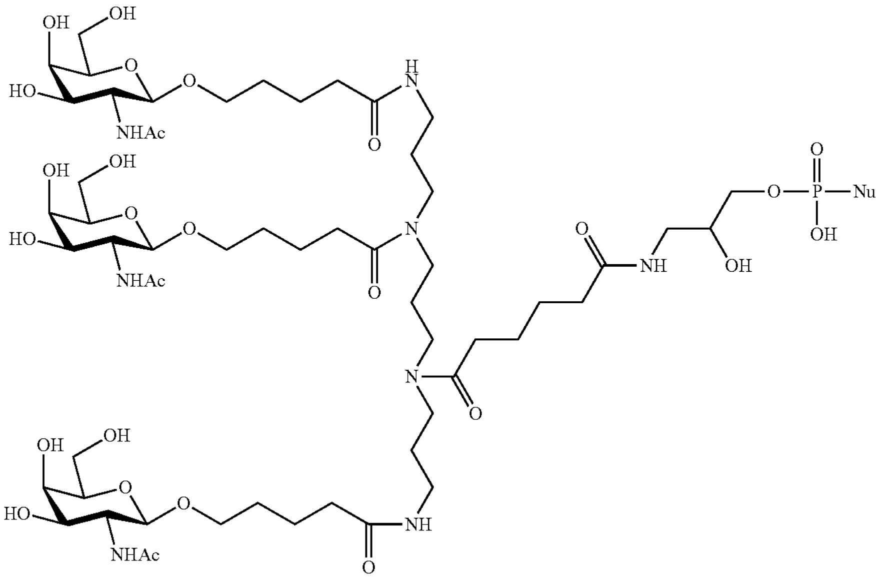
Formula (414)
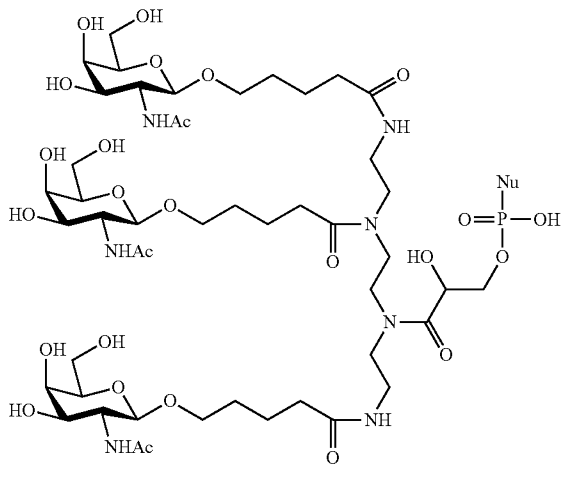
Formula (415)
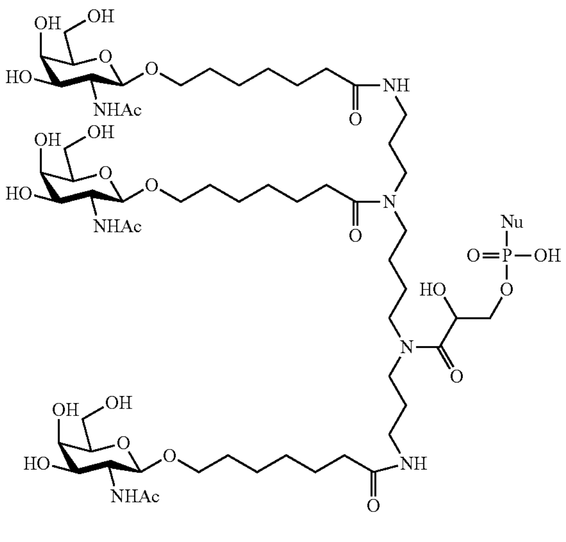

-continued
Formula (416)
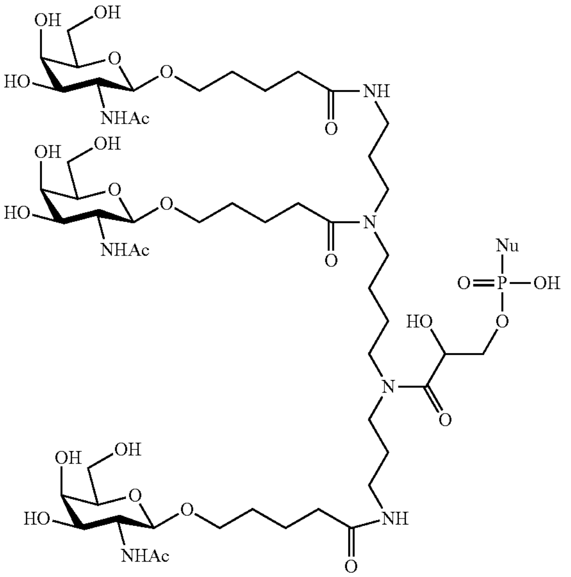
Formula (417)
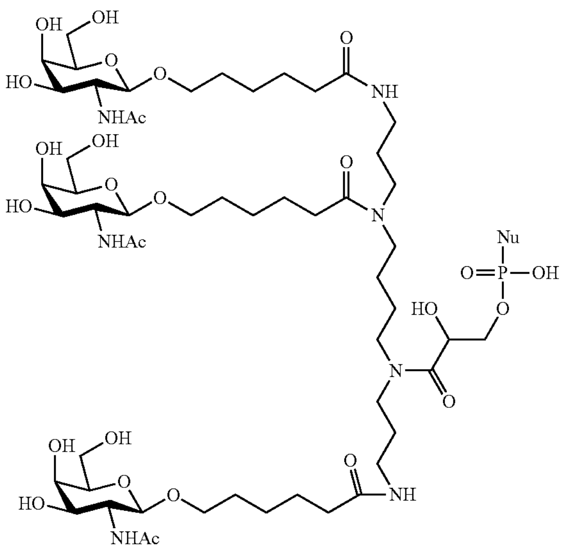
Formula (418)
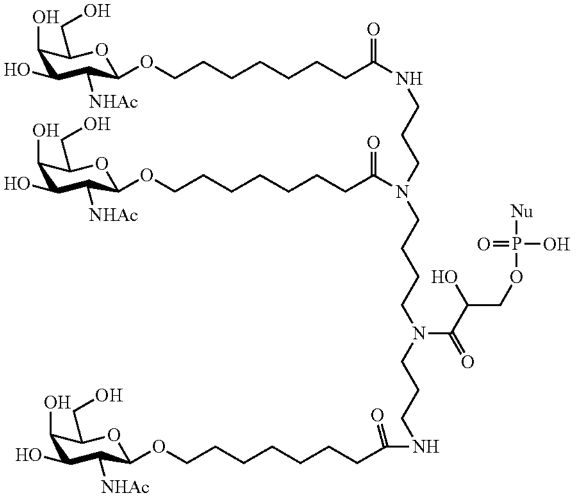
Formula (419)
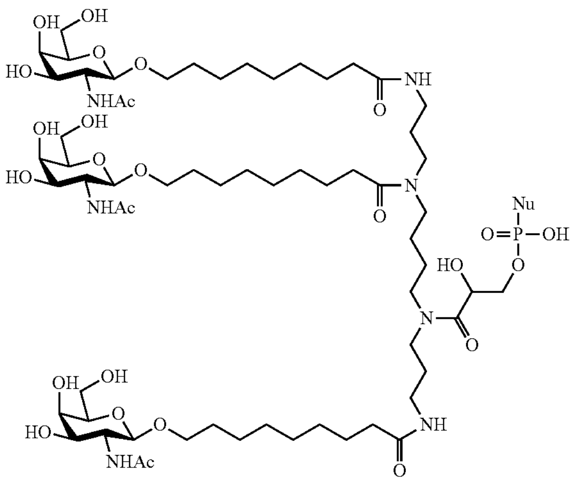

-continued

Formula (420)

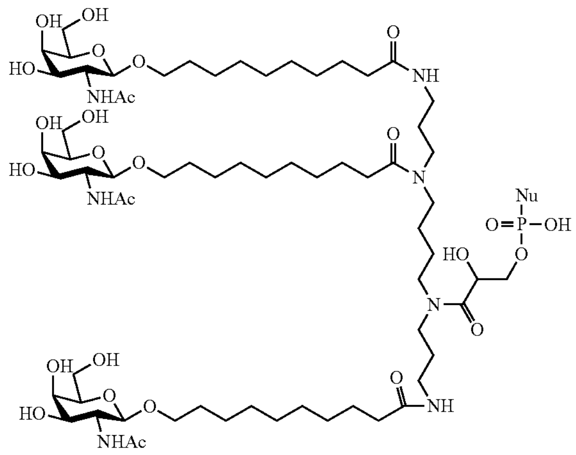

Formula (421)

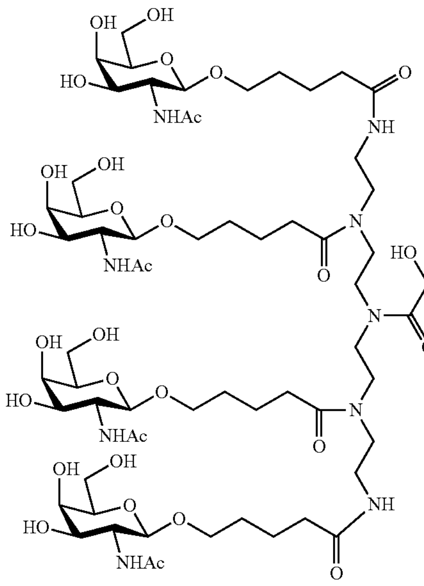

Formula (422)

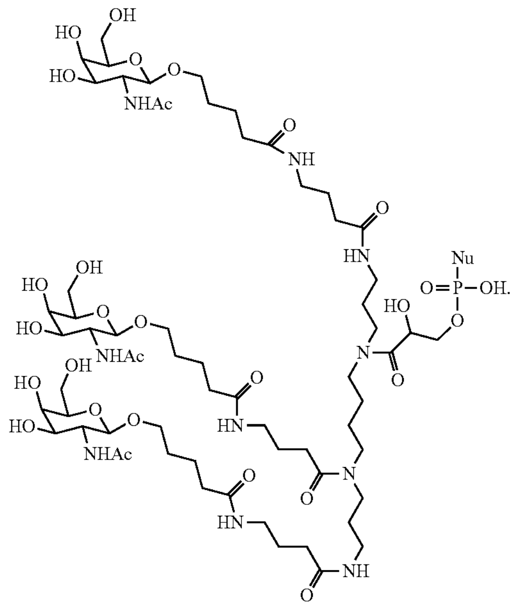

In some embodiments, the P atom in Formula A59 may be linked to any possible position in the siRNA sequence, for example, the P atom in Formula A59 may be linked to any nucleotide in the sense strand or the antisense strand of the siRNA. In some embodiments, the P atom in Formula A59 is linked to any nucleotide in the sense strand of the siRNA. In some embodiments, the P atom in Formula A59 is linked to an end of the sense strand or the antisense strand of the siRNA. In some embodiments, the P atom in Formula A59 is linked to an end of the sense strand of the siRNA. The end refers to the first 4 nucleotides counted from one terminal of the sense strand or antisense strand. In some embodiments, the P atom in Formula A59 is linked to the terminal of the sense strand or the antisense strand of the siRNA. In some embodiments, the P atom in Formula A59 is linked to 3' terminal of the sense strand of the siRNA. In the case where the P atom in Formula A59 is linked to the above position in the sense strand of the siRNA, after entering into cells, the siRNA conjugate as shown by Formula (308) can release a separate antisense strand of the siRNA during unwinding, thereby blocking the translation of the KNG mRNA into protein and inhibiting the expression of KNG gene.

In some embodiments, the P atom in Formula A59 may be linked to any possible position of a nucleotide in the siRNA, for example, to position 5', 2' or 3', or to the base of the nucleotide. In some embodiments, the P atom in Formula A59 may be linked to position 2', 3', or 5' of a nucleotide in the siRNA by forming a phosphodiester bond. In some embodiments, the P atom in Formula A59 is linked to an oxygen atom formed by dehydrogenation of 3' hydroxy of the nucleotide at 3' terminal of the sense strand of the siRNA (in this time, the P atom in Formula A59 may also be regarded as a P atom in a phosphate group contained in the siRNA), or the P atom in Formula A59 is linked to a nucleotide of the sense strand of the siRNA by substituting the hydrogen atom in the 2'-hydroxy of the nucleotide, or the P atom in Formula A59 is linked to a nucleotide at 5' terminal of the sense strand of the siRNA by substituting the hydrogen in the 5'-hydroxy of the nucleotide.

The inventors of the present disclosure have surprisingly found that the siRNA conjugate of the present disclosure has significantly improved stability in plasma and low off-target effect, and also shows higher silencing activity against KNG mRNA. In some embodiments, the siRNA of the present disclosure may be one of the siRNAs shown in Tables 1a-1f. The siRNA conjugates containing these siRNA show higher silencing activity against KNG mRNA.

TABLE 1a

First siRNA sequence of the present disclosure

| siRNA No. | SEQ ID NO: | Sequence direction 5' - 3' |
|---|---|---|
| siKNa1 | 9 | AAAGUAACAACCAGUUUGU |
| | 10 | ACAAACUGGUUGUUACUUUGG |
| siKNa2 | 11 | CCAAAGUAACAACCAGUUUGU |
| | 12 | ACAAACUGGUUGUUACUUUGGUU |
| siKNa1-M1 | 13 | AmAmAmGmUmAmAfCfAfAmCmCmAmGmUmUmUmGmUm |
| | 14 | AmCfAmAmAmCfUmGmGmUmUmGmUmUfAmCfUmUmUmGmGm |
| siKNa1-M2 | 15 | AmAmAmGmUfAmAfCfAfAmCmCmAmGmUmUmUmGmUm |
| | 16 | AmCfAmAmAmCfUmGfGfUmUmGmUmUfAmCfUmUmUmGmGm |
| siKNa1-M3 | 17 | AmAmAmGmUfAmAfCfAfAmCmCmAmGmUmUmUmGmUm |
| | 18 | AmCfAmAmAmCfUmGmGmUmUmGmUmUfAmCfUmUmUmGmGm |
| siKNa2-M1 | 19 | CmCmAmAmAmGmUmAmAfCfAfAmCmCmAmGmUmUmUmGmUm |
| | 20 | AmCfAmAmAmCfUmGmGmUmUmGmUmUfAmCfUmUmUmGmGmUmUm |
| siKNa2-M2 | 21 | CmCmAmAmAmGmUfAmAfCfAfAmCmCmAmGmUmUmUmGmUm |
| | 22 | AmCfAmAmAmCfUmGfGfUmUmGmUmUfAmCfUmUmUmGmGmUmUm |
| siKNa2-M3 | 23 | CmCmAmAmAmGmUfAmAfCfAfAmCmCmAmGmUmUmUmGmUm |
| | 24 | AmCfAmAmAmCfUmGmGmUmUmGmUmUfAmCfUmUmUmGmGmUmUm |
| siKNa1-M1S | 25 | AmsAmsAmGmUmAmAfCfAfAmCmCmAmGmUmUmUmGmUm |
| | 26 | AmsCfsAmAmAmCfUmGmGmUmUmGmUmUfAmCfUmUmUmsGmsGm |
| siKNa1-M2S | 27 | AmsAmsAmGmUfAmAfCfAfAmCmCmAmGmUmUmUmGmUm |
| | 28 | AmsCfsAmAmAmCfUmGfGfUmUmGmUmUfAmCfUmUmUmsGmsGm |
| siKNa1-M3S | 29 | AmsAmsAmGmUfAmAfCfAfAmCmCmAmGmUmUmUmGmUm |
| | 30 | AmsCfsAmAmAmCfUmGmGmUmUmGmUmUfAmCfUmUmUmsGmsGm |
| siKNa2-M1S | 31 | CmsCmsAmAmAmGmUmAmAfCfAfAmCmCmAmGmUmUmUmGmUm |
| | 32 | AmsCfsAmAmAmCfUmGmGmUmUmGmUmUfAmCfUmUmUmGmGmsUms Um |
| siKNa2-M2S | 33 | CmsCmsAmAmAmGmUfAmAfCfAfAmCmCmAmGmUmUmUmGmUm |
| | 34 | AmsCfsAmAmAmCfUmGfGfUmUmGmUmUfAmCfUmUmUmGmGmsUmsUm |
| siKNa2-M3S | 35 | CmsCmsAmAmAmGmUfAmAfCfAfAmCmCmAmGmUmUmUmGmUm |
| | 36 | AmsCfsAmAmAmCfUmGmGmUmUmGmUmUfAmCfUmUmUmGmGmsUms Um |
| siKNa1-M1P1 | 37 | AmAmAmGmUmAmAfCfAfAmCmCmAmGmUmUmUmGmUm |
| | 38 | P1AmCfAmAmAmCfUmGmGmUmUmGmUmUfAmCfUmUmUmGmGm |
| siKNa1-M2P1 | 39 | AmAmAmGmUfAmAfCfAfAmCmCmAmGmUmUmUmGmUm |
| | 40 | P1AmCfAmAmAmCfUmGfGfUmUmGmUmUfAmCfUmUmUmGmGm |
| siKNa1-M3P1 | 41 | AmAmAmGmUfAmAfCfAfAmCmCmAmGmUmUmUmGmUm |
| | 42 | P1AmCfAmAmAmCfUmGmGmUmUmGmUmUfAmCfUmUmUmGmGm |
| siKNa2-M1P1 | 43 | CmCmAmAmAmGmUmAmAfCfAfAmCmCmAmGmUmUmUmGmUm |
| | 44 | P1AmCfAmAmAmCfUmGmGmUmUmGmUmUfAmCfUmUmUmGmGmUmUm |
| siKNa2-M2P1 | 45 | CmCmAmAmAmGmUfAmAfCfAfAmCmCmAmGmUmUmUmGmUm |
| | 46 | P1AmCfAmAmAmCfUmGfGfUmUmGmUmUfAmCfUmUmUmGmGmUmUm |
| siKNa2-M3P1 | 47 | CmCmAmAmAmGmUfAmAfCfAfAmCmCmAmGmUmUmUmGmUm |
| | 48 | P1AmCfAmAmAmCfUmGmGmUmUmGmUmUfAmCfUmUmUmGmGmUmUm |
| siKNa1-M1SP1 | 49 | AmsAmsAmGmUmAmAfCfAfAmCmCmAmGmUmUmUmGmUm |
| | 50 | P1AmsCfsAmAmAmCfUmGmGmUmUmGmUmUfAmCfUmUmUmsGmsGm |

TABLE 1a-continued

First siRNA sequence of the present disclosure

| siRNA No. | SEQ ID NO: | Sequence direction 5' - 3' |
|---|---|---|
| siKNa1-M2SP1 | 51 | AmsAmsAmGmUfAmAfCfAfAmCmCmAmGmUmUmUmGmUm |
| | 52 | P1AmsCfsAmAmAmCfUmGfGfUmUmGmUmUfAmCfUmUmUmsGmsGm |
| siKNa1-M3SP1 | 53 | AmsAmsAmGmUfAmAfCfAfAmCmCmAmGmUmUmUmGmUm |
| | 54 | P1AmsCfsAmAmAmCfUmGmGmUmUmGmUmUfAmCfUmUmUmsGmsGm |
| siKNa2-M1SP1 | 55 | CmsCmsAmAmAmGmUmAmAfCfAfAmCmCmAmGmUmUmUmGmUm |
| | 56 | P1AmsCfsAmAmAmCfUmGmGmUmUmGmUmUfAmCfUmUmUmGmGmsUms Um |
| siKNa2-M2SP1 | 57 | CmsCmsAmAmAmGmUfAmAfCfAfAmCmCmAmGmUmUmUmGmUm |
| | 58 | P1AmsCfsAmAmAmCfUmGfGfUmUmGmUmUfAmCfUmUmUmGmGmsUms Um |
| siKNa2-M3SP1 | 59 | CmsCmsAmAmAmGmUfAmAfCfAfAmCmCmAmGmUmUmUmGmUm |
| | 60 | P1AmsCfsAmAmAmCfUmGmGmUmUmGmUmUfAmCfUmUmUmGmGmsUms Um |

TABLE 1b

Second siRNA sequence of the present disclosure

| siRNA No. | SEQ ID NO: | Sequence direction 5'- 3' |
|---|---|---|
| siKNb1 | 69 | AUUGAACUUUCGAAUUACC |
| | 70 | GGUAAUUCGAAAGUUCAAUCC |
| siKNb2 | 71 | GGAUUGAACUUUCGAAUUACC |
| | 72 | GGUAAUUCGAAAGUUCAAUCCAG |
| siKNb1-M1 | 73 | AmUmUmGmAmAmCfUfUfUmCmGmAmAmUmUmAmCmCm |
| | 74 | GmGfUmAmAmUfUmCmGmAmAmAmGmUfUmCfAmAmUmCmCm |
| siKNb1-M2 | 75 | AmUmUmGmAfAmCfUfUfUmCmGmAmAmUmUmAmCmCm |
| | 76 | GmGfUmAmAmUfUmCfGfAmAmAmGmUfUmCfAmAmUmCmCm |
| siKNb1-M3 | 77 | AmUmUmGmAfAmCfUfUfUmCmGmAmAmUmUmAmCmCm |
| | 78 | GmGfUmAmAmUfUmCmGmAmAmAmGmUfUmCfAmAmUmCmCm |
| siKNb2-M1 | 79 | GmGmAmUmUmGmAmAmCfUfUfUmCmGmAmAmUmUmAmCmCm |
| | 80 | GmGfUmAmAmUfUmCmGmAmAmAmGmUfUmCfAmAmUmCmCmAmGm |
| siKNb2-M2 | 81 | GmGmAmUmUmGmAfAmCfUfUfUmCmGmAmAmUmUmAmCmCm |
| | 82 | GmGfUmAmAmUfUmCfGfAmAmAmGmUfUmCfAmAmUmCmCmAmGm |
| siKNb2-M3 | 83 | GmGmAmUmUmGmAfAmCfUfUfUmCmGmAmAmUmUmAmCmCm |
| | 84 | GmGfUmAmAmUfUmCmGmAmAmAmGmUfUmCfAmAmUmCmCmAmGm |
| siKNb1-M1S | 85 | AmsUmsUmGmAmAmCfUfUfUmCmGmAmAmUmUmAmCmCm |
| | 86 | GmsGfsUmAmAmUfUmCmGmAmAmAmGmUfUmCfAmAmUmsCmsCm |
| siKNb1-M2S | 87 | AmsUmsUmGmAfAmCfUfUfUmCmGmAmAmUmUmAmCmCm |
| | 88 | GmsGfsUmAmAmUfUmCfGfAmAmAmGmUfUmCfAmAmUmsCmsCm |
| siKNb1-M3S | 89 | AmsUmsUmGmAfAmCfUfUfUmCmGmAmAmUmUmAmCmCm |
| | 90 | GmsGfsUmAmAmUfUmCmGmAmAmAmGmUfUmCfAmAmUmsCmsCm |
| siKNb2-M1S | 91 | GmsGmsAmUmUmGmAmAmCfUfUfUmCmGmAmAmUmUmAmCmCm |
| | 92 | GmsGfsUmAmAmUfUmCmGmAmAmAmGmUfUmCfAmAmUmCmCmsAmsGm |
| siKNb2-M2S | 93 | AmsUmsUmGmAfAmCfUfUfUmCmGmAmAmUmUmAmCmCm |
| | 94 | GmsGfsUmAmAmUfUmCfGfAmAmAmGmUfUmCfAmAmUmCmCmsAmsGm |
| siKNb2-M3S | 95 | GmsGmsAmUmUmGmAfAmCfUfUfUmCmGmAmAmUmUmAmCmCm |
| | 96 | GmsGfsUmAmAmUfUmCmGmAmAmAmGmUfUmCfAmAmUmCmCmsAmsGm |
| siKNb1-M1P1 | 97 | AmUmUmGmAmAmCfUfUfUmCmGmAmAmUmUmAmCmCm |
| | 98 | P1GmGfUmAmAmUfUmCmGmAmAmAmGmUfUmCfAmAmUmCmCm |

TABLE 1b-continued

| Second siRNA sequence of the present disclosure | | |
|---|---|---|
| siRNA No. | SEQ ID NO: | Sequence direction 5'- 3' |
| siKNb1-M2P1 | 99 | AmUmUmGmAfAmCfUfUfUmCmGmAmAmUmUmAmCmCm |
| | 100 | P1GmGfUmAmAmUfUmCfGfAmAmAmGmUfUmCfAmAmUmCmCm |
| siKNb1-M3P1 | 101 | AmUmUmGmAfAmCfUfUfUmCmGmAmAmUmUmAmCmCm |
| | 102 | P1GmGfUmAmAmUfUmCmGmAmAmAmGmUfUmCfAmAmUmCmCm |
| siKNb2-M1P1 | 103 | GmGmAmUmUmGmAmAmCfUfUfUmCmGmAmAmUmUmAmCmCm |
| | 104 | P1GmGfUmAmAmUfUmCmGmAmAmAmGmUfUmCfAmAmUmCmCmAmGm |
| siKNb2-M2P1 | 105 | GmGmAmUmUmGmAfAmCfUfUfUmCmGmAmAmUmUmAmCmCm |
| | 106 | P1GmGfUmAmAmUfUmCfGfAmAmAmGmUfUmCfAmAmUmCmCmAmGm |
| siKNb2-M3P1 | 107 | GmGmAmUmUmGmAfAmCfUfUfUmCmGmAmAmUmUmAmCmCm |
| | 108 | P1GmGfUmAmAmUfUmCmGmAmAmAmGmUfUmCfAmAmUmCmCmAmGm |
| siKNb1-M1SP1 | 109 | AmsUmsUmGmAmAmCfUfUfUmCmGmAmAmUmUmAmCmCm |
| | 110 | P1GmsGfsUmAmAmUfUmCmGmAmAmAmGmUfUmCfAmAmUmsCmsCm |
| siKNb1-M2SP1 | 111 | AmsUmsUmGmAfAmCfUfUfUmCmGmAmAmUmUmAmCmCm |
| | 112 | P1GmsGfsUmAmAmUfUmCfGfAmAmAmGmUfUmCfAmAmUmsCmsCm |
| siKNb1-M3SP1 | 113 | AmsUmsUmGmAfAmCfUfUfUmCmGmAmAmUmUmAmCmCm |
| | 114 | P1GmsGfsUmAmAmUfUmCmGmAmAmAmGmUfUmCfAmAmUmsCmsCm |
| siKNb2-M1SP1 | 115 | GmsGmsAmUmUmGmAmAmCfUfUfUmCmGmAmAmUmUmAmCmCm |
| | 116 | P1GmsGfsUmAmAmUfUmCmGmAmAmAmGmUfUmCfAmAmUmCmCmsAms Gm |
| siKNb2-M2SP1 | 117 | GmsGmsAmUmUmGmAfAmCfUfUfUmCmGmAmAmUmUmAmCmCm |
| | 118 | P1GmsGfsUmAmAmUfUmCfGfAmAmAmGmUfUmCfAmAmUmCmCmsAms Gm |
| siKNb2-M3SP1 | 119 | GmsGmsAmUmUmGmAfAmCfUfUfUmCmGmAmAmUmUmAmCmCm |
| | 120 | P1GmsGfsUmAmAmUfUmCmGmAmAmAmGmUfUmCfAmAmUmCmCmsAms Gm |

TABLE 1c

| Third siRNA sequence of the present disclosure | | |
|---|---|---|
| siRNA No. | SEQ ID NO: | Sequence direction 5'- 3' |
| siKNc1 | 129 | UCGAAUUACCUACUCAAUU |
| | 130 | AAUUGAGUAGGUAAUUCGAAA |
| siKNc2 | 131 | UUUCGAAUUACCUACUCAAUU |
| | 132 | AAUUGAGUAGGUAAUUCGAAAGU |
| siKNc1-M1 | 133 | UmCmGmAmAmUmUfAfCfCmUmAmCmUmCmAmAmUmUm |
| | 134 | AmAfUmUmGmAfGmUmAmGmGmUmAmAfUmUfCmGmAmAmAm |
| siKNc1-M2 | 135 | UmCmGmAmAfUmUfAfCfCmUmAmCmUmCmAmAmUmUm |
| | 136 | AmAfUmUmGmAfGmUfAfGmGmUmAmAfUmUfCmGmAmAmAm |
| siKNc1-M3 | 137 | UmCmGmAmAfUmUfAfCfCmUmAmCmUmCmAmAmUmUm |
| | 138 | AmAfUmUmGmAfGmUmAmGmGmUmAmAfUmUfCmGmAmAmAm |
| siKNc2-M1 | 139 | UmUmUmCmGmAmAmUmUfAfCfCmUmAmCmUmCmAmAmUmUm |
| | 140 | AmAfUmUmGmAfGmUmAmGmGmUmAmAfUmUfCmGmAmAmAmGmUm |
| siKNc2-M2 | 141 | UmUmUmCmGmAmAfUmUfAfCfCmUmAmCmUmCmAmAmUmUm |
| | 142 | AmAfUmUmGmAfGmUfAfGmGmUmAmAfUmUfCmGmAmAmAmGmUm |
| siKNc2-M3 | 143 | UmUmUmCmGmAmAfUmUfAfCfCmUmAmCmUmCmAmAmUmUm |
| | 144 | AmAfUmUmGmAfGmUmAmGmGmUmAmAfUmUfCmGmAmAmAmGmUm |
| siKNc1-M1S | 145 | UmsCmsGmAmAmUmUfAfCfCmUmAmCmUmCmAmAmUmUm |
| | 146 | AmsAfsUmUmGmAfGmUmAmGmGmUmAmAfUmUfCmGmAmsAmsAm |

TABLE 1c-continued

| Third siRNA sequence of the present disclosure | | |
|---|---|---|
| siRNA No. | SEQ ID NO: | Sequence direction 5'- 3' |
| siKNc1-M2S | 147 | UmsCmsGmAmAfUmUfAfCfCmUmAmCmUmCmAmAmUmUm |
| | 148 | AmsAfsUmUmGmAfGmUfAfGmGmUmAmAfUmUfCmGmAmsAmsAm |
| siKNc1-M3S | 149 | UmsCmsGmAmAfUmUfAfCfCmUmAmCmUmCmAmAmUmUm |
| | 150 | AmsAfsUmUmGmAfGmUmAmGmGmUmAmAfUmUfCmGmAmsAmsAm |
| siKNc2-M1S | 151 | UmsUmsUmCmGmAmAmUmUfAfCfCmUmAmCmUmCmAmAmUmUm |
| | 152 | AmsAfsUmUmGmAfGmUmAmGmGmUmAmAfUmUfCmGmAmAmAmsGms Um |
| siKNc2-M2S | 153 | UmsUmsUmCmGmAmAfUmUfAfCfCmUmAmCmUmCmAmAmUmUm |
| | 154 | AmsAfsUmUmGmAfGmUfAfGmGmUmAmAfUmUfCmGmAmAmAmsGmsUm |
| siKNc2-M3S | 155 | UmsUmsUmCmGmAmAfUmUfAfCfCmUmAmCmUmCmAmAmUmUm |
| | 156 | AmsAfsUmUmGmAfGmUmAmGmGmUmAmAfUmUfCmGmAmAmAmsGms Um |
| siKNc1-M1P1 | 157 | UmCmGmAmAmUmUfAfCfCmUmAmCmUmCmAmAmUmUm |
| | 158 | P1AmAfUmUmGmAfGmUmAmGmGmUmAmAfUmUfCmGmAmAmAm |
| siKNc1-M2P1 | 159 | UmCmGmAmAfUmUfAfCfCmUmAmCmUmCmAmAmUmUm |
| | 160 | P1AmAfUmUmGmAfGmUfAfGmGmUmAmAfUmUfCmGmAmAmAm |
| siKNc1-M3P1 | 161 | UmCmGmAmAfUmUfAfCfCmUmAmCmUmCmAmAmUmUm |
| | 162 | P1AmAfUmUmGmAfGmUmAmGmGmUmAmAfUmUfCmGmAmAmAm |
| siKNc2-M1P1 | 163 | UmUmUmCmGmAmAmUmUfAfCfCmUmAmCmUmCmAmAmUmUm |
| | 164 | P1AmAfUmUmGmAfGmUmAmGmGmUmAmAfUmUfCmGmAmAmAmGmUm |
| siKNc2-M2P1 | 165 | UmUmUmCmGmAmAfUmUfAfCfCmUmAmCmUmCmAmAmUmUm |
| | 166 | P1AmAfUmUmGmAfGmUfAfGmGmUmAmAfUmUfCmGmAmAmAmGmUm |
| siKNc2-M3P1 | 167 | UmUmUmCmGmAmAfUmUfAfCfCmUmAmCmUmCmAmAmUmUm |
| | 168 | P1AmAfUmUmGmAfGmUmAmGmGmUmAmAfUmUfCmGmAmAmAmGmUm |
| siKNc1-M1SP1 | 169 | UmsCmsGmAmAmUmUfAfCfCmUmAmCmUmCmAmAmUmUm |
| | 170 | P1AmsAfsUmUmGmAfGmUmAmGmGmUmAmAfUmUfCmGmAmsAmsAm |
| siKNc1-M2SP1 | 171 | UmsCmsGmAmAfUmUfAfCfCmUmAmCmUmCmAmAmUmUm |
| | 172 | P1AmsAfsUmUmGmAfGmUfAfGmGmUmAmAfUmUfCmGmAmsAmsAm |
| siKNc1-M3SP1 | 173 | UmsCmsGmAmAfUmUfAfCfCmUmAmCmUmCmAmAmUmUm |
| | 174 | P1AmsAfsUmUmGmAfGmUmAmGmGmUmAmAfUmUfCmGmAmsAmsAm |
| siKNc2-M1SP1 | 175 | UmsUmsUmCmGmAmAmUmUfAfCfCmUmAmCmUmCmAmAmUmUm |
| | 176 | P1AmsAfsUmUmGmAfGmUmAmGmGmUmAmAfUmUfCmGmAmAmAmsGms Um |
| siKNc2-M2SP1 | 177 | UmsUmsUmCmGmAmAfUmUfAfCfCmUmAmCmUmCmAmAmUmUm |
| | 178 | P1AmsAfsUmUmGmAfGmUfAfGmGmUmAmAfUmUfCmGmAmAmAmsGms Um |
| siKNc2-M3SP1 | 179 | UmsUmsUmCmGmAmAfUmUfAfCfCmUmAmCmUmCmAmAmUmUm |
| | 180 | P1AmsAfsUmUmGmAfGmUmAmGmGmUmAmAfUmUfCmGmAmAmAmsGms Um |

TABLE 1d

| Fourth siRNA sequence of the present disclosure | | |
|---|---|---|
| SIRNA No. | SEQ ID NO: | Sequence direction 5'- 3' |
| siKNd1 | 189 | GAUAAUGCAUACAUCGAUA |
| | 190 | UAUCGAUGUAUGCAUUAUCUG |
| siKNd2 | 191 | CAGAUAAUGCAUACAUCGAUA |
| | 192 | UAUCGAUGUAUGCAUUAUCUGUA |

TABLE 1d-continued

Fourth siRNA sequence of the present disclosure

| SIRNA No. | SEQ ID NO: | Sequence direction 5'- 3' |
|---|---|---|
| siKNd1-M1 | 193 | GmAmUmAmAmUmGfCfAfUmAmCmAmUmCmGmAmUmAm |
| | 194 | UmAfUmCmGmAfUmGmUmAmUmGmCmAfUmUfAmUmCmUmGm |
| siKNd1-M2 | 195 | GmAmUmAmAfUmGfCfAfUmAmCmAmUmCmGmAmUmAm |
| | 196 | UmAfUmCmGmAfUmGfUfAmUmGmCmAfUmUfAmUmCmUmGm |
| siKNd1-M3 | 197 | GmAmUmAmAfUmGfCfAfUmAmCmAmUmCmGmAmUmAm |
| | 198 | UmAfUmCmGmAfUmGmUmAmUmGmCmAfUmUfAmUmCmUmGm |
| siKNd2-M1 | 199 | CmAmGmAmUmAmAmUmGfCfAfUmAmCmAmUmCmGmAmUmAm |
| | 200 | UmAfUmCmGmAfUmGmUmAmUmGmCmAfUmUfAmUmCmUmGmUmAm |
| siKNd2-M2 | 201 | CmAmGmAmUmAmAfUmGfCfAfUmAmCmAmUmCmGmAmUmAm |
| | 202 | UmAfUmCmGmAfUmGfUfAmUmGmCmAfUmUfAmUmCmUmGmUmAm |
| siKNd2-M3 | 203 | CmAmGmAmUmAmAfUmGfCfAfUmAmCmAmUmCmGmAmUmAm |
| | 204 | UmAfUmCmGmAfUmGmUmAmUmGmCmAfUmUfAmUmCmUmGmUmAm |
| siKNd1-M1S | 205 | GmsAmsUmAmAmUmGfCfAfUmAmCmAmUmCmGmAmUmAm |
| | 206 | UmsAfsUmCmGmAfUmGmUmAmUmGmCmAfUmUfAmUmCmsUmsGm |
| siKNd1-M2S | 207 | GmsAmsUmAmAfUmGfCfAfUmAmCmAmUmCmGmAmUmAm |
| | 208 | UmsAfsUmCmGmAfUmGfUfAmUmGmCmAfUmUfAmUmCmsUmsGm |
| siKNd1-M3S | 209 | GmsAmsUmAmAfUmGfCfAfUmAmCmAmUmCmGmAmUmAm |
| | 210 | UmsAfsUmCmGmAfUmGmUmAmUmGmCmAfUmUfAmUmCmsUmsGm |
| siKNd2-M1S | 211 | CmsAmsGmAmUmAmAmUmGfCfAfUmAmCmAmUmCmGmAmUmAm |
| | 212 | UmsAfsUmCmGmAfUmGmUmAmUmGmCmAfUmUfAmUmCmUmGmsUms Am |
| siKNd2-M2S | 213 | CmsAmsGmAmUmAmAfUmGfCfAfUmAmCmAmUmCmGmAmUmAm |
| | 214 | UmsAfsUmCmGmAfUmGfUfAmUmGmCmAfUmUfAmUmCmUmGmsUmsAm |
| siKNd2-M3S | 215 | CmsAmsGmAmUmAmAfUmGfCfAfUmAmCmAmUmCmGmAmUmAm |
| | 216 | UmsAfsUmCmGmAfUmGmUmAmUmGmCmAfUmUfAmUmCmUmGmsUms Am |
| siKNd1-M1P1 | 217 | GmAmUmAmAmUmGfCfAfUmAmCmAmUmCmGmAmUmAm |
| | 218 | P1UmAfUmCmGmAfUmGmUmAmUmGmCmAfUmUfAmUmCmUmGm |
| siKNd1-M2P1 | 219 | GmAmUmAmAfUmGfCfAfUmAmCmAmUmCmGmAmUmAm |
| | 220 | P1UmAfUmCmGmAfUmGfUfAmUmGmCmAfUmUfAmUmCmUmGm |
| siKNd1-M3P1 | 221 | GmAmUmAmAfUmGfCfAfUmAmCmAmUmCmGmAmUmAm |
| | 222 | P1UmAfUmCmGmAfUmGmUmAmUmGmCmAfUmUfAmUmCmUmGm |
| siKNd2-M1P1 | 223 | CmAmGmAmUmAmAmUmGfCfAfUmAmCmAmUmCmGmAmUmAm |
| | 224 | P1UmAfUmCmGmAfUmGmUmAmUmGmCmAfUmUfAmUmCmUmGmUmAm |
| siKNd2-M2P1 | 225 | CmAmGmAmUmAmAfUmGfCfAfUmAmCmAmUmCmGmAmUmAm |
| | 226 | P1UmAfUmCmGmAfUmGfUfAmUmGmCmAfUmUfAmUmCmUmGmUmAm |
| siKNd2-M3P1 | 227 | CmAmGmAmUmAmAfUmGfCfAfUmAmCmAmUmCmGmAmUmAm |
| | 228 | P1UmAfUmCmGmAfUmGmUmAmUmGmCmAfUmUfAmUmCmUmGmUmAm |
| siKNd1-M1SP1 | 229 | GmsAmsUmAmAmUmGfCfAfUmAmCmAmUmCmGmAmUmAm |
| | 230 | P1UmsAfsUmCmGmAfUmGmUmAmUmGmCmAfUmUfAmUmCmsUmsGm |
| siKNd1-M2SP1 | 231 | GmsAmsUmAmAfUmGfCfAfUmAmCmAmUmCmGmAmUmAm |
| | 232 | P1UmsAfsUmCmGmAfUmGfUfAmUmGmCmAfUmUfAmUmCmsUmsGm |
| siKNd1-M3SP1 | 233 | GmsAmsUmAmAfUmGfCfAfUmAmCmAmUmCmGmAmUmAm |
| | 234 | P1UmsAfsUmCmGmAfUmGmUmAmUmGmCmAfUmUfAmUmCmsUmsGm |
| siKNd2-M1SP1 | 235 | CmsAmsGmAmUmAmAmUmGfCfAfUmAmCmAmUmCmGmAmUmAm |
| | 236 | P1UmsAfsUmCmGmAfUmGmUmAmUmGmCmAfUmUfAmUmCmUmGmsUms Am |
| siKNd2-M2SP1 | 237 | CmsAmsGmAmUmAmAfUmGfCfAfUmAmCmAmUmCmGmAmUmAm |
| | 238 | P1UmsAfsUmCmGmAfUmGfUfAmUmGmCmAfUmUfAmUmCmUmGmsUms Am |

TABLE 1d-continued

Fourth siRNA sequence of the present disclosure

| SIRNA No. | SEQ ID NO: | Sequence direction 5'- 3' |
|---|---|---|
| siKNd2-M3SP1 | 239 | CmsAmsGmAmUmAmAfUmGfCfAfUmAmCmAmUmCmGmAmUmAm |
| | 240 | P1UmsAfsUmCmGmAfUmGmUmAmUmGmCmAfUmUfAmUmCmUmGmsUmsAm |

TABLE 1e

Fifth siRNA sequence of the present disclosure

| siRNA No. | SEQ ID NO: | Sequence direction 5'- 3' |
|---|---|---|
| siKNe1 | 249 | GAAUAACGCAACUUUCUAU |
| | 250 | AUAGAAAGUUGCGUUAUUCUC |
| siKNe2 | 251 | GAGAAUAACGCAACUUUCUAU |
| | 252 | AUAGAAAGUUGCGUUAUUCUCUG |
| siKNe1-M1 | 253 | GmAmAmUmAmAmCfGfCfAmAmCmUmUmUmCmUmAmUm |
| | 254 | AmUfAmGmAmAfAmGmUmUmGmCmGmUfUmAfUmUmCmUmCm |
| siKNe1-M2 | 255 | GmAmAmUmAfAmCfGfCfAmAmCmUmUmUmCmUmAmUm |
| | 256 | AmUfAmGmAmAfAmGfUfUmGmCmGmUfUmAfUmUmCmUmCm |
| siKNe1-M3 | 257 | GmAmAmUmAfAmCfGfCfAmAmCmUmUmUmCmUmAmUm |
| | 258 | AmUfAmGmAmAfAmGmUmUmGmCmGmUfUmAfUmUmCmUmCm |
| siKNe2-M1 | 259 | GmAmGmAmAmUmAmAmCfGfCfAmAmCmUmUmUmCmUmAmUm |
| | 260 | AmUfAmGmAmAfAmGmUmUmGmCmGmUfUmAfUmUmCmUmCmUmGm |
| siKNe2-M2 | 261 | GmAmGmAmAmUmAfAmCfGfCfAmAmCmUmUmUmCmUmAmUm |
| | 262 | AmUfAmGmAmAfAmGfUfUmGmCmGmUfUmAfUmUmCmUmCmUmGm |
| siKNe2-M3 | 263 | GmAmGmAmAmUmAfAmCfGfCfAmAmCmUmUmUmCmUmAmUm |
| | 264 | AmUfAmGmAmAfAmGmUmUmGmCmGmUfUmAfUmUmCmUmCmUmGm |
| siKNe1-M1S | 265 | GmsAmsAmUmAmAmCfGfCfAmAmCmUmUmUmCmUmAmUm |
| | 266 | AmsUfsAmGmAmAfAmGmUmUmGmCmGmUfUmAfUmUmCmsUmsCm |
| siKNe1-M2S | 267 | GmsAmsAmUmAfAmCfGfCfAmAmCmUmUmUmCmUmAmUm |
| | 268 | AmsUfsAmGmAmAfAmGfUfUmGmCmGmUfUmAfUmUmCmsUmsCm |
| siKNe1-M3S | 269 | GmsAmsAmUmAfAmCfGfCfAmAmCmUmUmUmCmUmAmUm |
| | 270 | AmsUfsAmGmAmAfAmGmUmUmGmCmGmUfUmAfUmUmCmsUmsCm |
| siKNe2-M1S | 271 | GmsAmsGmAmAmUmAmAmCfGfCfAmAmCmUmUmUmCmUmAmUm |
| | 272 | AmsUfsAmGmAmAfAmGmUmUmGmCmGmUfUmAfUmUmCmUmCmsUmsGm |
| siKNe2-M2S | 273 | GmsAmsGmAmAmUmAfAmCfGfCfAmAmCmUmUmUmCmUmAmUm |
| | 274 | AmsUfsAmGmAmAfAmGfUfUmGmCmGmUfUmAfUmUmCmUmCmsUmsGm |
| siKNe2-M3S | 275 | GmsAmsGmAmAmUmAfAmCfGfCfAmAmCmUmUmUmCmUmAmUm |
| | 276 | AmsUfsAmGmAmAfAmGmUmUmGmCmGmUfUmAfUmUmCmUmCmsUmsGm |
| siKNe1-M1P1 | 277 | GmAmAmUmAmAmCfGfCfAmAmCmUmUmUmCmUmAmUm |
| | 278 | P1AmUfAmGmAmAfAmGmUmUmGmCmGmUfUmAfUmUmCmUmCm |
| siKNe1-M2P1 | 279 | GmAmAmUmAfAmCfGfCfAmAmCmUmUmUmCmUmAmUm |
| | 280 | P1AmUfAmGmAmAfAmGfUfUmGmCmGmUfUmAfUmUmCmUmCm |
| siKNe1-M3P1 | 281 | GmAmAmUmAfAmCfGfCfAmAmCmUmUmUmCmUmAmUm |
| | 282 | P1AmUfAmGmAmAfAmGmUmUmGmCmGmUfUmAfUmUmCmUmCm |
| siKNe2-M1P1 | 283 | GmAmGmAmAmUmAmAmCfGfCfAmAmCmUmUmUmCmUmAmUm |
| | 284 | P1AmUfAmGmAmAfAmGmUmUmGmCmGmUfUmAfUmUmCmUmCmUmGm |
| siKNe2-M2P1 | 285 | GmAmGmAmAmUmAfAmCfGfCfAmAmCmUmUmUmCmUmAmUm |
| | 286 | P1AmUfAmGmAmAfAmGfUfUmGmCmGmUfUmAfUmUmCmUmCmUmGm |

TABLE 1e-continued

Fifth siRNA sequence of the present disclosure

| siRNA No. | SEQ ID NO: | Sequence direction 5'- 3' |
|---|---|---|
| siKNe2-M3P1 | 287 | GmAmGmAmAmUmAfAmCfGfCfAmAmCmUmUmUmCmUmAmUm |
| | 288 | P1AmUfAmGmAmAfAmGmUmUmGmCmGmUfUmAfUmUmCmUmCmUmGm |
| siKNe1-M1SP1 | 289 | GmsAmsAmUmAmAmCfGfCfAmAmCmUmUmUmCmUmAmUm |
| | 290 | P1AmsUfsAmGmAmAfAmGmUmUmGmCmGmUfUmAfUmUmCmsUmsCm |
| siKNe1-M2SP1 | 291 | GmsAmsAmUmAfAmCfGfCfAmAmCmUmUmUmCmUmAmUm |
| | 292 | P1AmsUfsAmGmAmAfAmGfUfUmGmCmGmUfUmAfUmUmCmsUmsCm |
| siKNe1-M3SP1 | 293 | GmsAmsAmUmAfAmCfGfCfAmAmCmUmUmUmCmUmAmUm |
| | 294 | P1AmsUfsAmGmAmAfAmGmUmUmGmCmGmUfUmAfUmUmCmsUmsCm |
| siKNe2-M1SP1 | 295 | GmsAmsGmAmAmUmAmAmCfGfCfAmAmCmUmUmUmCmUmAmUm |
| | 296 | P1AmsUfsAmGmAmAfAmGmUmUmGmCmGmUfUmAfUmUmCmUmCmsUmsGm |
| siKNe2-M2SP1 | 297 | GmsAmsGmAmAmUmAfAmCfGfCfAmAmCmUmUmUmCmUmAmUm |
| | 298 | P1AmsUfsAmGmAmAfAmGfUfUmGmCmGmUfUmAfUmUmCmUmCmsUmsGm |
| siKNe2-M3SP1 | 299 | GmsAmsGmAmAmUmAfAmCfGfCfAmAmCmUmUmUmCmUmAmUm |
| | 300 | P1AmsUfsAmGmAmAfAmGmUmUmGmCmGmUfUmAfUmUmCmUmCmsUmsGm |

TABLE 1f

Sixth siRNA sequence of the present disclosure

| siRNA No. | SEQ ID NO: | Sequence direction 5'- 3' |
|---|---|---|
| siKNf1 | 309 | AACUUUCUAUUUCAAGAUU |
| | 310 | AAUCUUGAAAUAGAAAGUUGC |
| siKNf2 | 311 | GCAACUUUCUAUUUCAAGAUU |
| | 312 | AAUCUUGAAAUAGAAAGUUGCGU |
| siKNf1-M1 | 313 | AmAmCmUmUmUmCfUfAfUmUmUmCmAmAmGmAmUmUm |
| | 314 | AmAfUmCmUmUfGmAmAmAmUmAmGmAfAmAfGmUmUmGmCm |
| siKNf1-M2 | 315 | AmAmCmUmUfUmCfUfAfUmUmUmCmAmAmGmAmUmUm |
| | 316 | AmAfUmCmUmUfGmAfAfAmUmAmGmAfAmAfGmUmUmGmCm |
| siKNf1-M3 | 317 | AmAmCmUmUfUmCfUfAfUmUmUmCmAmAmGmAmUmUm |
| | 318 | AmAfUmCmUmUfGmAmAmAmUmAmGmAfAmAfGmUmUmGmCm |
| siKNf2-M1 | 319 | GmCmAmAmCmUmUmUmCfUfAfUmUmUmCmAmAmGmAmUmUm |
| | 320 | AmAfUmCmUmUfGmAmAmAmUmAmGmAfAmAfGmUmUmGmCmGmUm |
| siKNf2-M2 | 321 | GmCmAmAmCmUmUfUmCfUfAfUmUmUmCmAmAmGmAmUmUm |
| | 322 | AmAfUmCmUmUfGmAfAfAmUmAmGmAfAmAfGmUmUmGmCmGmUm |
| siKNf2-M3 | 323 | GmCmAmAmCmUmUfUmCfUfAfUmUmUmCmAmAmGmAmUmUm |
| | 324 | AmAfUmCmUmUfGmAmAmAmUmAmGmAfAmAfGmUmUmGmCmGmUm |
| siKNf1-M1S | 325 | AmsAmsCmUmUmUmCfUfAfUmUmUmCmAmAmGmAmUmUm |
| | 326 | AmsAfsUmCmUmUfGmAmAmAmUmAmGmAfAmAfGmUmUmsGmsCm |
| siKNf1-M2S | 327 | AmsAmsCmUmUfUmCfUfAfUmUmUmCmAmAmGmAmUmUm |
| | 328 | AmsAfsUmCmUmUfGmAfAfAmUmAmGmAfAmAfGmUmUmsGmsCm |
| siKNf1-M3S | 329 | AmsAmsCmUmUfUmCfUfAfUmUmUmCmAmAmGmAmUmUm |
| | 330 | AmsAfsUmCmUmUfGmAmAmAmUmAmGmAfAmAfGmUmUmsGmsCm |
| siKNf2-M1S | 331 | GmsCmsAmAmCmUmUmUmCfUfAfUmUmUmCmAmAmGmAmUmUm |
| | 332 | AmsAfsUmCmUmUfGmAmAmAmUmAmGmAfAmAfGmUmUmGmCmsGmsUm |
| siKNf2-M2S | 333 | GmsCmsAmAmCmUmUfUmCfUfAfUmUmUmCmAmAmGmAmUmUm |
| | 334 | AmsAfsUmCmUmUfGmAfAfAmUmAmGmAfAmAfGmUmUmGmCmsGmsUm |

TABLE 1f-continued

| Sixth siRNA sequence of the present disclosure | | |
|---|---|---|
| siRNA No. | SEQ ID NO: | Sequence direction 5'- 3' |
| siKNf2-M3S | 335 | GmsCmsAmAmCmUmUfUmCfUfAfUmUmUmCmAmAmGmAmUmUm |
| | 336 | AmsAfsUmCmUmUfGmAmAmAmUmAmGmAfAmAfGmUmUmGmCmsGmsUm |
| siKNf1-M1P1 | 337 | AmAmCmUmUmUmCfUfAfUmUmUmCmAmAmGmAmUmUm |
| | 338 | P1AmAfUmCmUmUfGmAmAmAmUmAmGmAfAmAfGmUmUmGmCm |
| siKNf1-M2P1 | 339 | AmAmCmUmUfUmCfUfAfUmUmUmCmAmAmGmAmUmUm |
| | 340 | P1AmAfUmCmUmUfGmAfAfAmUmAmGmAfAmAfGmUmUmGmCm |
| siKNf1-M3P1 | 341 | AmAmCmUmUfUmCfUfAfUmUmUmCmAmAmGmAmUmUm |
| | 342 | P1AmAfUmCmUmUfGmAmAmAmUmAmGmAfAmAfGmUmUmGmCm |
| siKNf2-M1P1 | 343 | GmCmAmAmCmUmUmUmCfUfAfUmUmUmCmAmAmGmAmUmUm |
| | 344 | P1AmAfUmCmUmUfGmAmAmAmUmAmGmAfAmAfGmUmUmGmCmGmUm |
| siKNf2-M2P1 | 345 | GmCmAmAmCmUmUfUmCfUfAfUmUmUmCmAmAmGmAmUmUm |
| | 346 | P1AmAfUmCmUmUfGmAfAfAmUmAmGmAfAmAfGmUmUmGmCmGmUm |
| siKNf2-M3P1 | 347 | GmCmAmAmCmUmUfUmCfUfAfUmUmUmCmAmAmGmAmUmUm |
| | 348 | P1AmAfUmCmUmUfGmAmAmAmUmAmGmAfAmAfGmUmUmGmCmGmUm |
| siKNf1-M1SP1 | 349 | AmsAmsCmUmUmUmCfUfAfUmUmUmCmAmAmGmAmUmUm |
| | 350 | P1AmsAfsUmCmUmUfGmAmAmAmUmAmGmAfAmAfGmUmUmsGmsCm |
| siKNf1-M2SP1 | 351 | AmsAmsCmUmUfUmCfUfAfUmUmUmCmAmAmGmAmUmUm |
| | 352 | P1AmsAfsUmCmUmUfGmAfAfAmUmAmGmAfAmAfGmUmUmsGmsCm |
| siKNf1-M3SP1 | 353 | AmsAmsCmUmUfUmCfUfAfUmUmUmCmAmAmGmAmUmUm |
| | 354 | P1AmsAfsUmCmUmUfGmAmAmAmUmAmGmAfAmAfGmUmUmsGmsCm |
| siKNf2-M1SP1 | 355 | GmsCmsAmAmCmUmUmUmCfUfAfUmUmUmCmAmAmGmAmUmUm |
| | 356 | P1AmsAfsUmCmUmUfGmAmAmAmUmAmGmAfAmAfGmUmUmGmCmsGmsUm |
| siKNf2-M2SP1 | 357 | GmsCmsAmAmCmUmUfUmCfUfAfUmUmUmCmAmAmGmAmUmUm |
| | 358 | P1AmsAfsUmCmUmUfGmAfAfAmUmAmGmAfAmAfGmUmUmGmCmsGmsUm |
| siKNf2-M3SP1 | 359 | GmsCmsAmAmCmUmUfUmCfUfAfUmUmUmCmAmAmGmAmUmUm |
| | 360 | P1AmsAfsUmCmUmUfGmAmAmAmUmAmGmAfAmAfGmUmUmGmCmsGmsUm |

wherein, capital letters C, G, U, and A indicate the base composition of the nucleotides; the lowercase m indicates that the nucleotide adjacent to the left side of the letter m is a methoxy modified nucleotide; the lowercase f indicates that the nucleotide adjacent to the left side of the letter f is a fluoro modified nucleotide; the lowercase letter s indicates that the two nucleotides adjacent to the left and right of the letter s are linked by phosphorothioate; and P1 represents that the nucleotide adjacent to the right side of P1 is a 5'-phosphate nucleotide or a 5'-phosphate analogue modified nucleotide. In some embodiments, P1 represents specifically modified VP, Ps or P, wherein the letter combination VP represents that the nucleotide adjacent to the right side of the letter combination VP is a 5'-(E)-vinylphosphonate (E-VP) modified nucleotide, the letter combination Ps represents that the nucleotide adjacent to the right side of the letter combination Ps is a phosphorothioate modified nucleotide, and the capital letter P represents that the nucleotide adjacent to the right side of the letter P is a 5'-phosphate nucleotide.

In the siRNA or the siRNA conjugate of the present disclosure, each pair of adjacent nucleotides is linked via a phosphodiester bond or phosphorothioate diester bond. The non-bridging oxygen atom or sulfur atom in the phosphodiester bond or phosphorothioate diester bond is negatively charged, and may be present in the form of hydroxy or sulfhydryl.

Moreover, the hydrogen ion in the hydroxy or sulfhydryl may be partially or completely substituted with a cation. The cation may be any cation, such as one of a metal cation, an ammonium ion $NH4^+$ or an organic ammonium cation. In order to increase solubility, in some embodiments, the cation is selected from one or more of an alkali metal ion, an ammonium cation formed by a tertiary amine and a quaternary ammonium cation. The alkali metal ion may be $K^+$ and/or $Na^+$, and the cation formed by the tertiary amine may be an ammonium ion formed by triethylamine and/or an ammonium ion formed by N,N-diisopropylethylamine. Thus, the siRNA or siRNA conjugate of the present disclosure may be at least partially present in the form of salt. In some embodiment, the non-bridging oxygen atom or sulfur atom in the phosphodiester bond or phosphorothioate diester bond at least partly binds to a sodium ion, and the siRNA or the siRNA conjugate of the present disclosure is present or partially present in the form of sodium salt.

Those skilled in the art clearly know that a modified nucleotide group may be introduced into the siRNA of the present disclosure by a nucleoside monomer having a corresponding modification. The methods for preparing the nucleoside monomer having the corresponding modification and the methods for introducing the modified nucleotide group into the siRNA are also well-known to those skilled in the art. All the modified nucleoside monomers may be either commercially available or prepared by known methods.

Preparation of the siRNA Conjugate as Shown by Formula (308)

The siRNA conjugate as shown by Formula (308) may be prepared by any appropriate synthetic routes.

In some embodiments, the siRNA conjugate as shown by Formula (308) may be prepared by the following method. The method comprises: successively linking nucleoside monomers in the direction from 3' to 5' according to the nucleotide types and sequences in the sense strand and antisense strand respectively under the condition of solid phase phosphoramidite synthesis, wherein the linking of each nucleoside monomer comprises a four-step reaction of deprotection, coupling, capping, and oxidation or sulfurization; isolating the sense strand and the antisense strand of the siRNA; and annealing; wherein the siRNA is the siRNA of the present disclosure mentioned above.

Moreover, the method further comprises: contacting the compound as shown by Formula (321) with a nucleoside monomer or a nucleotide sequence linked to a solid phase support under coupling reaction condition and in the presence of a coupling agent, thereby linking the compound as shown by Formula (321) to the nucleotide sequence through a coupling reaction. Hereinafter, the compound as shown by Formula (321) is also called a conjugating molecule.

Formula (321)

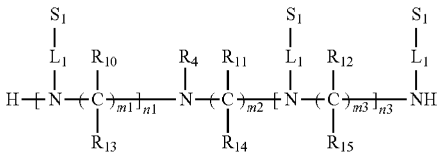

wherein:

$R_4$ is a group capable of binding to the siRNA represented by Nu in the compound as shown by Formula (308). In some embodiments, $R_4$ is a group capable of binding to the siRNA represented by Nu via a covalent bond. In some embodiments, $R_4$ is a group capable of being conjugated to any functional group of the siRNA represented by Nu via a phosphodiester bond by reaction;

Each $S_1$ is independently a group which is formed by substituting all active hydroxy in $M_1$ with YCOO— groups, wherein each Y is independently selected from one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. In some embodiments, Y is a methyl.

Definitions and options of n1, n3, m1, m2, m3, $R_{10}$, $R_{11}$, $R_{12}$, $R_{13}$, $R_{14}$, $R_{15}$, $L_1$, and $M_1$ are respectively as described above.

$R_4$ is selected to achieve the linkage to the N atom on a nitrogenous backbone and to provide a suitable reaction site for synthesizing the siRNA conjugate as shown by Formula (308). In some embodiments, $R_4$ comprises a $R_2$ linking group or a protected $R_2$ linking group, and a functional group that can react with siRNA to form the structure shown in A59.

In some embodiments, $R_4$ comprises a first functional group that can react with a group on an siRNA represented by Nu or a nucleoside monomer to form a phosphite ester, and a second functional group that can form a covalent bond with a hydroxy or an amino, or comprises a solid phase support linked via the covalent bond. In some embodiments, the first functional group is a phosphoramidite, a hydroxy or a protected hydroxy. In some embodiments, the second functional group is a phosphoramidite, a carboxyl or a carboxylate. In some embodiments, the second functional group is a solid phase support linked to the rest of the molecule via a covalent bond which is formed by a hydroxy or an amino. In some embodiments, the solid phase support is linked via a phosphoester bond, a carboxyl ester bond, or an amide bond. In some embodiments, the solid phase support is a resin.

In some embodiments, the first functional group comprises a hydroxy, —$OR_k$ or a group as shown by Formula (C3); and the second functional group comprises a group as shown by Formula (C1), (C2), (C3), (C1'), or (C3'):

(C1)

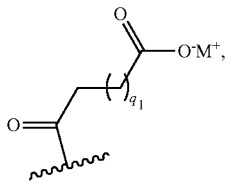

(C2)

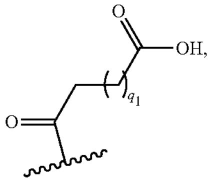

(C3)

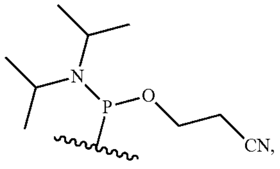

(C1')

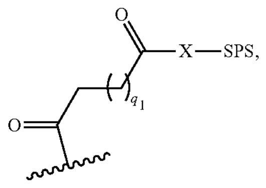

(C3')

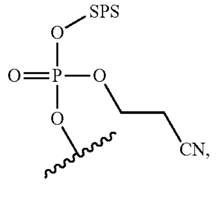

wherein $q_1$ is an integer of 1-4, X is O or NH, $M^+$ is a cation. $R_k$ is a hydroxy protecting group, SPS represents a solid phase support, and represents the site where a group is covalently linked.

In some embodiments, the first functional group comprises a phosphoramidite group as shown by Formula (C3). The phosphoramidite group can form a phosphite ester with a hydroxy at any position on a nucleotide such as a 2' or 3' hydroxy by a coupling reaction, and the phosphite ester can form a phosphodiester bond or phosphorothioate ester bond as shown by Formula (A59) via oxidation or sulfurization, so as to conjugate the conjugating molecule to the siRNA. In this case, even if the second functional group does not exist, the compound as shown by Formula (321) will still be able to be conjugated to the nucleotide, without affecting the acquisition of the siRNA conjugate as shown by Formula (308). Under such circumstances, after obtaining a sense strand or an antisense strand of the siRNA by a method such as solid phase phosphoramidite synthesis, the compound as shown by Formula (321) is reacted with a hydroxy on the terminal nucleotide of the nucleotide sequence, and phosphodiester bonding or phosphorothioate bonding is formed by a subsequent oxidation or sulfurization process, thereby conjugating the compound as shown by Formula (321) to the siRNA.

In some embodiments, the first functional group comprises a protected hydroxy. In some embodiments, the second functional group comprises a group that can react with a solid phase support to provide a conjugating molecule comprising the solid phase support. In some embodiments, the second functional group comprises a carboxyl, a carboxylate or a phosphoramidite as shown by Formula (C1), (C2) or (C3). When the second functional group comprises a carboxyl or a carboxylate, the compound as shown by Formula (321) reacts with a hydroxy or an amino on a solid phase support such as a resin via an esterification or an amidation reaction, to form a conjugating molecule comprising the solid phase support linked via a carboxyl ester bond. When the second functional group comprises a phosphoramidite functional group, the compound as shown by Formula (321) may be coupled with a hydroxy on a universal solid phase support, such as a resin, and form, by oxidation, a conjugating molecule comprising the solid phase support linked via a phosphodiester bond. Subsequently, starting from the above product linked to the solid phase support, the nucleoside monomers are linked sequentially by a solid phase phosphoramidite synthesis method, thereby obtaining a sense strand or an antisense strand of the siRNA linked to the conjugation group. During the solid phase phosphoramidite synthesis, the first functional group is deprotected, and then coupled with a phosphoramidite group on a nucleoside monomer under coupling reaction condition.

In some embodiments, the first functional group comprises a hydroxy or a protected hydroxy; and the second functional group comprises a solid phase support linked via a carboxyl ester bond, a solid phase support linked via an amide bond or a solid phase support linked via a phosphoester bond, as shown by Formula (C1') or (C3'). In this case, starting from the compound as shown by Formula (321) in place of the solid phase support, the nucleoside monomers are linked sequentially by a solid phase phosphoramidite synthesis, thereby obtaining a sense strand or an antisense strand of the siRNA linked to a conjugating group.

In some embodiments, the carboxylate may be expressed as —COO-M$^+$, wherein M$^+$ is a cation such as one of a metal cation, an ammonium cation NH4$^+$ and an organic ammonium cation. In one embodiment, the metal ion is selected from one of the alkali metal ions, such as K$^+$ or Na$^+$. In order to increase solubility and facilitate the reaction, in some embodiments, the organic ammonium ion is an ammonium cation formed by a tertiary amine, or a quaternary ammonium cation, such as an ammonium ion formed by triethylamine or an ammonium ion formed by N,N-diisopropylethylamine. In some embodiments, the carboxylate is a triethylamine carboxylate or an N,N-diisopropylethylamine carboxylate.

In some embodiments, $R_4$ comprises a structure as shown by Formula (B9), (B10), (B9'), (B10'), (B11), (B12), (B11') or (B12'):

(B9)

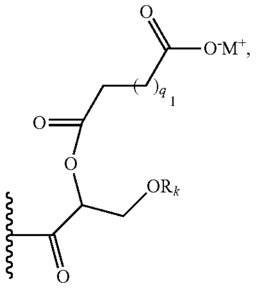

(B10)

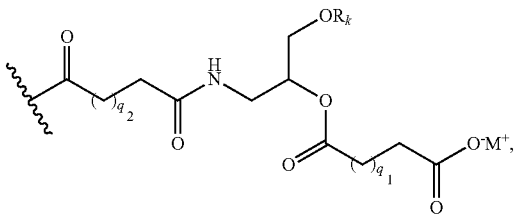

(B9')

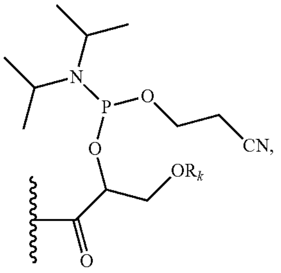

(B10')

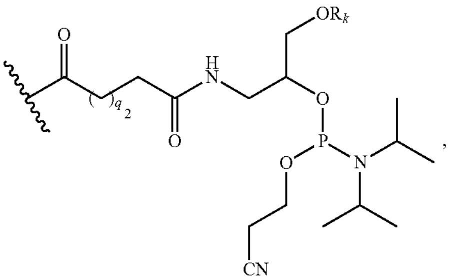

-continued (B11)

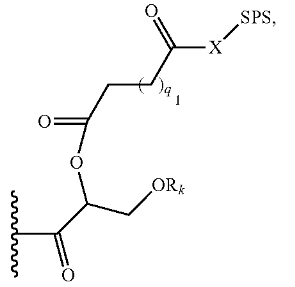

(B12)

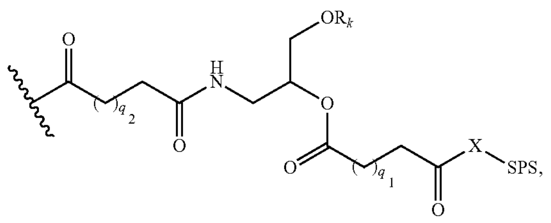

(B11')

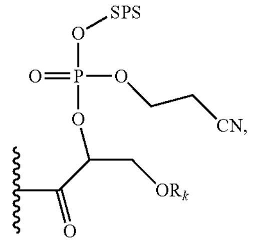

(B12')

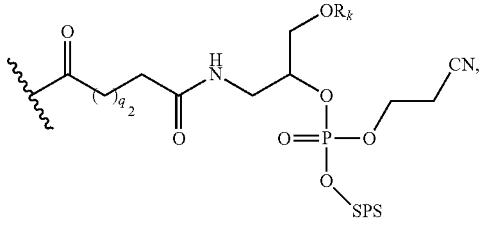

wherein $q_1$ is an integer of 1-4, $q_2$ is an integer of 1-10, X is O or NH, $M^+$ is a cation, $R_k$ is a hydroxy protecting group, SPS represents a solid phase support, and ~~~~ represents a site where a group is covalently linked. In some embodiments, $q_1$ is 1 or 2. In some embodiments, $q_2$ is an integer of 1-5. In some embodiments, $R_4$ comprises a structure as shown by Formula (B9) or (B10). In some embodiments, $R_4$ comprises a structure as shown by Formula (B11) or (B12).

In some embodiments, $R_k$ is one or more of Tr (trityl), MMTr (4-methoxytrityl), DMTr (4,4'-dimethoxytrityl), and TMTr (4,4',4"-trimethoxytrityl). In some embodiments, $R_k$ may be DMTr, i.e., 4,4'-dimethoxytrityl.

The definition of $L_1$ is as described above.

In some embodiments, $L_1$ is used to link the $M_1$ targeting group to the N atom on the nitrogenous backbone, thereby providing liver targeting function for the siRNA conjugate as shown by Formula (308). In some embodiments, $L_1$ comprises any one of A1-A26, or the combination thereof.

According to the description above, those skilled in the art would easily understand that as compared with the well-known solid phase phosphoramidite synthesis methods in the art, an siRNA conjugate as shown by Formula (308) in which a conjugating molecule is linked to any possible position of the nucleotide sequence can be obtained through the above first functional group and an optional second functional group. For example, the conjugating molecule is linked to an end of the nucleotide sequence or to a terminal of the nucleotide sequence. Correspondingly, unless otherwise specified, in the following description regarding the preparation of siRNA conjugate and/or conjugating molecule, when referring to the reactions such as "deprotection", "coupling", "capping", "oxidation", "sulfurization", it will be understood that the reaction conditions and agents involved in the well-known phosphoramidite nucleic acid solid phase synthesis methods in the art are also applicable to these reactions. Exemplary reaction conditions and agents will be described in detail hereinafter.

In some embodiments, each $S_1$ is independently an $M_1$. In some embodiments, each $S_1$ is independently a group formed by protecting at least one active hydroxy in $M_1$ with a hydroxy protecting group. In some embodiments, each $S_1$ is independently a group formed by protecting all active hydroxys in $M_1$ with hydroxy protecting groups. In some embodiments, any hydroxy protecting group known to those skilled in the art may be used to protect the active hydroxy in $M_1$. In some embodiments, the protected hydroxy may be expressed as the formula YCOO—, wherein each Y is independently selected from the group consisting of $C_1$-$C_{10}$ alkyl and $C_6$-$C_{10}$ aryl, wherein the $C_1$-$C_{10}$ alkyl and $C_6$-$C_{10}$ aryl are optionally substituted with one or more substituents selected from the group consisting of halo and $C_1$-$C_6$ alkyl. In some embodiments, each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and $C_1$-$C_6$ alkylphenyl.

In some embodiments, each $S_1$ is independently selected from the group consisting of Formulae A46-A54:

(A46)

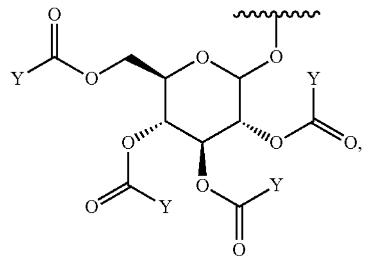

(A47)

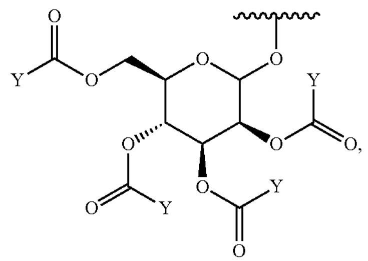

-continued (A48)

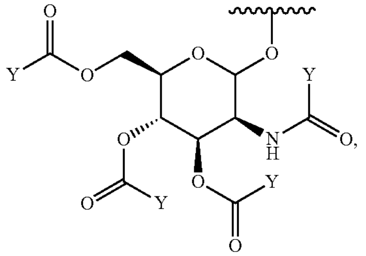

(A49)

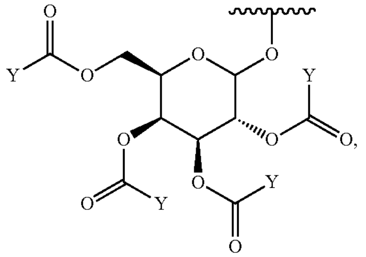

(A50)

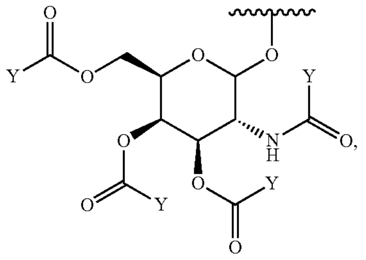

(A51)

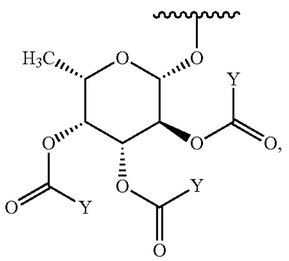

(A52)

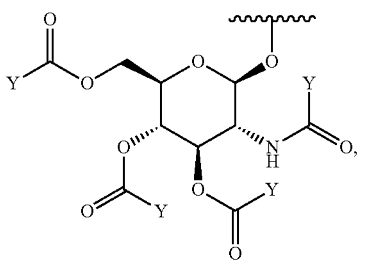

-continued (A53)

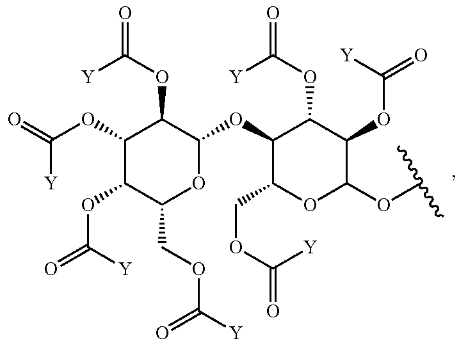

(A54)

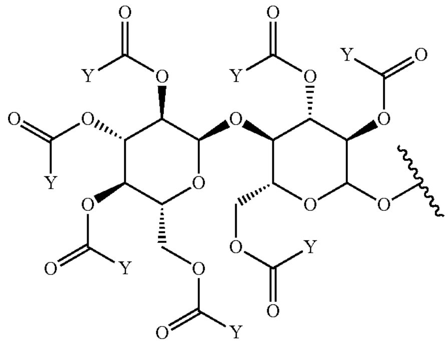

In some embodiments, $S_1$ is Formula A49 or A50.

In some embodiments, each Y is independently selected from one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. In some embodiments, Y is a methyl.

As mentioned previously, the method for preparing the siRNA conjugate as shown by Formula (308) further comprises the following steps of: synthesizing the other strand of the siRNA (for example, when the sense strand of the siRNA linked to the conjugating molecule is synthesized in the above steps, the method further comprises synthesizing the antisense strand of the siRNA by the solid phase synthesis method, and vice versa); isolating the sense strand and the antisense strand; and annealing. In particular, in the isolating step, the solid phase support linked to the nucleotide sequence and/or the conjugating molecule is cleaved and at the same time the necessary protecting group is removed (in this case, each $S_1$ group in the compound as shown by Formula (321) is converted to a corresponding $M_1$ targeting group), thereby providing the sense strand (or antisense strand) of the siRNA linked to the conjugating molecule and the corresponding antisense strand (or sense strand). The sense strand and the antisense strand are annealed to form a double-stranded RNA structure, thereby obtaining the siRNA conjugate as shown by Formula (308).

In some embodiments, the method for preparing the siRNA conjugate as shown by Formula (308) comprises the following steps of: contacting the compound as shown by Formula (321) with the first nucleoside monomer at 3' terminal of the sense strand or antisense strand under coupling reaction condition in the presence of a coupling agent, thereby linking the compound as shown by Formula (321) to the first nucleotide in the sequence; successively linking nucleoside monomers in the direction from 3' to 5' to synthesize the sense strand or the antisense strand of the siRNA according to the desired nucleotide type and sequence of the sense strand or antisense strand, under the condition of solid phase phosphoramidite synthesis; wherein the compound as shown by Formula (321) is a compound in which $R_4$ comprises a first functional group and a second functional group, the first functional group comprises a protected hydroxy and the second functional group has a structure as shown by Formula (C1') or (C3'), and the compound as shown by Formula (321) is deprotected before linking to the first nucleoside monomer; and the linking of each nucleoside monomer comprises a four-step reaction of deprotection, coupling, capping, and oxidation or sulfurization, thus obtaining a sense strand or an antisense strand of a nucleic acid linked to the conjugating molecule; successively linking the nucleoside monomers in the direction from 3' to 5' to synthesize the sense strand or antisense strand of the nucleic acid according to the nucleotide type and sequence of the sense strand or the antisense strand, under the condition of solid phase phosphoramidite synthesis; wherein the linking of each nucleoside monomer comprises a four-step reaction of deprotection, coupling, capping, and oxidation or sulfurization; removing the protecting groups and cleaving from the solid phase support; isolating and purifying to obtain the sense strand and the antisense strand; and annealing.

In some embodiments, the method for preparing the siRNA conjugate as shown by Formula (308) comprises the following steps of: successively linking nucleoside monomers in the direction from 3' to 5' to synthesize the sense strand or the antisense strand according to the nucleotide type and sequence of the sense strand or antisense strand in the double-stranded siRNA; wherein the linking of each nucleoside monomer comprises a four-step reaction of deprotection, coupling, capping, and oxidation or sulfurization, thus obtaining a sense strand linked to the solid phase support and an antisense strand linked to the solid phase support; contacting the compound as shown by Formula (321) with the sense strand linked to the solid phase support or the antisense strand linked to the solid phase support under coupling reaction condition in the presence of a coupling agent, thereby linking the compound as shown by Formula (321) to the sense strand or the antisense strand; wherein the compound as shown by Formula (321) is a compound in which $R_4$ comprises a the first functional group which is phosphoramidite group; removing the protecting groups and cleaving from the solid phase support; respectively isolating and purifying to obtain the sense strand or the antisense strand of the siRNA; and annealing; wherein the sense strand or the antisense strand of the siRNA is linked to a conjugating molecule.

In some embodiments, the P atom in Formula A59 is linked to the 3' terminal of the sense strand of the siRNA, and the method for preparing the siRNA conjugate as shown by Formula (308) comprises:

(1) removing the hydroxy protecting group $R_k$ in the compound as shown by Formula (321) (wherein the compound as shown by Formula (321) is a compound in which $R_4$ comprises a first functional group and a second function group, the first functional group comprises a protected hydroxy $OR_k$, and the second function group has a structure as shown by Formula (C1') or (C3')); and contacting the product obtained by deprotection with a nucleoside monomer to obtain a nucleoside monomer linked to a solid phase support via the conjugating molecule under a coupling reaction condition in the presence of a coupling agent;
(2) starting from the nucleoside monomer linked to the solid phase support via the conjugating molecule, synthesizing the sense strand of the siRNA in the direction from 3' to 5' by a solid phase phosphoramidite synthesis;
(3) synthesizing the antisense strand of the siRNA by a solid phase phosphoramidite synthesis method; and
(4) isolating the sense strand and the antisense strand of the siRNA, and annealing the same to obtain the siRNA conjugate as shown by Formula (308).

Wherein, in step (1), the method for removing the protecting group $R_k$ in the compound as shown by Formula (321) comprises contacting the compound as shown by Formula (321) with a deprotection agent under a deprotection condition. The deprotection condition comprises a temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments, the deprotection agent is dichloroacetic acid. The molar ratio of the deprotection agent to the compound as shown by Formula (321) may be 10:1 to 1000:1, and in some embodiments, 50:1 to 500:1.

The coupling reaction condition and the coupling agent may be any conditions and agents suitable for the above coupling reaction. In some embodiments, the same condition and agent as those of the coupling reaction in the solid phase synthesis method may be used.

In some embodiments, the coupling reaction condition comprises a reaction temperature of 0-50° C., and in some embodiments, 15-35° C. The molar ratio of the compound as shown by Formula (321) to the nucleoside monomer may be 1:1 to 1:50, and in some embodiments, 1:2 to 1:5. The molar ratio of the compound as shown by Formula (321) to the coupling agent may be 1:1 to 1:50, and in some embodiments, 1:3 to 1:10. The reaction time may be 200-3000 seconds, and in some embodiments, 500-1500 seconds. The coupling agent may be selected from one or more of 1H-tetrazole, 5-ethylthio-1H-tetrazole and 5-benzylthio-1H-tetrazole, and in some embodiments, is 5-ethylthio-1H-tetrazole. The coupling reaction may be carried out in an organic solvent, and the organic solvent may be selected from one or more of anhydrous acetonitrile, anhydrous DMF and anhydrous dichloromethane, and in some embodiments, is anhydrous acetonitrile. The amount of the organic solvent may be 3-50 L/mol, and in some embodiments, 5-20 L/mol, with respect to the compound as shown by Formula (321).

In step (2), a sense strand SS of the second siRNA conjugate is synthesized in the direction from 3' to 5' by the phosphoramidite nucleic acid solid phase synthesis method, starting with the nucleoside monomer linked to the solid phase support via the conjugating molecule prepared in the above steps. In this case, the conjugating molecule is linked to 3' terminal of the resultant sense strand.

Other conditions for the solid phase synthesis in steps (2) and (3), comprising the deprotection condition for the nucleoside monomer, the type and amount of the deprotection agent, the coupling reaction condition, the type and amount of the coupling agent, the capping reaction condition, the type and amount of the capping agent, the oxidation reaction condition, the type and amount of the oxidation agent, the sulfurization reaction condition, and the type and amount of the sulfurization agent, adopt various conventional agents, amounts, and conditions in the art.

For instance, in some embodiments, the solid phase synthesis in steps (2) and (3) may use the following conditions:

The deprotection condition for the nucleoside monomer comprises a temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments, the deprotection agent is dichloroacetic acid. The molar ratio of the deprotection agent to the protecting group 4,4'-dimethoxytrityl on the solid phase support is 2:1 to 100:1, and in some embodiments, is 3:1 to 50:1.

The coupling reaction condition comprises a reaction temperature of 0-50° C., and in some embodiments, 15-35° C. The molar ratio of the nucleic acid sequence linked to the solid phase support to the nucleoside monomer is 1:1 to 1:50, and in some embodiments, is 1:5 to 1:15. The molar ratio of the nucleic acid sequence linked to the solid phase support to the coupling agent is 1:1 to 1:100, and in some embodiments, is 1:50 to 1:80. The selection of the reaction time and the coupling agent can be same as above.

The capping reaction condition comprises a reaction temperature of 0-50° C., and in some embodiments, 15-35° C., and a reaction time of 5-500 seconds, and in some embodiments, 10-100 seconds. The selection of the capping agent can be same as above. The molar ratio of the total amount of the capping agent to the nucleic acid sequence linked to the solid phase support may be 1:100 to 100:1, and in some embodiments, is 1:10 to 10:1. In the case where the capping agent uses equimolar acetic anhydride and N-methylimidazole, the molar ratio of the acetic anhydride to the N-methylimidazole and the nucleic acid sequence linked to the solid phase support may be 1:1:10 to 10:10:1, and in some embodiments, is 1:1:2 to 2:2:1.

The oxidation reaction condition comprises a reaction temperature of 0-50° C., and in some embodiments, 15-35° C., and a reaction time of 1-100 seconds, and in some embodiments, 5-50 seconds. In some embodiments, the oxidation agent is iodine (in some embodiments, provided as iodine water). The molar ratio of the oxidation agent to the nucleic acid sequence linked to the solid phase support in the coupling step may be 1:1 to 100:1, and in some embodiments, is 5:1 to 50:1. In some embodiments, the oxidation reaction is performed in a mixed solvent in which the ratio of tetrahydrofuran:water:pyridine is 3:1:1 to 1:1:3. The sulfurization reaction condition comprises a reaction temperature of 0-50° C., and in some embodiments, 15-35° C., and a reaction time of 50-2000 seconds, and in some embodiments, 100-1000 seconds. In some embodiments, the sulfurization agent is xanthane hydride. The molar ratio of the sulfurization agent to the nucleic acid sequence linked to the solid phase support in the coupling step is 10:1 to 1000:1, and in some embodiments, is 10:1 to 500:1. In some embodiments, the sulfurization reaction is performed in a mixed solvent in which the ratio of acetonitrile:pyridine is 1:3 to 3:1.

The method further comprises isolating the sense strand and the antisense strand of the siRNA after linking all nucleoside monomers and before the annealing. Methods for isolation are well-known to those skilled in the art and generally comprise cleaving the synthesized nucleotide sequence from the solid phase support, removing protecting groups on the bases, phosphate groups and ligands, purifying and desalting.

The conventional cleavage and deprotection methods in the synthesis of siRNAs can be used to cleave the synthesized nucleotide sequence from the solid phase support, and remove the protecting groups on the bases, phosphate groups and ligands. For example, contact the resultant nucleotide sequence linked to the solid phase support with strong aqua; during deprotection, the protecting group YCOO— in groups A46-A54 is converted to a hydroxy, and the $S_1$ groups is converted to a corresponding $M_1$ group, providing the siRNA conjugate as shown by Formula (308); wherein the strong aqua may be aqueous ammonia at a concentration of 25-30% by weight. The amount of the strong aqua may be 0.2 ml/μmol-0.8 ml/μmol with respect to the target siRNA.

When there is at least one 2'-TBDMS protection on the synthesized nucleotide sequence, the method further comprises contacting the nucleotide sequence removed from the solid phase support with triethylamine trihydrofluoride to remove the 2'-TBDMS protection. In this case, the resultant target siRNA sequence comprises the corresponding nucleoside having free 2'-hydroxy. The amount of pure triethylamine trihydrofluoride is 0.4 ml/μmol-1.0 ml/μmol with respect to the target siRNA sequence. As such, the siRNA conjugate as shown by Formula (308) may be obtained.

Methods for purification and desalination are well-known to those skilled in the art. For example, nucleic acid purification may be performed using a preparative ion chromatography purification column with a gradient elution of NaBr or NaCl; after collection and combination of the product, the desalination may be performed using a reverse phase chromatography purification column.

The non-bridging oxygen atom or sulfur atom in the phosphodiester bond or phosphorothioate diester bond between the nucleotides in the resultant siRNA conjugate as shown by Formula (308) substantially binds to a sodium ion, and the siRNA conjugate as shown by Formula (308) is substantially present in the form of a sodium salt. The well-known ion-exchange methods may be used, in which the sodium ion may be replaced with hydrogen ion and/or other cations, thereby providing other forms of siRNA conjugates as shown by Formula (308). The cations are as described above.

During synthesis, the purity and molecular weight of the nucleic acid sequence may be determined at any time, so as to better control the synthesis quality, such detection methods are well-known to those skilled in the art. For example, the purity of the nucleic acid may be detected by ion exchange chromatography, and the molecular weight may be determined by liquid chromatography-mass spectrometry (LC-MS).

Methods for annealing are also well-known to those skilled in the art. For example, the synthesized sense strand (S strand) and antisense strand (AS strand) may be simply mixed in water for injection at an equimolar ratio, heated to 70-95° C., and then cooled at room temperature to form a double-stranded structure via hydrogen bond. As such, the siRNA conjugate as shown by Formula (308) may be obtained.

After obtaining the siRNA conjugate, in some embodiments, the siRNA conjugate as shown by Formula (308) thus synthesized can also be characterized by the means such as molecular weight detection using the methods such as liquid chromatography-mass spectrometry, to confirm that the synthesized siRNA conjugate is the designed siRNA conjugate as shown by Formula (308) of interest, and the sequence of the synthesized siRNA is the sequence of the siRNA sequence desired to be synthesized, for example, is one of the sequences listed in Tables 1.

The compound as shown by Formula (321) may be prepared by the following method comprising: contacting a compound as shown by Formula (313) with a cyclic anhydride in an organic solvent under esterification reaction condition in the presence of a base and an esterification catalyst; and isolating the compound as shown by Formula (321) by ion exchange:

Formula (313)

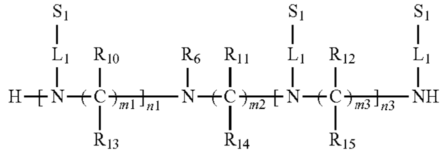

wherein the definitions and options of n1, n3, m1, m2, m3, $R_{10}$, $R_{11}$, $R_{12}$, $R_{13}$, $R_{14}$, $R_{15}$, $L_1$, and $S_1$ are respectively as described above;

$R_6$ is a group for providing $R_4$ of Formula (321). In some embodiments, $R_6$ comprises a structure as shown by Formula (A61):

(A61)

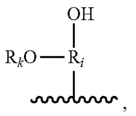

wherein, $R_i$ is any group capable of linking to the N atom on the nitrogenous backbone, linking to $R_kO$ and with a free hydroxy attached; and $R_k$ is a hydroxy protecting group. In this case, the compound as shown by Formula (321) is obtained, wherein $R_4$ comprises a first functional group as a hydroxy protecting group and a second functional group comprising a group as shown by Formula (C1) or (C2).

The esterification reaction condition comprises a reaction temperature of 0-100° C. and a reaction time of 8-48 hours. In some embodiments, the esterification reaction condition comprises a reaction temperature of 10-40° C. and a reaction time of 20-30 hours.

In some embodiments, the organic solvent comprises one or more of an epoxy solvent, an ether solvent, a haloalkane solvent, dimethyl sulfoxide, N,N-dimethylformamide, and N,N-diisopropylethylamine. In some embodiments, the epoxy solvent is dioxane and/or tetrahydrofuran, the ether solvent is diethyl ether and/or methyl tertbutyl ether, and the haloalkane solvent is one or more of dichloromethane, trichloromethane and 1,2-dichloroethane. In some embodiments, the organic solvent is dichloromethane. The amount of the organic solvent is 3-50 L/mol, and in some embodiments, 5-20 L/mol, with respect to the compound as shown by Formula (313).

In some embodiments, the cyclic anhydride is one of succinic anhydride, glutaric anhydride, adipic anhydride or pimelic anhydride, and in some embodiments, the cyclic anhydride is succinic anhydride. The molar ratio of the cyclic anhydride to the compound as shown by Formula (313) is 1:1 to 10:1, and in some embodiments, 2:1 to 5:1.

The esterification catalyst may be any catalyst capable of catalyzing this esterification, for example, the catalyst may be 4-dimethylaminopyridine. The molar ratio of the catalyst to the compound as shown by Formula (313) is 1:1 to 10:1, and in some embodiments, 2:1 to 5:1.

In some embodiments, the base may be any inorganic base, organic base or a combination thereof. Considering solubility and product stability, the base may be, for example, tertiary amine. In some embodiments, the tertiary amine is triethylamine or N,N-diisopropylethylamine. The molar ratio of the tertiary amine to the compound as shown by Formula (313) is 1:1 to 20:1, and in some embodiments, is 3:1 to 10:1.

The ion exchange serves the function of converting the compound as shown by Formula (321) into a desired form of carboxylic acid or carboxylic salt and the methods of ion exchange are well-known to those skilled in the art. The conjugating molecule having the cation $M^+$ may be obtained by using suitable ion exchange solution and ion exchange condition, which is not described here in detail. In some embodiments, a triethylamine phosphate solution is used in the ion exchange reaction, and the concentration of the triethylamine phosphate solution is 0.2-0.8 M. In some embodiments, the concentration of the triethylamine phosphate solution is 0.4-0.6 M. In some embodiments, the amount of the triethylamine phosphate solution is 3-6 L/mol, and in further embodiment, 4-5 L/mol, with respect to the compound as shown by Formula (313).

The compound as shown by Formula (321) may be isolated from the reaction mixture using any suitable isolation methods. In some embodiments, the compound as shown by Formula (321) may be isolated by removal of solvent via evaporation, followed by chromatography, for example, using the following two chromatographic conditions for the isolation: (1) normal phase purification silica gel: 200-300 mesh silica gel filler, and using gradient elution of 1 wt % triethylamine in dichloromethane:methanol=100:18 to 100:20; or (2) reverse phase purification: C18 and C8 reverse phase filler, and using gradient elution of methanol:acetonitrile=0.1:1 to 1:0.1. In some embodiments, the solvent may be directly removed to obtain a crude product of the compound as shown by Formula (321), which may be directly used in subsequent reactions.

In some embodiments, the method for preparing the compound as shown by Formula (321) further comprises: contacting the product obtained from the above ion exchanging reaction with a solid phase support containing amino or hydroxy in an organic solvent under condensation reaction condition in the presence of a condensing agent, a condensing catalyst and tertiary amine. In this case, the compound as shown by Formula (321) is obtained, wherein $R_4$ comprises a first functional group comprising a hydroxy protecting group and a second functional group having a structure as shown by Formula (C1').

The solid phase support is one of the carriers used in solid phase synthesis of siRNA, some of which are well-known to those skilled in the art. For example, the solid phase support may be selected from the solid phase supports containing an active hydroxy or amino functional group. In some embodiments, the solid phase support is an amino resin or hydroxy resin. In some embodiments, the amino or hydroxy resin has the following parameters: particle size of 100-400 mesh, and surface amino or hydroxy loading of 0.2-0.5 mmol/g. The usage ratio of the compound as shown by Formula (321) to the solid phase support is 10-400 mol compound per gram of solid phase support (μmol/g). In some embodiments, the usage ratio of the compound of Formula (321) to the solid phase support is 50-200 mol/g.

The organic solvent may be any suitable solvent or mixed solvents known to those skilled in the art. In some embodiments, the organic solvent comprises one or more of acetonitrile, an epoxy solvent, an ether solvent, a haloalkane solvent, dimethyl sulfoxide, N,N-dimethylformamide, and N,N-diisopropylethylamine. In some embodiments, the epoxy solvent is dioxane and/or tetrahydrofuran, the ether solvent is diethyl ether and/or methyl tertbutyl ether, and the haloalkane solvent is one or more of dichloromethane, trichloromethane and 1,2-dichloroethane. In some embodiments, the organic solvent is acetonitrile. The amount of the organic solvent may be 20-200 L/mol, and in some embodiments, 50-100 L/mol, with respect to the compound as shown by Formula (321).

In some embodiments, the condensing agent may be benzotriazol-1-yl-oxytripyrrolidino phosphonium hexafluorophosphate (PyBop), 3-(Diethoxyphosphoryloxy)-1,2,3-benzotriazin-4(3H)-one (DEPBT) and/or O-benzotriazol-1-yl-tetramethyluronium hexafluorophosphate. In some embodiments, the condensing agent is O-benzotriazol-1-yl-tetramethyluronium hexafluorophosphate. The molar ratio of the condensing agent to the compound as shown by Formula (321) is 1:1 to 20:1, and in some embodiments, 1:1 to 5:1.

In some embodiments, the tertiary amine is triethylamine and/or N,N-diisopropylethylamine, and in some embodiments, N,N-diisopropylethylamine. The molar ratio of the tertiary amine to the compound as shown by Formula (321) is 1:1 to 20:1, and in some embodiments, 1:1 to 5:1.

In some embodiments, the method for preparing the compound as shown by Formula (321) further comprises: contacting the resultant condensation product with a capping agent and an acylation catalyst in an organic solvent under capping reaction condition, and isolating the compound as shown by Formula (321). The capping reaction is used to remove any active functional group that does not completely react, so as to avoid producing unnecessary by products in subsequent reactions. The capping reaction condition comprises a reaction temperature of 0-50° C., and in some embodiments, 15-35° C., and a reaction time of 1-10 hours, and in some embodiments, 3-6 hours. The capping agent may be a capping agent used in solid phase synthesis of siRNA, and the capping agent used in solid phase synthesis of siRNA is well known to those skilled in the art.

In some embodiments, the capping agent is composed of a capping agent 1 (cap1) and a capping agent 2 (cap2). The cap1 is N-methylimidazole, and in some embodiments, provided as a mixed solution of N-methylimidazole in pyridine/acetonitrile, wherein the volume ratio of the pyridine to the acetonitrile is 1:10 to 1:1, and in some embodiments, 1:3 to 1:1. In some embodiments, the ratio of the total volume of the pyridine and acetonitrile to the volume of the N-methylimidazole is 1:1 to 10:1, and in some embodiments, 3:1 to 7:1. The capping agent 2 is acetic anhydride. In some embodiments, the capping agent 2 is provided as a solution of acetic anhydride in acetonitrile, wherein the volume ratio of the acetic anhydride to the acetonitrile is 1:1 to 1:10, and in some embodiments, 1:2 to 1:6.

In some embodiments, the ratio of the volume of the mixed solution of N-methylimidazole in pyridine/acetonitrile to the mass of the compound as shown by Formula (321) is 5 ml/g to 50 ml/g, and in some embodiments, 15 ml/g to 30 ml/g. The ratio of the volume of the solution of acetic anhydride in acetonitrile to the mass of the compound as shown by Formula (321) is 0.5 ml/g to 10 ml/g, and in some embodiments, 1 ml/g to 5 ml/g.

In some embodiments, the capping agent comprises equimolar acetic anhydride and N-methylimidazole. In some embodiments, the organic solvent comprises one or more of acetonitrile, an epoxy solvent, an ether solvent, a haloalkane solvent, dimethyl sulfoxide, N,N-dimethylformamide, and N,N-diisopropylethylamine. In some embodiments, the organic solvent is acetonitrile. The amount of the organic solvent may be 10-50 L/mol, and in some embodiments, 5-30 L/mol, with respect to the compound as shown by Formula (321).

In some embodiments, the acylation catalyst may be selected from any catalyst that may be used for esterification condensation or amidation condensation, such as alkaline heterocyclic compounds. In some embodiments, the acylation catalyst is 4-dimethylaminopyridine. The mass ratio of the catalyst to the compound as shown by Formula (321) may be 0.001:1 to 1:1, and in some embodiments, 0.01:1 to 0.1:1.

In some embodiments, the compound as shown by Formula (321) may be isolated from the reaction mixture using any suitable isolation methods. In some embodiments, the compound as shown by Formula (321) may be obtained by thoroughly washing with an organic solvent and filtering to remove unreacted reactants, excess capping agent and other impurities, wherein the organic solvent is selected from acetonitrile, dichloromethane, or methanol. In some embodiments, the organic solvent is acetonitrile.

In some embodiments, the preparation of the conjugating molecule as shown by Formula (321) comprises contacting a compound as shown by Formula (313) with a phosphorodiamidite in an organic solvent under coupling reaction condition in the presence of a coupling agent, and isolating the compound as shown by Formula (321). In this case, the compound as shown by Formula (321) is obtained, where $R_4$ comprises a first functional group comprising a hydroxy protecting group and a second functional group having a structure as shown by Formula (C3).

In some embodiments, the coupling reaction condition comprises that: a reaction temperature may be 0-50° C., such as 15-35° C.; the molar ratio of the compound as shown by Formula (313) to the phosphorodiamidite may be 1:1 to 1:50, such as 1:5 to 1:15; the molar ratio of the compound as shown by Formula (313) to the coupling agent may be 1:1 to 1:100, such as 1:50 to 80; the reaction time may be 200-3000 seconds, such as 500-1500 seconds. The phosphorodiamidite may be, for example, bis(diisopropylamino)(2-cyanoethoxy)phosphine, which may be commercially available or synthesized according to well-known methods in the art. The coupling agent is selected from one or more of 1H-tetrazole, 5-ethylthio-1H-tetrazole and 5-benzylthio-1H tetrazole, such as 5-ethylthio-1H-tetrazole. The coupling reaction may be performed in an organic solvent, and the organic solvent is selected from one or more of anhydrous acetonitrile, anhydrous DMF and anhydrous dichloromethane, such as anhydrous acetonitrile. In some embodiments, the amount of the organic solvent may be 3-50 L/mol, such as 5-20 L/mol, with respect to the compound as shown by Formula (313). By performing the coupling reaction, the hydroxy in the compound as shown by Formula (313) reacts with the phosphorodiamidite to form a phosphoramidite group. In some embodiments, the solvent may be directly removed to obtain a crude product of the compound as shown by Formula (321), which may be directly used in subsequent reactions.

In some embodiments, the method for preparing the compound as shown by Formula (321) further comprises: further contacting the isolated product with a solid phase support containing hydroxy in an organic solvent under coupling reaction condition in the presence of a coupling agent, followed by capping, oxidation, and isolation, to obtain the compound as shown by Formula (321). In this case, the compound as shown by Formula (321) is obtained, where $R_4$ comprises a first functional group comprising a hydroxy protecting group and a second functional group having a structure as shown by Formula (C3').

In some embodiments, the solid phase support is a well-known solid phase support in the art for solid phase synthesis of a nucleic acid, such as a commercially available universal solid phase support after deprotection reaction (NittoPhase®HL UnyLinker™ 300 Oligonucleotide Synthesis Support, Kinovate Life Sciences, as shown by Formula B80):

(B80)

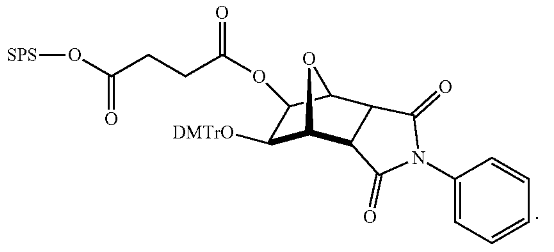

A deprotection reaction is well-known in the art. In some embodiments, the deprotection condition comprises a temperature of 0-50° C., such as 15-35° C.; and a reaction time of 30-300 seconds, such as 50-150 seconds. The deprotection agent may be selected from one or more of trifluoroacetic acid, trichloroacetic acid, dichloroacetic acid, and monochloroacetic acid. In some embodiments, the deprotection agent is dichloroacetic acid. The molar ratio of the deprotection agent to the protecting group -DMTr (4,4'-dimethoxytrityl) on the solid phase may be 2:1 to 100:1, such as 3:1 to 50:1. By such deprotection, free hydroxyl groups with reactivity are obtained on the surface of the solid phase support, for facilitating the subsequent coupling reaction.

The coupling reaction condition and the coupling agent may be selected as above. By performing the coupling reaction, the free hydroxy formed in the deprotection reaction reacts with the phosphoramidite group, so as to form a phosphite ester linkage.

In some embodiments, the capping reaction condition comprises a reaction temperature of 0-50° C., such as 15-35° C., and a reaction time of 5-500 seconds, such as 10-100 seconds. The capping reaction is performed in the presence of a capping agent. The selection and amount of the capping agent are as above.

The oxidation reaction condition may comprise a temperature of 0-50° C., such as 15 35° C., and a reaction time of 1-100 seconds, such as 5-50 seconds. The oxidation agent may be, for example, iodine (in some embodiments, provided as iodine water). In some embodiments, the molar ratio of the oxidation agent to the nucleic acid sequence linked to the solid phase support is 1:1 to 100:1, such as 5:1 to 50:1. In some embodiments, the oxidation reaction is performed in a mixed solvent in which the ratio of tetrahydrofuran:water:pyridine is 3:1:1 to 1:1:3.

In some embodiments, $R_6$ is a group as shown by Formula B7 or B8:

(B7)

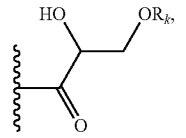

(B8)

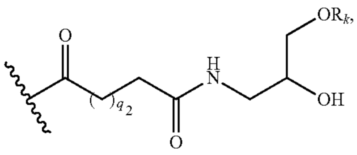

wherein the definitions of $q_2$ and $R_k$ are as described above.

In this case, the compound as shown by Formula (313) may be prepared by the following method: contacting a compound as shown by Formula (314) with a compound as shown by Formula (A-1) or a compound as shown by Formula (A-2) in an organic solvent under amidation reaction condition in the presence of an agent for amidation condensation and tertiary amine, and followed by isolating:

Formula (314)

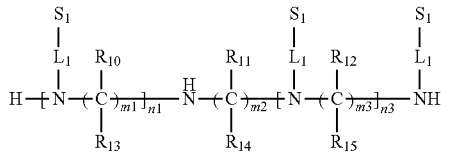

(A-1)

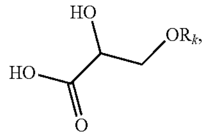

(A-2)

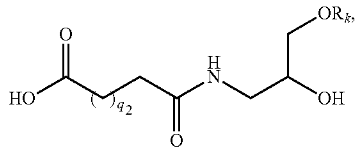

wherein the definitions and options of n1, n3, m1, m2, m3, $R_{10}$, $R_{11}$, $R_{12}$, $R_{13}$, $R_{14}$, $R_{15}$, $L_1$, $S_1$, $q_2$ and $R_k$ are respectively as described above.

The amidation reaction condition may comprise a reaction temperature of 0-100° C. and a reaction time of 1-48 hours. In some embodiments, the amidation reaction condition comprises a reaction temperature of 10-40° C. and a reaction time of 2-16 hours.

In some embodiments, the organic solvent is one or more of an alcohol solvent, an epoxy solvent, an ether solvent, a haloalkane solvent, dimethyl sulfoxide, N,N-dimethylformamide, and N,N-diisopropylethylamine. In some embodiments, the alcohol solvent is one or more of methanol, ethanol and propanol, and in some embodiments, ethanol. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments, 3-20 L/mol, with respect to the compound as shown by Formula (314).

In some embodiments, the agent for amidation condensation is benzotriazol-1-yl-oxytripyrrolidinophosphonium hexafluorophosphate, 3-(Diethoxyphosphoryloxy)-1,2,3-benzotriazin-4(3H)-one, 4-(4,6-dimethoxytriazin-2-yl)-4-methylmorpholine hydrochloride, 2-ethoxy-1-ethoxycarbonyl-1,2-dihydroquinoline (EEDQ) or 0-benzotriazol-1-yl-tetramethyluronium hexafluorophosphate, and in further embodiments, 3-(Diethoxyphosphoryloxy)-1,2,3-benzotriazin-4(3H)-one. The molar ratio of the agent for amidation condensation to the compound as shown by Formula (314) may be 1:1 to 10:1, and in some embodiments, 2.5:1 to 5:1.

In some embodiments, the tertiary amine is triethylamine and/or N,N-diisopropylethylamine, and in further embodiments, N,N-diisopropylethylamine. The molar ratio of the tertiary to the compound as shown by Formula (314) is 3:1 to 20:1, and in some embodiments, is 5:1 to 10:1.

In some embodiments, the compounds as shown by Formula (A-1) and Formula (A-2) may be prepared by any suitable methods. For example, when $R_k$ is a DMTr group, the compound as shown by Formula (A-1) may be prepared by reacting calcium glycerate with DMTrCl. Similarly, the compound as shown by Formula (A-2) may be prepared by contacting 3-amino-1,2-propanediol with a cyclic anhydride and then reacting with DMTrCl, wherein the cyclic anhydride may be a cyclic anhydride having 4-13 carbon atoms, and in some embodiments, 4-8 carbon atoms. Those skilled in the art would readily understand that the selections of the cyclic anhydride correspond to different values for $q_2$ in the compound as shown by Formula (A-2). For example, when the cyclic anhydride is succinic anhydride, $q_2$-1; when the cyclic anhydride is glutaric anhydride, $q_2$=2, and so on.

In some variants, the compound as shown by Formula (313) can also be prepared by successively reacting the compound as shown by Formula (314) with the cyclic anhydride, 3-amino-1,2 propanediol, and DMTrCl. Those skilled in the art would readily understand that these variants would not affect the structure and function of the compound as shown by Formula (313), and these variants can be readily achieved by those skilled in the art on the basis of the above methods.

Similarly, the compound as shown by Formula (313) may be isolated from the reaction mixture by any suitable isolation methods. In some embodiments, the compound as shown by Formula (313) may be isolated by removal of solvent via evaporation, followed by chromatography, for example, using the following two chromatographic conditions for isolation: (1) normal phase purification silica gel: 200-300 mesh silica gel filler, and using gradient elution of petroleum ether:ethyl acetate:dichloromethane:N,N-dimethylformamide=1:1:1:0.5-1:1:1:0.6; and (2) reverse phase purification: C18 and C8 reverse phase fillers, and using gradient elution of methanol:acetonitrile=0.1:1 to 1:0.1. In some embodiments, the solvent may be directly removed to obtain a crude product of the compound as shown by Formula (313), which may be directly used in subsequent reactions.

In some embodiments, the compound as shown by Formula (314) may be prepared by the following method comprising: contacting a compound as shown by Formula (320) with a compound as shown by Formula (316) in an organic solvent under condensation reaction condition in the presence of an agent for amidation condensation and tertiary amine, and followed by isolating:

Formula (316)

$$S_1—L_1—OH$$

Formula (320)

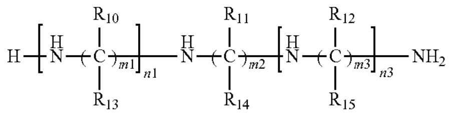

wherein the definitions and options of n1, n3, m1, m2, m3, $R_{10}$, $R_{11}$, $R_{12}$, $R_{13}$, $R_{14}$, and $R_{15}$ are respectively as described above.

The compound as shown by Formula (316) can be, such as, those disclosed in J. Am. Chem. Soc. 2014, 136, 16958-16961, or, the compound as shown by Formula (316) may be prepared by those skilled in the art via various methods. For example, some compound as shown by Formula (316) may be prepared according to the methods as disclosed in Example 1 of U.S. Pat. No. 8,106,022 B2, the entire contents of the above documents are incorporated herein by reference in their entirety.

In some embodiments, the condensation reaction condition comprises a reaction temperature of 0-100° C. and a reaction time of 0.1-24 hours. In some embodiments, the condensation reaction condition comprises a reaction temperature is 10-40° C. and a reaction time is 0.5-16 hours.

Considering the structure of the desired compound as shown by Formula (314), the molar ratio of the compound as shown by Formula (316) to the compound as shown by Formula (320) should be determined based on the sum of n1 and n3 in Formula (320). In some embodiments, for example, when n1+n3=3, in order to ensure that the reaction is complete and not excessive, the molar ratio of the compound as shown by Formula (316) to the compound as shown by Formula (320) may be 3:1 to 3.5:1, and in some embodiments, is 3.01:1 to 3.15:1.

In some embodiments, the organic solvent is one or more of acetonitrile, an epoxy solvent, an ether solvent, a haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in some embodiments, 5-20 L/mol, with respect to the compound as shown by Formula (320).

In some embodiments, the agent for amidation condensation is benzotriazol-1-yl-oxytripyrrolidinophosphonium hexafluorophosphate, 3-(Diethoxyphosphoryloxy)-1,2,3-benzotriazin-4(3H)-one (DEPBT), O-benzotriazol-1-yl-tetramethyluronium hexafluorophosphate, 4-(4,6-dimethoxytriazin-2-yl)-4-methylmorpholine hydrochloride or 1-hydroxybenzotriazole, and in further embodiments, is a mixture of the benzotriazol-1-yl-oxytripyrrolidinophosphonium hexafluorophosphate and the 1-hydroxybenzotriazole, wherein the benzotriazol-1-yl-oxytripyrrolidinophosphonium hexafluorophosphate and the 1-hydroxybenzotriazole are equimolar. The molar ratio of the total agent for amidation condensation to the compound as shown by Formula (316) may be 1:1 to 3:1, and in some embodiments, is 1.05:1 to 1.5:1.

The tertiary amine may be N-methylmorpholine, triethylamine or N,N-diisopropylethylamine, and in some embodiments, N-methylmorpholine. The molar ratio of the tertiary amine to the compound as shown by Formula (316) may be 2:1 to 10:1, and in some embodiments, is 2:1 to 5:1.

Similarly, the compound as shown by Formula (314) may be isolated from the reaction mixture by any suitable isolation methods. In some embodiments, the compound as shown by Formula (314) is isolated by removal of solvent via evaporation, followed by chromatography, for example, using the following two chromatographic conditions for isolation: (1) normal phase purification silica gel: 200-300 mesh silica gel filler, and using gradient elution of dichloromethane:methanol=100:5 to 100:7; and (2) reverse phase purification: C18 and C8 reverse phase fillers, and using gradient elution of methanol:acetonitrile=0.1:1 to 1:0.1. In some embodiments, the solvent is directly removed to obtain a crude product of the compound as shown by Formula (314), and the crude product can be directly used in subsequent reactions.

The compound as shown by Formula (320) may be commercially available, or obtained by those skilled in the art via the known methods. For example, in the case that m1=m2=m3=3, n1=1, n3=2, and each of $R_{10}$, $R_{11}$, $R_{12}$, $R_{13}$, $R_{14}$, and $R_{15}$ is H, the compound as shown by Formula (320) is commercially available from Alfa Aesar Inc.

The siRNA conjugate of the present disclosure may also be used in combination with other pharmaceutically acceptable excipients, which may be one or more of the various conventional formulations or compounds in the art. For details, please refer to the above description of the pharmaceutical compositions of the present disclosure.

Use of the siRNA, the Pharmaceutical Composition and the siRNA Conjugate of the Present Disclosure In some embodiments, the present disclosure provides the use of the siRNA, and/or the pharmaceutical composition, and/or the siRNA of the present disclosure in the manufacture of a medicament for treating and/or preventing septicemia.

According to some embodiments, the present disclosure provides a method for preventing and/or treating septicemia, comprising administering an effective amount of the siRNA and/or the pharmaceutical composition and/or the siRNA conjugate of the present disclosure to a subject in need.

It is possible to achieve the purpose of preventing and/or treating septicemia based on a mechanism of RNA interference by administering the active ingredients of the siRNA of the present disclosure to the subject in need. Thus, the siRNA and/or the pharmaceutical composition and/or the siRNA conjugate of the present disclosure may be used for preventing and/or treating septicemia, or for the manufacture of a medicament for preventing and/or treating septicemia.

In some embodiments, the septicemia usually refers to a systemic inflammatory response syndrome caused by infection, which is essentially a body's response to infectious factors. In some embodiments, the septicemia often occurs in patients suffering from severe diseases, such as severe burns, multiple injuries, after surgery, or the like. In some embodiments, the septicemia is also common in patients suffering from chronic diseases such as diabetes, chronic obstructive bronchus, leukemia, aplastic anemia and urinary calculi.

As used herein, the term "administration/administer" refers to the delivery of the siRNA, the pharmaceutical composition, and/or the siRNA conjugate of the present disclosure into a subject by a method or a route that at least partly locates the siRNA, the pharmaceutical composition, and/or the siRNA conjugate of the present disclosure at a desired site to produce a desired effect. Suitable administration routes for the methods of the present disclosure comprise topical administration and systemic administration. In general, the topical administration results in the delivery of more siRNA conjugate to a particular site compared with the systemic circulation of the subject; whereas the systemic administration results in the delivery of the siRNA, the pharmaceutical composition, and/or the siRNA conjugate of the present disclosure to the substantial systemic circulation of the subject. Considering that the present disclosure can provide a means for preventing and/or treating septicemia diseases, in some embodiments, an administration mode capable of delivering drugs to liver is used.

The administration to a subject may be achieved by any suitable routes known in the art, including but not limited to, oral or parenteral route, such as intravenous administration, intramuscular administration, subcutaneous administration, transdermal administration, intratracheal administration (aerosol), pulmonary administration, nasal administration, rectal administration and topical administration (including buccal administration and sublingual administration). The administration frequency may be once or more times daily, weekly, biweekly, triweekly, monthly, bimonthly, trimonthly, semiannually or annually.

The dose of the siRNA, the pharmaceutical composition, or the siRNA conjugate of the present disclosure may be a conventional dose in the art, and the dose may be determined according to various parameters, especially age, weight and gender of a subject. Toxicity and efficacy may be measured in cell cultures or experimental animals by standard pharmaceutical procedures, for example, by determining $LD_{50}$ (the lethal dose that causes 50% population death), and $ED_{50}$ (the dose that can cause 50% of the maximum response intensity in a quantitative response, and that causes 50% of the experimental subjects to have a positive response in a qualitative response). The dose range for human may be derived based on the data obtained from cell culture analysis and animal studies.

When administrating the siRNA, the pharmaceutical composition or the siRNA conjugate of the present disclosure, for example, to male or female, 6-12 weeks old, C57BL/6J mice of 18-25 g body weight or ob/ob mice of 30-45 g, and calculating based on the amount of the siRNA: (i) for the siRNA conjugate, the dosage of the siRNA thereof may be 0.001-100 mg/kg body weight, and in some embodiments, is 0.01-50 mg/kg body weight, and in some embodiments, is 0.05-20 mg/kg body weight, in some other embodiments is 0.1-15 mg/kg body weight, and in some other embodiments, is 0.1-10 mg/kg body weight; and (ii) for a pharmaceutical composition formed by an siRNA and a pharmaceutically acceptable carrier, the dosage of the siRNA thereof may be 0.001-50 mg/kg body weight, in some embodiments, is 0.01-10 mg/kg body weight, in some embodiments, is 0.05-5 mg/kg body weight, and in some embodiments, is 0.1-3 mg/kg body weight.

In some embodiments, the present disclosure provides a method for inhibiting the expression of a KNG gene in a hepatocyte. The method comprises contacting an effective amount of the siRNA and/or the pharmaceutical composition and/or the siRNA conjugate of the present disclosure with the hepatocyte, introducing the siRNA and/or the pharmaceutical composition and/or the siRNA conjugate of the present disclosure into the hepatocyte, and achieving the purpose of inhibiting the expression of the KNG gene in the hepatocyte through a mechanism of RNA interference. The hepatocyte may be selected from SMMC-7721, HepG2, Huh7 and other hepatoma cell lines or isolated primary hepatocytes.

In the case where the expression of the KNG gene in the cell is inhibited by using the method provided by the present disclosure, the amount of the siRNA in the modified siRNA, the pharmaceutical composition, and/or the siRNA conjugate provided is typically: an amount sufficient to reduce the expression of the target mRNA and result in an extracellular concentration of 1 pM to 1 μM, or 0.01 nM to 100 nM, or 0.05 nM to 50 nM or 0.05 nM to about 5 nM on the surface of the target cell. The amount required to achieve this local concentration will vary with various factors, including the delivery method, the delivery site, the number of cell layers between the delivery site and the target cells or tissues, the delivery route (topical or systemic), etc. The concentration at the delivery site may be significantly higher than that on the surface of the target cells or tissues.

Kit

The present disclosure provides a kit, wherein the kit comprises an effective amount of at least one of the siRNA, the pharmaceutical composition, and the siRNA conjugate of the present disclosure.

In some embodiments, the kit disclosed herein may provide a modified siRNA in a container. In some embodiments, the kit of the present disclosure may comprise a container providing pharmaceutically acceptable excipients. In some embodiments, the kit may further comprise additional ingredients, such as stabilizers or preservatives. In some embodiments, the kit herein may comprise at least one additional therapeutic agent in other container than the container providing the modified siRNA described herein. In some embodiments, the kit may comprise an instruction for mixing the modified siRNA with the pharmaceutically acceptable carrier and/or excipients or other ingredients (if any).

In the kit of the present disclosure, the siRNA and the pharmaceutically acceptable carrier and/or the excipients as well as the siRNA, the pharmaceutical composition, and/or the siRNA conjugate and/or the pharmaceutically acceptable excipients may be provided in any form, e.g., in a liquid form, a dry form, or a lyophilized form. In some embodiments, the siRNA and the pharmaceutically acceptable carrier and/or the excipients as well as the pharmaceutical composition and/or the siRNA conjugate and optional pharmaceutically acceptable excipients are substantially pure and/or sterile. In some embodiments, sterile water may be provided in the kit of the present disclosure.

Hereinafter, the present disclosure will be further described by examples, but is not limited thereto in any respect.

EXAMPLES

Unless otherwise specified, the agents and culture media used in following examples are all commercially available, and the operations used such as nucleic acid electrophoresis and real-time PCR are all performed according to methods described in Molecular Cloning (Cold Spring Harbor Laboratory Press (1989)).

The Lipofectamine™2000(Invitrogen) is used as the transfection reagent when the siRNA and the siRNA conjugate against KNG gene synthesized in the present disclosure or the siRNA and the siRNA conjugate as negative control transfect cells, and the specific operation refers to the instructions provided by the manufacturer.

Unless otherwise specified, ratios of reagents provided below are all calculated by volume ratio (v/v).

Unless otherwise specified, the following experimental data of the in vivo/in vitro are all expressed as X±SEM, and the data analysis is carried out by using Graphpad prism5.0 statistical analysis software.

Preparation Example 1

Preparation of siRNA Conjugate L10-siKNa1M1SP

In this preparation example, the siRNA conjugate L10-siKNa1M1SP was synthesized.

An siRNA conjugated in the siRNA conjugate has sense strand and antisense strand sequences corresponding to the siRNA conjugate L10-siKNa1M1SP in Table 3.

(1-1) Synthesis of Compound L-10

The compound L-10 was synthesized according to the following method:

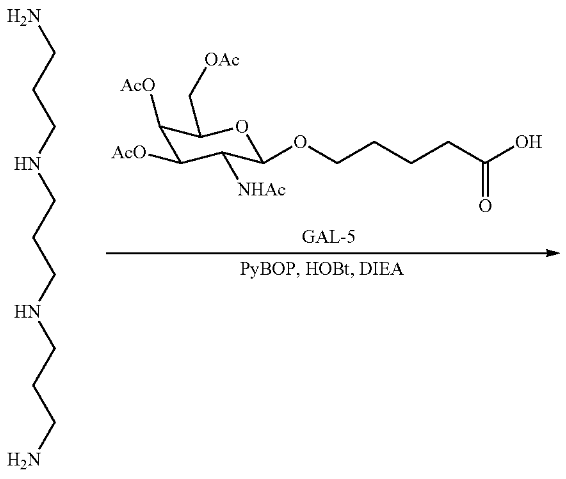

J-0

-continued
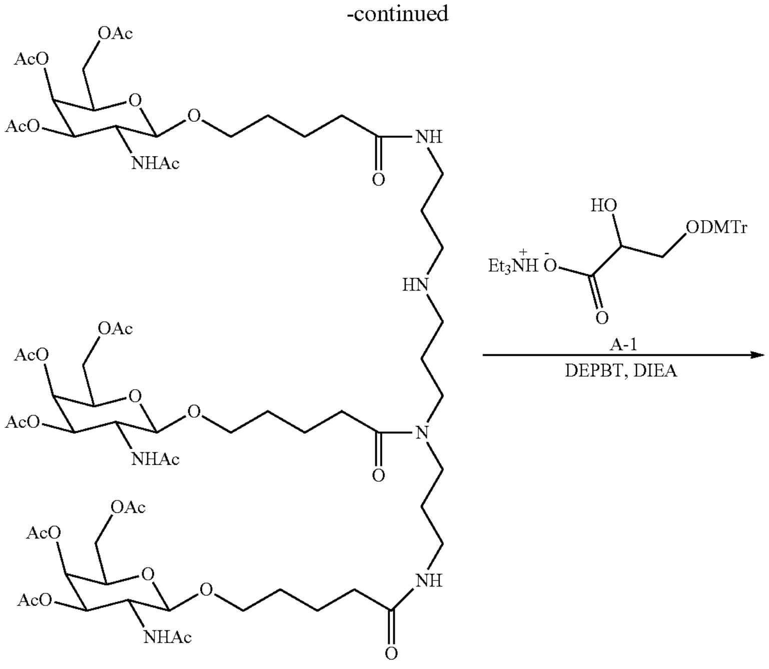
L-8
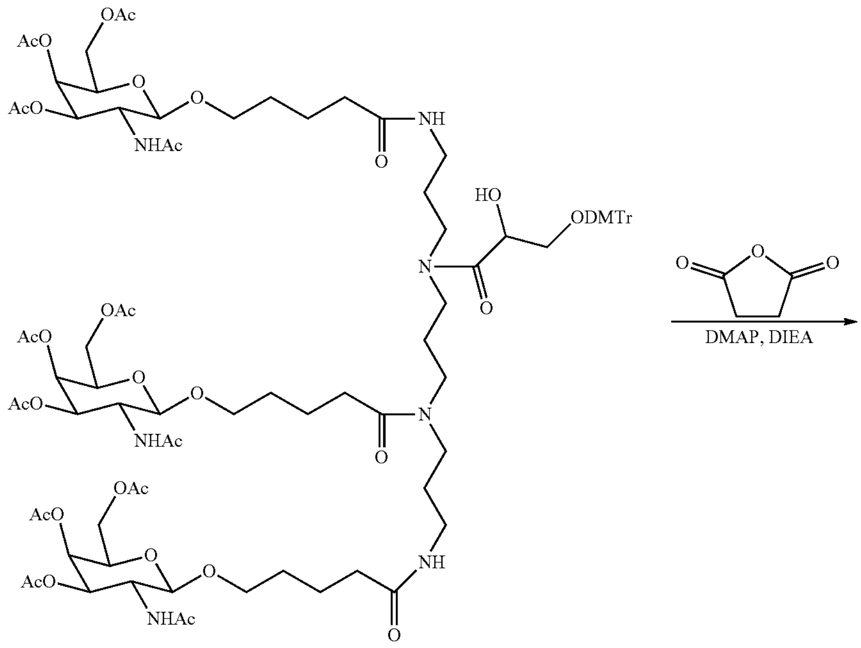
L-7

-continued
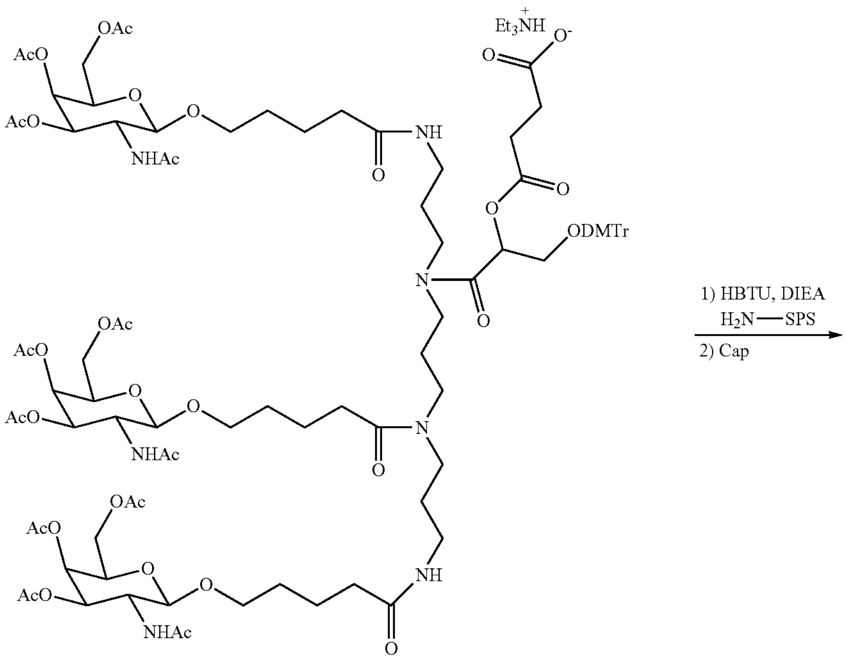
L-9
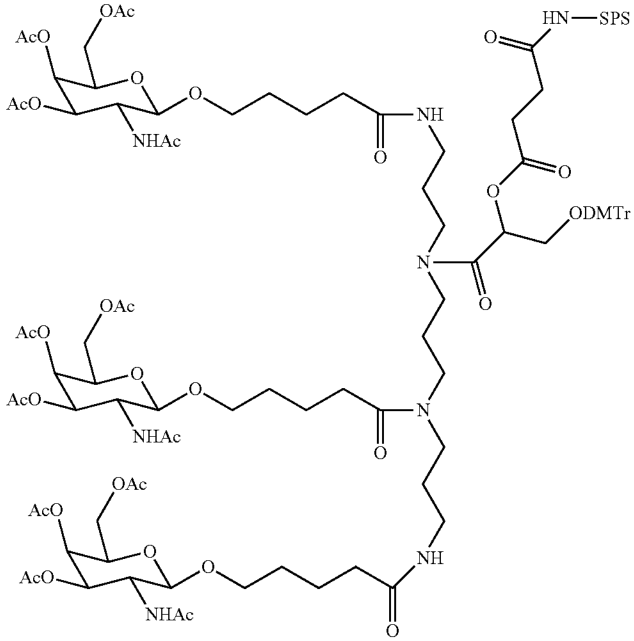
L-10

(1-1-1) Synthesis of GAL-5 (a Terminal Segment of the Conjugating Molecule)

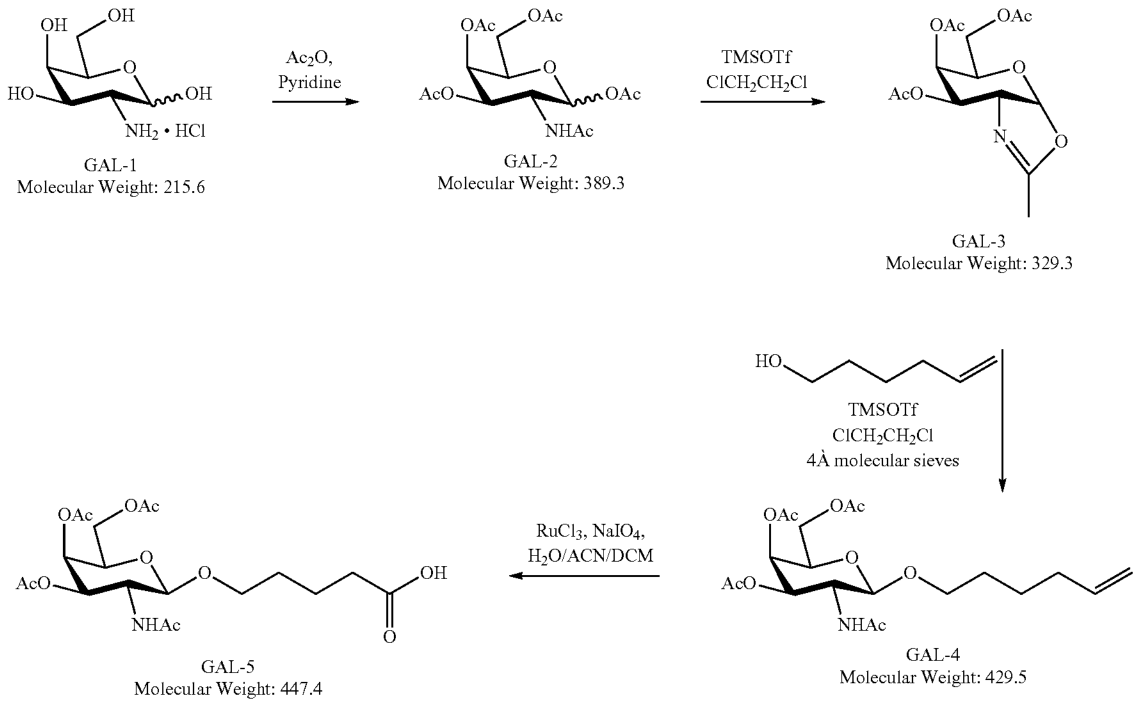

(1-1-1a) Synthesis of GAL-2

100.0 g of GAL-1 (N-acetyl-D-galactosamine hydrochloride, CAS No.: 1772-03-8, purchased from Ningbo Hongxiang Bio-Chem Co., Ltd., 463.8 mmol) was dissolved in 1000 ml of anhydrous pyridine, to which 540 ml of acetic anhydride (purchased from Enox Inc., 5565.6 mmol) was added in an ice water bath to react under stirring at room temperature for 1.5 hours. The resultant reaction solution was poured into 10 L of ice water and subjected to suction filtration under reduced pressure. The filter mass was washed with 2 L of ice water, and then added with a mixed solvent of acetonitrile/toluene (v/v ratio of acetonitrile:toluene=1:1) until completely dissolved. The solvent was removed by evaporation to give 130.0 g of product GAL-2 as a white solid.

(1-1-1b) Synthesis of GAL-3

GAL-2 (35.1 g, 90.0 mmol) obtained in step (1-1-1a) was dissolved in 213 ml of anhydrous 1,2-dichloroethane, to which 24.0 g of TMSOTf (CAS No.: 27607-77-8, purchased from Macklin Inc., 108.0 mmol) was added under an ice water bath and nitrogen protection to react at room temperature overnight.

400 ml of dichloromethane was added to the reaction solution for dilution, filtered with diatomite, and then added with 1 L of saturated aqueous sodium bicarbonate solution and stirred evenly. An organic phase was isolated. An aqueous phase remained was extracted twice, each time with 300 ml of dichloroethane, and all organic phases were combined and washed with 300 ml of saturated aqueous sodium bicarbonate solution and 300 ml of saturated brine, respectively. The organic phase resulted from washing was isolated and dried with anhydrous sodium sulfate. The solvent was removed by evaporation under reduced pressure to give 26.9 g of product GAL-3 as a light yellow viscous syrup.

(1-1-1c) Synthesis of GAL-4

GAL-3 (26.9 g, 81.7 mmol) obtained in step (1-1-1b) was dissolved in 136 ml of anhydrous 1,2-dichloroethane, added with 30 g of dry 4 Å molecular sieve powder followed by 9.0 g of 5-hexen-1-ol (CAS No.: 821-41-0, purchased from Adamas-beta Inc., 89.9 mmol), and stirred at room temperature for 30 minutes. 9.08 ml of TMSOTf (40.9 mmol) was added in an ice bath and nitrogen protection to react under stirring at room temperature overnight. The 4 Å molecular sieve powder was removed by filtration. The filtrate was added with 300 ml of dichloroethane for dilution, filtered with diatomite, and then added with 500 ml of saturated aqueous sodium bicarbonate solution and stirred for 10 minutes for washing. An organic phase was isolated. An aqueous phase was extracted once with 300 ml of dichloroethane. All organic phases were combined and washed with 300 ml of saturated aqueous sodium bicarbonate solution and 300 ml of saturated brine respectively. The organic phase resulted from the washing was isolated and dried with anhydrous sodium sulfate. The solvent was removed by evaporation under reduced pressure to give 41.3 g of product GAL-4 as a yellow syrup, which was directly used in the next oxidation reaction without purification.

(1-1-1d) Synthesis of GAL-5

GAL-4 (14.9 g, 34.7 mmol) obtained according to the method described in step (1-1 1c) was dissolved in a mixed solvent of 77 ml of dichloromethane and 77 ml of acetonitrile, added with 103 ml of deionized water and 29.7 g of sodium periodate (CAS No.: 7790-28-5, purchased from Aladdin Inc., 138.8 mmol) respectively, and stirred in an ice bath for 10 minutes. Ruthenium trichloride (CAS No.: 14898-67-0, purchased from Energy Chemical, 238 mg, 1.145 mmol) was added to react at room temperature overnight. The resultant reaction solution was diluted by adding 300 ml of water under stirring, and adjusted to a pH of about 7.5 by adding saturated sodium bicarbonate. An organic phase was isolated and discarded. An aqueous phase was extracted three times, each time with 200 ml of dichloromethane, and the organic phase resulted from the extraction was discarded. The aqueous phase resulted from the extraction was adjusted to a pH of about 3 with citric acid solids and extracted three times, each time with 200 ml of dichloromethane, and the resultant organic phases were combined and dried with anhydrous sodium sulfate. The solvent is removed by evaporation under reduced pressure to give 6.85 g of product GAL-5 as a white foamy solid. $^1H$ NMR (400 MHz, DMSO) δ 12.01 (br, 1H), 7.83 (d, J=9.2 Hz, 1H), 5.21 (d, J=3.2 Hz, 1H), 4.96 (dd, J=11.2, 3.2 Hz, 1H), 4.49 (d, J=8.4 Hz, 1H), 4.07-3.95 (m, 3H), 3.92-3.85 (m, 1H), 3.74-3.67 (m, 1H), 3.48-3.39 (m, 1H), 2.20 (t, J=6.8 Hz, 2H), 2.11 (s, 3H), 2.00 (s, 3H), 1.90 (s, 3H), 1.77 (s, 3H), 1.55-1.45 (m, 4H).

(1-1-2) Synthesis of L-8

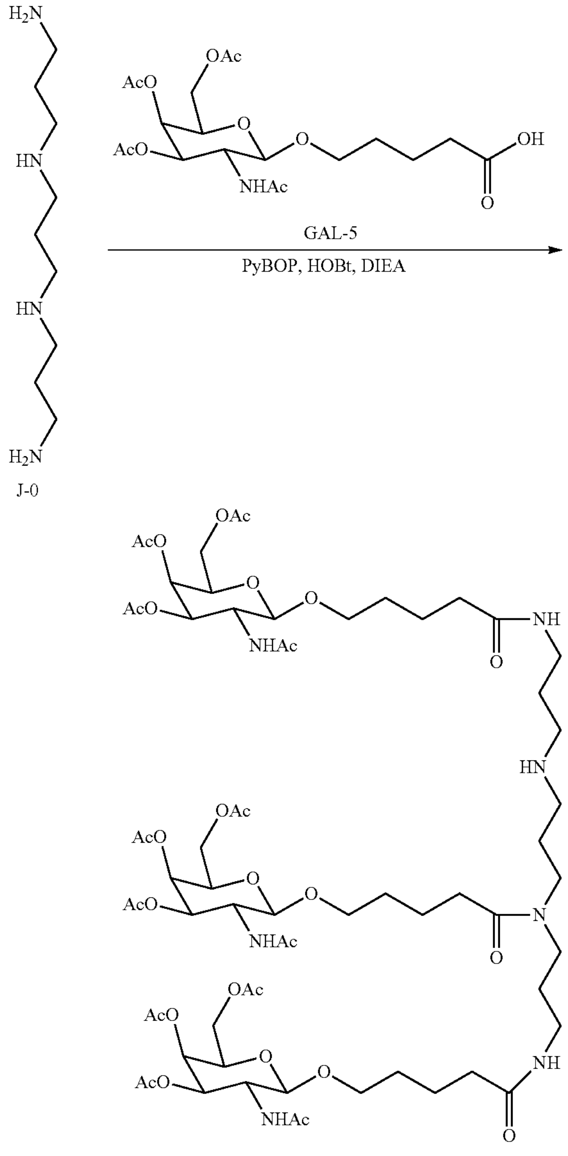

J-0

L-8

J-0 (9.886 g, 52.5 mmol, purchased from AlfaAesar Inc.) and GAL-5 (72.819 g, 162.75 mmol, obtained by combining the products of multiple batches) obtained in step (1-1-1) were dissolved in 525 ml of dichloromethane, added with diisopropylethylamine (DIEA, 44.782 g, 346.50 mmol), benzotriazol-1-yl-oxytripyrrolidino phosphonium hexafluorophosphate (PyBop, 90.158 g, 173.25 mmol) and hydroxybenzotriazole (HOBt, 23.410 g, 173.25 mmol) to react at room temperature for 4 hours, and then added with 20 ml of saturated sodium bicarbonate and 200 ml of saturated brine for washing. An aqueous phase was extracted twice, each time with 100 ml of dichloromethane, and the resultant organic phases were combined and dried with anhydrous sodium sulfate. After filtration, the solvent was removed by evaporation under reduced pressure to give a crude product. The crude product was purified by using a normal phase silica gel column (200-300 mesh). The column was added with 10 wt % triethylamine for neutralizing the acidity of silica gel and equilibrated with 1 wt % triethylamine, and eluted with a gradient elution of dichloromethane:methanol=100:25 to 100:40. The eluate was collected, and the solvent was removed by evaporation under reduced pressure to give 38.8 g of pure product L-8. $^1H$ NMR (400 MHz, DMSO) δ 7.84 (d, J=9.0 Hz, 3H), 7.27-7.23 (m, 1H), 7.13-7.18 (m, 1H), 5.22 (d, J=3.1 Hz, 3H), 4.97 (dd, J=11.3, 3.1 Hz, 3H), 4.48 (d, J=8.4 Hz, 3H), 4.09-3.98 (m, 9H), 3.88 (dd, J=19.3, 9.3 Hz, 3H), 3.75-3.66 (m, 3H), 3.44-3.38 (m, 3H), 3.17-3.30 (m, 4H), 3.10-2.97 (m, 4H), 2.35-2.20 (m, 6H), 2.15-2.08 (m, 9H), 2.07-1.98 (m, 13H), 1.94-1.87 (m, 9H), 1.81-1.74 (m, 9H), 1.65-1.42 (m, 18H). MS m/z: $C_{85}H_{119}N_7O_{30}$, $[M+H]^+$, theoretical: 1477.59, measured: 1477.23.

(1-1-3a) Synthesis of A-1

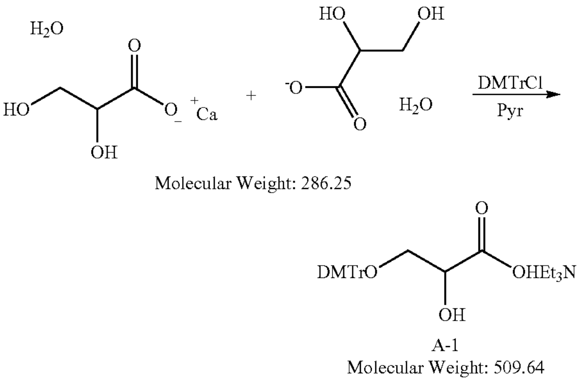

A-1

DMTrCl (4,4'-dimethoxytrityl chloride, 101.65 g, 300 mmol) was dissolved in 1000 ml of anhydrous pyridine, and added with calcium DL-glycerate hydrate (28.63 g, 100 mmol) to react at 45° C. for 20 hours. The reaction solution was filtered. The filter mass was rinsed with 200 ml of DCM, and the filtrate was concentrated to dryness under reduced pressure. The residue was redissolved in 500 ml of dichloromethane and washed twice, each time with 200 ml of 0.5 M triethylamine phosphate (pH=7-8). An aqueous phase isolated was extracted twice, each time with 200 ml of dichloromethane. All organic phases were combined, dried with anhydrous sodium sulfate, and filtered. The solvent was removed by evaporation under reduced pressure, and the residue was purified by using a normal phase silica gel column (200-300 mesh) which was eluted with a gradient elution of petroleum ether:ethyl acetate:dichloromethane:

methanol=1:1:1:0.35 to 1:1:1:0.55. The eluate was collected, and the solvent was removed by evaporation under reduced pressure. The residue was redissolved in 600 ml of dichloromethane, and washed once with 200 ml of 0.5 M triethylamine phosphate. The aqueous phase isolated was extracted once with 200 ml of dichloromethane. All organic phases were combined, dried with anhydrous sodium sulfate, and filtered. The solvent was removed by evaporation under reduced pressure and overnight under reduced pressure in a vacuum oil pump to give 50.7 g of product A-1 as a white solid. $^1$H NMR (400 MHz, DMSO-d6) δ 7.46 (ddd, J=6.5, 2.3, 1.1 Hz, 1H), 7.40-7.28 (m, 7H), 6.89-6.81 (m, 4H), 4.84 (d, J=5.0 Hz, 1H), 4.36-4.24 (m, 1H), 4.29 (s, 6H), 3.92 (dd, J=12.4, 7.0 Hz, 1H), 3.67 (dd, J=12.3, 7.0 Hz, 1H), 2.52 (q, J=6.3 Hz, 6H), 1.03 (t, J=6.3 Hz, 9H). MS m/z: $C_{24}H_{23}O_6$, $[M-H]^+$, theoretical: 407.15, measured: 406.92.

(1-1-3b) Synthesis of L-7

L-8 (40 g, 27.09 mmol, obtained by combining the products of multiple batches) obtained in step (1-1-2) and A-1 (41.418 g, 81.27 mmol) obtained in step (1-1-3a) were mixed and dissolved in 271 ml of dichloromethane, added with 3-(Diethoxyphosphoryloxy)-1,2,3-benzotriazin-4(3H)-one (DEPBT, 24.318 g, 81.37 mmol), and further added with diisopropylethylamine (21.007 g, 162.54 mmol) to react under stirring at 25° C. for 1.5 hours. An organic phase was washed with 800 ml of saturated sodium bicarbonate. An aqueous phase isolated was extracted three times, each time with 50 ml of dichloromethane. The organic phase was washed with 150 ml of saturated brine, and the aqueous phase was extracted once with 50 ml of dichloromethane. The resultant organic phases were combined and dried with anhydrous sodium sulfate. After filtration, the solvent was removed by evaporation under reduced pressure and the residue was foam-dried in a vacuum oil pump overnight to

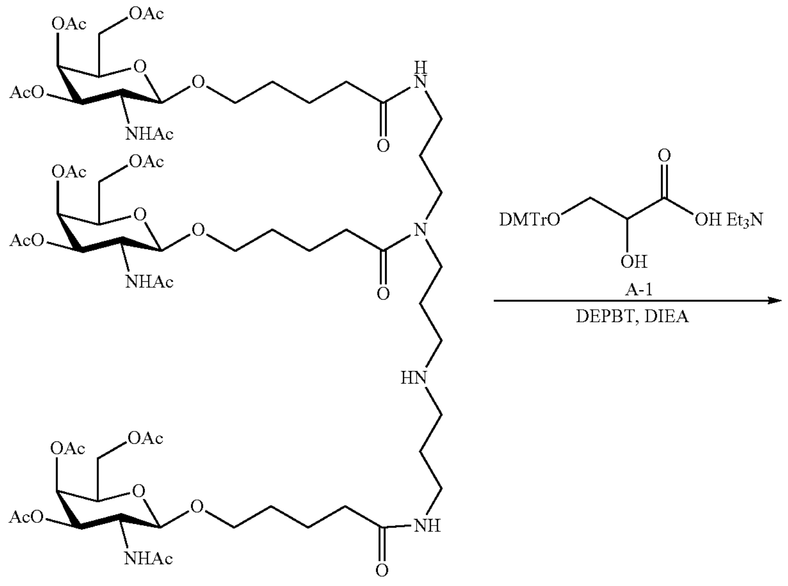

L-8

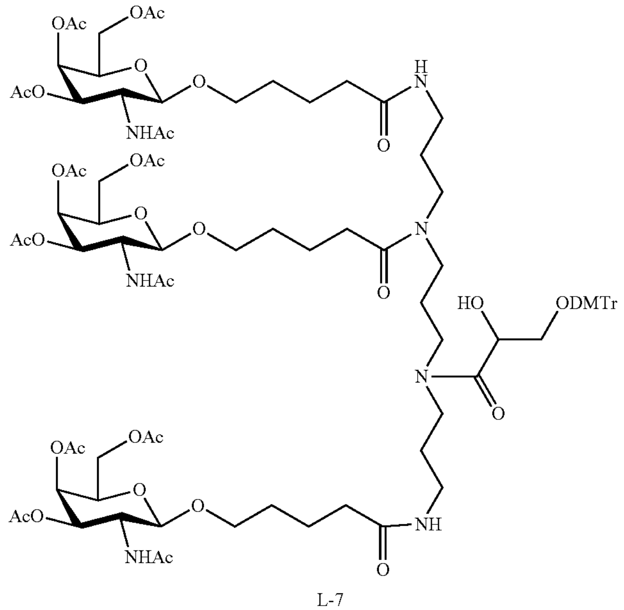

L-7 give a crude product. The crude product was subjected to a column purification, the column was filled with 2 kg of normal phase silica gel (200-300 mesh), added with 200 ml of triethylamine for neutralizing the acidity of the silica gel, equilibrated with petroleum ether containing 1 wt % triethylamine, and eluted with a gradient elution of petroleum ether:ethyl acetate:dichloromethane: N,N-dimethylformamide=1:1:1:0.5 to 1:1:1:0.6. The eluate was collected, and the solvent was removed by evaporation under reduced pressure to give 40.4 g of pure product L-7. $^{1}$H NMR (400 MHz, DMSO) δ7.90-7.78 (m, 4H), 7.75-7.64 (m, 1H), 7.38-7.18 (m, 9H), 6.91-6.83 (m, 4H), 5.25-5.10 (m, 4H), 4.97 (dd, J=11.2, 3.2 Hz, 3H), 4.48-4.30 (m, 4H), 4.02 (s, 9H), 3.93-3.84 (m, 3H), 3.76-3.66 (m, 9H), 3.45-3.35 (m, 3H), 3.24-2.98 (m, 10H), 2.30-2.20 (m, 2H), 2.11-1.88 (m, 31H), 1.80-1.40 (m, 28H). MS m/z: $C_{90}H_{128}N_7O_{35}$, [M-DMTr]$^+$, theoretical: 1564.65, measured: 1564.88.

(1-1-4) Synthesis of L-9

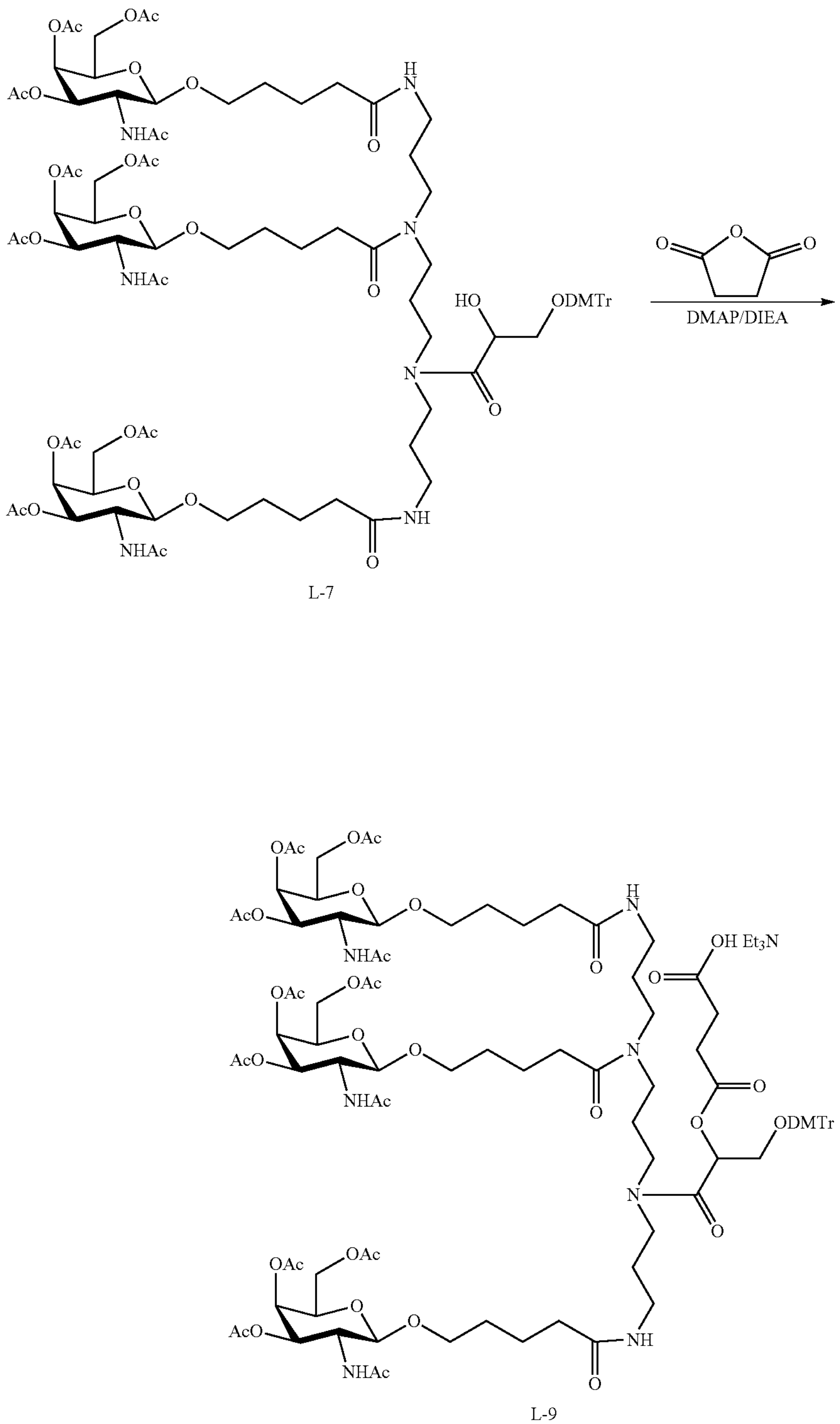

L-7

L-9

L-7 (40 g, 21.4247 mmol) obtained in step (1-1-3b), succinic anhydride (4.288 g, 42.8494 mmol) and 4-dimethylaminopyridine (DMAP, 5.235 g, 42.8494 mmol) were mixed and dissolved in 215 ml of dichloromethane, further added with diisopropylethylamine (DIEA, 13.845 g, 107.1235 mmol), and stirred at 25° C. for 24 hours. The reaction solution was washed with 800 ml of 0.5 M triethylamine phosphate. An aqueous phase was extracted three times, each time with 5 ml of dichloromethane. All organic phases were combined, and the solvent was evaporated under reduced pressure to give a crude product. The crude product was subjected to a column purification, the column was filled with 1 kg normal phase silica gel (200-300 mesh), added with 1 wt % triethylamine for neutralizing the acidity of the silica gel, equilibrated with dichloromethane and eluted with a gradient elution of 1 wt % triethylamine-containing dichloromethane:methanol=100:18 to 100:20. The eluate was collected, and the solvent was evaporated under reduced pressure to give 31.0 g of pure product of L-9 conjugating molecule. $^{1}H$ NMR (400 MHz, DMSO) δ 8.58 (d, J=4.2 Hz, 1H), 7.94-7.82 (m, 3H), 7.41-7.29 (m, 5H), 7.22 (d, J=8.1 Hz, 5H), 6.89 (d, J=8.3 Hz, 4H), 5.49-5.37 (m, 1H), 5.21 (d, J=3.0 Hz, 3H), 4.97 (d, J=11.1 Hz, 3H), 4.49 (d, J=8.2 Hz, 3H), 4.02 (s, 9H), 3.88 (dd, J=19.4, 9.4 Hz, 3H), 3.77-3.65 (m, 9H), 3.50-3.39 (m, 6H), 3.11-2.90 (m, 5H), 2.61-2.54 (m, 4H), 2.47-2.41 (m, 2H), 2.26-2.17 (m, 2H), 2.15-1.95 (m, 22H), 1.92-1.84 (m, 9H), 1.80-1.70 (m, 10H), 1.65-1.35 (m, 17H), 1.31-1.19 (m, 4H), 0.96 (t, J=7.1 Hz, 9H). MS m/z: $C_{94}H_{132}N_7O_{38}$, $[M-DMTr]^+$, theoretical: 1664.72, measured: 1665.03.

(1-1-5) Synthesis of Compound L-10

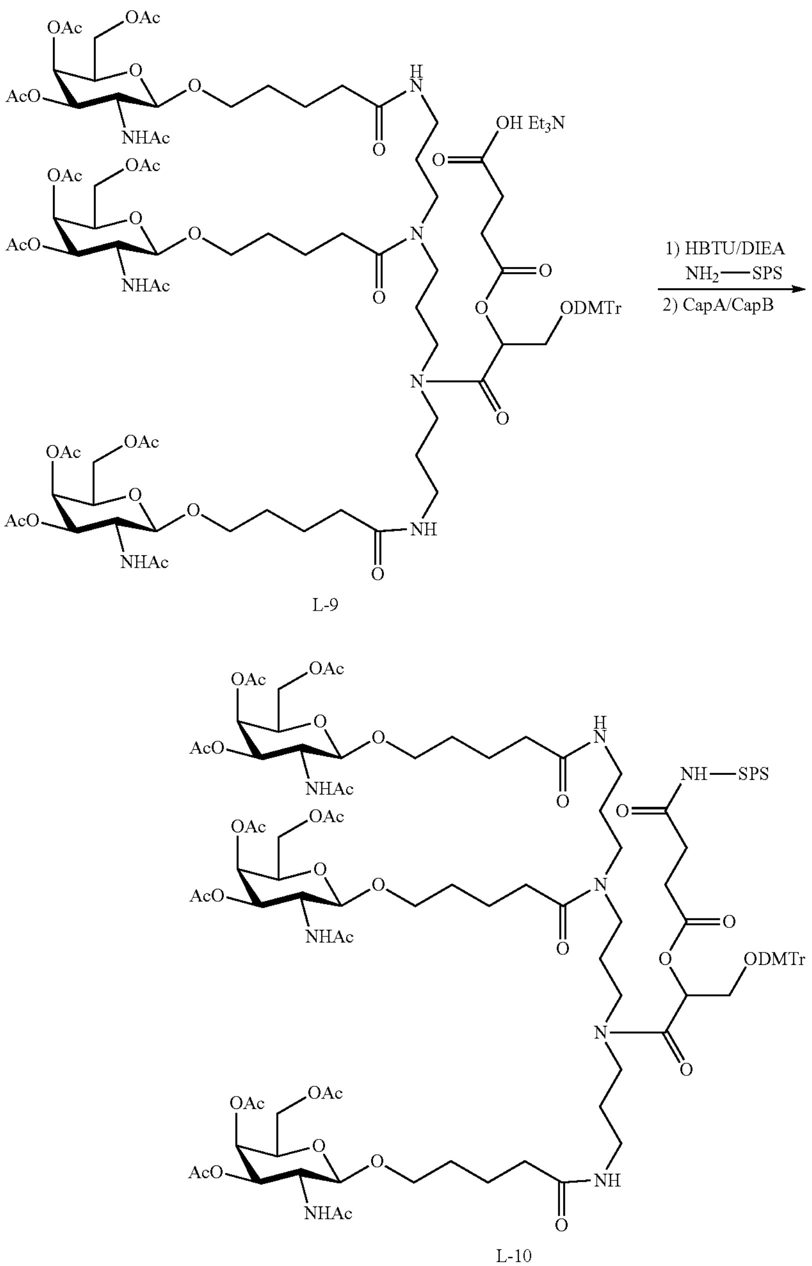

L-9

L-10

In this step, the compound L-10 was prepared by linking the L-9 conjugating molecule to a solid phase support.

The L-9 conjugating molecule (22.751 g, 11 mmol) obtained in step (1-1-4), 0-benzotriazol-1-yl-tetramethyluronium hexafluorophosphate (HBTU, 6.257 g, 16.5 mmol) and diisopropylethylamine (DIEA, 2.843 g, 22 mmol) were mixed and dissolved in 900 ml of acetonitrile, and stirred at room temperature for 5 minutes. Aminomethyl resin (88 g, 100-200 mesh, amino loading: 400 mol/g, purchased from Tianjin Nankai HECHENG S&T Co., Ltd.) was added into the reaction liquid. A reaction was performed on a shaker at 25° C. and 150 rpm/min for 18 hours, followed by filtration. The filter mass was rinsed twice, each time with 300 ml of DCM, and rinsed three times, each time with 300 ml of acetonitrile, and dried for 18 hours with a vacuum oil pump. Then a capping reaction was performed by adding starting materials (CapA, CapB, 4-dimethylaminopyridine (DMAP) and acetonitrile) according to the charge ratio shown in Table 2. A reaction was performed on a shaker at 25° C. and 150 rpm/min for 5 hours. The reaction liquid was filtrated. The filter mass was rinsed three times, each time with 300 ml of acetonitrile, the solvent was evaporated to dryness under a reduced pressure, and the residue was dried overnight under a reduced pressure with a vacuum oil pump to give 102 g of compound L-10 (i.e., the L-9 conjugating molecule linked to the solid phase support), with a loading of 90.8 mol/g.

in dichloromethane (3% v/v) as a deprotection agent, and a molar ratio of the dichloroacetic acid to the protecting group 4,4'-dimethoxytrityl on the solid phase support of 5:1.

The condition for coupling reaction in each step was identical, comprising a temperature of 25° C., a molar ratio of the nucleic acid sequence linked to the solid phase support to the nucleoside monomers of 1:10, a molar ratio of the nucleic acid sequence linked to the solid phase support to a coupling agent of 1:65, a reaction time of 600 seconds, and 0.5 M acetonitrile solution of 5-ethylthio-1H-tetrazole (ETT) as a coupling agent.

The condition for capping reaction in each step was identical, comprising a temperature of 25° C. and a reaction time of 15 seconds. A capping agent was a mixed solution of Cap A and Cap B in a molar ratio of 1:1, and a molar ratio of the capping agent to the nucleic acid sequence linked to the solid phase support was 1:1:1 (anhydride:N-methylimidazole: the nucleic acid sequence linked to the solid phase support).

The condition for oxidation reaction in each step was identical, comprising a temperature of 25° C., a reaction time of 15 seconds, and 0.05 M iodine water as an oxidation agent. A molar ratio of iodine to the nucleic acid sequence linked to the solid phase support in the coupling step was 30:1. The reaction was carried out in a mixed solvent in which the ratio of tetrahydrofuran:water:pyridine was 3:1:1.

TABLE 2

The charge ratio of capping reaction

| Starting materials | Amount | Grade | Lot No. | Manufacturer |
|---|---|---|---|---|
| CapA | 1980 ml | — | — | — |
| CapB | 220 ml | — | — | — |
| DMAP | 1.100 g | Analytical pure | I1422139 | Aladdin |
| Acetonitrile | 220 ml | Spectroscopic pure | O15161001 | CINC (Shanghai) Co., Ltd |

In the above table, CapA and CapB are solutions of capping agents. CapA is a solution of 20% by volume of N-methylimidazole in a mixture of pyridine/acetonitrile, wherein the volume ratio of the pyridine to the acetonitrile is 3:5. CapB is a solution of 20% by volume of acetic anhydride in acetonitrile.

(1-2) Synthesis of the Sense Strand of siRNA Conjugate L10-siKNa1M1SP

Nucleoside monomers were linked one by one in the direction from 3' to 5' according to the arrangement sequence of nucleotides in the sense strand corresponding to L10-siKNa1M1SP in Table 3 by the solid phase phosphoramidite method, starting the cycles from the Compound L-10 prepared in the above step. The linking of each nucleoside monomer comprised a four-step reaction of deprotection, coupling, capping, and oxidation or sulfurization. Wherein, when two nucleotides are linked via a phosphoester, a four-step reaction of deprotection, coupling, capping, and oxidation was comprised during linking of the later nucleoside monomer. When two nucleotides are linked via a phosphorothioate, a four-step reaction of deprotection, coupling, capping, and sulfurization was comprised during linking of the later nucleoside monomer. The synthesis condition was given as follows.

The nucleoside monomers were provided in a 0.1 M acetonitrile solution. The condition for deprotection reaction in each step was identical, i.e., a temperature of 25° C., a reaction time of 70 seconds, a solution of dichloroacetic acid After the last nucleoside monomer was linked, the nucleic acid sequence linked to the solid phase support was cleaved, deprotected, purified and desalted in turn, and then freeze-dried to obtain the sense strand, wherein, the conditions for cleavage and deprotection were as follows: adding the synthesized nucleotide sequence linked to the support into 25 wt % aqueous ammonia to react for 16 hours at 55° C., wherein the aqueous ammonia was in an amount of 0.5 ml/mol; filtering to remove the remaining support, and concentrating the supernatant in vacuum to dryness.

The conditions for purification and desalination were as follows: purifying the nucleic acid by using a preparative ion chromatography column (Source 15Q) with a gradient elution of NaCl. Specifically, eluent A: 20 mM sodium phosphate (pH 8.1), solvent: water/acetonitrile=9:1 (v/v); eluent B: 1.5 M sodium chloride, 20 mM sodium phosphate (pH 8.1), solvent: water/acetonitrile=9:1 (v/v); elution gradient: eluent A: eluent B=100:0 to 50:50. The eluate was collected, combined and desalted by using a reverse phase chromatography purification column. The specific conditions comprised using a Sephadex column (filler: Sephadex-G25) for desalination and deionized water for eluting.

The detection method was as follows: determining the purity of the sense strand above by ion exchange chromatography (IEX-HPLC); and analyzing the molecular weight by Liquid Chromatography-Mass Spectrometry (LC-MS). The measured value was in conformity with the theoretical value, indicating that a sense strand SS conjugated with L-9 conjugating molecule at 3' terminal was synthesized.

(1-3) Synthesis of the Antisense Strand of siRNA Conjugate L10-siKNa1M1SP

The antisense strands of the siRNA conjugate L10-siKNa1M1SP was synthesized by starting the cycles using a universal solid phase support (UnyLinker™ loaded NittoPhase®HL Solid Supports, Kinovate Life Sciences Inc.) by the solid phase phosphoramidite method and according to the antisense strand nucleotide sequence corresponding to L10-siKNa1M1SP in Table 3. The reaction conditions of deprotection, coupling, capping, oxidation or sulfurization, cleavage and deprotection, purification and desalting in the solid phase synthesis method were the same as those in the synthesis of the sense strand. The difference was in that: the antisense strand had 5'-phosphate nucleotide at the first nucleotide of the 5'-terminal. Therefore, in the process of preparing the antisense strand according to the solid phase phosphoramidite method, a CPR-I monomer (Suzhou GenePharma, article number Cat #13-2601-XX) was linked to the 5' terminal of the antisense strand to form 5'-phosphate nucleotide modification by four steps of deprotection, coupling, capping and oxidation after the last nucleoside monomer of the antisense strand was linked.

(CPR-I)

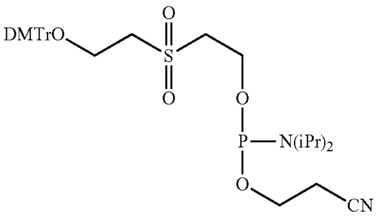

In this linkage, the conditions used of deprotection, coupling, capping and oxidation reaction, cleavage and deprotection, purification and desalting were the same as those in the synthesis of the sense strand. The obtained product was freeze-dried to obtain the antisense strand subsequently. The purity of the antisense strand was detected by ion exchange chromatography (IEX-HPLC), and the molecular weight was analyzed by liquid chromatography-mass spectrometry (LC-MS). The measured value was in conformity with the theoretical value, indicating that an antisense strand AS having a target sequence was synthesized.

(1-4) Synthesis of siRNA Conjugate L10-siKNa1M1SP

The sense strand and the antisense strand obtained in steps (1-2) and (1-3) were respectively dissolved in water for injection to give a solution of 40 mg/mL, the obtained solutions were mixed with equimolar sense strand and antisense strand, heated at 50° C. for 15 minutes, and then cooled at room temperature, such that an annealed product was obtained and then freeze-dried to obtain lyophilized powder. The siRNA conjugate was diluted to a concentration of 0.2 mg/mL with ultra-pure water (prepared by Milli-Q ultra-pure water instrument, with resistivity of 18.2M2*cm (25° C.)). The molecular weight was measured by Liquid Chromatography-Mass Spectrometry (LC-MS, purchased from Waters Corp., model: LCT Premier). The measured value was in conformity with the theoretical value, indicating that the synthesized siRNA conjugate was the designed double stranded nucleic acid sequence of interest with the L-9 conjugating molecule. The structure thereof was as shown by Formula (403). The siRNA conjugate has sense strand and antisense strand sequences corresponding to the siRNA conjugate L10-siKNa1M1SP in Table 3.

TABLE 3 siRNA conjugates

| Preparation Example No. | SIRNA conjugate No. | Sequence direction 5'-3' | | SEQ ID NO |
|---|---|---|---|---|
| Preparation Example 1 | L10-siKNa1M1SP | Sense strand | AmsAmsAmGmUmAmAfCfAfAmCmCmAm GmUmUmUmGmUm | 361 |
| | | Antisense strand | PAmsCfsAmAmAmCfUmGmGmUmUmGm UmUfAmCfUmUmUmsGmsGm | 362 |
| Preparation Example 2 | L10-siKNb1M1SP | Sense strand | AmsUmsUmGmAmAmCfUfUfUmCmGmAm AmUmUmAmCmCm | 363 |
| | | Antisense strand | PGmsGfsUmAmAmUfUmCmGmAmAmAm GmUfUmCfAmAmUmsCmsCm | 364 |
| Preparation Example 3 | L10-siKNc1M1SP | Sense strand | UmsCmsGmAmAmUmUfAfCfCmUmAmCm UmCmAmAmUmUm | 365 |
| | | Antisense strand | PAmsAfsUmUmGmAfGmUmAmGmGmUm AmAfUmUfCmGmAmsAmsAm | 366 |
| Preparation Example 4 | L10-siKNd1M1SP | Sense strand | GmsAmsUmAmAmUmGfCfAfUmAmCmAm UmCmGmAmUmAm | 367 |
| | | Antisense strand | PUmsAfsUmCmGmAfUmGmUmAmUmGm CmAfUmUfAmUmCmsUmsGm | 368 |
| Preparation Example 5 | L10-siKNe1M1SP | Sense strand | GmsAmsAmUmAmAmCfGfCfAmAmCmUm UmUmCmUmAmUm | 369 |
| | | Antisense strand | PAmsUfsAmGmAmAfAmGmUmUmGmCm GmUfUmAfUmUmCmsUmsCm | 370 |

TABLE 3-continued

| siRNA conjugates | | | | |
|---|---|---|---|---|
| Preparation Example No. | SIRNA conjugate No. | Sequence direction 5'-3' | | SEQ ID NO |
| Preparation Example 6 | L10-siKNf1M1SP | Sense strand | AmsAmsCmUmUmUmCfUfAfUmUmUmCm AmAmGmAmUmUm | 371 |
| | | Antisense strand | PAmsAfsUmCmUmUfGmAmAmAmUmAm GmAfAmAfGmUmUmsGmsCm | 372 |

wherein, capital letters C, G, U, and A indicated the base composition of the nucleotides; the lowercase m indicated that the nucleotide adjacent to the left side of the letter m was a methoxy modified nucleotide; the lowercase f indicated that the nucleotide adjacent to the left side of the letter f was a fluoro modified nucleotide; the lowercase letter s indicated that the two nucleotides adjacent to the left and right of the letter s were linked by phosphorothioate; and the capital letter P indicated that the nucleotide adjacent to the right side of the letter P was a 5'-phosphate nucleotide.

Preparation Examples 2-6

Synthesis of the siRNA Conjugates of the Present Disclosure

The siRNA conjugates of the present disclosure shown in Table 3 comprising L10-siKNb1M1SP, L10-siKNc1M1SP, L10-siKNd1M1SP, L10-siKNe1M1SP and L10-siKNf1M1SP were synthesized by the same method as that in Preparation Example 1. The siRNAs comprised in these siRNA conjugates respectively have the sense strand and antisense strand sequences corresponding to each siRNA conjugate in Table 3. The difference between the preparation methods was only in that the sense strands and the antisense strands were respectively synthesized according to the sense strand and the antisense strand sequences corresponding to each siRNA conjugate in Table 3.

After preparation, the molecular weights of the prepared siRNA conjugates were respectively detected according to the method of the Preparation Example 1, and the measured values were consistent with the theoretical values, indicating that the synthesized siRNA conjugate was a designed double-stranded nucleic acid sequence of interest with the L-9 conjugating molecule. The structures thereof were all as shown by Formula (403).

The siRNAs contained in these siRNA conjugates respectively have the sequences corresponding to the siRNA conjugates L10-siKNb1M1SP, L10-siKNc1M1SP, L10-siKNd1M1SP, L10-siKNe1M1SP and L10-siKNf1M1SP in Table 3.

Preparation Examples 7-14 and Comparative Preparation Examples 15 and 16

Synthesis of siRNA Sequences

The sense strands or the antisense strands of the siRNA sequences listed in Table 4 were respectively synthesized by a solid phase synthesis method, and DEPC water was used to dissolve an equimolar mixture of the sense strands and antisense strands, and then followed by annealing to obtain the following siRNAs: siKNa1M1S, siKNb1M1S, siKNc1M1S, siKNd1M1S, siKNe1M1S, siKNf1M1S, siKNa0, siKNc0, siKNa0-com, and NC.

TABLE 4

| siRNA sequences | | | | |
|---|---|---|---|---|
| Preparation Example No. | siRNA No. | | Sequence direction 5'-3' | SEQ ID NO |
| Preparation Example 7 | siKNa1M1S | Sense strand | AmsAmsAmGmUmAmAfCfAfAmCmCmAmGmUm UmUmGmUm | 373 |
| | | Antisense strand | AmCfAmAmAmCfUmGmGmUmUmGmUmUfAmCf UmUmUmsGmsGm | 374 |
| Preparation Example 8 | siKNb1M1S | Sense strand | AmsUmsUmGmAmAmCfUfUfUmCmGmAmAmUm UmAmCmCm | 375 |
| | | Antisense strand | GmGfUmAmAmUfUmCmGmAmAmAmGmUfUmC fAmAmUmsCmsCm | 376 |
| Preparation Example 9 | siKNc1M1S | Sense strand | UmsCmsGmAmAmUmUfAfCfCmUmAmCmUmCm AmAmUmUm | 377 |
| | | Antisense strand | AmAfUmUmGmAfGmUmAmGmGmUmAmAfUmU fCmGmAmsAmsAm | 378 |
| Preparation Example 10 | siKNd1M1S | Sense strand | GmsAmsUmAmAmUmGfCfAfUmAmCmAmUmCm GmAmUmAm | 379 |
| | | Antisense strand | UmAfUmCmGmAfUmGmUmAmUmGmCmAfUmU fAmUmCmsUmsGm | 380 |
| Preparation Example 11 | siKNe1M1S | Sense strand | GmsAmsAmUmAmAmCfGfCfAmAmCmUmUmUm CmUmAmUm | 381 |
| | | Antisense strand | AmUfAmGmAmAfAmGmUmUmGmCmGmUfUmA fUmUmCmsUmsCm | 382 |

TABLE 4-continued siRNA sequences

| Preparation Example No. | siRNA No. | | Sequence direction 5'-3' | SEQ ID NO |
|---|---|---|---|---|
| Preparation Example 12 | siKNf1M1S | Sense strand | AmsAmsCmUmUmUmCfUfAfUmUmUmCmAmAmGmAmUmUm | 383 |
| | | Antisense strand | AmAfUmCmUmUfGmAmAmAmUmAmGmAfAmAfGmUmUmsGmsCm | 384 |
| Preparation Example 13 | siKNa0 | Sense strand | AAAGUAACAACCAGUUUGU | 385 |
| | | Antisense strand | ACAAACUGGUUGUUACUUU | 386 |
| Preparation Example 14 | siKNc0 | Sense strand | UCGAAUUACCUACUCAAUU | 387 |
| | | Antisense strand | AAUUGAGUAGGUAAUUCGA | 388 |
| Comparative Preparation Example 15 | siKNa0-com | Sense strand | CCAAAGUAACAACCAGUUU | 389 |
| | | Antisense strand | AAACUGGUUGUUACUUUGG | 390 |
| Comparative Preparation Example 16 | NC | Sense strand | UUCUCCGAACGUGUCACGUdTdT | 391 |
| | | Antisense strand | ACGUGACACGUUCGGAGAAdTdT | 392 |

Wherein, capital letters C, G, U, and A indicated the base composition of the nucleotides; the lowercase m indicated that the nucleotide adjacent to the left side of the letter m was a methoxy modified nucleotide; the lowercase f indicated that the nucleotide adjacent to the left side of the letter f was a fluoro modified nucleotide; and the lowercase letter s indicated that the two nucleotides adjacent to the left and right of the letter s were linked by phosphorothioate.

In the preparation process of the sequences above, when the target sequence contained an unmodified nucleotide, under the conditions of cleavage and deprotection, after aqueous ammonia treatment, 0.4 ml/mol N-methyl pyrrolidone was used to dissolve the product, and then 0.3 ml/mol triethylamine and 0.6 ml/mol triethylamine trihydrofluoride were added to remove 2'-TBDMS protection on ribose, with respect to the amount of the single-stranded nucleic acid. The molecular weights of the above siRNAs were respectively detected according to the method of Preparation Example 1, and the measured values were consistent with the theoretical values, confirming that the obtained siRNAs had sequences corresponding to each siRNA shown in Table 4.

After the siRNA or siRNA conjugate of the present disclosure above was prepared, the siRNA or siRNA conjugate was freeze-dried into solid powder for later use. When in use, for example, water for injection, normal saline (NS), phosphate buffer (PB) or phosphate buffered saline (PBS) could be used to redissolve the siRNA or siRNA conjugate into a solution with the required concentration for use.

Experimental Example 1

In Vitro Inhibitory Activity of the siRNA of the Present Disclosure

HEK293A cells (purchased from Nanjing COBIOER Biotechnology Co., Ltd.) were cultured in H-DMEM complete media (HyClone company) containing 10% fetal bovine serum (FBS, Hyclone company) and 0.2 v % Penicillin-Streptomycin (Gibco, Invitrogen company) at 37° C. in an incubator containing 5% $CO_2$/95% air.

According to the methods described in Kumico Ui-Tei et. al., Functional dissection of siRNA sequence DNA substitution: modified siRNA with a DNA seed arm is a powerful tool for mammalian gene silencing with significantly reduced off-target effect. Nucleic Acids Research, 2008.36 (7), 2136-2151, detection plasmids were constructed, and co-transfected into the HEK293A cells together with the to-be-tested siRNAs, and the inhibitory activity of the siRNA was reflected by the expression level of double luciferase reporter gene. The specific steps were as follows:

[1] Construction of Detection Plasmids

Detection plasmids were constructed using psiCHECK™-2 (Promega™) plasmid. Each plasmid comprised one target sequence, i.e., the target sequence of the siRNA. For each to-be-tested siRNA, the target sequences were respectively as shown below:

The target sequence of the siKNa0 was:

(SEQ ID NO: 393)
AAAGTAACAACCAGTTTGT

The target sequence of the siKNc0 was:

(SEQ ID NO: 394)
TCGAATTACCTACTCAATT

The target sequence was cloned into the Xho I/Not I site of the psiCHECK™-2 plasmid.

[2] Transfection

HEK293A cells were seeded in a 96-well plate with $8\times10^3$ cells/well. After 16 hours, when the growth density of the cells reached 70-80%, the H-DMEM complete media in the culture wells were sucked up, and 80 μl of Opti-MEM media (GIBCO company) was added to each well to continue the culture for 1.5 hours.

For each siRNA, the corresponding detection plasmid was diluted into 200 ng/μl detection plasmid working solution with DEPC water. For each siRNA, DEPC water was used to prepare the siRNA into siRNA working solutions with concentrations (calculated by siRNA) of 10 nM, 3 nM and 1 nM respectively.

A 1A1 solution was prepared, and each part of the 1A1 solution contained 1 μl of siRNA working solution with a concentration of 10 nM, 0.05 μl of detection plasmid working solution (containing 10 ng of detection plasmids) and 10 μl of Opti-MEM media.

A 1A2 solution was prepared, and each part of the 1A2 solution contained 1 μl of siRNA working solution with a concentration of 3 nM, 0.05 μl of detection plasmid working solution (containing 10 ng of detection plasmids) and 10 μl of Opti-MEM media.

A 1A3 solution was prepared, and each part of the 1A3 solution contained 1 μl of siRNA working solution with a concentration of 1 nM, 0.05 μl of detection plasmid working solution (containing 10 ng of detection plasmids) and 10 μl of Opti-MEM media.

A 1B solution was prepared, and each part of the 1B solution contained 0.2 μl of Lipofectamine™ 2000 and 10 μl of Opti-MEM media.

A 1C solution was prepared, and each part of the 1C solution contained 0.05 μl of detection plasmid working solution (containing 10 ng of detection plasmids) and 10 μl of Opti-MEM media For each siRNA, one part of the 1B solution was mixed with one part of the 1A1 solution, one part of the 1A2 solution and one part of the 1A3 solution, and incubated for 20 minutes at room temperature to obtain transfection complexes 1X1, 1X2 and 1X3 respectively. One part of the 1B solution was mixed with one part of the 1C solution and incubated for 20 minutes at room temperature to obtain a transfection complex 1X4.

For each siRNA, the transfection complex 1X1 was respectively added into three culture wells, and evenly mixed, with an addition amount of 20 μl/well, to obtain a co-transfection mixture with the final concentration of the siRNA about 0.1 nM, which was labeled as test group 1.

For each siRNA, the transfection complex 1X2 was respectively added into another three culture wells, and evenly mixed, with an addition amount of 20 μl/well, to obtain a co-transfection mixture with the final concentration of the siRNA about 0.03 nM, which was labeled as test group 2.

For each siRNA, the transfection complex 1X3 was respectively added into another three culture wells, and evenly mixed, with an addition amount of 20 μl/well, to obtain a co-transfection mixture with the final concentration of the siRNA about 0.01 nM, which was labeled as test group 3.

The transfection complex 1X4 was respectively added into another three culture wells, and evenly mixed, with an addition amount of 20 μl/well, to obtain a transfection mixture not containing the siRNA, which was labeled as a control group.

The co-transfection mixture containing the siRNA and the transfection mixture not containing the siRNA were co-transfected in culture wells for 4 hours, and then 100 μl of H-DMEM complete medium containing 20% FBS was added to each well. The 96-well plate was placed in a $CO_2$ incubator to continuously culture for 24 hours.

[3] Detection

The media in the culture wells were sucked off, and 150 μl of a mixed solution of Dual-Glo® Luciferase and H-DMEM (volume ratio of 1:1) was added to each well, thoroughly mixed, and incubated at room temperature for 10 minutes, then 120 μl of the mixed solution was transferred to a 96-well enzyme-labeled plate, and a Firefly chemiluminescence value (Fir) was read by using Synergy II multifunctional microplate reader (BioTek company); then, 60 μl of Dual-Glo® Stop & Glo® reagent was added to each well, thoroughly mixed, incubated at room temperature for 10 minutes, then the *Renilla* chemiluminescence value (Ren) in each culture well was read with a microplate reader according to the arrangement of reading the Fir.

The luminous ratio (Ratio=Ren/Fir) of each well was calculated, and the luminous Ratio (test) or Ratio (control) of each test group or control group was the average value of the Ratio of three culture wells; on the basis of the luminous ratio of the control group, the luminous ratio of each test group was normalized to obtain the ratio R of the Ratio (test)/Ratio (control), which was used to express the expression level of *Renilla* reporter gene, i.e., the residual activity. Inhibition percentage of the siRNA=(1-R)×100%.

FIG. 1 shows the residual activity of *Renilla* reporter genes in HEK293A cells after transfection of siKNa0 and siKNc0 respectively.

Comparative Experimental Example 1

In vitro inhibitory activity of reference siRNA

According to the method of Experimental Example 2, the residual activities of the reference siRNA NC and siKNa0-com in the psiCHECK system were also investigated.

The only difference was in that the tested siRNAs were the reference siRNA NC and the siKNa0-com respectively.

The target sequence of the siKNa0-com was:

```
                                    (SEQ ID NO: 395)
CCAAAGTAACAACCAGTTT
```

The target sequence of the NC was the same as the target sequence of the siKNa0.

The results were as shown in FIG. 1.

The results in FIG. 1 show that the siRNA of the present disclosure has good inhibitory activity to the target sequences in HEK293A cells, and the inhibition percentage shows a concentration dependence. Especially, the inhibition percentages of the siKNa0 and siKNc0 both reach above 75% when the concentration of the siRNA is 0.1 nM, showing a good effect of inhibiting the expression of KNG genes. In sharp contrast, although the sequence of the reference siKNa0-com is very similar to the siKNa0, the inhibition percentage thereof to the target sequence is less than 50% even under the siRNA concentration of 0.1 nM, which indicates that the siRNA of the present disclosure unexpectedly shows a good effect of inhibiting the expression of the KNG genes.

Experimental Example 2

$IC_{50}$ Detection of Target Sequence of siRNA in psiCHECK

HEK293A (purchased from Nanjing COBIOER Biotechnology Co., Ltd.) were cultured in H-DMEM complete media (HyClone company) containing 10% fetal bovine serum (FBS, Hyclone company) and 0.2 v % Penicillin-Streptomycin (Gibco, Invitrogen company) at 37° C. in an incubator containing 5% $CO_2$/95% air.

According to the methods disclosed in Kumico Ui-Tei et. al., Functional dissection of siRNA sequence by systematic DNA substitution: modified siRNA with a DNA seed arm is a powerful tool for mammalian gene silencing with significantly reduced off-target effect. Nucleic Acids Research, 2008.36(7), 2136-2151, detection plasmids were constructed. The detection plasmids and the to-be-tested siRNA were co-transfected into HEK293A cells, and the inhibition activity of the target sequence of the siRNA was reflected by the expression level of the double luciferase reporter gene. The specific steps were as follows:

[1] Construction of Detection Plasmids

Detection plasmids were constructed using psiCHECK™-2 (Promega™) plasmid. The plasmid comprised one target sequence, i.e., the target sequence of the siRNA. For the to-be-tested siRNAs, the target sequences were respectively as shown below:

The target sequence of the siKNa1M1S was:

```
                                        (SEQ ID NO: 396)
CATGGCCACGGAAAACATAAAAATAAAGGCAAAAGAATGGAAAGCA

CAATGGTTGGAAAACAGAGCATTTGGCAAGCTCTTCTGAAGACAGTACTAC

ACCTTCTGCACAGACACAAGAGAAGACAGAAGGGCCAACACCCATCCCTT

CCCTAGCCAAGCCAGGTGTAACAGTTACCTTTTCTGACTTTCAGGACTCTG

ATCTCATTGCAACTATGATGCCTCCTATATCACCAGCTCCCATACAGAGTG

ATGACGATTGGATCCCTGATATCCAGATAGACCCAAATGGCCTTTCATTTA

ACCCAATATCAGATTTTCCAGACACGACCTCCCCAAAATGTCCTGGACGCC

CCTGGAAGTCAGTTAGTGAAATTAATCCAACCACACAAATGAAAGAATCTT

ATTATTTCGATCTCACTGATGGCCTTTCTTAATTTAAGTGGCTATGGGTAT

TTCTTTCATACTTTATTAAAGTATCAATATCCCTCTCTCCATTGTCCAGAT

GAAAATATCCTGATATAATGCACCAAAAACCATGCAGCTTCGGAACAGTCT

AAAGAGAAGTGGTGAGACTCCCAGTGGAGACACC
```

The target sequences of the siKNb1M1S, siKNc1M1S, siKNd1M1S, siKNe1M1S and siKNf1M1S were:

```
                                        (SEQ ID NO: 397)
CATGGCCACGGAAAACATAAAAATAAAGGCAAAAGAATGGAAAGCA

CAATGGTTGGAAAACAGAGCATTTGGCAAGCTCTTCTGAAGACAGTACTAC

ACCTTCTGCACAGACACAAGAGAAGACAGAAGGGCCAACACCCATCCCTT

CCCTAGCCAAGCCAGGTGTAACAGTTACCTTTTCTGACTTTCAGGACTCTG

ATCTCATTGCAACTATGATGCCTCCTATATCACCAGCTCCCATACAGAGTG

ATGACGATTGGATCCCTGATATCCAGATAGACCCAAATGGCCTTTCATTTA

ACCCAATATCAGATTTTCCAGACACGACCTCCCCAAAATGTCCTGGACGCC

CCTGGAAGTCAGTTAGTGAAATTAATCCAACCACACAAATGAAAGAATCTT

ATTATTTCGATCTCACTGATGGCCTTTCTTAATTTAAGTGGCTATGGGTAT

TTCTTTCATACTTTATTAAAGTATCAATATCCCTCTCTCCATTGTCCAGAT

GAAAATATCCTGATATAATGCACCAAAAACCATGCAGCTTCGGAACAGTCT

AAAGAGAAGTGGTGAGACTCCCAGTGGAGACACC
```

The above target sequences were all gene fragments of genes encoding human KNG mRNA.

The target sequence was cloned into the Xho I/Not I site of the psiCHECK™-2 plasmid.

[2] Transfection

HEK293A cells were seeded in a 96-well plate with $8\times10^3$ cells/well. After 16 hours, when the growth density of the cells reached 70-80%, the H-DMEM complete media in the culture wells were sucked up, and 80 μl of Opti-MEM media (GIBCO company) was added to each well to continue the culture for 1.5 hours.

The above detection plasmid was diluted into 200 ng/μl detection plasmid working solution with DEPC water. DEPC water was used to prepare each siRNA in the following siRNAs into siRNA working solutions with nine different concentrations of 100 nM, 50 nM, 25 nM, 12.5 nM, 6.25 nM, 3.125 nM, 1.5625 nM, 0.7813 nM and 0.3906 nM respectively, and the siRNAs used were respectively siKNa1M1S, siKNb1M1S, siKNc1M1S, siKNd1M1S, siKNe1M1S and siKNf1M1S.

For each siRNA, 2A1-2A9 solutions were respectively prepared, and each part of the 2A1-2A9 solutions contained 1 μl of the above siRNA working solutions with nine concentrations in turn, 0.05 μl of detection plasmid working solution (containing 10 ng of detection plasmids) and 10 μl of Opti-MEM media.

One part of the 1B solution was respectively mixed with one part of the obtained 2A1-2A9 solutions of each siRNA, and incubated at room temperature for 20 minutes respectively to obtain the transfection complexes 2X1-2X9 of each siRNA.

The transfection complexes 2X1-2X9 of each siRNA were respectively added in the culture wells, and evenly mixed, with an addition amount of 20 μl/well, to obtain transfection complexes respectively with the final concentrations of the siRNA about 1 nM, 0.5 nM, 0.25 nM, 0.125 nM, 0.0625 nM, 0.03125 nM, 0.015625 nM, 0.007813 nM and 0.003906 nM. The transfection complexes 2X1-2X9 of each siRNA were respectively transfected with three culture wells to obtain a co-transfection mixture containing the siRNA, which was labeled as the test group.

The transfection complex 1X3 was respectively added into another three culture wells, and evenly mixed, with an addition amount of 20 μl/well, to obtain a co-transfection mixture not containing the siRNA, which was labeled as a control group.

The co-transfection mixture containing the siRNA and the co-transfection mixture not containing the siRNA were co-transfected in culture wells for 4 hours, and then 100 μl of H-DMEM complete media containing 20% FBS was added to each well. The 96-well plate was placed in a $CO_2$ incubator to continuously culture for 24 hours.

[3] Detection

The media in the culture wells were sucked off, and 150 μl of a mixed solution of Dual-Glo® Luciferase reagent and H-DMEM (volume ratio 1:1) was added to each well, thoroughly mixed, and incubated at room temperature for 10 minutes, then 120 μl of the mixed solution was transferred to a 96-well enzyme-labeled plate, and a Firefly chemiluminescence value (Fir) in each culture well on the 96-well enzyme-labeled plate was read by using Synergy II multifunctional microplate reader (BioTek company); then, 60 μl of Dual-Glo® Stop & Glo® reagent was added to each well on the 96-well enzyme-labeled plate, thoroughly mixed, incubated at room temperature for 10 minutes, then a *Renilla* chemiluminescence value (Ren) in each culture well was read with a microplate reader according to the arrangement of reading the Fir.

The luminous ratio (Ratio=Ren/Fir) of each well on the 96-well enzyme-labeled plate was calculated, and the luminous Ratio (test) or Ratio (control) of each test group or control group was the average value of the Ratio of three culture wells; on the basis of the luminous ratio of the control group, the luminous ratio of each test group was normalized to obtain the ratio R of the Ratio (test)/Ratio (control), which was used to expresse the expression level of *Renilla* reporter gene, i.e., the residual activity. Inhibition percentage of the siRNA to the target sequence=(1−R)× 100%.

According to the relative residual activity of *Renilla* in HEK293A cells transfected with different concentrations of to-be-tested siRNAs, the log(inhibitor) vs. response-Variable slope (four parameters) dose-response curve was fitted by using a nonlinear regression analysis function of Graphpad 5.0 software. FIGS. 2A-2F showed the dose-response curves of the siKNa1M1S, siKNb1M1S, siKNc1M1S, siKNd1M1S, siKNe1M1S and siKNf1M1S in turn. Wherein, a common logarithmic value (lg nM) of the siRNA final concentration was used as the abscissa and the relative residual activity (%) of *Renilla* was used as the ordinate, each dot represented the mean value of the relative residual activity of *Renilla* in three culture wells of the test group compared with the control group.

The $IC_{50}$ value of the target sequence of the to-be-tested siRNA was calculated according to a function corresponding to the fitted dose-effect curve, wherein the function was as follows:

$$Y = Bot + \frac{\text{Top} - Bot}{1 + 10^{(X'-X)\times HillSlope}}$$

wherein:

Y is the ratio R, i.e., the relative residual activity of *Renilla*,

X is the logarithmic value of the concentration of the transfected siRNA,

Bot is the Y value at the bottom of the steady stage,

Top is the Y value at the top of the steady stage, and

X' is the corresponding X value when Y is median value between the bottom and the top, and HillSlope is the slope of the curve at X'.

According to the dose-effect curve and the corresponding function, the corresponding $X_{50}$ value when Y=50% was determined, and the $IC_{50}$ value of each siRNA was calculated to be 10^X50 (nM). The $IC_{50}$ value is summarized in Table 5.

TABLE 5

$IC_{50}$ of siRNA conjugates

| Preparation Example No. | No. | $IC_{50}$ |
|---|---|---|
| Preparation Example 1 | L10-siKNa1M1SP | 0.1054 nM |
| Preparation Example 2 | L10-siKNb1M1SP | 0.1914 nM |
| Preparation Example 3 | L10-siKNc1M1SP | 0.2328 nM |
| Preparation Example 4 | L10-siKNd1M1SP | 0.1096 nM |
| Preparation Example 5 | L10-siKNe1M1SP | 0.0048 nM |
| Preparation Example 6 | L10-siKNf1M1SP | 0.0186 nM |

It can be seen from the results in FIGS. 2A-2F and the Table 5 above that the siRNA conjugate provided by the present disclosure has high inhibitory activity for target sequence in HEK293A cells in vitro, and the $IC_{50}$ is between 0.0048 nM and 0.2328 nM.

Experimental Example 3

Determination of Activity of the siRNA Conjugate Provided by the Present Disclosure in Humanized Mice (In Vivo)

The humanized mice used in this experimental example were constructed by HEMATOLOGY CENTER, CYRUS TANG MEDICAL INSTITUTE, SOOCHOW UNIVERSITY The humanized mice aged 6-8 weeks were randomly divided into 5 groups, with 4 mice in each group (2 males and 2 females). The mice in each group were given siRNA conjugates L10-siKNa1M1SP, L10-siKNc1M1SP, L10-siKNe1M1SP, L10-siKNf1M1SP and normal saline (control) at a dose of 6 mg/kg (based on siRNA) via single subcutaneous injection. Each siRNA conjugate was provided in the form of 0.9% sodium chloride aqueous solution at 0.6 mg/ml (based on siRNA), and the administration volume was 10 ml/kg.

Then, the animals were sacrificed on the $28^{th}$ day, and liver tissues of each mouse were collected respectively. About 100 mg of the left lobe of the liver was taken per mouse, and preserved by RNA later (Sigma Aldrich company). Then, for the liver tissue of each mouse, the liver tissues were respectively homogenated with a tissue homogenizer, and the total RNA of the liver tissue of each mouse was extracted with Trizol (Thermo Fisher company) according to the operation steps described in the instruction.

According to the method of the Experimental Example 2, fluorescence quantitative PCR was performed and the relative expression level and inhibition percentages of KNG mRNA were detected. The only difference was in that the extracted total RNA was reversely transcribed into cDNA by using ImProm-II™ reverse transcription kit (Promega company) according to the instructions thereof to obtain a solution containing cDNA, and then the expression level of KNG mRNA in the liver tissues was detected by fluorescence quantitative PCR kit (Beijing CoWin Biosciences). In this fluorescence quantitative PCR method, β-actin gene was used as internal reference genes, and KNG and β-actin genes were detected by using primers for KNG and for β-actin gene respectively. The sequences of the detection primers were shown in Table 6. In the calculation of the expression level and inhibition percentage of the KNG mRNA, the control group referred to the control group mice given PBS in this experiment, and each test group referred to the mice given different siRNA conjugates. The expression level of the KNG mRNA in the control group was recorded as 100%, and accordingly, the inhibition percentage to the expression level of the KNG mRNA was recorded as 0%. The test results were normalized by the expression level of the KNG mRNA in the control group, and the results were shown in Table 6.

TABLE 6

Sequences of the Detection Primers

| Name of gene | Type of primer | Nucleotide sequence (5'-3') | SEQ ID NO. |
|---|---|---|---|
| Human KNG | Upstream primer | CTACCCAGACCTGCCAGATTACTC | 398 |
| | Downstream primer | GATATAGGATGCACACAGCCGAG | 399 |

TABLE 6-continued

| Sequences of the Detection Primers | | | |
|---|---|---|---|
| Name of gene | Type of primer | Nucleotide sequence (5'-3') | SEQ ID NO. |
| β-actin | Upstream primer | GTGCTATGTTGCTCTAGACTTCG | 400 |
| | Downstream primer | ATGCCACAGGATTCCATACC | 401 |

Comparative Ct (ΔΔCt) method was used to calculate the relative quantitative expression of the target gene KNG in each test group and the control group. The calculation method was as follows:

ΔCt(test group)=Ct(target gene of test group)−Ct(internal reference gene of test group)

ΔCt(control group)=Ct(target gene of control group)−Ct(internal reference gene of control group)

ΔΔCt(test group)=ΔCt(test group)−ΔCt(mean value of control group)

ΔΔCt(control group)=ΔCt(control group)−ΔCt(mean value of control group)

wherein, ΔCt(mean value of control group) was the arithmetic mean value of ΔCt(control group) of each mouse of the control group. Therefore, each mouse of the test group and the control group corresponded to one ΔΔCt value.

On the basis of the control group, the expression level of KNG mRNA in the test group was normalized, and the expression level of KNG mRNA in the control group was defined as 100%.

The relative expression level of KNG mRNA in the test group=$2^{-\Delta\Delta ct(test\ group)}$×100%.

For the siRNAs of the same test group, the mean value of the relative expression level of the KNG mRNA of the test group was the arithmetic mean value of the relative expression level of each group of mice at this concentration.

The test results were normalized by the expression level of KNG mRNA of the control group, and the results were shown in Table 7. In Table 7, the inhibition percentage of human KNG mRNA was the mean value of the inhibition percentage of human KNG mRNA of one group of mice given corresponding siRNA conjugates and a standard deviation thereof.

TABLE 7

| Inhibition percentage of the siRNA conjugate of the present disclosure on KNG mRNA in humanized mice | | |
|---|---|---|
| Preparation Example No. | siRNA conjugate No. | Inhibition percentage on human KNG mRNA % (±standard deviation) |
| Preparation Example 1 | L10-siKNa1M1SP | 52.75 ± 29.52 |
| Preparation Example 3 | L10-siKNc1M1SP | 56.29 ± 14.47 |
| Preparation Example 5 | L10-siKNe1M1SP | 54.13 ± 16.22 |
| Preparation Example 6 | L10-siKNf1M1SP | 48.35 ± 6.49 |

It can be seen from Table 7 that the siRNA conjugates of the present disclosure show good inhibitory effect on human KNG mRNA in the livers of the humanized mice, and the inhibition percentage on KNG mRNA is 48.35%-56.29%.

Experimental Example 4

Determination of Influence of the siRNA Conjugate Provided by the Present Disclosure on KNG Protein Concentration in Humanized Mice (In Vivo)

The humanized mice used in this experimental example were the same as those in Experimental Example 3. In the test group, two humanized mice aged 6-8 weeks were used, and each mouse was given 6 mg/kg (based on siRNA) of the siRNA conjugate L10-siKNa1M1SP via single subcutaneous injection. The siRNA conjugate L10-siKNa1M1SP was provided in the form of 0.9% sodium chloride aqueous solution at 0.6 mg/ml (based on siRNA), and the administration volume was 10 ml/kg body weight of mouse. The other humanized mouse was given 1×PBS, and the administration volume was 10 mL/kg body weight of mouse, which was used as the control group.

Blood samples were collected from the mice on the day of administration and on the $7^{th}$, $14^{th}$, $21^{st}$ and $28^{th}$ days after administration (the above time points were marked as DO, D7, D14, D21 and D28 in turn) to obtain whole blood samples. 3.8 wt % sodium citrate aqueous solution anticoagulant was added to the whole blood sample of each mouse at a volume ratio of anticoagulant to the whole blood of 1:9 (v/v), and the sample was centrifuged to obtain supernatant, i.e., to-be-tested plasma sample, which was saved at −80° C.

6×protein loading buffer (containing DTT, purchased from Beijing BioDee Biotechnology Co., Ltd., article number DE0105-1 mL) was diluted into 2×protein loading buffer with sterile water. 5 μL of to-be-tested plasma samples from each of the three mice in the test group and the control group were respectively added to different 1.5 mL centrifuge tubes, and then 5 μL of sterile water and 15 μL of 2×protein loading buffer were added to each centrifuge tube, thoroughly mixed, and then denatured at 100° C. in metal bath for 10 minutes to obtain protein sample solution.

10% separation gle and 4% stacking gle were prepared. 200 mL of 5×SDS-PAGE electrophoresis buffer (purchased from Beijing BioDee Biotechnology Co., Ltd., article number DE0100-500) was taken and was added with water till the volume reached 800 mL, and blended to obtain a diluted buffer. The diluted buffer was poured into an electrophoresis tank. 10 μL of each prepared protein sample solution was taken out, and added into different gel pores of SDS-PAGE gel respectively. In another gel pore, protein marker (Spectra Multcolor Broad Range Protein Ladder, Thermo Scientific company, No. 26634) was added for electrophoresis for 80 minutes at a constant voltage of 120 V, and then the electrophoresis was terminated.

100 mL of 10×protein electrophoresis transfer buffer (Beijing BioDee Biotechnology Co., Ltd., article number DE0181-500 mL) was taken and added with water till the volume reached 800 mL, then added with 200 mL of absolute methanol, and blended to obtain a diluted transfer buffer. After soaking a polyvinyl-difluoride membrane (hereinafter referred to as PVDF membrane) with methanol for 2 minutes, the diluted transfer buffer was used to soak sponge, filter paper and the PVDF membrane. The gel was taken out from gel plates, and a splint was prepared from bottom to top according to the order of negative plate (black)-sponge-filter paper-gel-PVDF membrane-filter paper-positive plate (white), and put into a transfer membrane tank. The transfer membrane tank was placed in an ice box, and the membrane was transferred at a constant voltage of 100 V for 1 hour.

The PVDF membrane after membrane transfer was taken out, and a PVDF membrane corresponding to a protein marker 80-150 KD interval was cut, and the cut PVDF membrane was soaked in 5 wt % skimmed milk (the skimmed milk powder was purchased from Beijing Solarbio Science and Technology Co., Ltd., article number D8340), and blocked in a table concentrator for 2 hours. A first antibody (anti-h-KNG (purchased from HEMATOLOGY CENTER, CYRUS TANG MEDICAL INSTITUTE, SOOCHOW UNIVERSITY)) was diluted with 5 wt % skimmed milk at a volume ratio of 1:1500, and incubated overnight at 4° C. to obtain the incubated PVDF membrane.

50 ml of 20×TBS buffer (purchased from Beijing BioDee Biotechnology Co., Ltd., article number DE0190-500) was diluted with water till the volume reached 1 μL, and then added with 1000 μL of Tween-20 (purchased from Beijing Solarbio Science and Technology Ltd., article number T8220) to prepare a TBST buffer.

The incubated PVDF membrane described above was eluted with excessive TBST buffer for 3 times, and 5 minutes in each time, a secondary antibody (horseradish peroxidase labeled goat anti-rabbit IgG(H+L) (purchased from Beijing ZSGB-BIO Co., Ltd., article number ZB-2301)) was diluted with 5 wt % skimmed milk at a volume ratio of 1:2000, incubated in a table concentrator at room temperature for 1 hour, and then the PVDF membrane was eluted with excessive TBST buffer for 3 times, and 5 minutes in each time. Then, the cleaned PVDF membrane was obtained.

Western luminescence detection kit (purchased from Vigorous Biotechnology (Beijing) Co., Ltd., article number P004) was used to take Western blots according to the steps described in the manual, and the specific steps were as follows: mixing solution A and solution B (included in the Western luminescence detection kit) at a ratio of 1:1 (v/v) to obtain horseradish peroxidase reaction substrate solution (HRP reaction substrate), and coating the cleaned PVDF membrane with the HRP reaction substrate.

The PVDF membrane coated with the HRP reaction substrate was placed in an imager, and the protein marker was photographed in bright field mode according to the method described in the manual. Protein luminescence bands were photographed in chemiluminescence mode, and the exposure time was 10 minutes.

It could be known from the photographing results of protein marker that the control group and each test group at different time points showed clear protein markers. Then, the protein markers were analyzed by ImageJ software, and light intensity values of western blot bands of the control group and each test group at different time points were obtained. It could be known through analysis that the light intensity values of the western blot bands of each test group at different time points after administration were significantly reduced in comparison to the data of the control group and DO.

Furthermore, based on the light intensity value of the western blot band of the control group, the light intensity values of KNG western blot bands of each test group at each time point were standardized, the protein expression level of the control group was defined as 100%, and the relative expression level of the KNG protein of the test group was calculated by the following equation:

Relative expression level of KNG protein=(light intensity value of KNG western blot band of test group/light intensity value of KNG western blot band of control group)×100%

Inhibition percentage on expression of KNG protein=(1−relative expression level of KNG protein)×100%

For the test groups, the relative expression level and the inhibition percentage were the arithmetic mean values of the test results of two mice.

Figure 3:
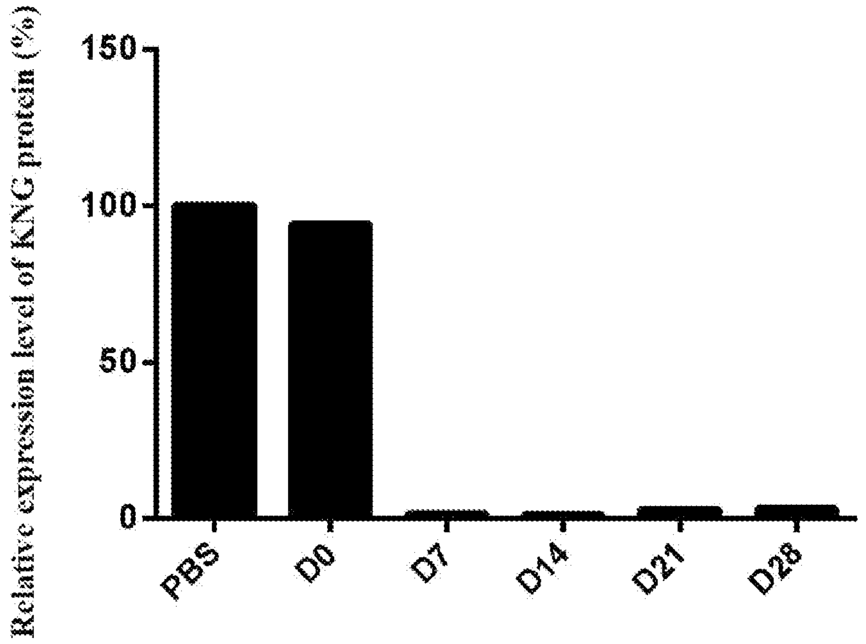
FIG. 3 is a histogram showing relative expression levels of KNG protein in mice at different time points after administration of an siRNA conjugate.

FIG. 3 shows the relative expression level of KNG proteins in samples of the control group and the test groups at different blood sampling time points.

It can be seen from the results in FIG. 3 that the siRNA conjugate provided by the present disclosure shows a good inhibitory effect on KNG protein in the to-be-tested plasma samples in mice. For the siRNA conjugate provided by the present disclosure, the inhibition percentage on KNG protein in the to-be-tested plasma samples reaches over 97%, even up to about 99% for up to 28 days, and the inhibition effect is remarkable. Therefore, it is shown that the siRNA conjugate of the present disclosure can effectively inhibit the expression of KNG protein, thus showing excellent application prospect for treating KNG related diseases, especially septicemia.

Some embodiments of the present disclosure are described in detail above, but the present disclosure is not limited to the specific details of the above-described embodiments. Various simple variations of the technical solution of the present disclosure can be made within the scope of the technical concept of the present disclosure, and these simple variations are within the protection scope of the present disclosure.

In addition, it is to be noted that each of the specific technical features described in the above embodiments can be combined in any suitable manner as long as no contradiction is caused. In order to avoid unnecessary repetition, the various possible combination manners are no longer described in the present disclosure.

In addition, the various different embodiments of the present disclosure may also be carried out in any combination as long as it does not contravene the idea of the present disclosure, which should also be regarded as the disclosure of the present disclosure.

The invention claimed is:

1. An siRNA conjugate having a structure as shown by Formula (308):

Formula (308)

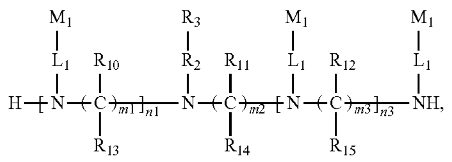

wherein:

n1 is an integer selected from 1-3, and n3 is an integer selected from 0-4;

each of m1, m2, or m3 is independently an integer selected from 2-10;

each of $R_{10}$, $R_{11}$, $R_{12}$, $R_{13}$, $R_{14}$ or $R_{15}$ is independently H or selected from the group consisting of $C_1$-$C_{10}$ alkyl, $C_1$-$C_{10}$ haloalkyl and $C_1$-$C_{10}$ alkoxy; and $R_3$ is a group having a structure as shown by Formula A59:

(A59)

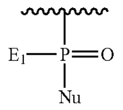

wherein, E1 is OH, SH or $BH_2$, and Nu is the siRNA;

wherein the siRNA comprises a sense strand and an antisense strand, and each nucleotide in the siRNA is independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; and the nucleotide sequence I and the nucleotide sequence II are selected from a group of sequences shown in the following i)-vi):

i) the nucleotide sequence I has the same length as and no more than three nucleotide differences from the nucleotide sequence shown in SEQ ID NO:1; and the nucleotide sequence II has the same length as and no more than three nucleotide differences from the nucleotide sequence shown in SEQ ID NO:2:

(SEQ ID NO: 1)
5'-AAAGUAACAACCAGUUUGZ$_1$-3';

(SEQ ID NO: 2)
5'-Z$_2$CAAACUGGUUGUUACUUU-3', wherein, $Z_1$ is U, and $Z_2$ is A; and the nucleotide sequence I comprises a nucleotide $Z_3$ at a corresponding site to $Z_1$, the nucleotide sequence II comprises a nucleotide $Z_4$ at a corresponding site to $Z_2$, and $Z_4$ is the first nucleotide from the 5' terminal of the antisense strand, $Z_3$ is the first nucleotide from the 3' terminal of the sense strand; the nucleotide difference between the nucleotide sequence II and the nucleotide sequence shown in SEQ ID NO: 2 comprises a difference at the site of $Z_4$, and $Z_4$ is selected from U, C or G;

ii) the nucleotide sequence I has the same length as and no more than three nucleotide differences from the nucleotide sequence shown in SEQ ID NO: 61; and the nucleotide sequence II has the same length as and no more than three nucleotide differences from the nucleotide sequence shown in SEQ ID NO: 62:

(SEQ ID NO: 61)
5'-AUUGAACUUUCGAAUUACZ$_5$-3';

(SEQ ID NO: 62)
5'-Z$_6$GUAAUUCGAAAGUUCAAU-3', wherein, $Z_5$ is C, and $Z_6$ is G; and the nucleotide sequence I comprises a nucleotide $Z_7$ at a corresponding site to $Z_5$, the nucleotide sequence II comprises a nucleotide $Z_8$ at a corresponding site to $Z_6$, and $Z_8$ is the first nucleotide from the 5' terminal of the antisense strand, $Z_7$ is the first nucleotide from the 3' terminal of the sense strand; the nucleotide difference between the nucleotide sequence II and the nucleotide sequence shown in SEQ ID NO: 62 comprises a difference at the site of $Z_8$, and $Z_8$ is selected from A, U or C;

iii) the nucleotide sequence I has the same length as and no more than three nucleotide differences from the nucleotide sequence shown in SEQ ID NO: 121; and the nucleotide sequence II has the same length as and no more than three nucleotide differences from the nucleotide sequence shown in SEQ ID NO: 122:

(SEQ ID NO: 121)
5'-UCGAAUUACCUACUCAAUZ$_9$-3';

(SEQ ID NO: 122)
5'-Z$_{10}$AUUGAGUAGGUAAUUCGA-3', wherein, $Z_9$ is U, and $Z_{10}$ is A; and the nucleotide sequence I comprises a nucleotide Zu at a corresponding site to $Z_9$, the nucleotide sequence II comprises a nucleotide $Z_{12}$ at a corresponding site to $Z_{10}$, and $Z_{12}$ is the first nucleotide from the 5' terminal of the antisense strand, $Z_{11}$ is the first nucleotide from the 3' terminal of the sense strand: the nucleotide difference between the nucleotide sequence II and the nucleotide sequence shown in SEQ ID NO: 122 comprises a difference at the site of $Z_{12}$, and $Z_{12}$ is selected from U, C or G;

iv) the nucleotide sequence I has the same length as and no more than three nucleotide differences from the nucleotide sequence shown in SEQ ID NO: 181; and the nucleotide sequence II has the same length as and no more than three nucleotide differences from the nucleotide sequence shown in SEQ ID NO: 182:

(SEQ ID NO: 181)
5'-GAUAAUGCAUACAUCGAUZ$_{13}$-3';

(SEQ ID NO: 182)
5'-Z$_{14}$AUCGAUGUAUGCAUUAUC-3', wherein, $Z_{13}$ is A, and $Z_{14}$ is U; and the nucleotide sequence I comprises a nucleotide $Z_{15}$ at a corresponding site to $Z_{13}$, the nucleotide sequence II comprises a nucleotide $Z_{16}$ at a corresponding site to $Z_{14}$, and $Z_{16}$ is the first nucleotide from the 5' terminal of the antisense strand, $Z_{15}$ is the first nucleotide from the 3' terminal of the sense strand: the nucleotide difference between the nucleotide sequence II and the nucleotide sequence shown in SEQ ID NO: 182 comprises a difference at the site of $Z_{16}$, and $Z_{16}$ is selected from A, C or G;

v) the nucleotide sequence I has the same length as and no more than three nucleotide differences from the nucleotide sequence shown in SEQ ID NO: 241; and the nucleotide sequence II has the same length as and no more than three nucleotide differences from the nucleotide sequence shown in SEQ ID NO: 242:

(SEQ ID NO: 241)
5'-GAAUAACGCAACUUUCUAZ$_{17}$-3';

(SEQ ID NO: 242)
5'-Z$_{18}$UAGAAAGUUGCGUUAUUC-3', wherein, $Z_{17}$ is U, and $Z_{18}$ is A; and the nucleotide sequence I comprises a nucleotide $Z_{19}$ at a corresponding site to $Z_{17}$, the nucleotide sequence II comprises a nucleotide $Z_{20}$ at a corresponding site to $Z_{18}$, and $Z_{20}$ is the first nucleotide from the 5' terminal of the antisense strand, $Z_{19}$ is the first nucleotide from the 3' terminal of the sense strand: the nucleotide difference between the nucleotide sequence II and the nucleotide sequence shown in SEQ ID NO: 242 comprises a difference at the site of $Z_{20}$, and $Z_{20}$ is selected from U, C or G;

vi) the nucleotide sequence I has the same length as and no more than three nucleotide differences from the nucleotide sequence shown in SEQ ID NO: 301; and the nucleotide sequence II has the same length as and no more than three nucleotide differences from the nucleotide sequence shown in SEQ ID NO: 302:

(SEQ ID NO: 301)
5'-AACUUUCUAUUUCAAGAUZ$_{21}$-3';

(SEQ ID NO: 302)
5'-Z$_{22}$AUCUUGAAAUAGAAAGUU-3', wherein, $Z_{21}$ is U, and $Z_{22}$ is A; and the nucleotide sequence I comprises a nucleotide $Z_{23}$ at a corresponding site to $Z_{21}$, the nucleotide sequence II comprises a nucleotide $Z_{24}$ at a corresponding site to $Z_{22}$, and $Z_{24}$ is the first nucleotide from the 5' terminal of the antisense strand; wherein "corresponding site" means being at the same site in the nucleotide sequence by counting from the same terminal of the nucleotide sequence, $Z_{23}$ is the first nucleotide from the 3' terminal of the sense strand: the nucleotide difference between the nucleotide sequence II and the nucleotide sequence shown in SEQ ID NO: 302 comprises a difference at the site of $Z_{24}$, and $Z_{24}$ is selected from U, C or G;

$R_2$ is a linear alkylene of 1-20 carbon atoms in length, wherein one or more carbon atoms are optionally replaced with any one or more selected from the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene; and wherein $R_2$ can optionally have any one or more substituents in the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo substituent, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —$CO_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —NH$SO_2$($C_1$-$C_{10}$ alkyl), —NH$SO_2$(phenyl), and —NH$SO_2$($C_1$-$C_{10}$ haloalkyl);

each $L_1$ is a linear alkylene of 1-70 carbon atoms in length, wherein one or more carbon atoms are optionally replaced with any one or more selected from the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene; and wherein $L_1$ can optionally have any one or more substituents in the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo substituent, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —$CO_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-

$C_{10}$ alkyl), $—SO_2NH$(phenyl), $—NHSO_2(C_1\text{-}C_{10}$ alkyl), $—NHSO_2$(phenyl), and $—NHSO_2(C_1\text{-}C_{10}$ haloalkyl);

represents the site where a group is covalently linked; and

M1 represents a targeting group.

2. The siRNA conjugate according to claim 1, wherein each $L_1$ is independently selected from the group consisting of groups A1-A26 and any combinations thereof:

(A1)

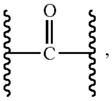

(A2)

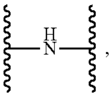

(A3)

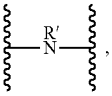

(A4)

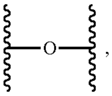

(A5)

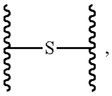

(A6)

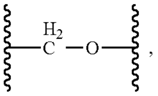

(A7)

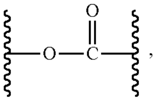

(A8)

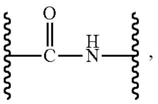

(A9)

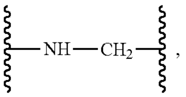

(A10)

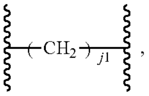

(A11)

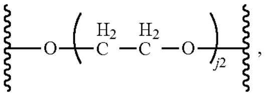

(A12)

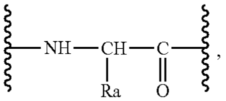

-continued (A13)

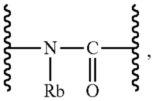

(A14)

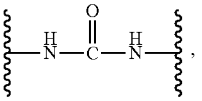

(A15)

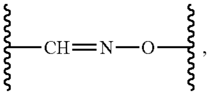

(A16)

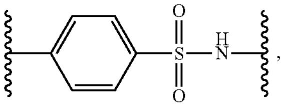

(A17)

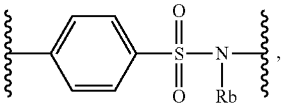

(A18)

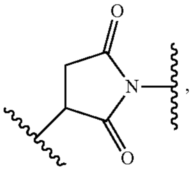

(A19)

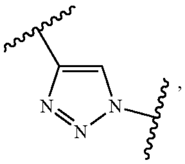

(A20)

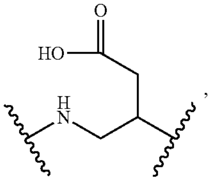

(A21)

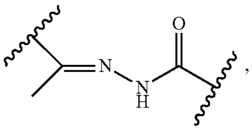

(A22)

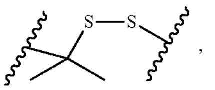

(A23)

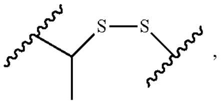

(A24)

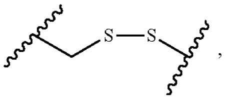

-continued
(A25)
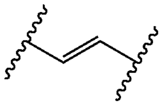,
(A26)
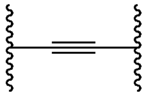;
wherein, each j1 is independently an integer of 1-20;
each j2 is independently an integer of 1-20;
each R' is independently a $C_1$-$C_{10}$ alkyl; and
each Ra is independently selected from the group consisting of groups A27-A45 and any combinations thereof:
(A27)
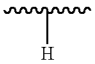,
(A28)
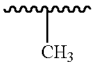,
(A29)
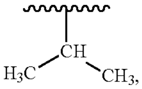
(A30)
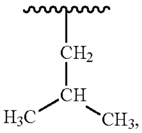
(A31)
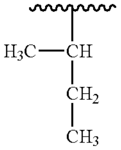,
(A32)
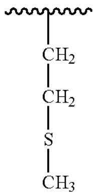,
(A33)
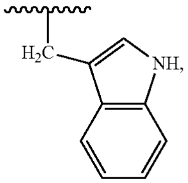
(A34)
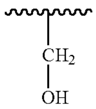,
-continued
(A35)
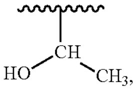
(A36)
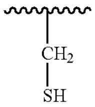,
(A37)
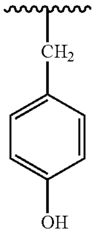,
(A38)
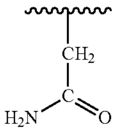,
(A39)
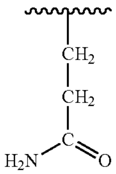,
(A40)
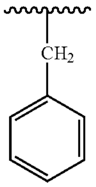,
(A41)
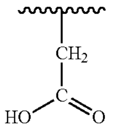,
(A42)
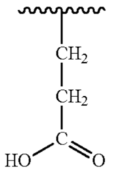,
(A43)
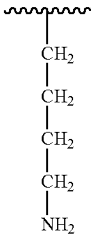, -continued (A44)

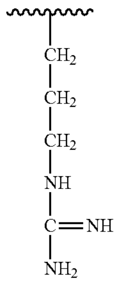

or (A45)

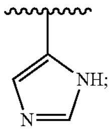

each Rb is independently a $C_1$-$C_{10}$ alkyl; and represents a site where the group is covalently linked.

3. The siRNA conjugate according to claim 2, wherein L1 is selected from the group consisting of groups A1, A4, A5, A6, A8, A10, A11, A13 and the connection combinations thereof, or L1 is the connection combinations of at least two of groups A1, A4, A8, A10, and A11.

4. The siRNA conjugate according to claim 1, wherein the length of L1 is 3-25 atoms; or the length of L1 is 4-15 atoms.

5. The siRNA conjugate according to claim 1, wherein each of m1, m2 or m3 is independently an integer of 2-5; or m1=m2=m3.

6. The siRNA conjugate according to claim 1, wherein each of the targeting groups is independently a ligand that has affinity with the asialoglycoprotein receptor on a surface of a mammalian hepatocyte; or at least one or each of the targeting groups is galactose or N-acetylgalactosamine.

7. The siRNA conjugate according to claim 1, wherein the siRNA conjugate has a structure as shown by Formula (403), (404), (405), (406), (407), (408), (409), (410), (411), (412), (413), (414), (415), (416), (417), (418), (419), (420), (421) or (422):

Formula (403)

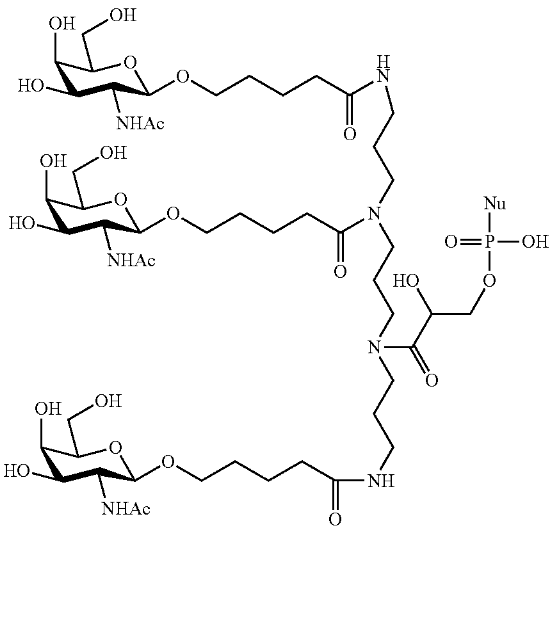

-continued
Formula (404)
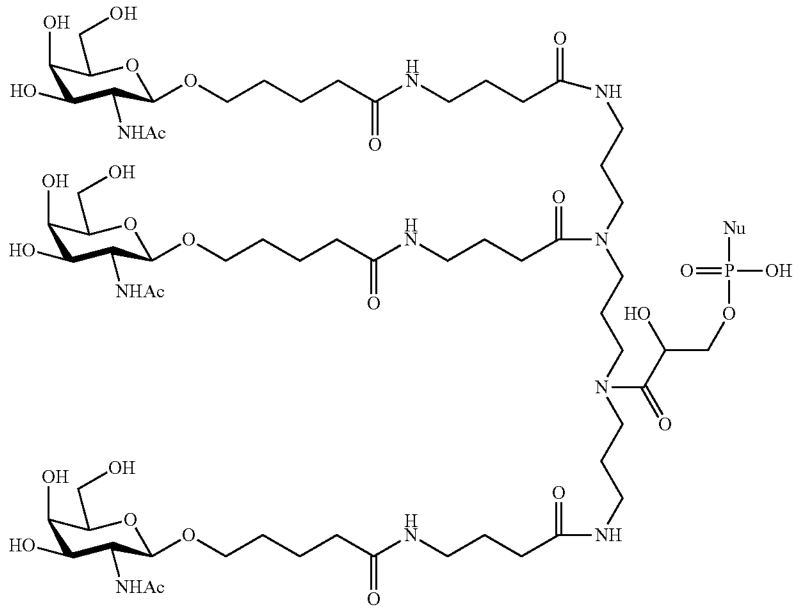
Formula (405)
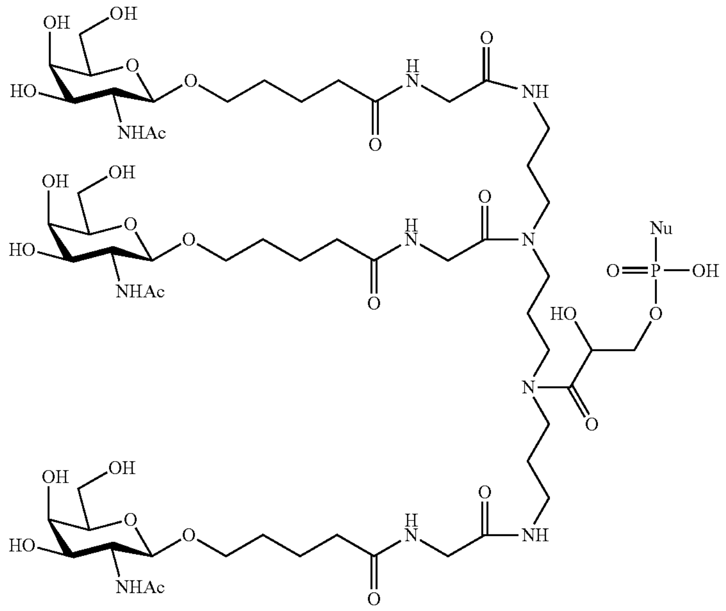

-continued
Formula (406)
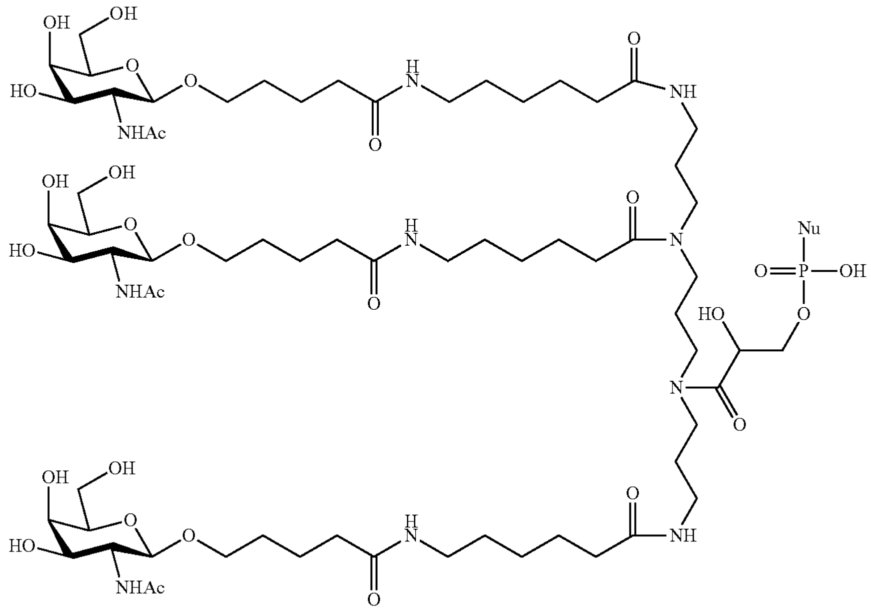
Formula (407)
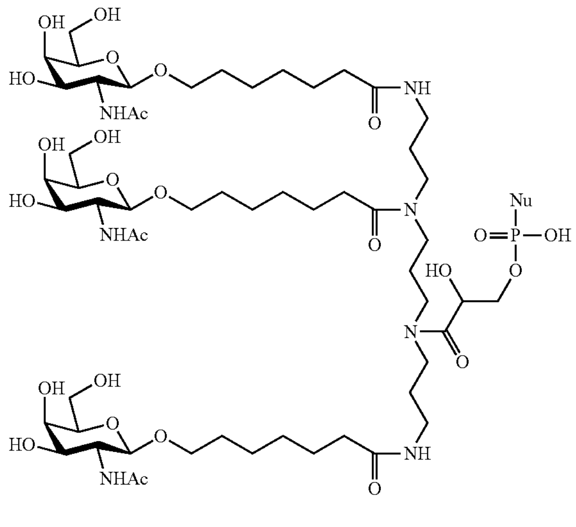
Formula (408)
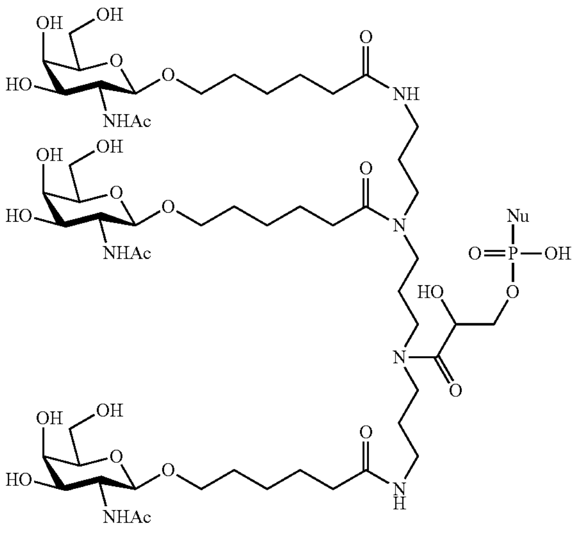
Formula (409)
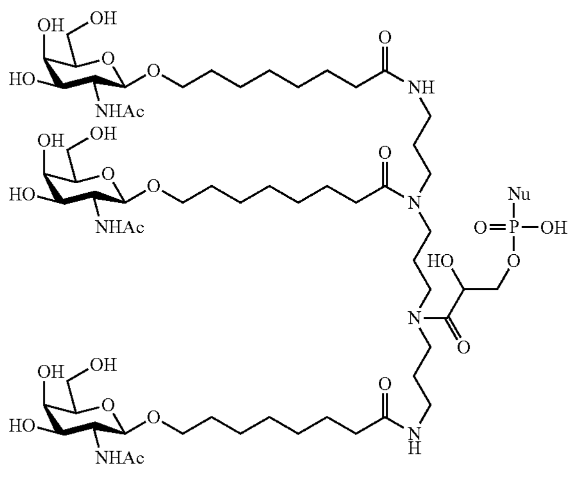
Formula (410)
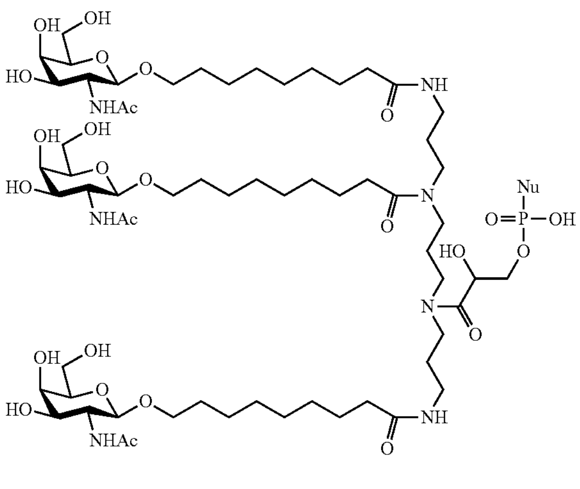

-continued
Formula (411)
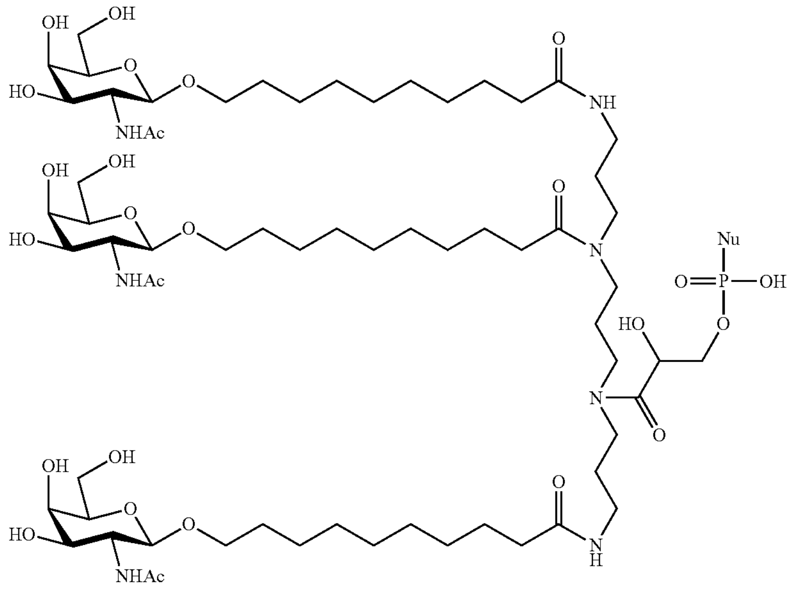
Formula (412)
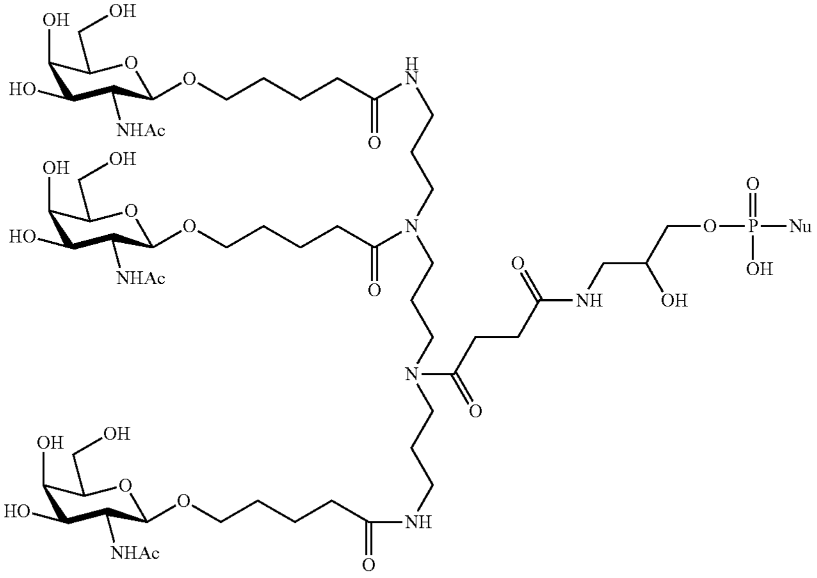

-continued
Formula (413)
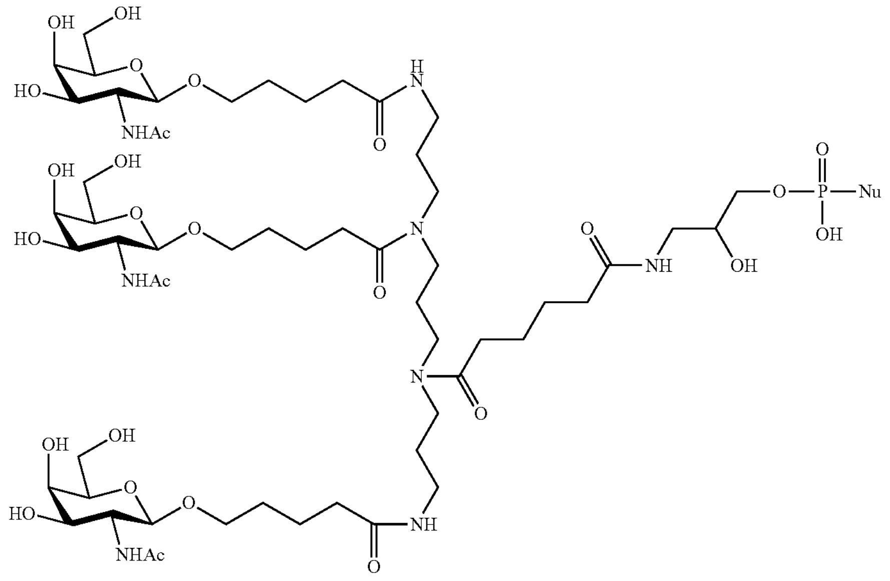
Formula (414)
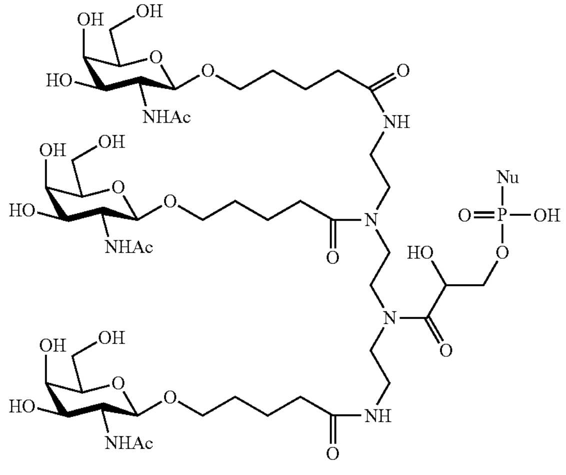
Formula (415)
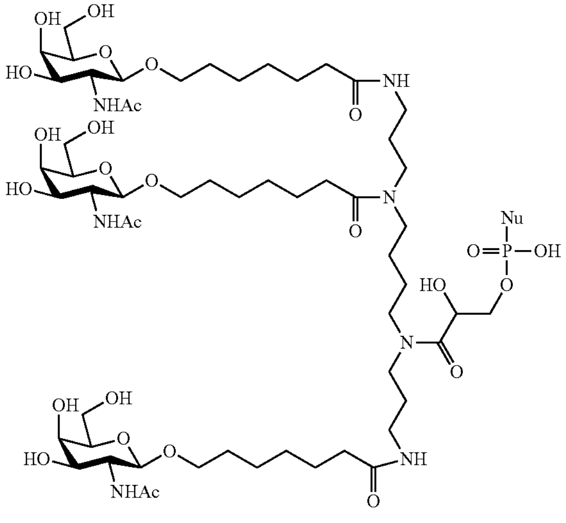

-continued
Formula (416)
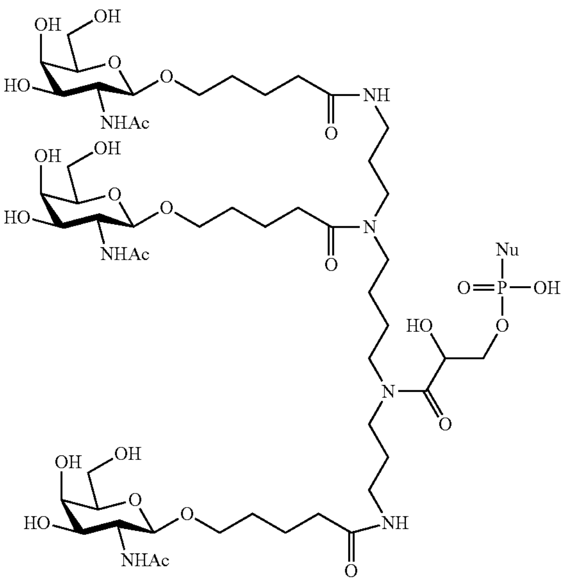
Formula (417)
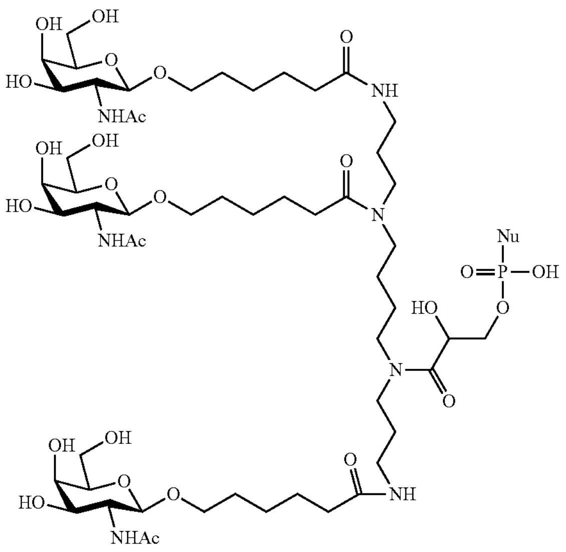
Formula (418)
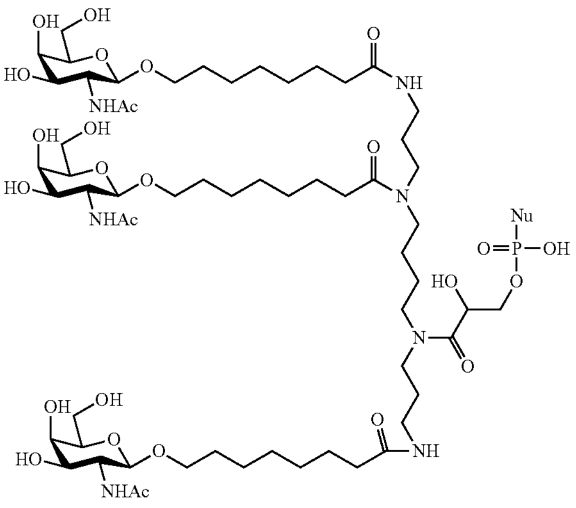
Formula (419)
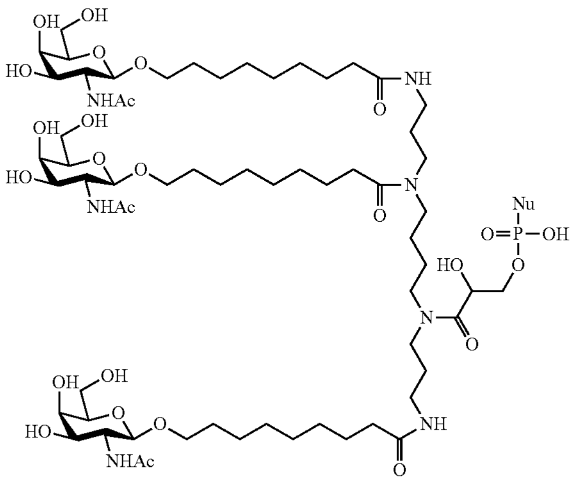

-continued
Formula (420)
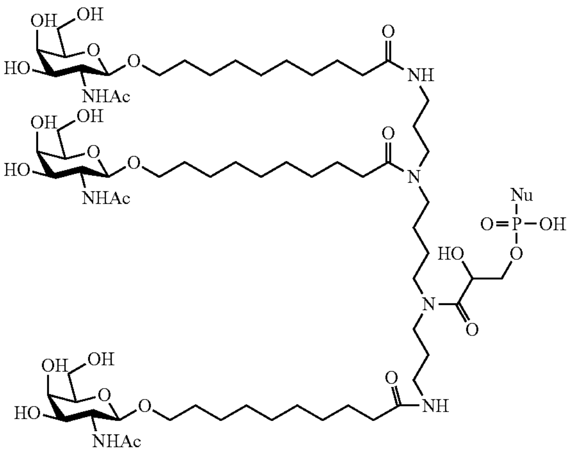
Formula (421)
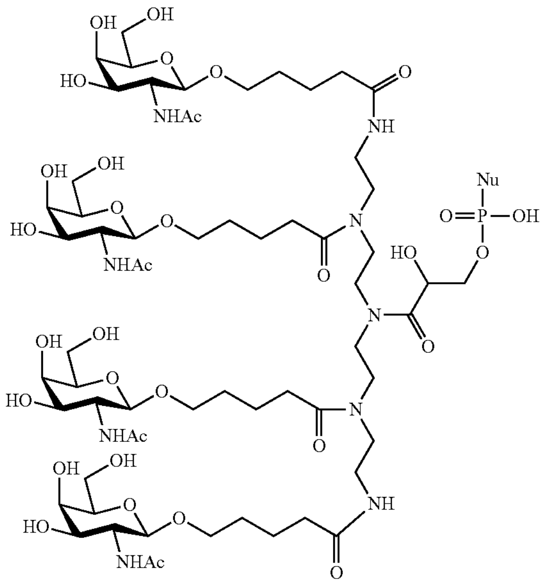
Formula (422)
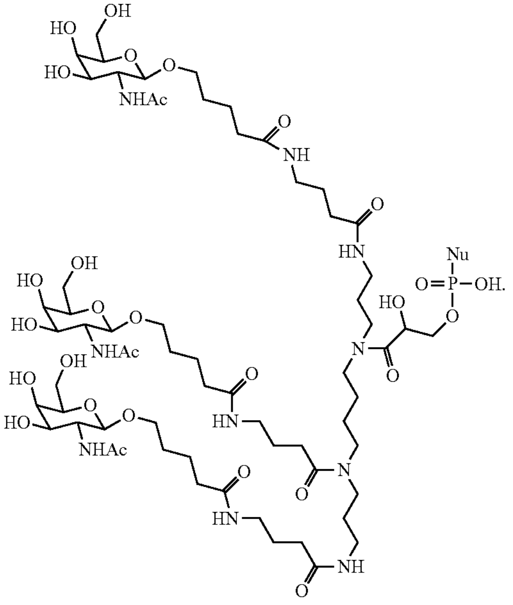
8. The siRNA conjugate according to claim 1, wherein the P atom in Formula A59 is linked to a 3' terminal of the sense strand of the siRNA.
* * * * *